United States Patent
Koehler et al.

(10) Patent No.: US 10,106,555 B2
(45) Date of Patent: Oct. 23, 2018

(54) MAX BINDERS AS MYC MODULATORS AND USES THEREOF

(71) Applicant: Massachusetts Institute of Technology, Cambridge, MA (US)

(72) Inventors: Angela N. Koehler, Belmont, MA (US); Eric Stefan, Boston, MA (US); Francisco Caballero, Brookline, MA (US); Dylan Vijith Neel, Providence, RI (US); Nicholas B. Struntz, Cambridge, MA (US); Helen L. Evans, Cambridge, MA (US); Andrew Chen, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 15/435,003

(22) Filed: Feb. 16, 2017

(65) Prior Publication Data

US 2017/0233405 A1 Aug. 17, 2017

Related U.S. Application Data

(60) Provisional application No. 62/295,996, filed on Feb. 16, 2016.

(51) Int. Cl.
*C07D 223/28* (2006.01)
*C07D 491/107* (2006.01)
(Continued)

(52) U.S. Cl.
CPC ......... *C07D 498/04* (2013.01); *C07D 233/28* (2013.01); *C07D 491/107* (2013.01); *C07D 498/10* (2013.01)

(58) Field of Classification Search
CPC .............. C07D 233/28; C07D 491/107; C07D 498/04; C07D 498/10
See application file for complete search history.

(56) References Cited

U.S. PATENT DOCUMENTS

| | | | |
|---|---|---|---|
| 5,965,574 A | 10/1999 | Chen et al. | |
| 6,452,014 B1 | 9/2002 | Akama et al. | |

(Continued)

FOREIGN PATENT DOCUMENTS

| | | |
|---|---|---|
| EP | 1 746 097 A1 | 1/2007 |
| JP | H02191695 A | 7/1990 |

(Continued)

OTHER PUBLICATIONS

International Search Report and Written Opinion for PCT/US2015/065044, dated Feb. 22, 2016.

(Continued)

*Primary Examiner* — Bruck Kifle
(74) *Attorney, Agent, or Firm* — Wolf, Greenfield & Sacks, P.C.

(57) ABSTRACT

The present disclosure provides compounds of Formula (I'), Formula (I), Formula (II), Formula (II-A), Formula (III), and Formula (IV). The compounds described herein are MAX binders and/or modulators of Myc, Mad, or Mxi1 (e.g., inhibitors of Myc, Mad, or Mxi1), and may be useful in treating a subject with a disease associated with Myc, such as proliferative diseases (e.g., cancer). Also provided in the present disclosure are pharmaceutical compositions and kits including the compounds described herein, as well as methods of using and uses of the compounds, compositions, and kits.

(I')

(I)

(II)

(II-A)

(Continued)

-continued

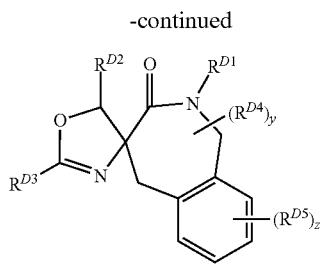

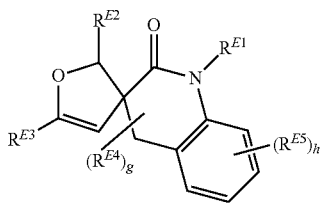

23 Claims, 32 Drawing Sheets

(51) Int. Cl.
*C07D 498/04* (2006.01)
*C07D 498/10* (2006.01)
*C07D 233/28* (2006.01)

(56) References Cited

U.S. PATENT DOCUMENTS

| | | | |
|---|---|---|---|
| 8,642,660 | B2 | 2/2014 | Goldfarb |
| 2006/0074124 | A1 | 4/2006 | Napper et al. |
| 2011/0152240 | A1 | 6/2011 | Haddach et al. |
| 2013/0184240 | A1 | 7/2013 | Tonogaki et al. |
| 2014/0296307 | A1 | 10/2014 | Fletcher et al. |
| 2016/0168165 | A1 | 6/2016 | Koehler et al. |

FOREIGN PATENT DOCUMENTS

| | | |
|---|---|---|
| JP | H02196887 A | 8/1990 |
| JP | H02208392 A | 8/1990 |
| JP | H02222488 A | 9/1990 |
| JP | H02227489 A | 9/1990 |
| JP | H02227490 A | 9/1990 |
| JP | H02227491 A | 9/1990 |
| JP | H02242882 A | 9/1990 |
| JP | H02247280 A | 10/1990 |
| JP | H02247282 A | 10/1990 |
| JP | H02255793 A | 10/1990 |
| JP | H02255794 A | 10/1990 |
| JP | H08231541 A | 9/1996 |
| JP | 2003-057783 A | 2/2003 |
| JP | 2003-075955 A | 3/2003 |
| JP | 2003-075957 A | 3/2003 |
| JP | 2004-131463 A | 4/2004 |
| JP | 2006-084592 A | 3/2006 |
| JP | 2007-217298 A | 8/2007 |
| JP | 2010-207767 A | 9/2010 |
| WO | H02194085 A | 7/1990 |
| WO | WO 00/023451 A1 | 4/2000 |
| WO | WO 2004/080989 A1 | 9/2004 |
| WO | WO 2005/002503 A2 | 1/2005 |
| WO | WO 2005/026112 A2 | 3/2005 |
| WO | WO 2005/033090 A1 | 4/2005 |
| WO | WO 2006/031894 A2 | 3/2006 |
| WO | WO 2007/047604 A2 | 4/2007 |
| WO | WO 2007/146712 A2 | 12/2007 |
| WO | WO 2008/012010 A1 | 1/2008 |
| WO | WO 2009/092764 A1 | 7/2009 |
| WO | WO 2009/108905 A2 | 9/2009 |
| WO | WO 2010/054398 A1 | 5/2010 |
| WO | WO 2010/075282 A1 | 7/2010 |
| WO | WO 2012/153780 A1 | 11/2012 |
| WO | WO 2013/038650 A1 | 3/2013 |
| WO | WO 2013/177241 A1 | 11/2013 |
| WO | WO 2014/132971 A1 | 9/2014 |
| WO | WO 2015/089180 A1 | 6/2015 |

OTHER PUBLICATIONS

International Preliminary Report on Patentability for PCT/US2015/065044, dated Jun. 22, 2017.
CAS Registry No. 444693-02-1, STN Entry Date Aug. 22, 2002.
CAS Registry No. 444714-90-3, STN Entry Date Aug. 22, 2002.
CAS Registry No. 444653-79-6, STN Entry Date Aug. 22, 2002.
CAS Registry No. 497836-62-1, STN Entry Date Mar. 11, 2003.
CAS Registry No. 675830-23-6, STN Entry Date Apr. 16, 2004.
CAS Registry No. 1458427-65-0, STN Entry Date Oct. 15, 2013.
CAS Registry No. 439814-35-4, STN Entry Date Jul. 23, 2002.
CAS Registry No. 83490-12-4, STN Entry Date Nov. 16, 1984.
CAS Registry No. 920536-51-2, STN Entry Date Feb. 12, 2007.
Boxer et al., Translocations involving c-myc and c-myc function. Oncogene. Sep. 10, 2001;20(40):5595-610.
Dang et al., c-Myc target genes involved in cell growth, apoptosis, and metabolism. Mol Cell Biol. Jan. 1999;19(1):1-11.
Dang et al., The c-Myc target gene network.Semin Cancer Biol. Aug. 2006;16(4):253-64. Epub Jul. 25, 2006.
Duffner et al., A pipeline for ligand discovery using small-molecule microarrays. Curr Opin Chem Biol. Feb. 2007;11(1):74-82. Epub Dec. 13, 2006.
Eilers et al., Myc's broad reach. Genes Dev. Oct. 15, 2008;22(20):2755-66. doi: 10.1101/gad.1712408.
Felsher et al., Reversible tumorigenesis by MYC in hematopoietic lineages.Mol Cell. Aug. 1999;4(2):199-207.
Frost et al., Comparative immunohistochemical analysis of pediatric Burkitt lymphoma and diffuse large B-cell lymphoma. Am J Clin Pathol. Mar. 2004;121(3):384-92.
Frye et al., The art of the chemical probe. Nat Chem Biol. Mar. 2010;6(3):159-161.
Leskov et al., Rapid generation of human B-cell lymphomas via combined expression of Myc and Bcl2 and their use as a preclinical model for biological therapies. Oncogene. Feb. 21, 2013;32(8):1066-72. doi: 10.1038/onc.2012.117. Epub Apr. 9, 2012.
Nitsche et al., Thiazolidinone-peptide hybrids as dengue virus protease inhibitors with antiviral activity in cell culture. J Med Chem. Nov. 14, 2013;56(21):8389-403. doi: 10.1021/jm400828u.
Norgren et al., On-Resin Click-Glycoconjugation of Peptoids. Synthesis. 2009; 3: 488-94.
Pajic et al., Cell cycle activation by c-myc in a burkitt lymphoma model cell line. Int J Cancer. Sep. 15, 2000;87(6):787-93.
Seiler et al., ChemBank: a small-molecule screening and cheminformatics resource database. Nucleic Acids Res. Jan. 2008;36(Database issue):D351-9. Epub Oct. 18, 2007.
Sekar et al., S-arylation of mercaptobenzimidazoles using Cu(I) catalysts-experimental and theoretical observations. Tetrahedron Letters. 2011;52:3347-52.
Soucek et al., Inhibition of Myc family proteins eradicates KRas-driven lung cancer in mice. Genes Dev. Mar. 1, 2013;27(5):504-13. doi: 10.1101/gad.205542.112.
Vanriggelen et al., MYC as a regulator of ribosome biogenesis and protein synthesis. Nat Rev Cancer. Apr. 2010;10(4):301-9. doi: 10.1038/nrc2819.
Vita et al., The Myc oncoprotein as a therapeutic target for human cancer. Semin Cancer Biol. Aug. 2006;16(4):318-30. Epub Aug. 3, 2006.
International Search Report and Written Opinion for PCT/US2017/018162, dated Apr. 20, 2017.
Huang et al., Photocycloadditions of substituted oxazoles with isoquinoline-1,3,4-trione—chemo, regio-, diastereoselectivities and transformation of the photocycloadducts. Org Biomol Chem. Aug 14, 2013;11(30):5023-33. doi: 10.1039/c3ob40645h. Epub Jun. 26, 2013.

(56) References Cited

OTHER PUBLICATIONS

Mitchell et al., A structurally diverse library of polycyclic lactams resulting from systematic placement of proximal functional groups. Angew Chem Int Ed Engl. Mar. 3, 2006;45(11):1722-6.
Wang et al., Small-molecule reagents for cellular pull-down experiments. Bioconjug Chem. Mar. 2008;19(3):585-7. doi: 10.1021/bc700297j. Epub Jan. 15, 2008.
CAS Registry No. 641607-16-1, STN Entry Date Jan. 26, 2004.
CAS Registry No. 1024883-05-3, STN Entry Date Jun. 3, 2008.
Verma et al., Design and Synthesis of Benzimidazole-Linked meta-Substituted Benzylidenes/Benzyls as Biologically Significant New Chemical Entities. Synthetic Communications 2013; 43(14):1882-95.

Legend: Bio-MS2 (compound 5); Bio-MS2 + MS2 (compound 5 and compound 1)

Legend: EB (empty beads); Me-Bio (methylated biotin); KI-MS2-005 (compound 5)

Western Blot for Max

Coomassie Total Protein Stain

IV administration:
20μM in saline
+0.1% DMSO
150 μL daily

MAX BINDERS AS MYC MODULATORS AND USES THEREOF

RELATED APPLICATIONS

This application claims priority under 35 U.S.C. § 119(e) to U.S. Provisional Application, U.S. Ser. No. 62/295,996, filed Feb. 16, 2016, which is incorporated herein by reference.

GOVERNMENT SUPPORT

This invention was made with government support under grant numbers R01 CA160860 and P30 CA014051 awarded by the National Institutes of Health. The government has certain rights in the invention.

BACKGROUND OF THE INVENTION

MAX (MYC associated factor X) is a member of the basic helix-loop-helix leucine zipper (bHLHZ) family of transcription factors. It is able to form homodimers and heterodimers with other family members, which include Mad, Mxi1, and Myc. The homodimers and heterodimers compete for a common DNA target site (the E box), and rearrangement among these dimeric forms provides a complex system of transcriptional regulation. Activation of c-MYC is one of the most common oncogenic events in human malignancies [1, 2]. In normal cells, the Myc family of transcription factors (MYC, MYCL, and MYCN) regulates a diverse set of biological processes including DNA replication, gene transcription, and protein translation. Consequently, numerous cellular processes are regulated by Myc, including growth, proliferation, apoptosis, metabolism, differentiation, self-renewal, and angiogenesis [3, 4, 5]. In malignant cells, Myc activation can occur through several mechanisms such as point mutation, somatic gene amplification, chromosomal translocation, overexpression, enhanced translation, and increased protein stability [2]. The report that the inhibition of Myc in vivo had eradicated lung cancer in mice [6] suggests that Myc may be a promising therapeutic target in treating cancer. However, the Myc protein is difficult to target using small molecule probes due to its disordered conformational structure and the difficulty of finding specific probes. Since Myc and MAX dimerize in order to bind DNA and initiate transcription, Myc can be indirectly targeted by using compounds that bind MAX. If these compounds reduce Myc transcriptional activity in human cancers, they may also cause tumor regression. Thus, MAX binding compounds have potential in cancer treatment and may provide an indirect way of targeting of Myc in treating cancer and other proliferative diseases.

SUMMARY OF THE INVENTION

In one aspect, described herein are compounds of Formula (I'), Formula (I), Formula (II), Formula (II-A), Formula (III), Formula (IV), and pharmaceutically acceptable salts, solvates, hydrates, polymorphs, co-crystals, tautomers, stereoisomers, isotopically labeled derivatives, and prodrugs thereof. The compounds described herein may be binders of MAX and/or modulators (e.g., inhibitors) of Myc (e.g., c-Myc, L-Myc, N-Myc), Mad, or Mxi1. The compounds may be useful in modulating (e.g., inhibiting) the activity of Myc, Mad, or Mxi1 in a subject in need thereof, treating diseases associated with Myc (e.g., diseases associated with aberrant activity (e.g., increased activity) of Myc) in a subject in need thereof, treating diseases in a subject in need thereof (e.g., proliferative diseases), preventing diseases associated with Myc (e.g., diseases associated with aberrant activity (e.g., increased activity) of Myc) in a subject in need thereof, preventing diseases in a subject in need thereof (e.g., proliferative diseases), and/or as research tools (e.g., for studying Myc and Myc-associated transcription (e.g., studying the activity of Myc) in a subject, biological sample, tissue, or cell). Also provided are pharmaceutical compositions, kits, methods, and uses including a compound described herein (e.g., a compound of Formula (I'), Formula (I), Formula (II), Formula (II-A), Formula (III), or Formula (IV)).

In one aspect, the present invention provides compounds of Formula (I'):

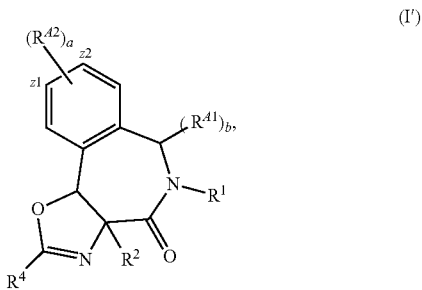

(I')

and pharmaceutically acceptable salts, solvates, hydrates, polymorphs, co-crystals, tautomers, stereoisomers, isotopically labeled derivatives, and prodrugs thereof, wherein $R^1$, $R^2$, $R^4$, $R^{41}$, $R^{42}$, a, and b are as defined herein.

In one aspect, the present disclosure provides compounds of Formula (I):

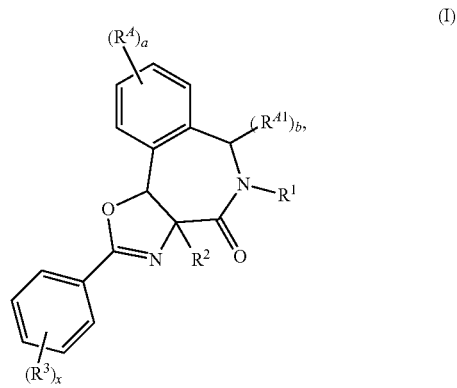

(I)

and pharmaceutically acceptable salts, solvates, hydrates, polymorphs, co-crystals, tautomers, stereoisomers, isotopically labeled derivatives, and prodrugs thereof, wherein $R^1$, $R^2$, $R^3$, $R^4$, $R^{41}$, a, b, and x are as defined herein.

Exemplary compounds of Formulae (I') and (I) include, but are not limited to:

3
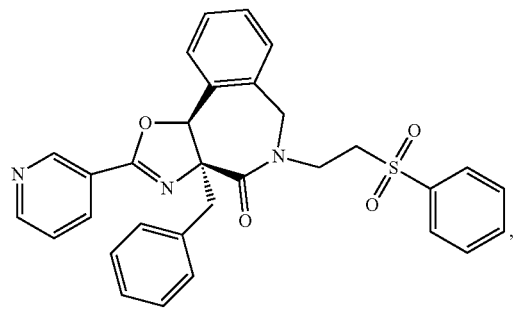
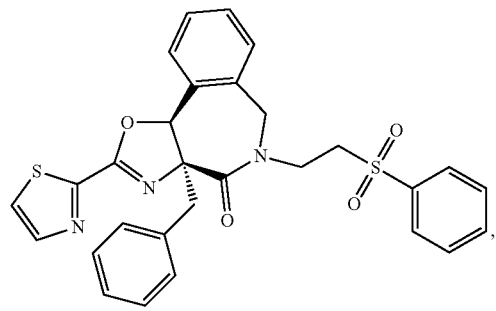
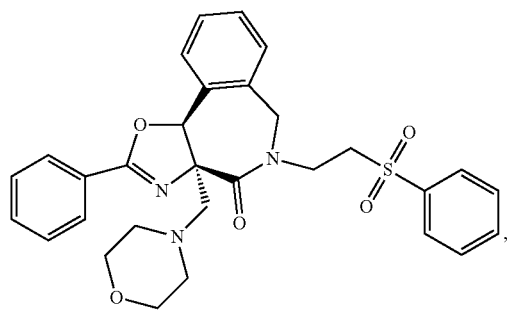
4
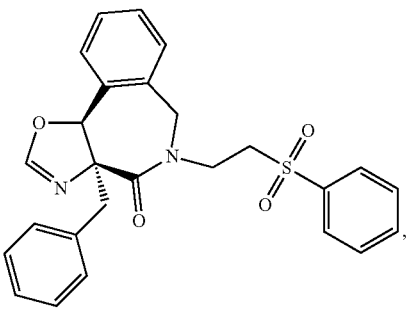
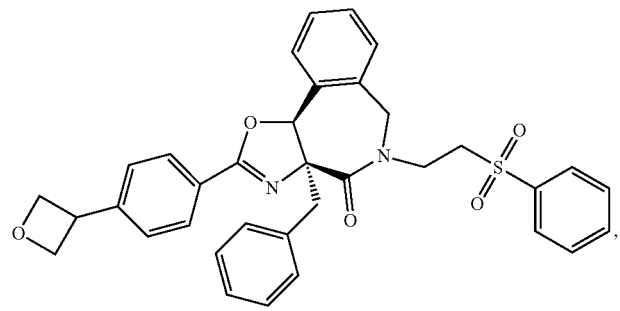
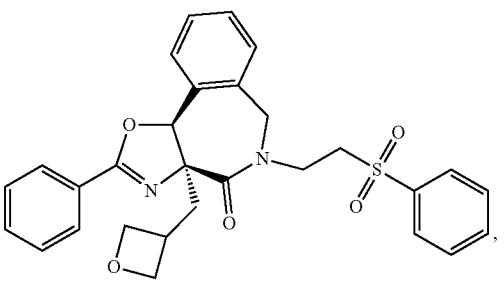
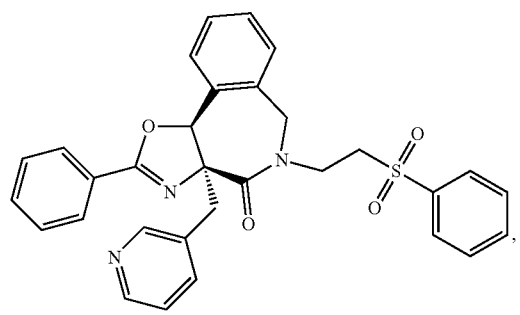
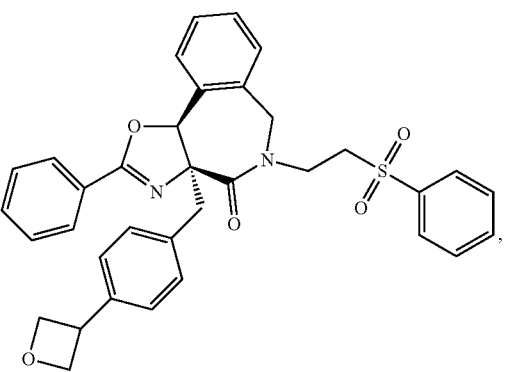
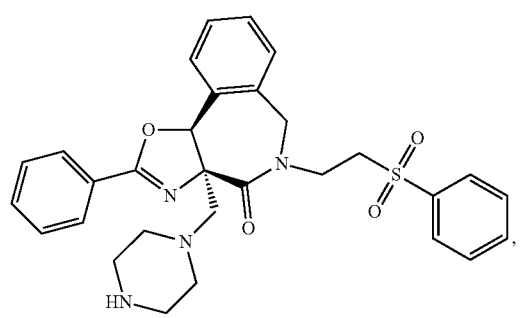
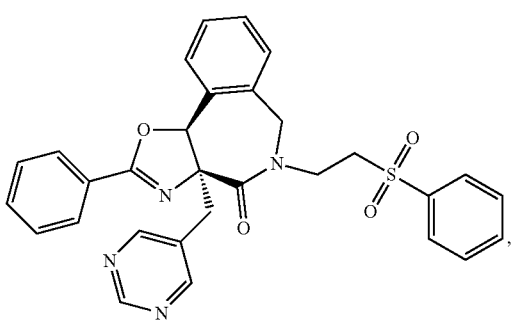

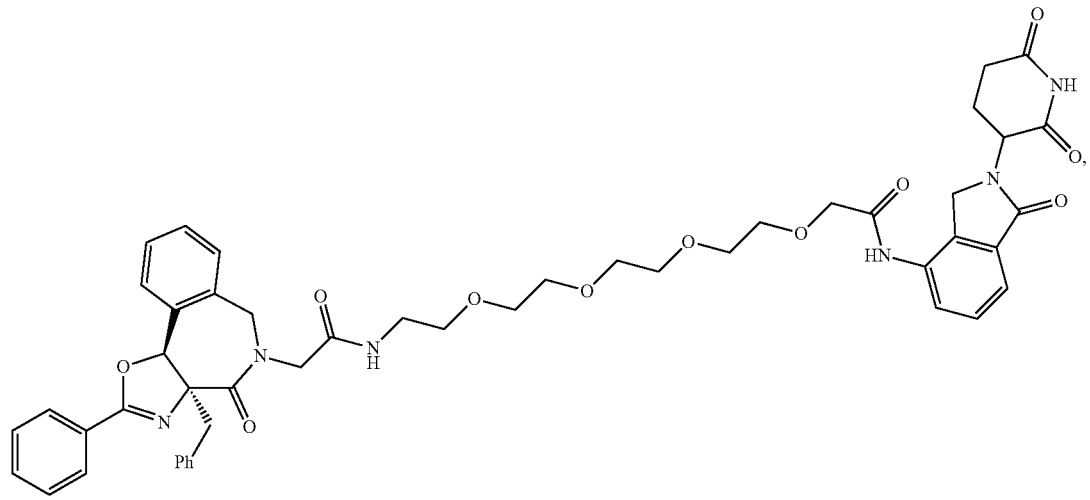
(MS2-090)
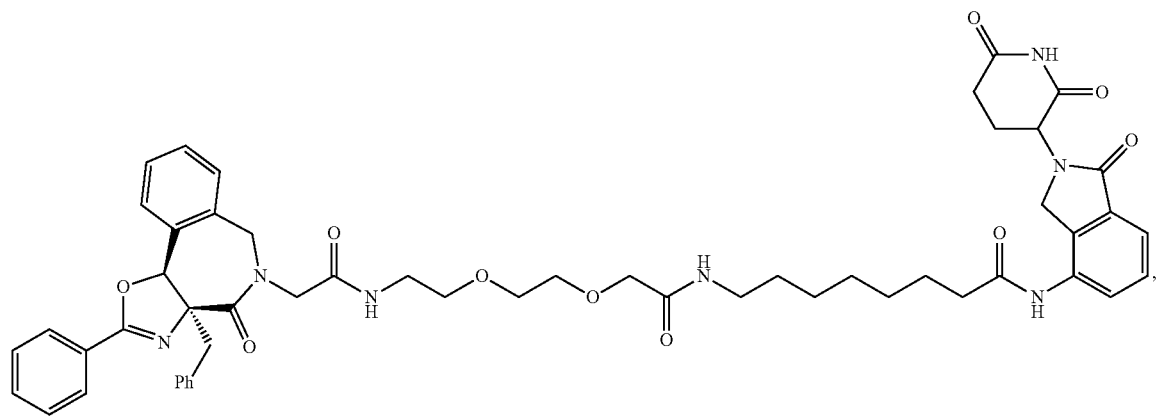
(MS2-096)
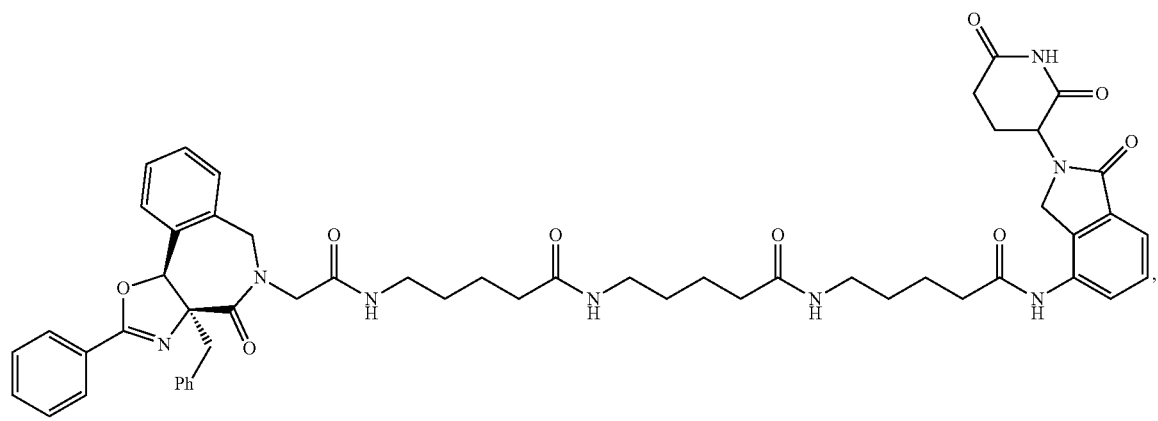
(MS2-095)

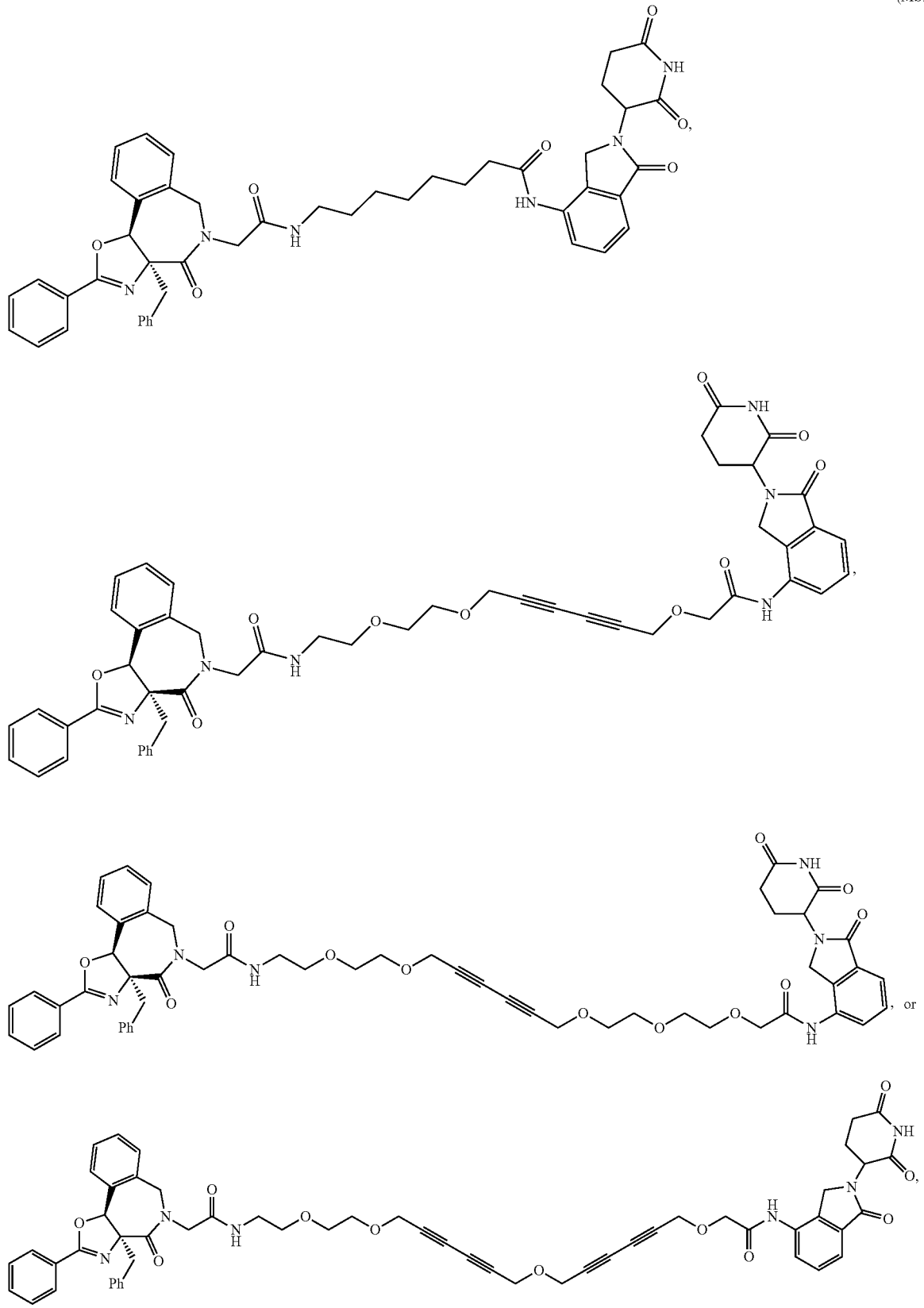
or a pharmaceutically acceptable salt thereof.

Exemplary compounds of Formulae (I') and (I) include, but are not limited to:
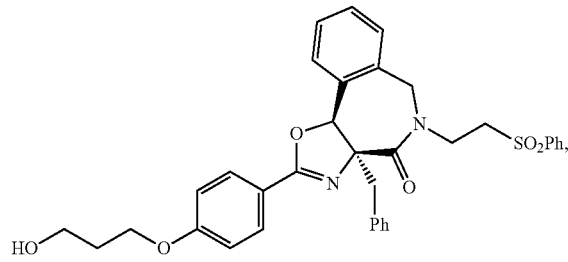
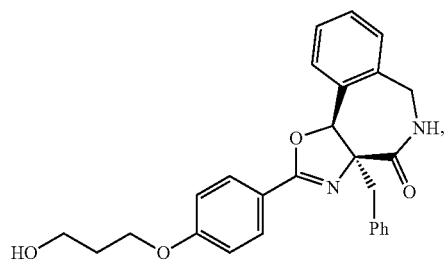
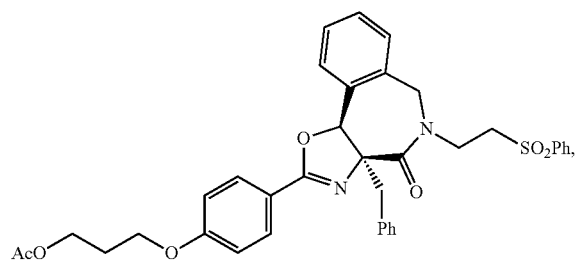
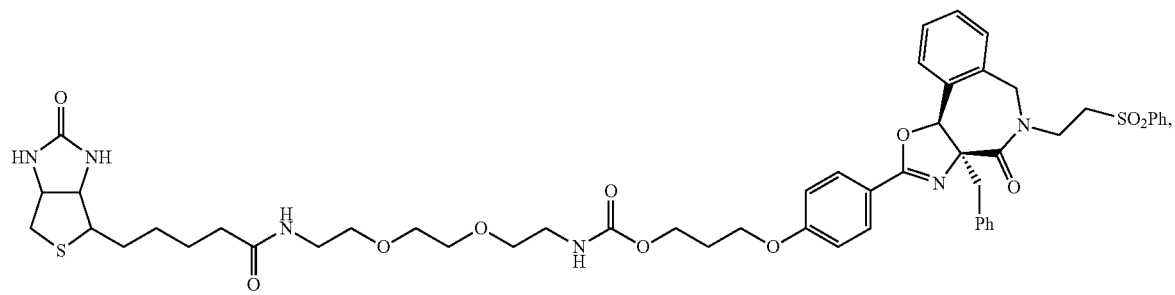
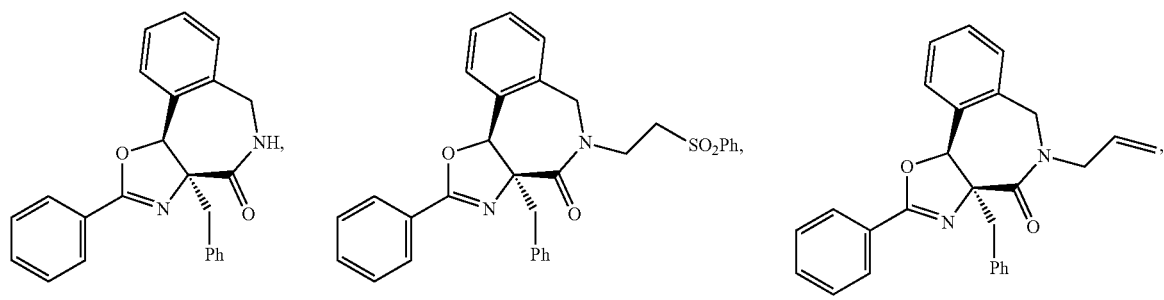
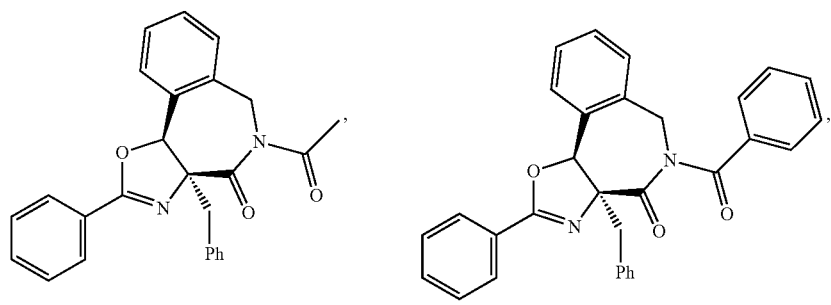

11 12
-continued
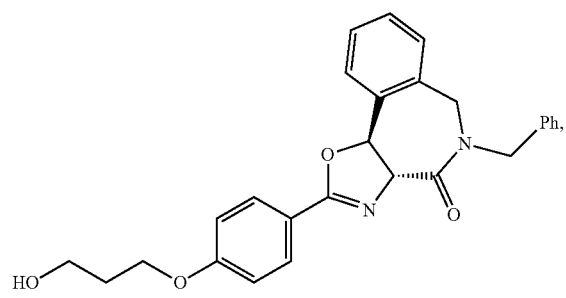
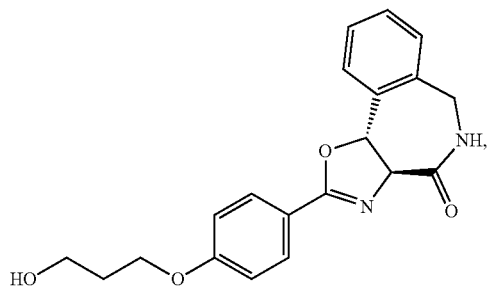
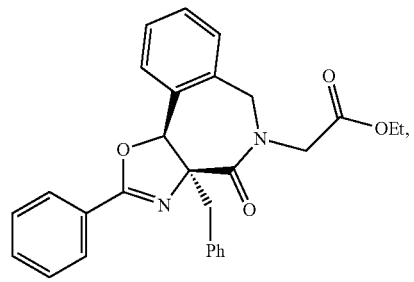
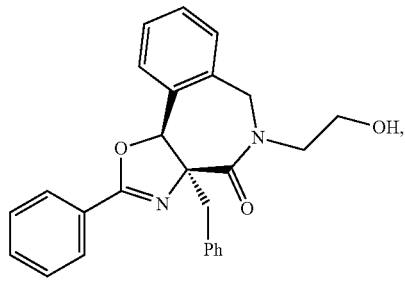
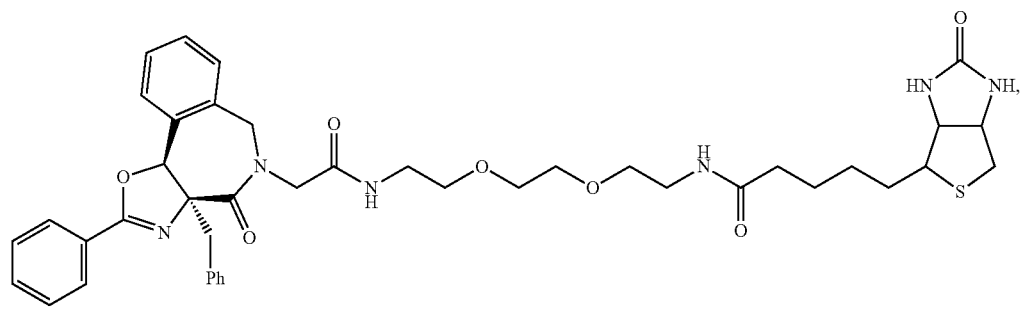
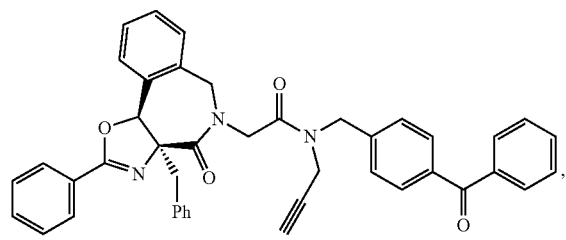
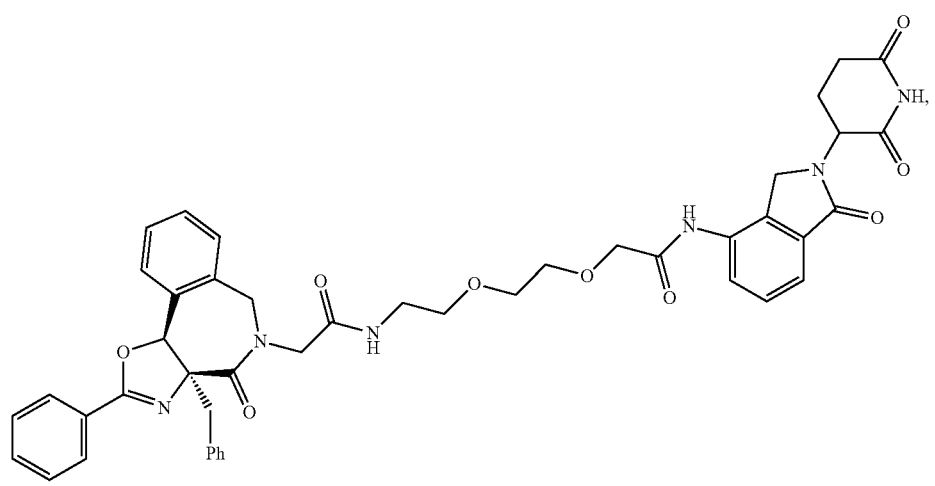

and pharmaceutically acceptable salts, solvates, hydrates, polymorphs, co-crystals, tautomers, stereoisomers, isotopically labeled derivatives, and prodrugs thereof.

In another aspect, the present disclosure provides compounds of Formula (II):

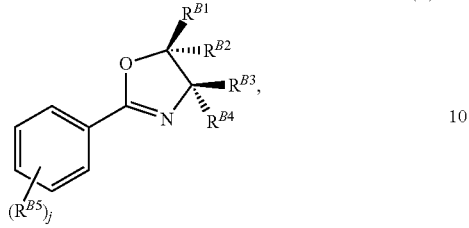

(II)

and pharmaceutically acceptable salts, solvates, hydrates, polymorphs, co-crystals, tautomers, stereoisomers, isotopically labeled derivatives, and prodrugs thereof, wherein $R^{B1}$, $R^{B2}$, $R^{B3}$, $R^{B4}$, $R^{B5}$, and j are as defined herein.

Exemplary compounds of Formula (II) include, but are not limited to:

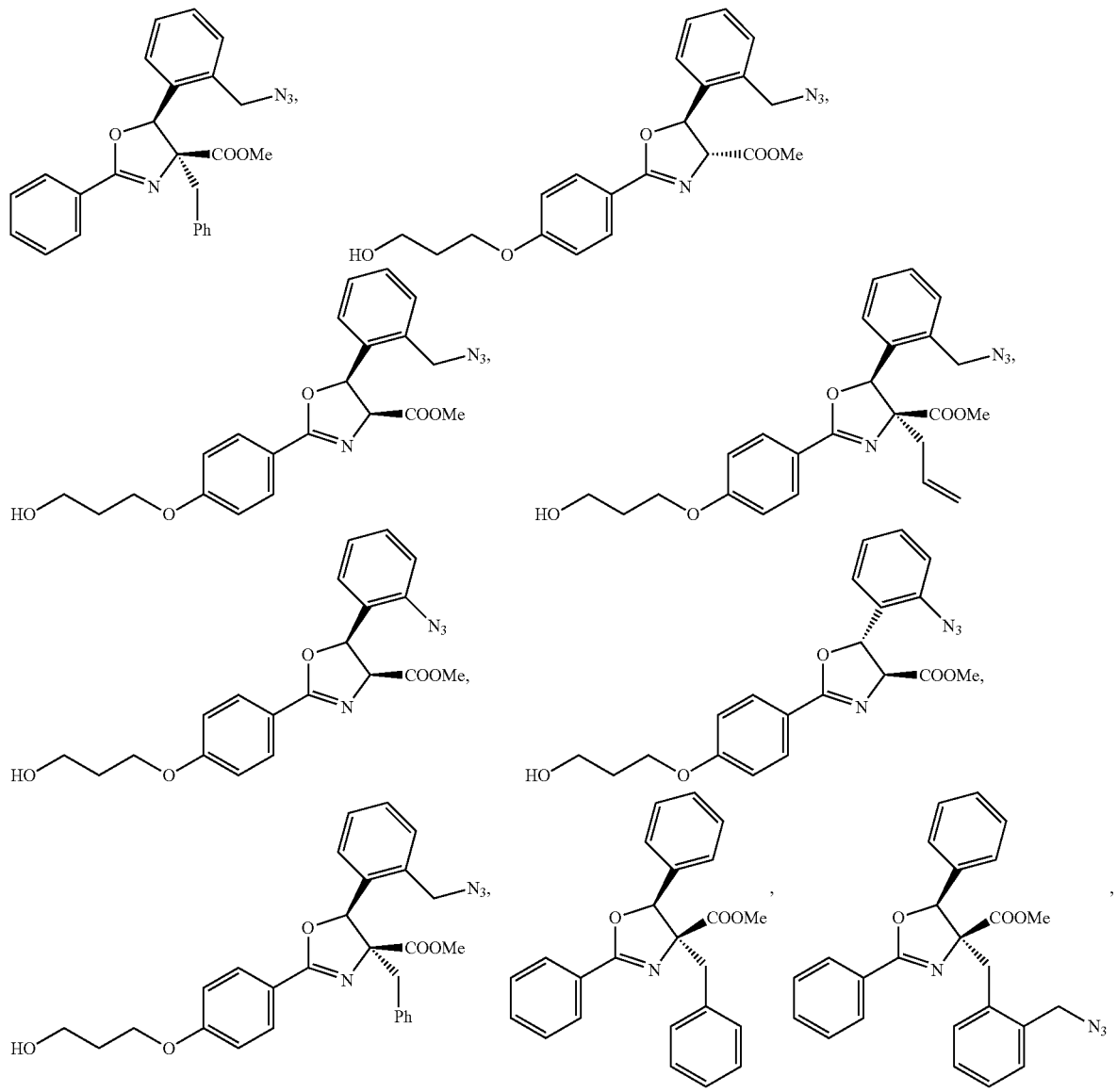

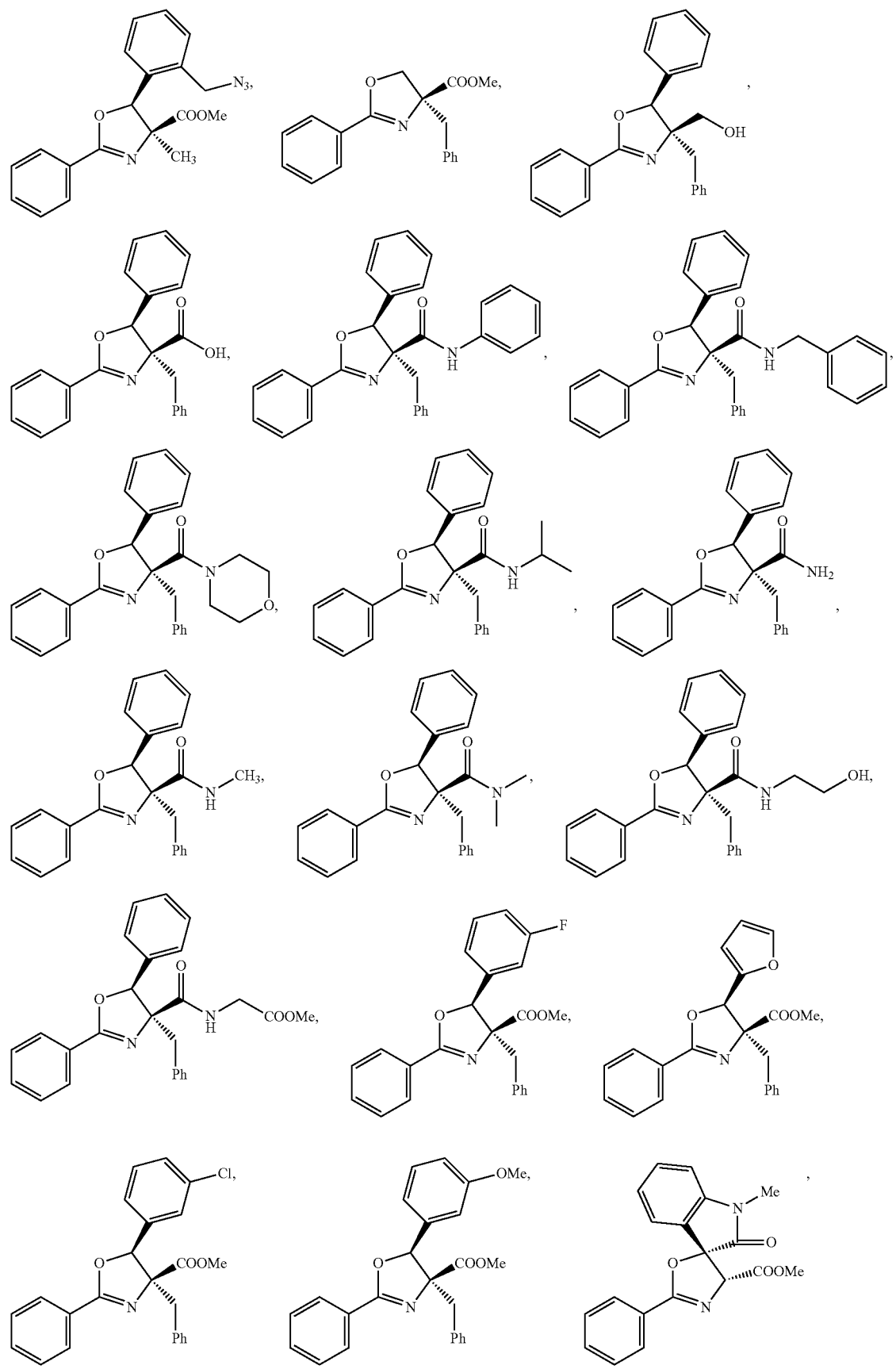

-continued
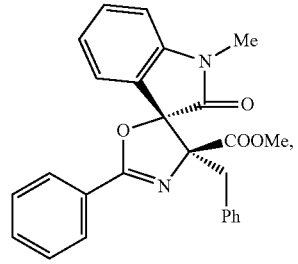 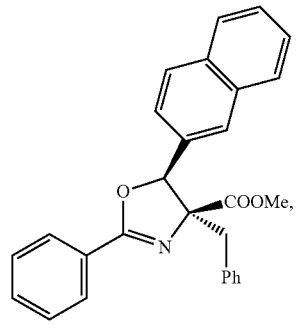 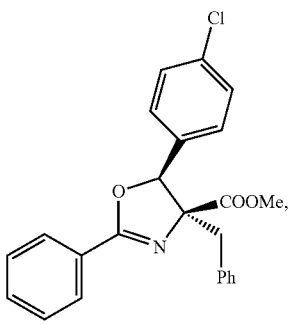
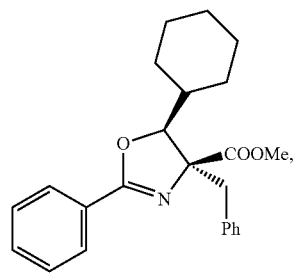 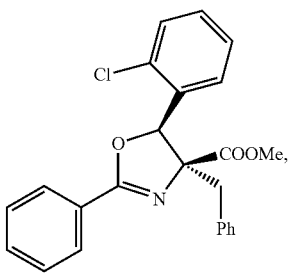 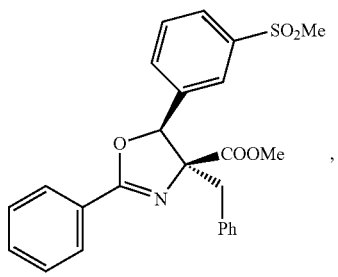
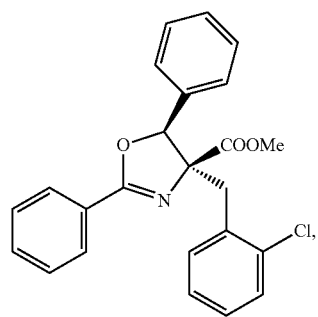 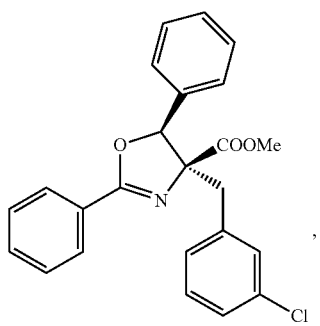 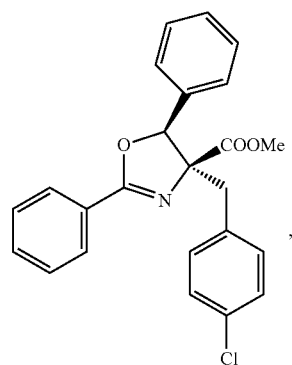
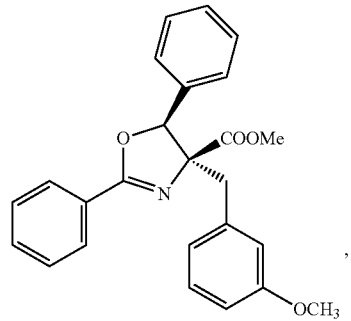 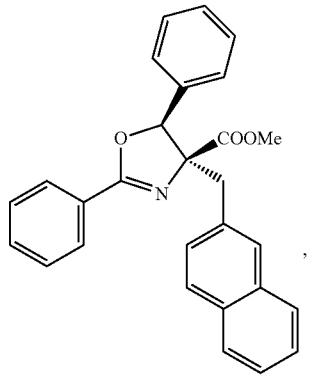 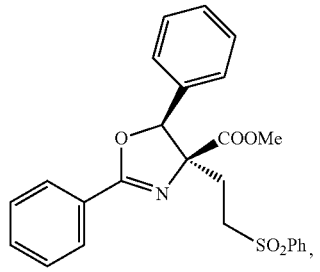
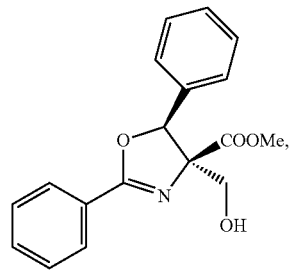 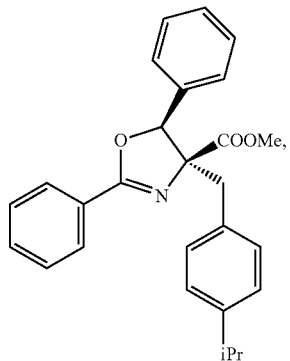

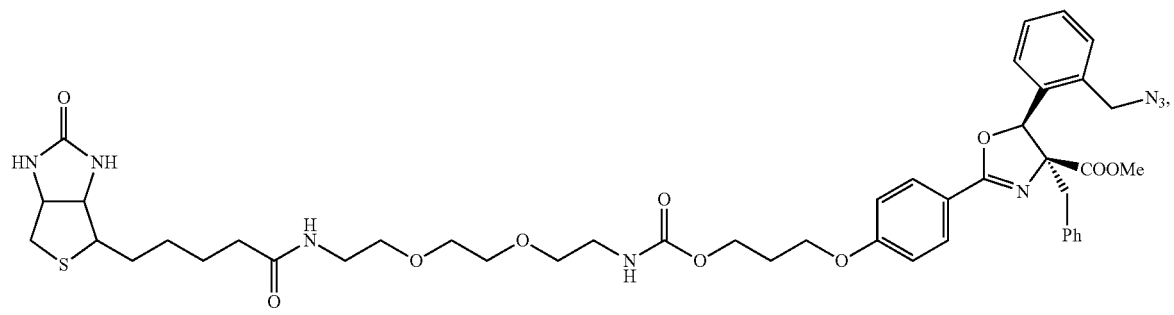
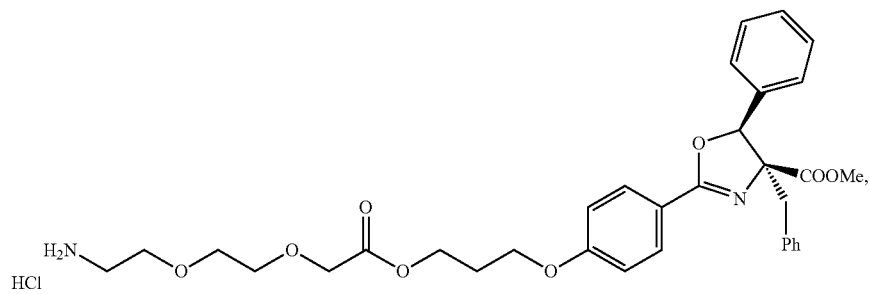
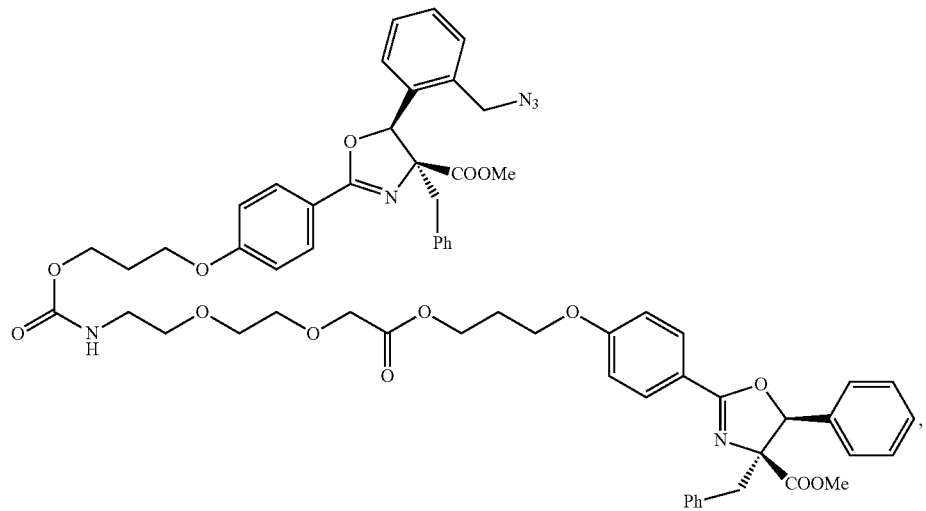
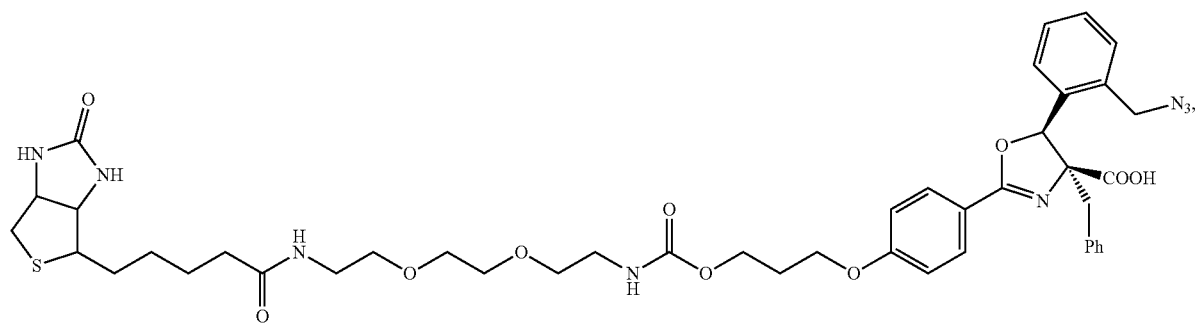

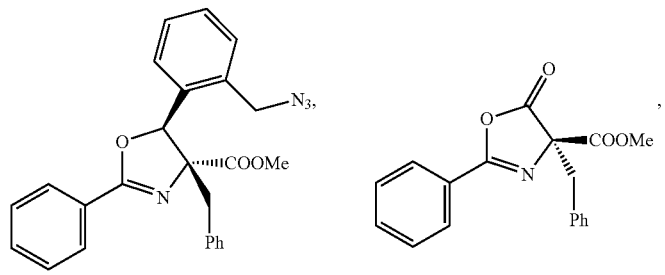

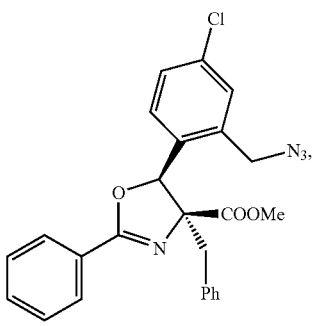

and pharmaceutically acceptable salts, solvates, hydrates, polymorphs, co-crystals, tautomers, stereoisomers, isotopically labeled derivatives, and prodrugs thereof.

In yet another aspect, the present disclosure provides compounds of Formula (II-A):

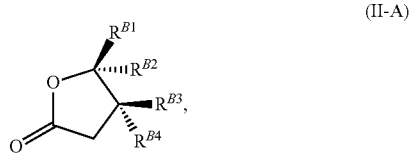

(II-A)

and pharmaceutically acceptable salts, solvates, hydrates, polymorphs, co-crystals, tautomers, stereoisomers, isotopically labeled derivatives, and prodrugs thereof, wherein $R^{B1}$, $R^{B2}$, $R^{B3}$, and $R^{B4}$ are as defined herein.

Exemplary compounds of Formula (II-A) include, but are not limited to:

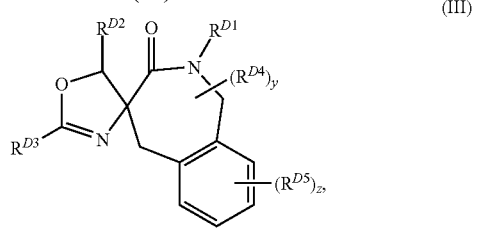

and pharmaceutically acceptable salts, solvates, hydrates, polymorphs, co-crystals, tautomers, stereoisomers, isotopically labeled derivatives, and prodrugs thereof.

In still another aspect, the present disclosure provides compounds of Formula (III):

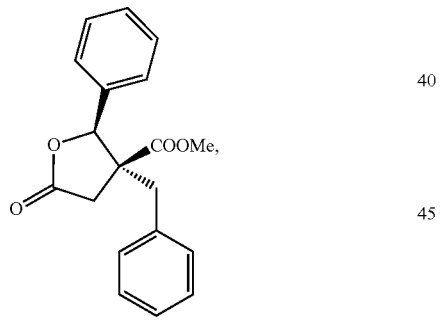

(III)

and pharmaceutically acceptable salts, solvates, hydrates, polymorphs, co-crystals, tautomers, stereoisomers, isotopically labeled derivatives, and prodrugs thereof, wherein $R^{D1}$, $R^{D2}$, $R^{D3}$, $R^{D4}$, $R^{D5}$, y, and z are as defined herein.

Exemplary compounds of Formula (III) include, but are not limited to:

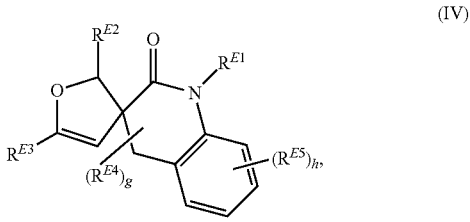

pharmaceutically acceptable salts, solvates, hydrates, polymorphs, co-crystals, tautomers, stereoisomers, isotopically labeled derivatives, and prodrugs thereof.

In another aspect, the present disclosure provides compounds of Formula (IV):

(IV)

and pharmaceutically acceptable salts, solvates, hydrates, polymorphs, co-crystals, tautomers, stereoisomers, isotopically labeled derivatives, and prodrugs thereof, wherein $R^{E1}$, $R^{E2}$, $R^{E3}$, $R^{E4}$, $R^{E5}$, g, and h are as defined herein.

Exemplary compounds of Formula (IV) include, but are not limited to:

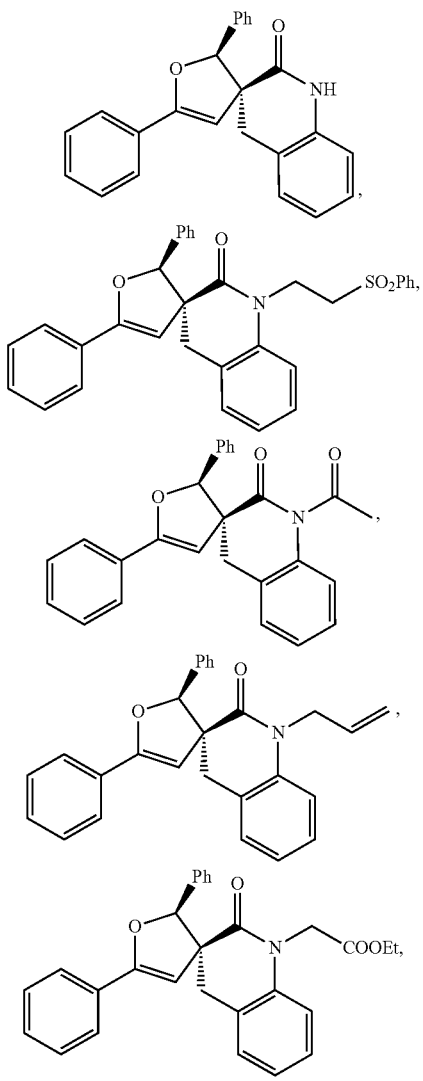

and pharmaceutically acceptable salts, solvates, hydrates, polymorphs, co-crystals, tautomers, stereoisomers, isotopically labeled derivatives, and prodrugs thereof.

In another aspect, described herein are pharmaceutical compositions including a compound described herein, and optionally a pharmaceutically acceptable excipient. In certain embodiments, a pharmaceutical composition described herein includes an effective amount (e.g., therapeutically effective amount or prophylactically effective amount) of a compound described herein. The pharmaceutical compositions may be useful in modulating (e.g., inhibiting) the activity of Myc, Mad, or Mxi1 in a subject in need thereof, treating diseases associated with Myc (e.g., diseases associated with aberrant activity (e.g., increased activity) of Myc) in a subject in need thereof, treating diseases in a subject in need thereof (e.g., proliferative disease), preventing diseases associated with Myc (e.g., diseases associated with aberrant activity (e.g., increased activity) of Myc) in a subject in need thereof, preventing diseases in a subject in need thereof (e.g., proliferative disease), and/or as research tools (e.g., for studying Myc (e.g., studying the activity of Myc, studying transcription modulated by Myc) in a subject, biological sample, tissue, or cell). In another aspect, described herein is a use of compounds described herein to treat and/or prevent a disease in a subject in need thereof, the use comprising administering to the subject an effective amount of compounds described herein.

In certain embodiments, the disease being treated and/or prevented by a compound described herein is a proliferative disease. In certain embodiments, the disease is associated with aberrant activity (e.g., increased or decreased activity) of Myc. In certain embodiments, the disease is associated with increased activity of Myc. In certain embodiments, the disease is associated with increased stability of Myc. In certain embodiments, the disease is cancer (e.g., lung cancer, brain cancer, or lymphoma). The pharmaceutical compositions described herein are useful in treating and/or preventing proliferative diseases (e.g., cancer (e.g., lung cancer, breast cancer, leukemia, lymphoma, melanoma, multiple myeloma, Ewing's sarcoma, osteosarcoma, brain cancer, neuroblastoma), benign neoplasms, angiogenesis, inflammatory diseases, autoinflammatory diseases, and autoimmune diseases) in a subject, biological sample, tissue, or cell. In another aspect, described herein are kits including a container with a compound or pharmaceutical composition described herein. A kit described herein may include a single dose or multiple doses of the compound or pharmaceutical composition described herein. The described kits may be useful in modulating (e.g., inhibiting) the activity of Myc, Mad, or Mxi1, treating and/or preventing diseases (e.g., proliferative diseases, diseases associated with Myc, aberrant activity (e.g., increased activity) of Myc) in a subject in need thereof, and useful as research tools (e.g., for studying Myc (e.g., studying the activity of Myc) in a subject, biological sample, tissue, or cell). In certain embodiments, a kit described herein further includes instructions for using the compound or pharmaceutical composition included in the kit.

Another aspect of the present disclosure relates to methods of treating and/or preventing a disease in a subject in need thereof, the methods comprising administering to the subject in need thereof an effective amount of a compound or pharmaceutical composition described herein.

In another aspect, the present disclosure provides compounds and pharmaceutical compositions described herein for use in a method of the disclosure (e.g., for use treating and/or preventing a disease (e.g. proliferative disease)).

Definitions

Definitions of specific functional groups and chemical terms are described in more detail below. The chemical elements are identified in accordance with the Periodic Table of the Elements, CAS version, *Handbook of Chemistry and Physics*, 75th Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5th Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3rd Edition, Cambridge University Press, Cambridge, 1987. The disclosure is not intended to be limited in any manner by the exemplary listing of substituents described herein.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, *Tables of Resolving Agents and Optical Resolutions* p. 268 (E. L. Eliel, Ed., Univ. of Notre Dame Press, Notre Dame, Ind. 1972). The disclosure additionally encompasses compounds described herein as individual isomers substantially free of other isomers, and alternatively, as mixtures of various isomers.

When a range of values is listed, it is intended to encompass each value and sub-range within the range. For example "$C_{1-6}$" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

The term "aliphatic" includes both saturated and unsaturated, straight chain (i.e., unbranched), branched, acyclic, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, the term "alkyl" includes straight, branched and cyclic alkyl groups. An analogous convention applies to other generic terms such as "alkenyl", "alkynyl", and the like. Furthermore, the terms "alkyl", "alkenyl", "alkynyl", and the like encompass both substituted and unsubstituted groups. In certain embodiments, "lower alkyl" is used to indicate those alkyl groups (cyclic, acyclic, substituted, unsubstituted, branched or unbranched) having 1-6 carbon atoms.

In certain embodiments, the alkyl, alkenyl, and alkynyl groups employed in the disclosure contain 1-20 aliphatic carbon atoms. In certain other embodiments, the alkyl, alkenyl, and alkynyl groups employed in the disclosure contain 1-10 aliphatic carbon atoms. In yet other embodiments, the alkyl, alkenyl, and alkynyl groups employed in the disclosure contain 1-8 aliphatic carbon atoms. In still other embodiments, the alkyl, alkenyl, and alkynyl groups employed in the disclosure contain 1-6 aliphatic carbon atoms. In yet other embodiments, the alkyl, alkenyl, and alkynyl groups employed in the disclosure contain 1-4 carbon atoms. Illustrative aliphatic groups thus include, but are not limited to, for example, methyl, ethyl, n-propyl, isopropyl, cyclopropyl, —CH$_2$-cyclopropyl, vinyl, allyl, n-butyl, sec-butyl, isobutyl, tert-butyl, cyclobutyl, —CH$_2$-cyclobutyl, n-pentyl, sec-pentyl, isopentyl, tert-pentyl, cyclopentyl, —CH$_2$-cyclopentyl, n-hexyl, sec-hexyl, cyclohexyl, —CH$_2$-cyclohexyl moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl, and the like.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$) and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-10}$ alkyl (such as unsubstituted $C_{1-6}$ alkyl, e.g., —CH$_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu), unsubstituted isobutyl (i-Bu)). In certain embodiments, the alkyl group is a substituted $C_{1-10}$ alkyl (such as substituted $C_{1-6}$ alkyl, e.g., —CF$_3$, Bn).

"Alkenyl" refers to a radical of a straight-chain or branched hydrocarbon group having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl. In an alkenyl group, a C=C double bond for which the stereochemistry is not specified (e.g., —CH=CHCH$_3$ or

)

may be an (E)- or (Z)-double bond.

"Alkynyl" refers to a radical of a straight-chain or branched hydrocarbon group having from 2 to 20 carbon atoms, one or more carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

"Carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclic ring, as defined above, is fused with one or more aryl or heteroaryl groups wherein the point of attachment is on the carbocyclic ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged, or spiro ring system, such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclic ring, as defined above, is fused with one or more carbocyclyl groups wherein the point of attachment is either on the carbocyclyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiiranyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, and dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14 pi electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Aralkyl" is a subset of alkyl and aryl and refers to an optionally substituted alkyl group substituted by an optionally substituted aryl group. In certain embodiments, the aralkyl is optionally substituted benzyl. In certain embodiments, the aralkyl is benzyl. In certain embodiments, the aralkyl is optionally substituted phenethyl. In certain embodiments, the aralkyl is phenethyl.

"Heteroaryl" refers to a radical of a 5-10 membered monocyclic or bicyclic 4n+2 aromatic ring system (e.g., having 6 or 10 pi electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl, and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Heteroaralkyl" is a subset of alkyl and heteroaryl and refers to an optionally substituted alkyl group substituted by an optionally substituted heteroaryl group.

"Unsaturated" or "partially unsaturated" refers to a group that includes at least one double or triple bond. A "partially unsaturated" ring system is further intended to encompass rings having multiple sites of unsaturation, but is not intended to include aromatic groups (e.g., aryl or heteroaryl groups). Likewise, "saturated" refers to a group that does not contain a double or triple bond, i.e., contains all single bonds.

Alkyl, alkenyl, alkynyl, carbocyclyl, heterocyclyl, aryl, and heteroaryl groups, which are divalent bridging groups, are further referred to using the suffix -ene, e.g., alkylene, alkenylene, alkynylene, carbocyclylene, heterocyclylene, arylene, and heteroarylene.

An atom, moiety, or group described herein may be unsubstituted or substituted, as valency permits, unless otherwise provided expressly. The term "optionally substituted" refers to substituted or unsubstituted.

A group is optionally substituted unless expressly provided otherwise. The term "optionally substituted" refers to being substituted or unsubstituted. In certain embodiments, alkyl, alkenyl, alkynyl, carbocyclyl, heterocyclyl, aryl, and heteroaryl groups are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl, or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present disclosure contemplates any and all such combinations in order to arrive at a stable compound. For purposes of this disclosure, heteroatoms such as nitrogen may have hydrogen substituents and/or any suitable substituent as described herein which satisfy the valencies of the heteroatoms and results in the formation of a stable moiety. In certain embodiments, the substituent is a carbon atom substituent. In certain embodiments, the substituent is a nitrogen atom substituent. In certain embodiments, the substituent is an oxygen atom substituent. In certain embodiments, the substituent is a sulfur atom substituent.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —P(=O)(OR$^{cc}$)$_2$, —OP(=O)(R$^{aa}$)$_2$, —OP(=O)(OR$^{cc}$)$_2$, —P(=O)(N(R$^{bb}$)$_2$)$_2$, —OP(=O)(N(R$^{bb}$)$_2$)$_2$, —NR$^{bb}$P(=O)(R$^{aa}$)$_2$, —NR$^{bb}$P(=O)(OR$^{cc}$)$_2$, —NR$^{bb}$P(=O)(N(R$^{bb}$)$_2$)$_2$, —P(R$^{cc}$)$_2$, —P(OR$^{cc}$)$_2$, —P(R$^{cc}$)$_3^+$X$^-$, —P(OR$^{cc}$)$_3^+$X$^-$, —P(R$^{cc}$)$_4$, —P(OR$^{cc}$)$_4$, —OP(R$^{cc}$)$_2$, —OP(R$^{cc}$)$_3^+$X$^-$, —OP(OR$^{cc}$)$_2$, —OP(OR$^{cc}$)$_3^+$X$^-$, —OP(R$^{cc}$)$_4$, —OP(OR$^{cc}$)$_4$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups; wherein X$^-$ is a counterion;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(OR$^{cc}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups; wherein X$^-$ is a counterion;

each instance of $R^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)(OR$^{ee}$)$_2$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal $R^{dd}$ substituents can be joined to form =O or =S; wherein X$^-$ is a counterion;

each instance of $R^{ee}$ is, independently, selected from C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of $R^{ff}$ is, independently, selected from hydrogen, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl and 5-10 membered heteroaryl, or two R$^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH (OH), —SH, —SC$_{1-6}$ alkyl, —SS(C$_{1-6}$ alkyl), —C(=O) (C$_{1-6}$ alkyl), —CO$_2$H, —CO$_2$(C$_1$ alkyl), —OC(=O)(C$_{1-6}$ alkyl), —OCO$_2$(C$_{1-6}$ alkyl), —C(=O)NH$_2$, —C(=O)N (C$_{1-6}$ alkyl)$_2$, —OC(=O)NH(C$_{1-6}$ alkyl), —NHC(=O) (C$_{1-6}$ alkyl), —N(C$_{1-6}$ alkyl)C(=O)(C$_{1-6}$ alkyl), —NHCO$_2$ (C$_1$ alkyl), —NHC(=O)N(C$_{1-6}$ alkyl)$_2$, —NHC(=O)NH (C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH) NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_1$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C (=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S) SC$_{1-6}$ alkyl, —P(=O)(OC$_{1-6}$ alkyl)$_2$, —P(=O)(C$_{1-6}$ alkyl)$_2$, —OP(=O)(C$_{1-6}$ alkyl)$_2$, —OP(=O)(OC$_{1-6}$ alkyl)$_2$, C$_1$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, 5-10 membered heteroaryl; or two geminal R$^{gg}$ substituents can be joined to form =O or =S; wherein X is a counterion.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., F$^-$, Cl$^-$, Br$^-$, F$^-$), NO$_3$$^-$, ClO$_4$$^-$, OH$^-$, H$_2$PO$_4$$^-$, HSO$_4$$^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), BF$_4$$^-$, PF$_4$$^-$, PF$_6$$^-$, AsF$_6$$^-$, SbF$_6$$^-$, B[3,5-(CF$_3$)$_2$C$_6$H$_3$]$_4$]$^-$, BPh$_4$$^-$, Al(OC(CF$_3$)$_3$)$_4$$^-$, and a carborane anion (e.g., CB$_{11}$H$_{12}$$^-$ or (HCB$_{11}$Me$_5$Br$_6$)$^-$). Exemplary counterions which may be multivalent include CO$_3$$^{2-}$, HPO$_4$$^{2-}$, PO$_4$$^{3-}$, B$_4$O$_7$$^{2-}$, SO$_4$$^{2-}$, S$_2$O$_3$$^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

"Halo" or "halogen" refers to fluorine (fluoro, —F), chlorine (chloro, —Cl), bromine (bromo, —Br), or iodine (iodo, —I).

"Acyl" refers to a moiety selected from the group consisting of —C(=O)R$^{aa}$, —CHO, —CO$_2$R$^{aa}$, —C(=O)N (R$^{bb}$)$_2$, —C(=NR$^{bb}$)R$^{aa}$, —C(=NR$^{bb}$)OR$^{aa}$, —C(=NR$^{bb}$) N(R$^{bb}$)$_2$, —C(=O)NR$^{bb}$SO$_2$R$^{aa}$, —C(=S)N(R$^{bb}$)$_2$, —C(=O)SR$^{aa}$, or —C(=S)SR$^{aa}$, wherein R$^{aa}$ and R$^{bb}$ are as defined herein.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O) N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(OR$^{cc}$)$_2$, —P(=O)(R$^{aa}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$, and $R^{dd}$ are as defined above.

In certain embodiments, the substituent present on a nitrogen atom is a nitrogen protecting group (also referred to as an amino protecting group). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, $C_{1-10}$ alkyl (e.g., aralkyl, heteroaralkyl), $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, and o-(benzoyloxymethyl)benzamide.

Nitrogen protecting groups such as carbamate groups (e.g., —C(=O)OR$^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)

phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

Exemplary oxygen atom substituents include, but are not limited to, —$R^{aa}$, —C(=O)$SR^{aa}$, —C(=O)$R^{aa}$, —$CO_2R^{aa}$, —C(=O)N($R^{bb}$)$_2$, —C(=$NR^{bb}$)$R^{aa}$, —C(=$NR^{bb}$)$OR^{aa}$, —C(=$NR^{bb}$)N($R^{bb}$)$_2$, —S(=O)$R^{aa}$, —$SO_2R^{aa}$, —Si($R^{aa}$)$_3$, —P($R^{cc}$)$_2$, —P($R^{cc}$)$_3^+X^-$, —P($OR^{cc}$)$_2$, —P($OR^{cc}$)$_3^+X^-$, —P(=O)($R^{aa}$)$_2$, —P(=O)($OR^{cc}$)$_2$, and —P(=O)(N($R^{bb}$)$_2$)$_2$, wherein $X^-$, $R^{aa}$, $R^{bb}$, and $R^{cc}$ are as defined herein. In certain embodiments, the oxygen atom substituent present on an oxygen atom is an oxygen protecting group (also referred to as a hydroxyl protecting group). Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference. Exemplary oxygen protecting groups include, but are not limited to, methyl, t-butyloxycarbonyl (BOC or Boc), methoxylmethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl) ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, ca-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris (levulinoyloxyphenyl)methyl, 4,4',4"-tris (benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

Exemplary sulfur atom substituents include, but are not limited to, —$R^{aa}$, —C(=O)$SR^{aa}$, —C(=O)$R^{aa}$, —$CO_2R^{aa}$, —C(=O)N($R^{bb}$)$_2$, —C(=$NR^{bb}$)$R^{aa}$, —C(=$NR^{bb}$)$OR^{aa}$, —C(=$NR^{bb}$)N($R^{bb}$)$_2$, —S(=O)$R^{aa}$, —$SO_2R^{aa}$, —Si($R^{aa}$)$_3$, —P($R^{cc}$)$_2$, —P($R^{cc}$)$_3^+X^-$, —P($OR^{cc}$)$_2$, —P($OR^{cc}$)$_3^+X^-$, —P(=O)($R^{aa}$)$_2$, —P(=O)($OR^{cc}$)$_2$, and —P(=O)(N($R^{bb}$)$_2$)$_2$, wherein $R^{aa}$, $R^{bb}$, and $R^{cc}$ are as defined herein. In certain embodiments, the sulfur atom substituent present on a sulfur atom is a sulfur protecting group (also referred to as a thiol protecting group). Sulfur protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

The term "leaving group" is given its ordinary meaning in the art of synthetic organic chemistry and refers to an atom or a group capable of being displaced by a nucleophile. See, for example, Smith, *March Advanced Organic Chemistry* 6th ed. (501-502). Examples of suitable leaving groups include, but are not limited to, halogen (such as F, Cl, Br, or I (iodine)), alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, N,O-dimethylhydroxyamino, pixyl, and haloformates. In some cases, the leaving group is an activated substituted hydroxyl group (e.g., —OC(=O)$SR^{aa}$, —OC(=O)$R^{aa}$, —$OCO_2R^{aa}$, —OC(=O)N($R^{bb}$)$_2$, —OC(=$NR^{bb}$)$R^{aa}$, —OC(=$NR^{bb}$)$OR^{aa}$, —OC(=$NR^{bb}$)N($R^{bb}$)$_2$, —OS(=O)$R^{aa}$, —$OSO_2R^{aa}$, —OP($R^{cc}$)$_2$, —OP($R^{cc}$)$_3$, —OP(=O)$_2R^{aa}$, —OP(=O)($R^{aa}$)$_2$, —OP(=O)($OR^{cc}$)$_2$, —OP(=O)$_2$N($R^{bb}$)$_2$, and —OP(=O)(N($R^{bb}$)$_2$)$_2$, wherein $R^{aa}$, $R^{bb}$, and $R^{cc}$ are as defined herein). In some cases, the leaving group is a sulfonic acid ester, such as toluenesulfonate (tosylate, —OTs), methanesulfonate (mesylate, —OMs), p-bromobenzenesulfonyloxy (brosylate, —OBs), —OS(=O)$_2$(CF$_2$)$_3$CF$_3$ (nonaflate, —ONf), or trifluoromethanesulfonate (triflate, —OTf). In some cases, the leaving group is a brosylate, such as p-bromobenzenesulfonyloxy. In some cases, the leaving group is a nosylate, such as 2-nitrobenzenesulfonyloxy. In some embodiments, the leaving group is a sulfonate-containing group. In some embodiments, the leaving group is a tosylate group. The leaving group may also be a phosphineoxide (e.g., formed during a Mitsunobu reaction) or an internal leaving group such as an epoxide or cyclic sulfate. Other non-limiting examples of leaving groups are water, ammonia, alcohols, ether moieties, thioether moieties, zinc halides, magnesium moieties, diazonium salts, and copper moieties.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences*, 1977, 66, 1-19, incorporated herein by reference. Pharmaceutically acceptable salts of the compounds described herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, and ammonium salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound, or a salt thereof, that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula R·x H$_2$O, wherein R is the compound, and x is a number greater than 0. A given compound may form more than one type of hydrate, including, e.g., monohydrates (x is 1), lower hydrates (x is a number greater than 0 and smaller than 1, e.g., hemihydrates (R·0.5H$_2$O)), and polyhydrates (x is a number greater than 1, e.g., dihydrates (R·2 H$_2$O) and hexahydrates (R·6H$_2$O)).

The term "tautomers" or "tautomeric" refers to two or more interconvertible compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorphs" refers to a crystalline form of a compound (or a salt, hydrate, or solvate thereof). All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "prodrugs" refers to compounds that have cleavable groups and become by solvolysis or under physiological conditions the compounds described herein, which are pharmaceutically active in vivo. Such examples include, but are not limited to, choline ester derivatives and the like, N-alkylmorpholine esters and the like. Other derivatives of the compounds described herein have activity in both their acid and acid derivative forms, but in the acid sensitive form often offer advantages of solubility, tissue compatibility, or delayed release in the mammalian organism (see, Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds described herein are particular prodrugs. In some cases it is desirable to prepare double ester type prodrugs such as (acyloxy)alkyl esters or ((alkoxycarbonyl)oxy)alkylesters. $C_1$-$C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds described herein may be preferred.

The term "small molecule" refers to molecules, whether naturally-occurring or artificially created (e.g., via chemical synthesis) that have a relatively low molecular weight. Typically, a small molecule is an organic compound (i.e., it contains carbon). The small molecule may contain multiple carbon-carbon bonds, stereocenters, and other functional groups (e.g., amines, hydroxyl, carbonyls, and heterocyclic rings, etc.). In certain embodiments, the molecular weight of a small molecule is not more than about 1,000 g/mol, not more than about 900 g/mol, not more than about 800 g/mol, not more than about 700 g/mol, not more than about 600 g/mol, not more than about 500 g/mol, not more than about 400 g/mol, not more than about 300 g/mol, not more than about 200 g/mol, or not more than about 100 g/mol. In certain embodiments, the molecular weight of a small molecule is at least about 100 g/mol, at least about 200 g/mol, at least about 300 g/mol, at least about 400 g/mol, at least about 500 g/mol, at least about 600 g/mol, at least about 700 g/mol, at least about 800 g/mol, or at least about 900 g/mol, or at least about 1,000 g/mol. Combinations of the above ranges (e.g., at least about 200 g/mol and not more than about 500 g/mol) are also possible. In certain embodiments, the small molecule is a therapeutically active agent such as a drug (e.g., a molecule approved by the U.S. Food and Drug Administration as provided in the Code of Federal Regulations (C.F.R.)). The small molecule may also be complexed with one or more metal atoms and/or metal ions. Preferred small molecules are biologically active in that they produce a biological effect in animals, preferably mammals, more preferably humans. Small molecules include, but are not limited to, radionuclides and imaging agents. In certain embodiments, the small molecule is a drug. Preferably, though not necessarily, the drug is one that has already been deemed safe and effective for use in humans or animals by the appropriate governmental agency or regulatory body. For example, drugs approved for human use are listed by the FDA under 21 C.F.R. §§ 330.5, 331 through 361, and 440 through 460, incorporated herein by reference; drugs for veterinary use are listed by the FDA under 21 C.F.R. §§ 500 through 589, incorporated herein by reference. All listed drugs are considered acceptable for use in accordance with the present invention.

The term "inhibition", "inhibiting", "inhibit," or "inhibitor" refer to the ability of a compound to reduce, slow, halt, or prevent activity of a particular biological process (e.g., activity of Myc) in a cell relative to vehicle.

When a compound, pharmaceutical composition, method, use, or kit is referred to as "selectively," "specifically," or "competitively" modulating (e.g., inhibiting) a Myc, the compound, pharmaceutical composition, method, use, or kit inhibits the Myc to a greater extent (e.g., not less than 2-fold, not less than 5-fold, not less than 10-fold, not less than 30-fold, not less than 100-fold, not less than 1,000-fold, or not less than 10,000-fold; and/or not more than 2-fold, not more than 5-fold, not more than 10-fold, not more than 30-fold, not more than 100-fold, not more than 1,000-fold, or not more than 10,000-fold) than inhibiting a different Myc and/or a different transcription factor.

The term "aberrant activity" refers to activity deviating from normal activity. In certain embodiments, the aberrant activity is increased activity. In certain embodiments, the aberrant activity is decreased activity. The term "increased activity" refers to activity higher than normal activity. The term "decreased activity" refers to activity lower than normal activity.

The terms "composition" and "formulation" are used interchangeably.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. In certain embodiments, the non-human animal is a mammal (e.g., primate (e.g., cynomolgus monkey or rhesus monkey), commercially relevant mammal (e.g., cattle, pig, horse, sheep, goat, cat, or dog), or bird (e.g., commercially relevant bird, such as chicken, duck, goose, or turkey)). In certain embodiments, the non-human animal is a fish, reptile, or amphibian. The non-human animal may be a male or female at any stage of development. The non-human animal may be a transgenic animal or genetically engineered animal. A "patient" refers to a human subject in need of treatment of a disease (e.g., proliferative disease).

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments or organelles (such as obtained by lysing cells and separating the components thereof by centrifugation or otherwise). Other examples of biological samples include blood, serum, urine, semen, fecal matter, cerebrospinal fluid, interstitial fluid, mucous, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample.

The terms "administer," "administering," or "administration" refers to implanting, absorbing, ingesting, injecting, inhaling, or otherwise introducing a compound described herein, or a composition thereof, in or on a subject.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen). Treatment may also be continued after symptoms have resolved, for example, to delay or prevent recurrence.

The term "prevent," "preventing," or "prevention" refers to a prophylactic treatment of a subject who is not and was not with a disease but is at risk of developing the disease or who was with a disease, is not with the disease, but is at risk of regression of the disease. In certain embodiments, the subject is at a higher risk of developing the disease or at a higher risk of regression of the disease than an average healthy member of a population.

The terms "condition," "disease," and "disorder" are used interchangeably.

An "effective amount" of a compound described herein refers to an amount sufficient to elicit the desired biological response. An effective amount of a compound described herein may vary depending on such factors as the desired biological endpoint, the pharmacokinetics of the compound, the condition being treated, the mode of administration, and the age and health of the subject. In certain embodiments, an effective amount is a therapeutically effective amount. In certain embodiments, an effective amount is a prophylactic treatment. In certain embodiments, an effective amount is the amount of a compound described herein in a single dose. In certain embodiments, an effective amount is the combined amounts of a compound described herein in multiple doses.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent. In certain embodiments, a therapeutically effective amount is effective for modulating (e.g., inhibiting) the activity of Myc. In certain embodiments, a therapeutically effective amount is effective for treating a disease (e.g., proliferative disease). In certain embodiments, a therapeutically effective amount is effective for modulating (e.g., inhibiting) the activity of Myc and effective for treating a disease (e.g., proliferative disease).

A "prophylactically effective amount" of a compound described herein is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent. In certain embodiments, a prophylactically effective amount is effective for modulating (e.g., inhibiting) the activity of Myc. In certain embodiments, a prophylactically effective amount is effective for preventing a disease (e.g., proliferative disease). In certain embodiments, a prophylactically effective amount is effective for modulating (e.g., inhibiting) the activity of Myc and effective for preventing a disease (e.g., proliferative disease).

The term "transcription factor" refers to is a protein that binds to specific DNA sequences, thereby controlling the rate of transcription of genetic information from DNA to messenger RNA. Transcription factors perform their functions alone or with other proteins in a complex, by promoting (as an activator), or blocking (as a repressor) the recruitment of RNA polymerase to specific genes. A feature of transcription factors is that they contain one or more DNA-binding domains (DBDs), which attach to specific sequences of DNA adjacent to the genes that they regulate. Additional proteins such as coactivators, chromatin remodelers, histone acetylases, deacetylases, kinases, and methylases, while also playing crucial roles in gene regulation, lack DNA-binding domains, and, therefore, are not classified as transcription factors. In certain embodiments, a transcription factor described herein is Myc. In certain embodiments, a transcription factor described herein is c-Myc. In certain embodiments, a transcription factor described herein is Mad. In certain embodiments, a transcription factor described herein is Mxi1. In certain embodiments, a transcription factor described herein is SP1, AP-1, C/EBP, heat shock factor, ATF/CREB, Oct-1, or NF-1.

The term "Myc" refers to the Myc family of transcription factors and the genes encoding the Myc family of transcription factors. In certain embodiments, the Myc is c-Myc (encoded by the MYC gene (HomoloGene: 31092; ChEMBL: 1250348; GeneCards: MYC Gene)). In certain embodiments, the Myc is L-Myc (encoded by the MYCL gene (HomoloGene: 3921; GeneCards: MYCL Gene)) or N-Myc (encoded by the MYCN gene (HomoloGene: 3922; GeneCards: MYCN Gene)). In certain embodiments, the Myc is MYC. In certain embodiments, the Myc is MYCL or MYCN.

A "proliferative disease" refers to a disease that occurs due to abnormal growth or extension by the multiplication of cells (Walker, *Cambridge Dictionary of Biology*; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as the matrix metalloproteinases (e.g., collagenases, gelatinases, and elastases); or 4) the pathological angiogenesis as in proliferative retinopathy and tumor metastasis. Exemplary proliferative diseases include cancers (i.e., "malignant neoplasms"), benign neoplasms, angiogenesis, inflammatory diseases, and autoimmune diseases.

The term "angiogenesis" refers to the physiological process through which new blood vessels form from pre-existing vessels. Angiogenesis is distinct from vasculogenesis, which is the de novo formation of endothelial cells from mesoderm cell precursors. The first vessels in a developing embryo form through vasculogenesis, after which angiogenesis is responsible for most blood vessel growth during normal or abnormal development. Angiogenesis is a vital process in growth and development, as well as in wound healing and in the formation of granulation tissue. However, angiogenesis is also a fundamental step in the transition of tumors from a benign state to a malignant one, leading to the use of angiogenesis inhibitors in the treatment of cancer. Angiogenesis may be chemically stimulated by angiogenic proteins, such as growth factors (e.g., VEGF). "Pathological angiogenesis" refers to abnormal (e.g., excessive or insufficient) angiogenesis that amounts to and/or is associated with a disease.

The terms "neoplasm" and "tumor" are used herein interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristics slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites. The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue.

The term "cancer" refers to a class of diseases characterized by the development of abnormal cells that proliferate uncontrollably and have the ability to infiltrate and destroy normal body tissues. See, e.g., *Stedman's Medical Dictionary*, 25th ed.; Hensyl ed.; Williams & Wilkins: Philadelphia, 1990. Exemplary cancers include, but are not limited to, hematological malignancies. Additional exemplary cancers include, but are not limited to, lung cancer (e.g., bronchogenic carcinoma, small cell lung cancer (SCLC), non-small cell lung cancer (NSCLC), adenocarcinoma of the lung); kidney cancer (e.g., nephroblastoma, a.k.a. Wilms' tumor, renal cell carcinoma); acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; ocular cancer (e.g., intraocular melanoma, retinoblastoma); familiar hyperesosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); heavy chain disease (e.g., alpha chain disease, gamma chain disease, mu chain disease; hemangioblastoma; hypopharynx cancer; inflammatory myofibroblastic tumors; immunocytic amyloidosis; liver cancer (e.g., hepatocellular cancer (HCC), malignant hepatoma); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendoctrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva). The term "hematological malignancy" refers to tumors that affect blood, bone marrow, and/or lymph nodes. Exemplary hematological malignancies include, but are not limited to, leukemia, such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma, such as Hodgkin lymphoma (HL) (e.g., B-cell HL, T-cell HL) and non-Hodgkin lymphoma (NHL) (e.g., B-cell NHL, such as diffuse large cell lymphoma (DLCL) (e.g., diffuse large B-cell lymphoma (DLBCL, e.g., activated B-cell (ABC) DLBCL (ABC-DLBCL))), follicular lymphoma, chronic lymphocytic leukemia/small lymphocytic lymphoma (CLL/SLL), mantle cell lymphoma (MCL), marginal zone B-cell lymphoma (e.g., mucosa-associated lymphoid tissue (MALT) lymphoma, nodal marginal zone B-cell lymphoma, splenic marginal zone B-cell lymphoma), primary mediastinal B-cell lymphoma, Burkitt's lymphoma, Waldenström's macroglobulinemia (WM, lymphoplasmacytic lymphoma), hairy cell leukemia (HCL), immunoblastic large cell lymphoma, precursor B-lymphoblastic lymphoma, central nervous system (CNS) lymphoma (e.g., primary CNS lymphoma and secondary CNS lymphoma); and T-cell NHL, such as precursor T-lymphoblastic lymphomalleukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); lymphoma of an immune privileged site (e.g., cerebral lymphoma, ocular lymphoma, lymphoma of the placenta, lymphoma of the fetus, testicular lymphoma); a mixture of one or more leukemia/lymphoma as described above; myelodysplasia; and multiple myeloma (MM).

The structure of Compound 1 is:

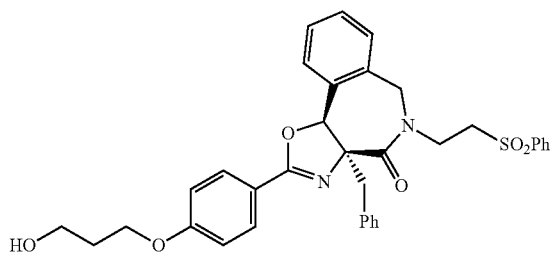

Figure 2:
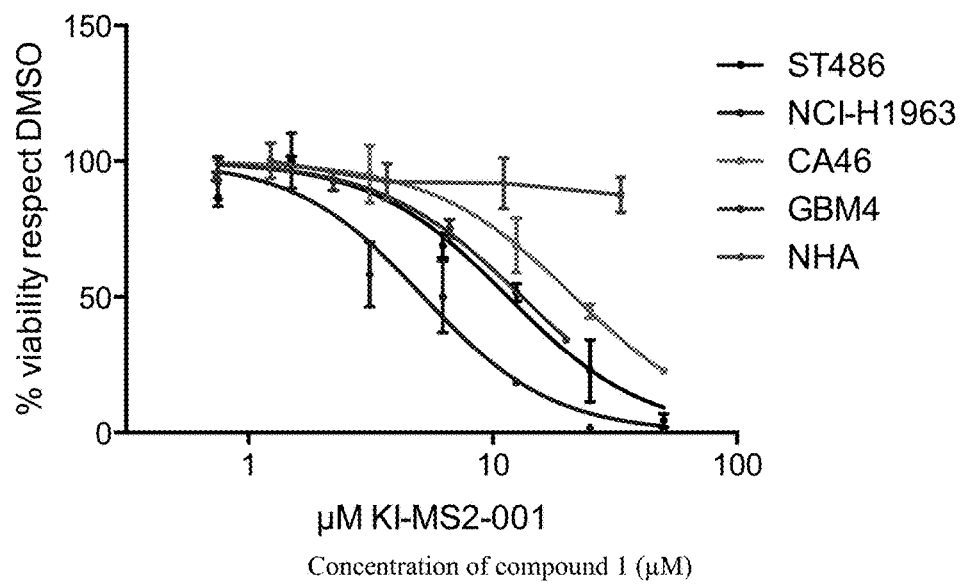

FIG. 2 shows exemplary results of a cell viability assay of Compound 1. Compound 1 affected cell viability after treatment with Compound 1 for 3 days (and 4 days for GBM4 and NHA), as measured using CELL TITER GLO (Promega) in 4 different cancer cell lines: ST486 (Burkitt's lymphoma; FIG. 2), CA46 (Burkitt's lymphoma; FIG. 2), NCI-H1963 (small cell lung cancer; FIG. 2), and GBM4 (glioblastoma; FIG. 2). The cell viability of normal human astrocytes (NHA) was also assayed. Results were expressed as a mean+/−SEM (n=2).

Figure 3A:
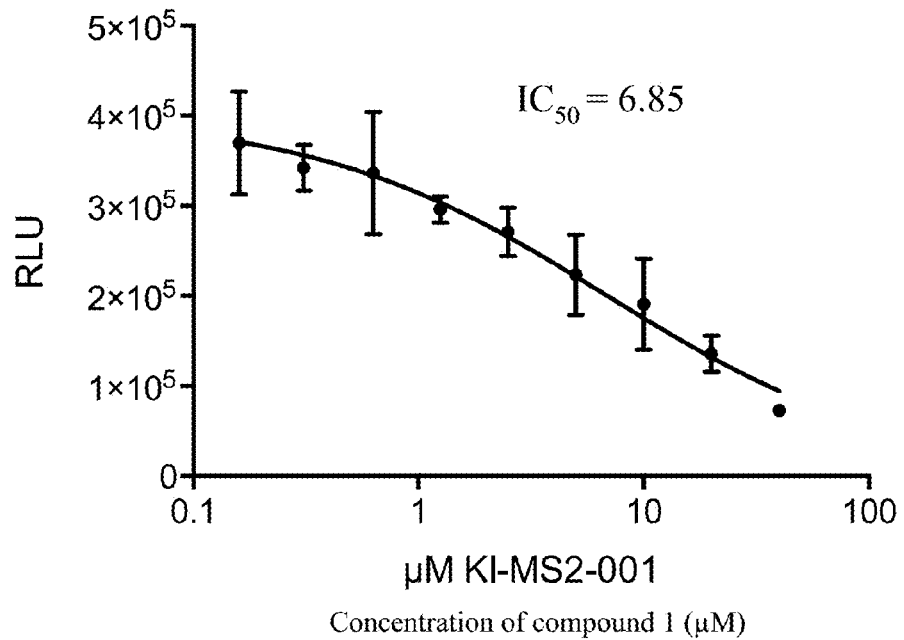
Figure 3B:
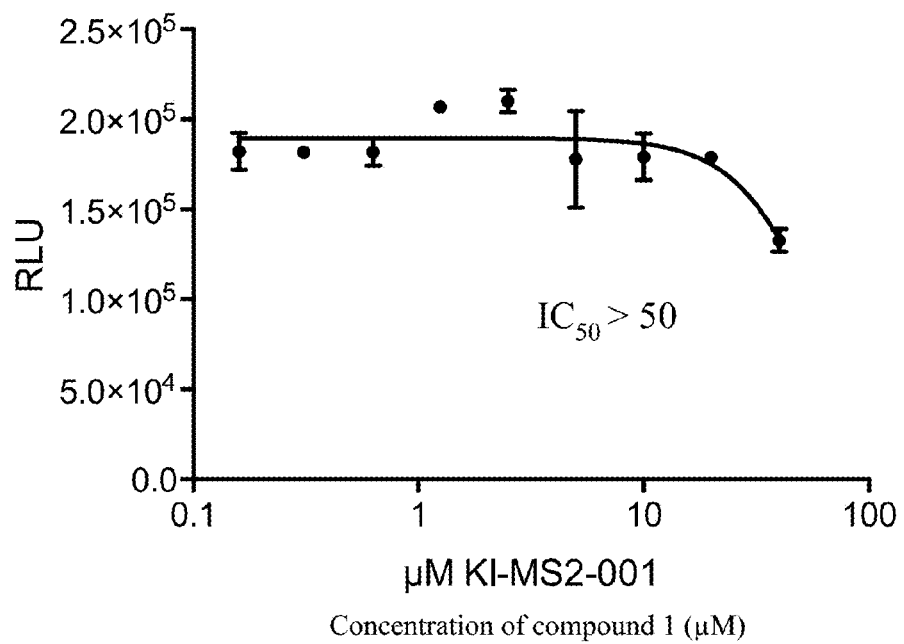

FIGS. 3A to 3B show exemplary results of an assay of cell viability and the selectivity of Compound 1 for cells expressing Myc and non-Myc expressing cells. Compound 1 affected cell viability after treatment with Compound 1 for 3 days, as measured using CELL TITER GLO (Promega) in a cancer cell line (P493-6, derived from human B-cells), where Myc is ON (FIG. 3A) or Myc is OFF (FIG. 3B). Results were expressed as a mean+/−SEM (n=3). RLU: Relative Luminescence Units.

Figure 4A:
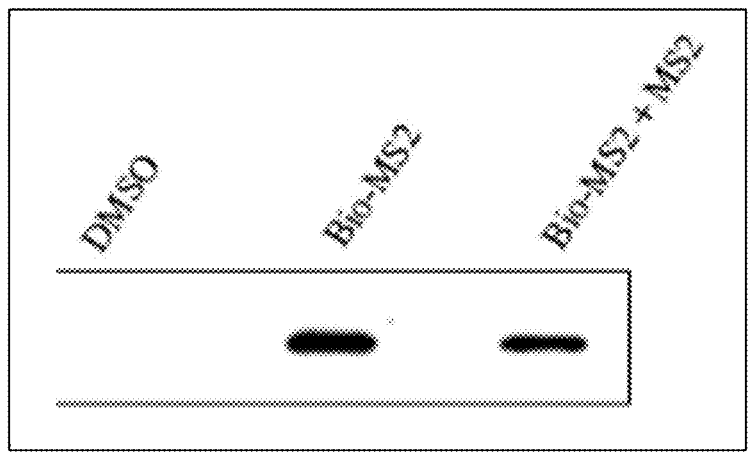
Figure 4B:
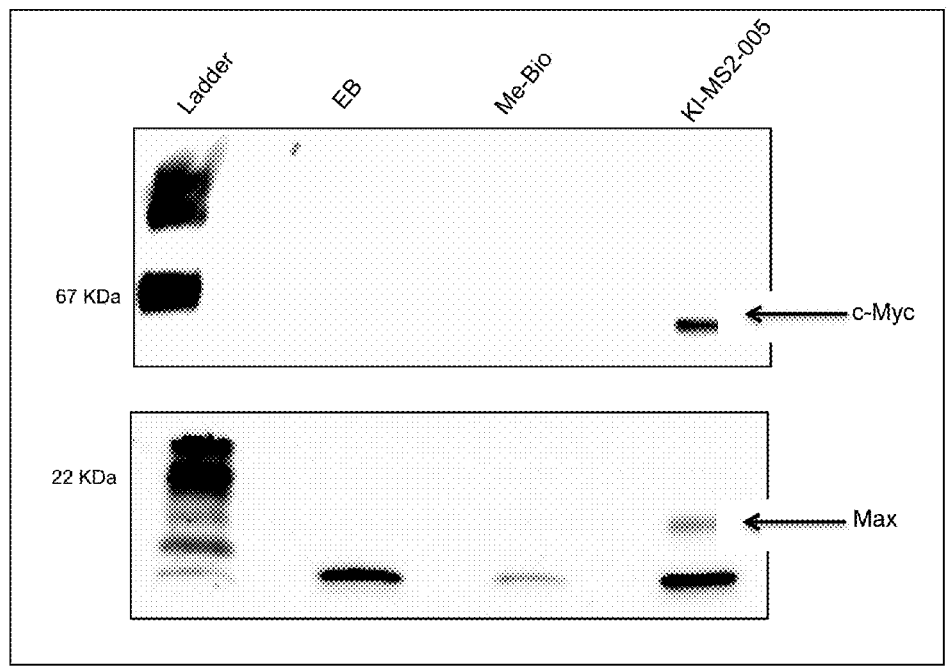
Figure 5:
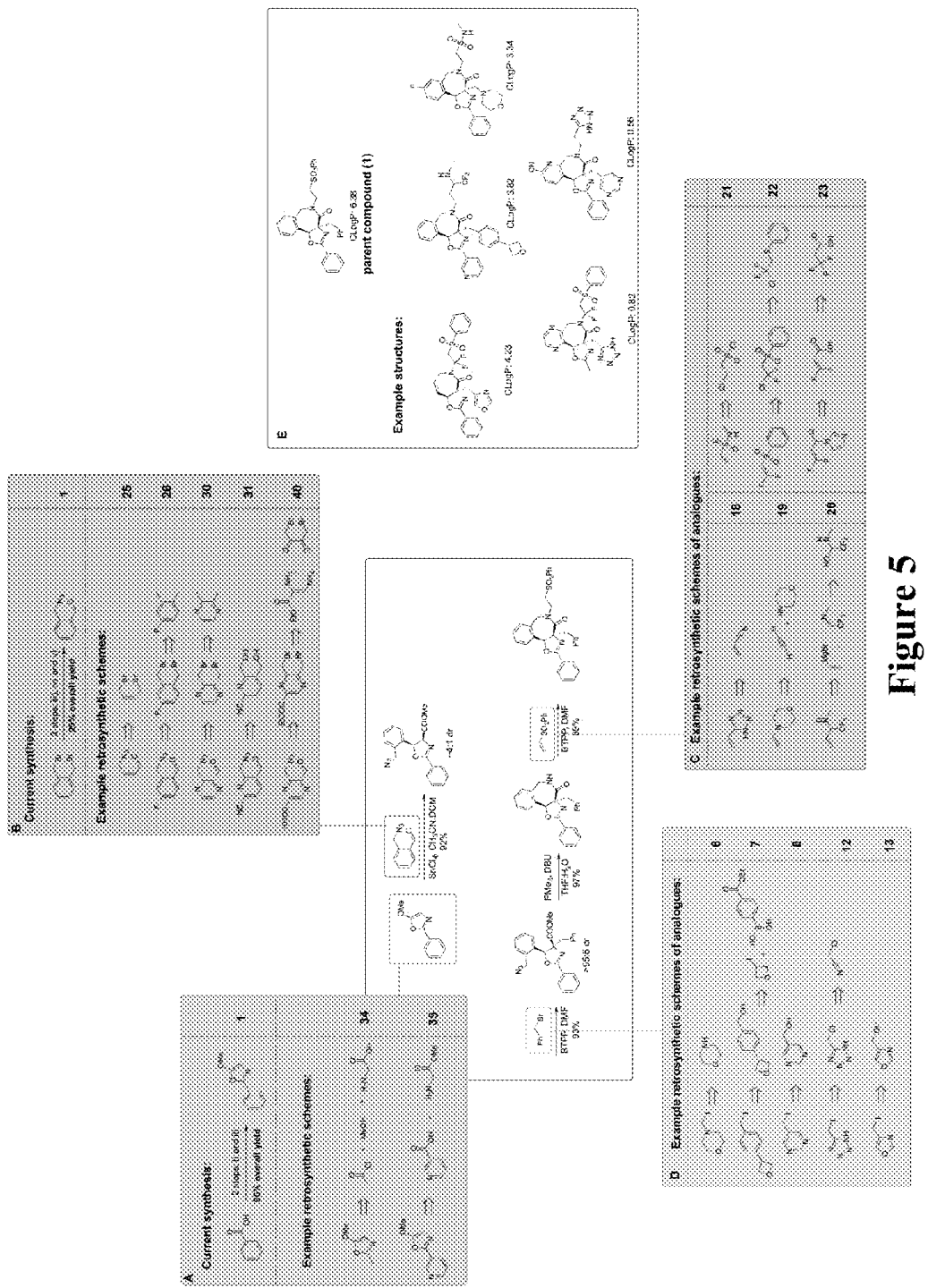

FIGS. 4A to 4B show exemplary Western blotting results of Compound 1-mediated pull downs of MAX where free Compound 1 is used as a soluble competitor. Compound 5 beads (FIGS. 4A-4B) were used. The structure of Compound 5 is:

FIGS. 5A to 5B show the synthesis of KI-MS2-008 and proposed retrosynthetic schemes for making synthetic analogues. 5A) Current synthesis of 5-methoxy-2-phenyloxazole from benzoic acid; (i) glycine methyl ester HCl, EDC, HOBt, DIPEA, 98%. (ii) $I_2$, $PPh_3$, $Et_3N$, 98%, and example structures and retrosynthetic schemes of analogues of 5-methoxy-2-phenyloxazole; 5B) Current synthesis of 2-(azidomethyl)benzaldehyde from 1,2-bis(bromomethyl)benzene; (iv) $NaN_3$, DMF, 80° C. (v) $H_2O$, $K_2CO_3$, acetone, reflux. (vi) PCC and example structures and retrosynthetic schemes of analogues of 2-(azidomethyl)benzaldehyde; 5C) Example structures and retrosynthetic schemes of analogues of (vinylsulfonyl)benzene; 5D) Example structures and retrosynthetic schemes of analogues of benzyl bromide; 5E) Example structures of proposed final compounds, combining the proposed modifications at each R group, along with the calculated C Log P values.

Figure 6:
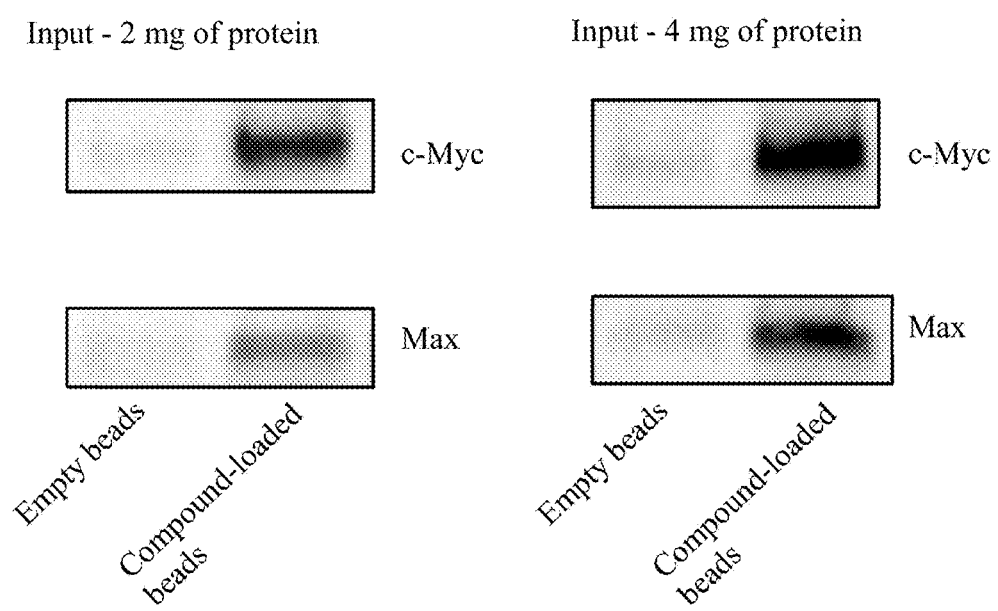

FIG. 6 shows proteins visualized by immunoblotting (c-Myc: 9E10, Santa Cruz Biotechnology; Max: C-124, Santa Cruz Biotechnology). KI-MS2-081 loaded beads pulled down significantly more c-Myc and Max compared to empty beads when 2 or 4 mg of total protein were incubated with beads. P493-6 cells were washed twice with cold PBS and resuspended in modified RIPA buffer (200 mM NaCl, 50 mM Tris, 1% NP-40, 0.1 g/100 mL sodium deoxycholate, protease inhibitor cocktail, phosphatase inhibitor, 0.4 µL benzonase per 10 mL buffer, pH 7.5) at a density of about 50 million cells per mL of modified RIPA buffer. Cell resuspensions were vortexed briefly and left on ice for 20 min. The mixture was spun down at 14,000 g for 10 min at 4° C. The supernatant following centrifugation was the whole cell lysate. Protein concentrations were estimated via Bradford assay and the same amount of lysate was incubated with either KI-MS2-081 loaded beads or empty beads at 4° C. for 1 hour. Beads were collected and washed three times with 500 µL wash buffer. Finally, proteins were eluted off of beads with 50 µL of 2× Laemmli sample buffer with 2-mercaptoethanol and boiling at 90° C. for 1 hour. Proteins were visualized by immunoblotting (c-Myc: 9E10, Santa Cruz Biotechnology; Max: C-124, Santa Cruz Biotechnology). KI-MS2-081 loaded beads pulled down significantly more c-Myc and Max compared to empty beads when 2 or 4 mg of total protein were incubated with beads.

Figure 7:
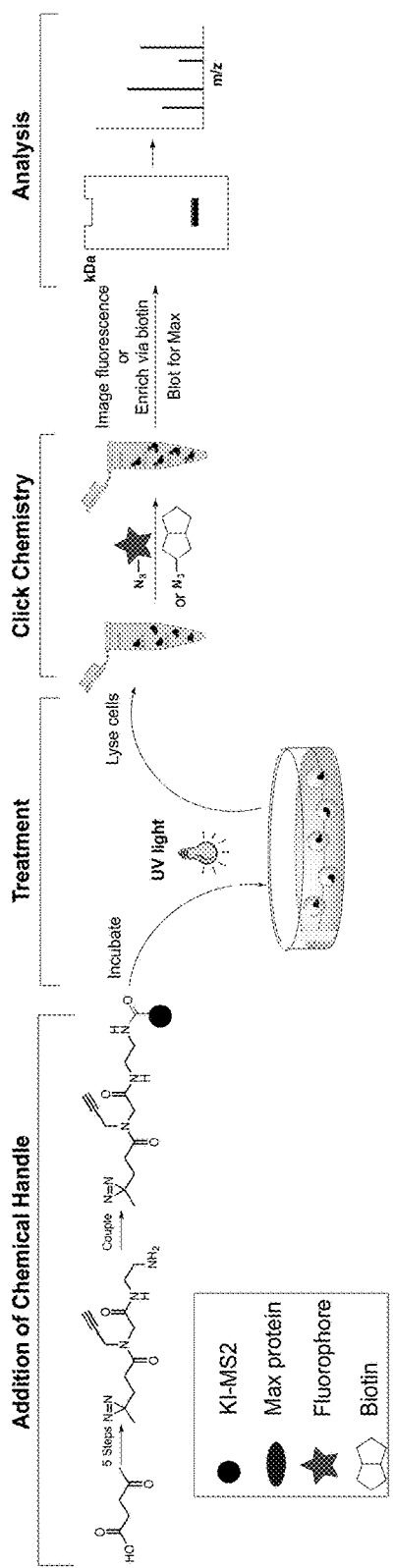

FIG. 7 shows an overview of a target engagement study in live cells using KI-MS2-085. Cells were treated with a biologically active photoprobe followed by irradiation and installation of Alexa Fluor 647 azide or biotin azide via click chemistry and were analyzed by fluorescence or enriched and analyzed by western-blot. The diazirine alkyne analogue KI-MS2-085 retained cellular activity and was further utilized in the target engagement studies.

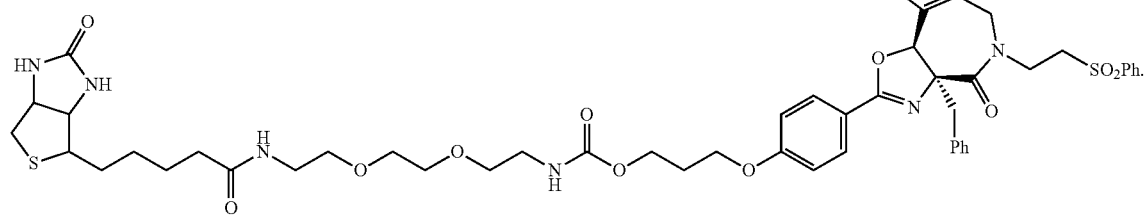

Figure 8A:
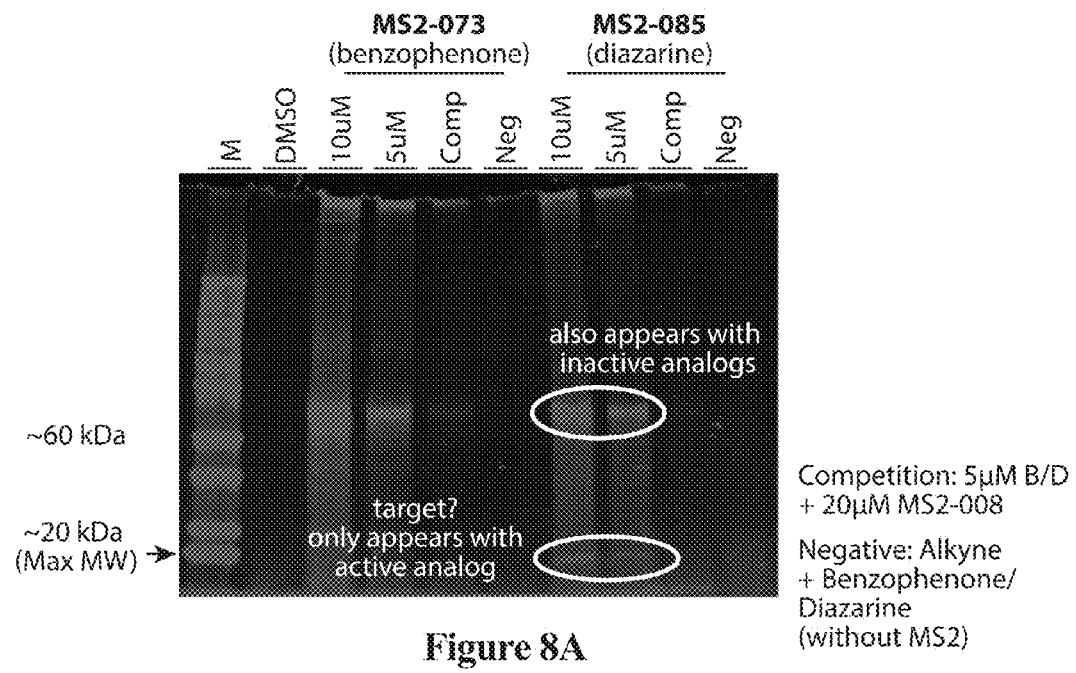
Figure 8B:
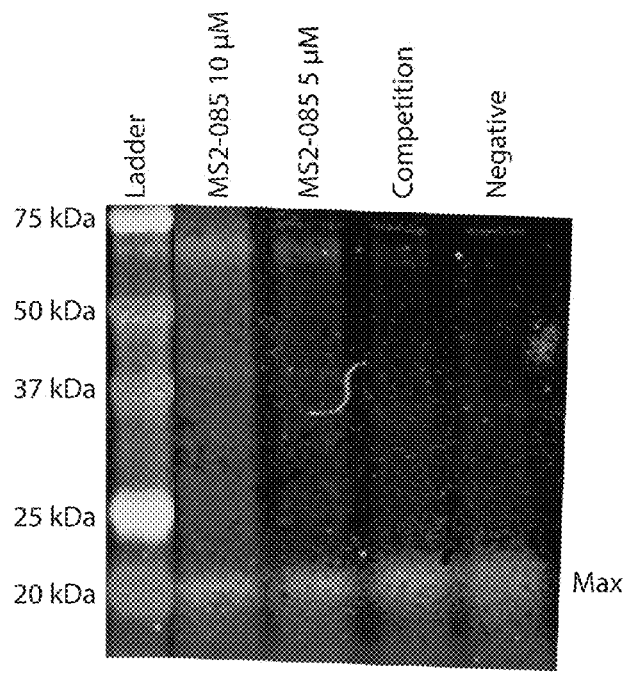

FIGS. 8A to 8B show target engagement in live cells using KI-MS2-085 clicked on AlexaFluor. An inactive benzophenone (KI-MS2-073) and an active diazirine compound (KI-MS2-085) are shown in FIG. 8A. Clicking on AlexaFluor to KI-MS2-085 illuminates a 20 kDa band in live cell treatments. The active compound illuminates two bands at 20 kDa, which is the molecular weight of two Max isoforms. These bands overlap with western blot detection of Max (FIG. 8B). The interaction is competed when 20 μM soluble KI-MS2-008 compound is present. Another non-selective band appears for both the active and inactive analogues.

Figure 9A:
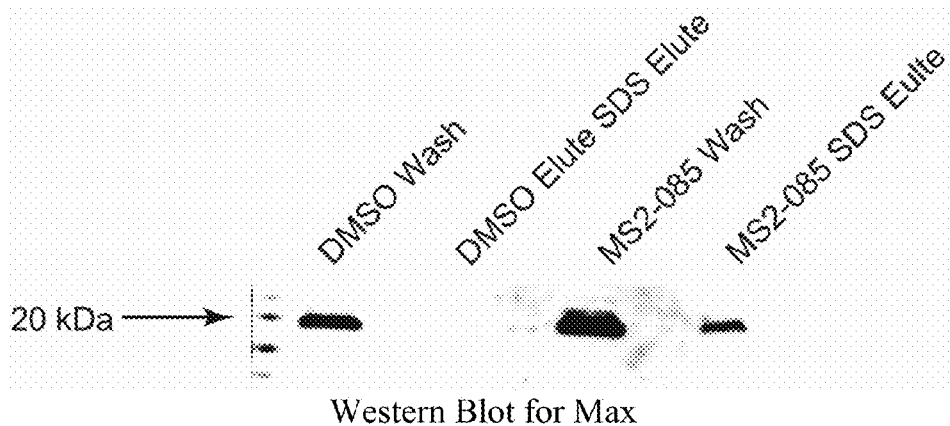
Figure 9B:
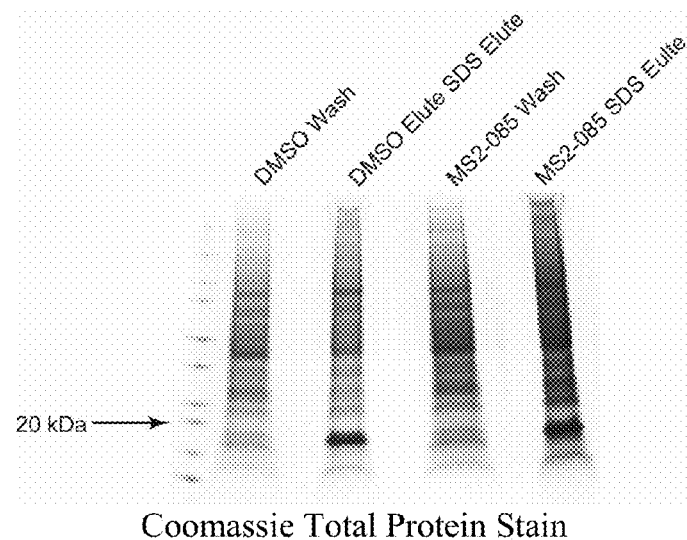

FIGS. 9A to 9B show target engagement in live cells using KI-MS2-085 clicked on Biotin with Streptavidin Enrichment. Clicking on Biotin to KI-MS2-085 followed by Streptavidin enrichment yielded Max protein enrichment by western-blot (FIG. 9A). A coomassie total protein stain is also shown (FIG. 9B).

Figure 10:
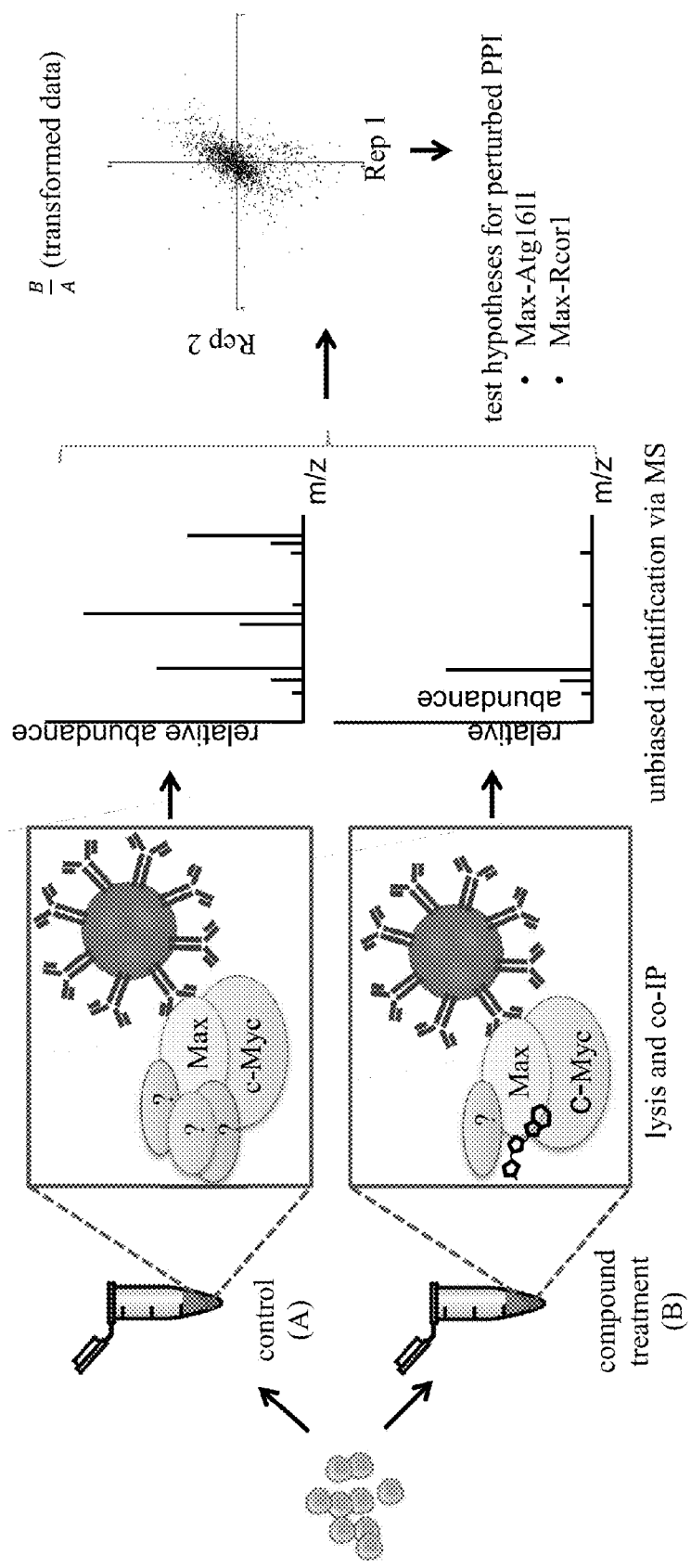

FIG. 10 shows a general schematic for Co—IP MS experiment to investigate mechanism of action of KI-MS2-008: Whole cell lysate was generated and a Max-anchored co-immunoprecipitation was performed when KI-MS2-008 was or was not added to the cell lysate. Proteins bound to anti-Max beads were identified via mass spec with tandem mass tagging (TMT) based quantification.

Figure 11:
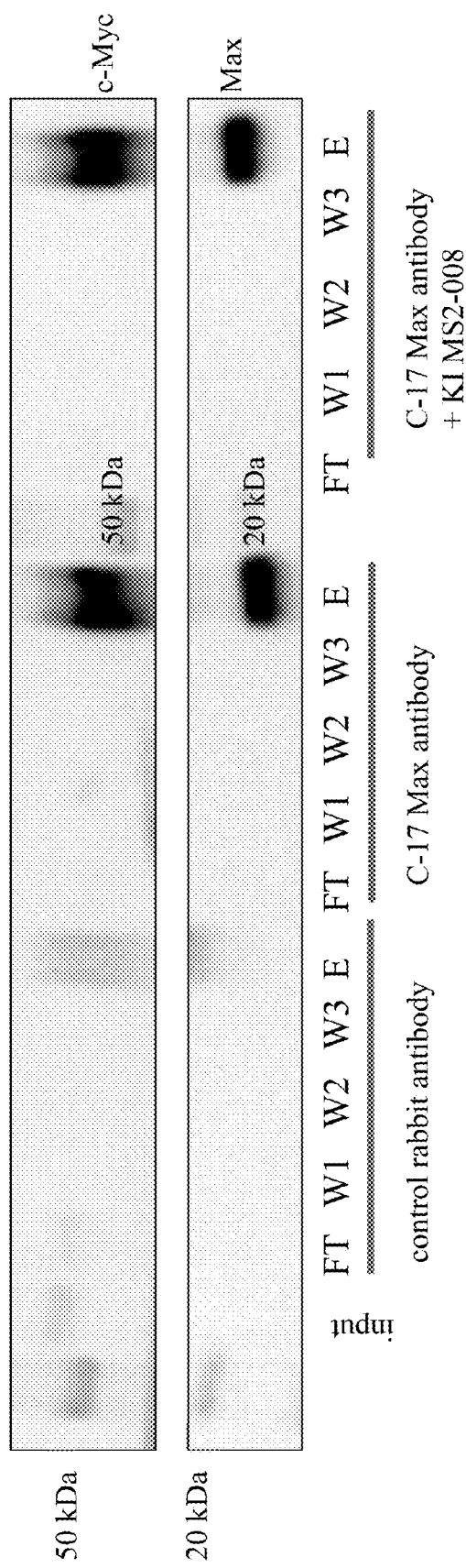

FIG. 11 shows an immunoblot against c-Myc and Max (c-Myc: 9E10, Santa Cruz Biotechnology; Max: H-2, Santa Cruz Biotechnology). Max was immunoprecipitated and c-Myc was co-immunoprecipitated using the α-Max antibody both in the presence and absence of KI-MS2-008, but not with control antibody. P493-6 cells were washed twice with cold PBS and resuspended in modified RIPA buffer (200 mM NaCl, 50 mM Tris, 1% NP-40, 0.1 g/100 mL sodium deoxycholate, protease inhibitor cocktail, phosphatase inhibitor, 0.4 μL benzonase per 10 mL buffer, pH 7.5) at a density of about 50 million cells per mL of modified RIPA buffer. Cell resuspensions were vortexed briefly and left on ice for 20 min. The mixture was spun down at 14,000 g for 10 min at 4° C. The supernatant following centrifugation was the whole cell lysate. Protein concentrations were estimated via Bradford assay and 4 mg of total protein was incubated with 2 μL DMSO or 10 mM KI-MS2-008 for 30 min before adding α-Max antibody or control antibody. After an overnight incubation at 4° C., 50 μL of washed Dynabeads® Protein G for Immunoprecipitation (Thermo-Fisher Scientific) were added and allowed to incubate for 1 hour at 4° C. Beads were collected and washed three times with wash buffer. For one replicate of beads, 30 μL of 2× Laemmli sample buffer with 2-mercaptoethanol was added and boiled at 90° C. for 5 min to elute. Samples were run on a gel and an immunoblot against c-Myc and Max was generated (c-Myc: 9E10, Santa Cruz Biotechnology; Max: H-2, Santa Cruz Biotechnology). Max was immunoprecipitated and c-Myc was co-immunoprecipitated using the α-Max antibody both in the presence and absence of KI-MS2-008, but not with control antibody.

Figure 12:
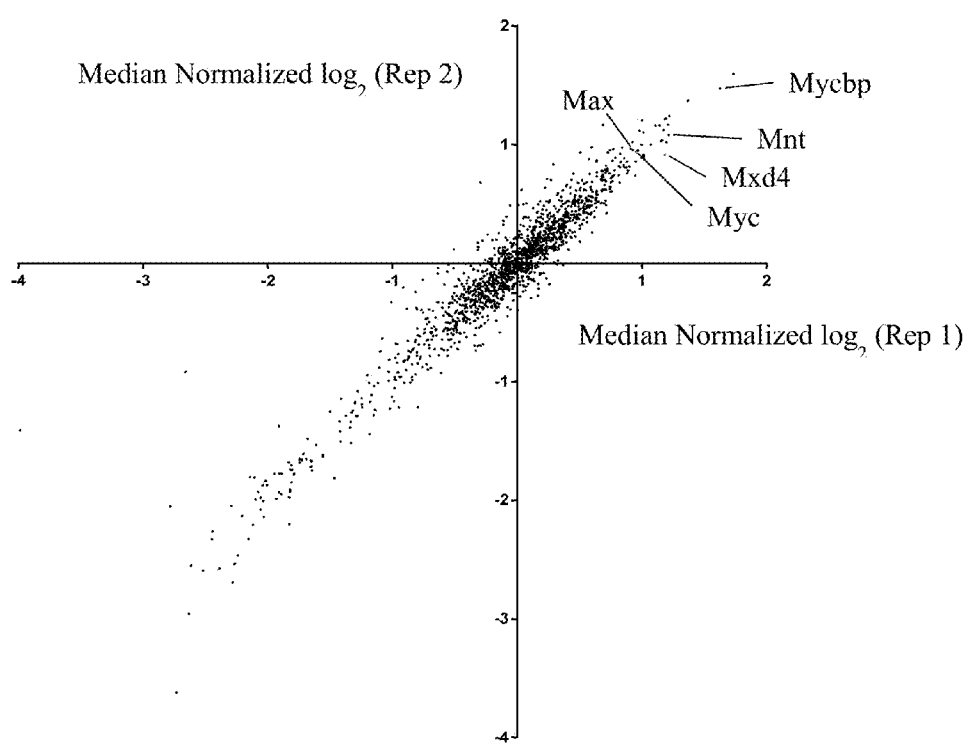

FIG. 12 shows interactomics data of α-Max Ab (−KI-MS2-008)/control IgG in a scatterplot. In this scatterplot, each dot represents a protein. Proteins that appear in the upper right quadrant are enriched in the first condition, while those that appear in the bottom left quadrant are enriched in the second condition. Some known interactors of Max are shown enriched in the Max Co—IP.

Figure 13:
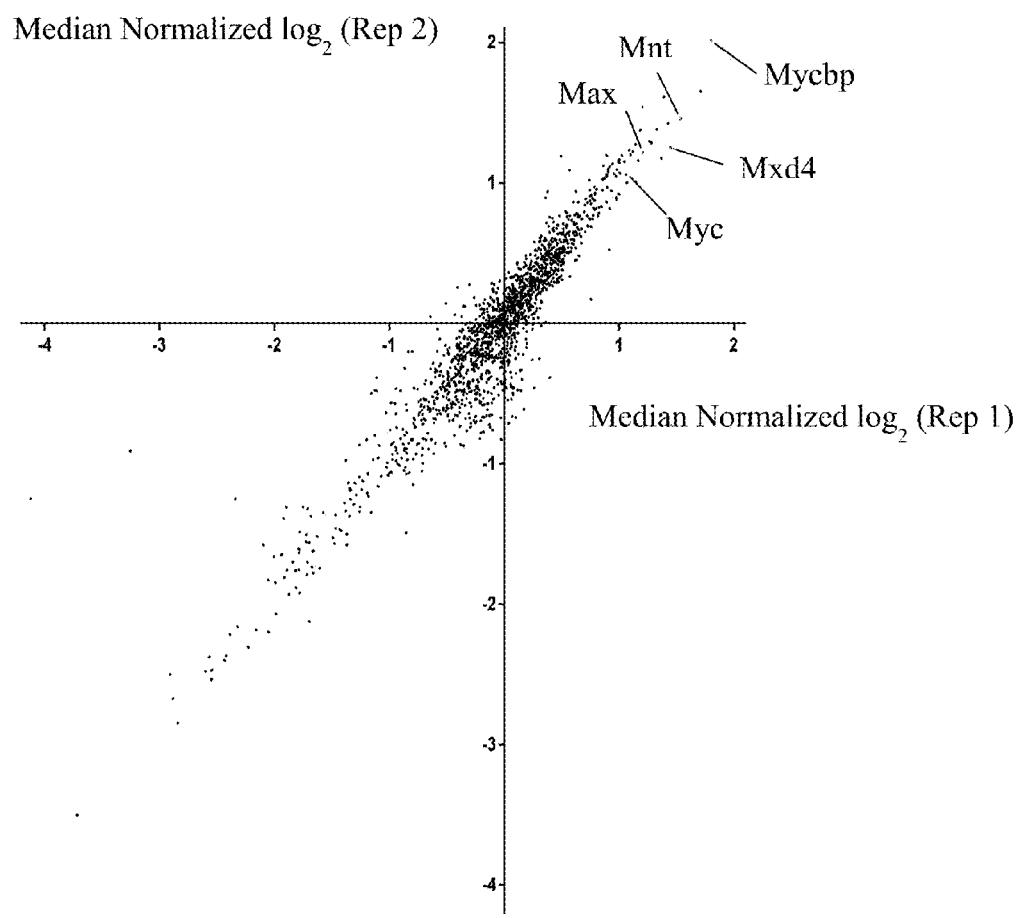

FIG. 13 shows interactomics data of α-Max Ab (+KI-MS2-008)/control IgG in a scatterplot. In the presence of KI-MS2-008, similar proteins are enriched when α-Max antibody is used compared to the control antibody.

Figure 14:
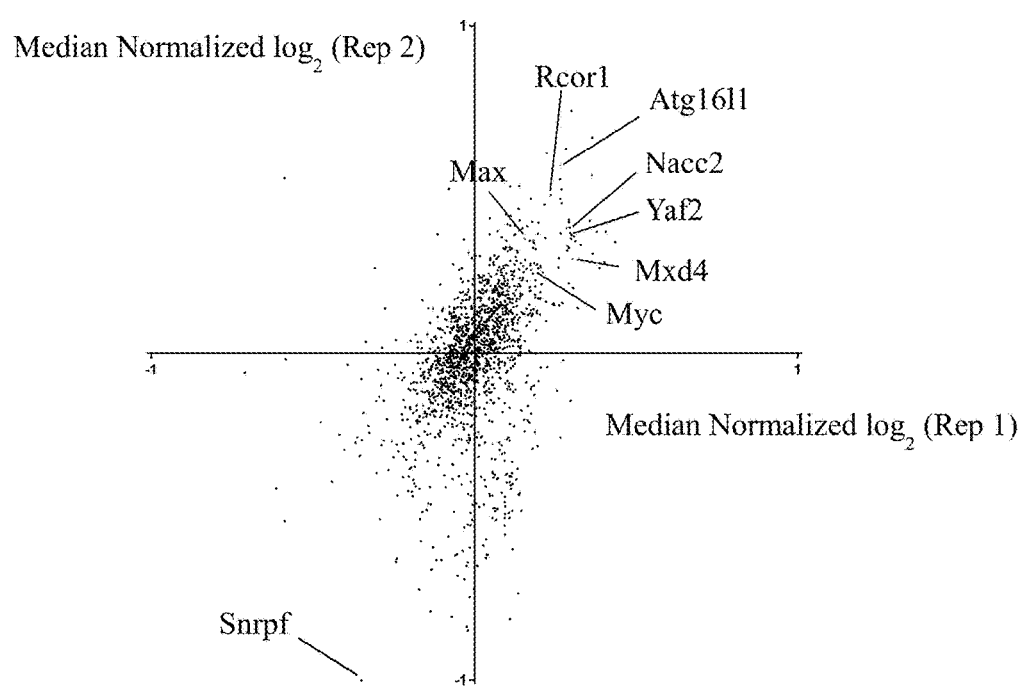

FIG. 14 shows the impact of KI-MS2-008 on Max interactome in a scatterplot. When comparing the Max interactome in the presence of KI-MS2-008 compared to its absence, perturbed proteins can be identified for follow-up studies.

Figure 15A:
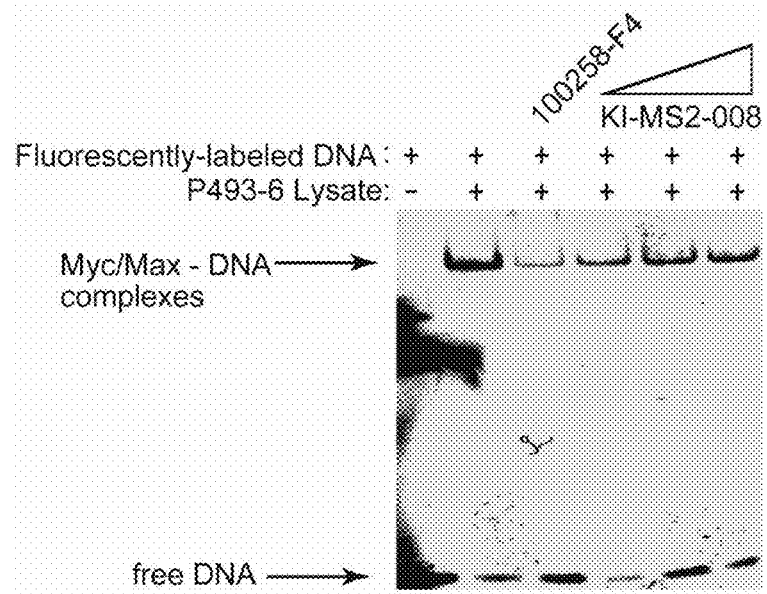
Figure 15B:
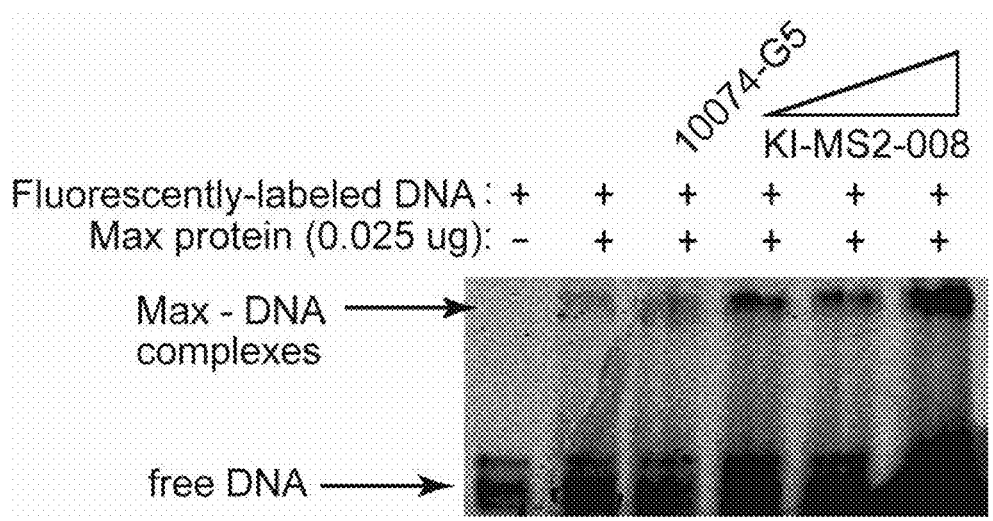
Figure 15C:
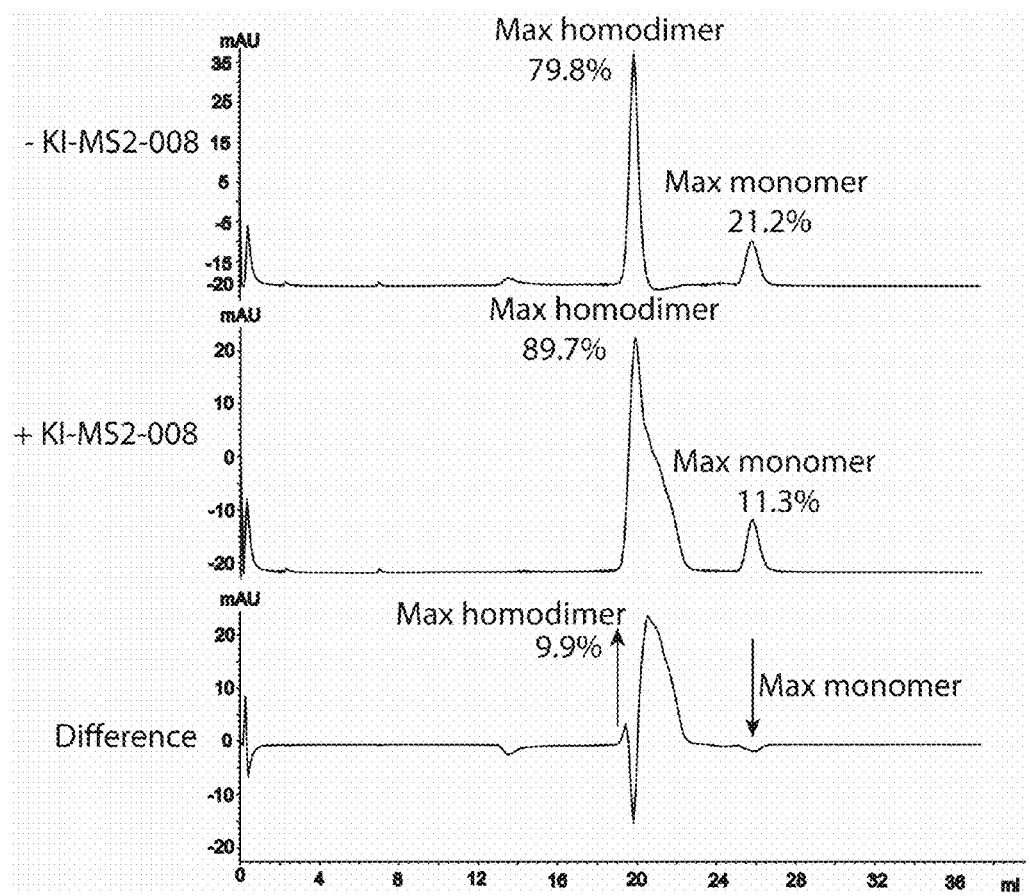

FIGS. 15A to 15C show KI-MS2-008 Max Homodimer Stabilization Hypothesis for MoA. FIG. 15A shows electrophoretic mobility shift assays (EMSAs), which demonstrate that KI-MS2-008 does not disrupt the c-Myc/Max heterodimer. FIG. 15B shows an EMSA experiment with recombinant Max, which revealed a dose-dependent increase of Max homodimer binding to DNA. This leads to a hypothesize that KI-MS2-008 stabilizes the Max homodimer. FIG. 15C shows further evidence of this by quantifying the relative populations of the Max monomer vs. Max homodimer by fPLC. Addition of KI-MS2-008 induced dimerization of the Max homodimer by 9.9%.

Figure 16A:
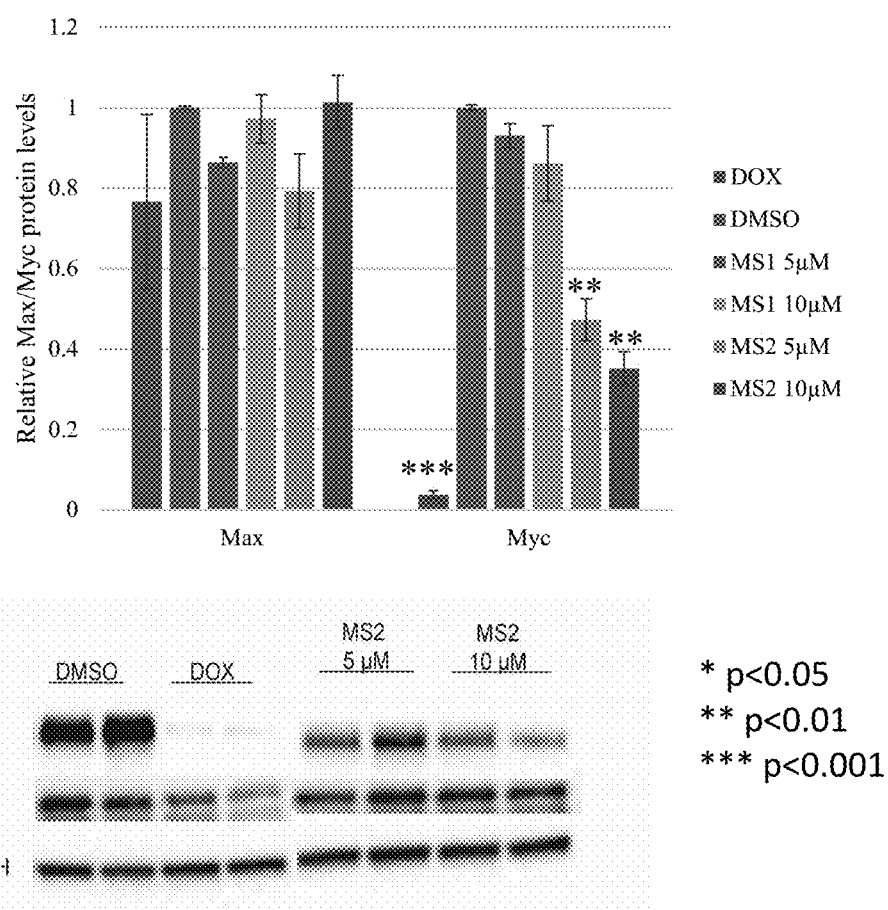
Figure 16B:
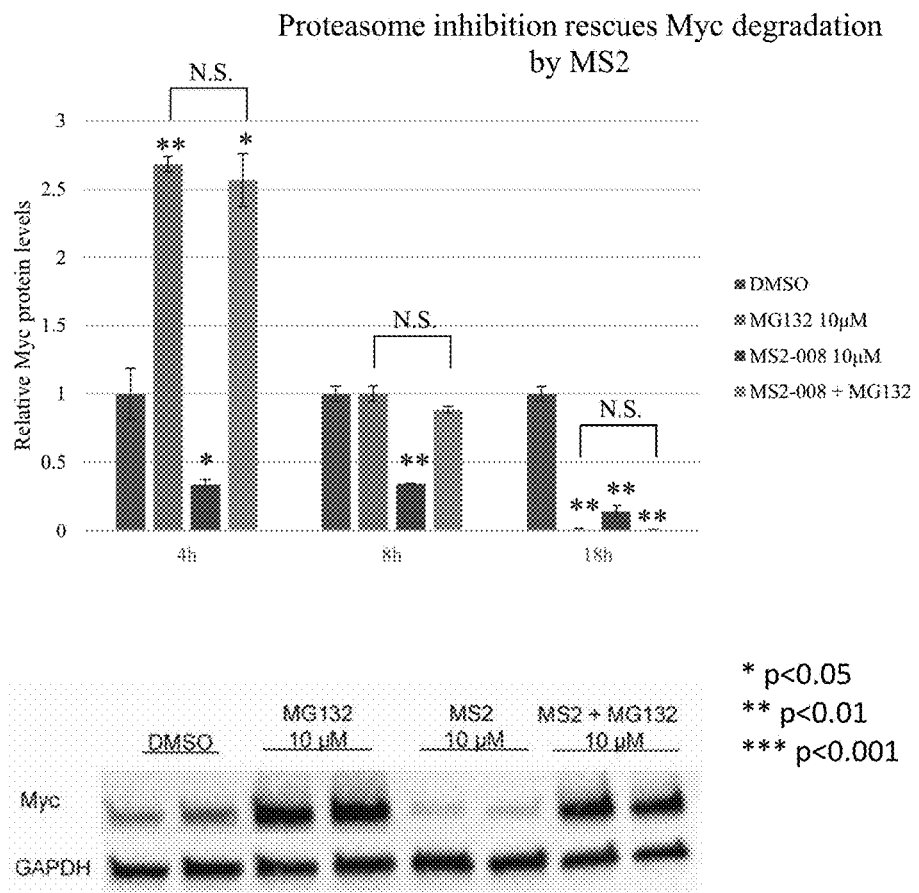

FIGS. 16A to 16B show that KI-MS2-008 decreases Myc protein levels (FIG. 16A), which can be recovered by Proteasome inhibition (FIG. 16B).

Figure 17:
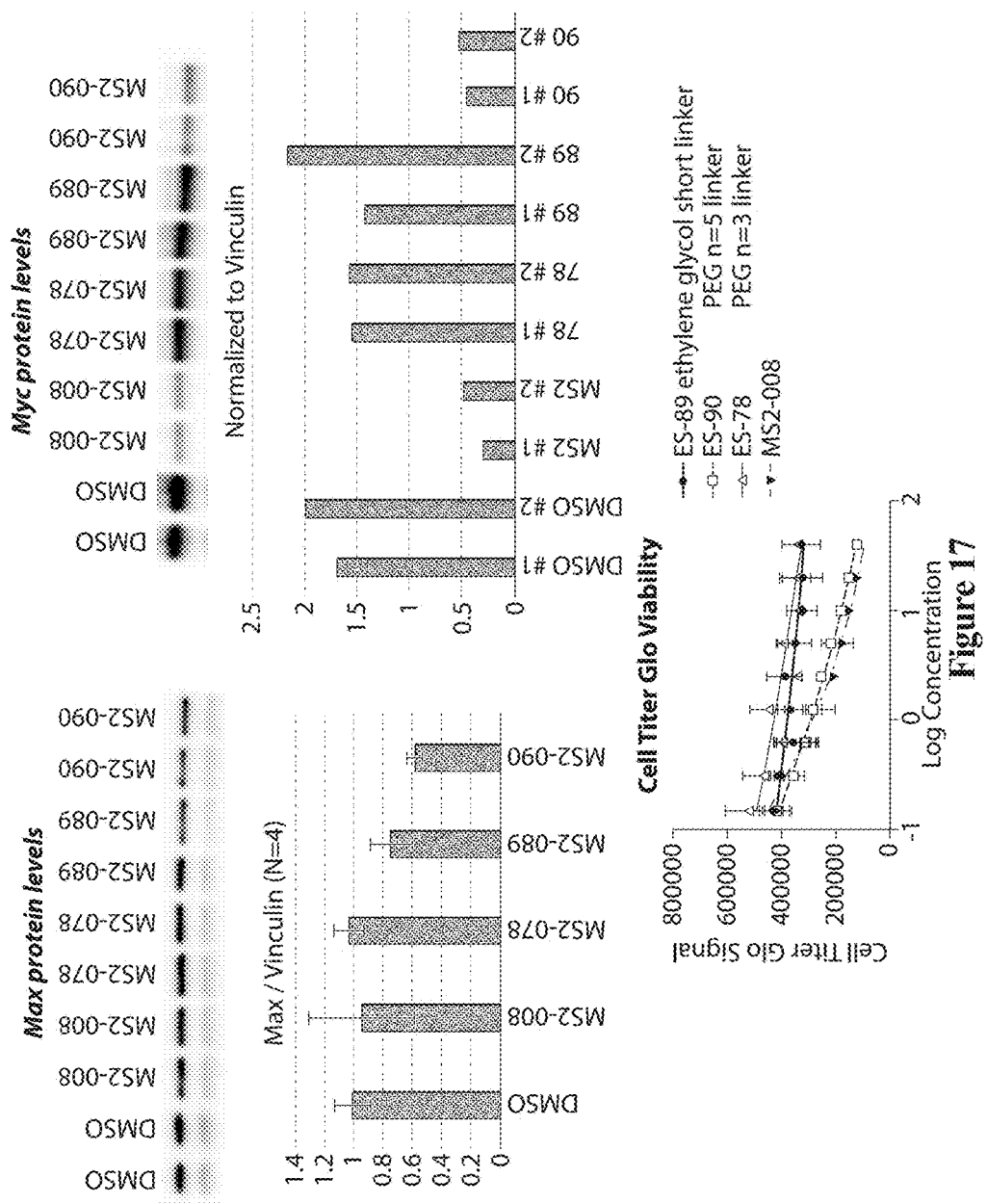

FIG. 17 shows data for MS2 degronimids first-generation molecules.

Figure 18:
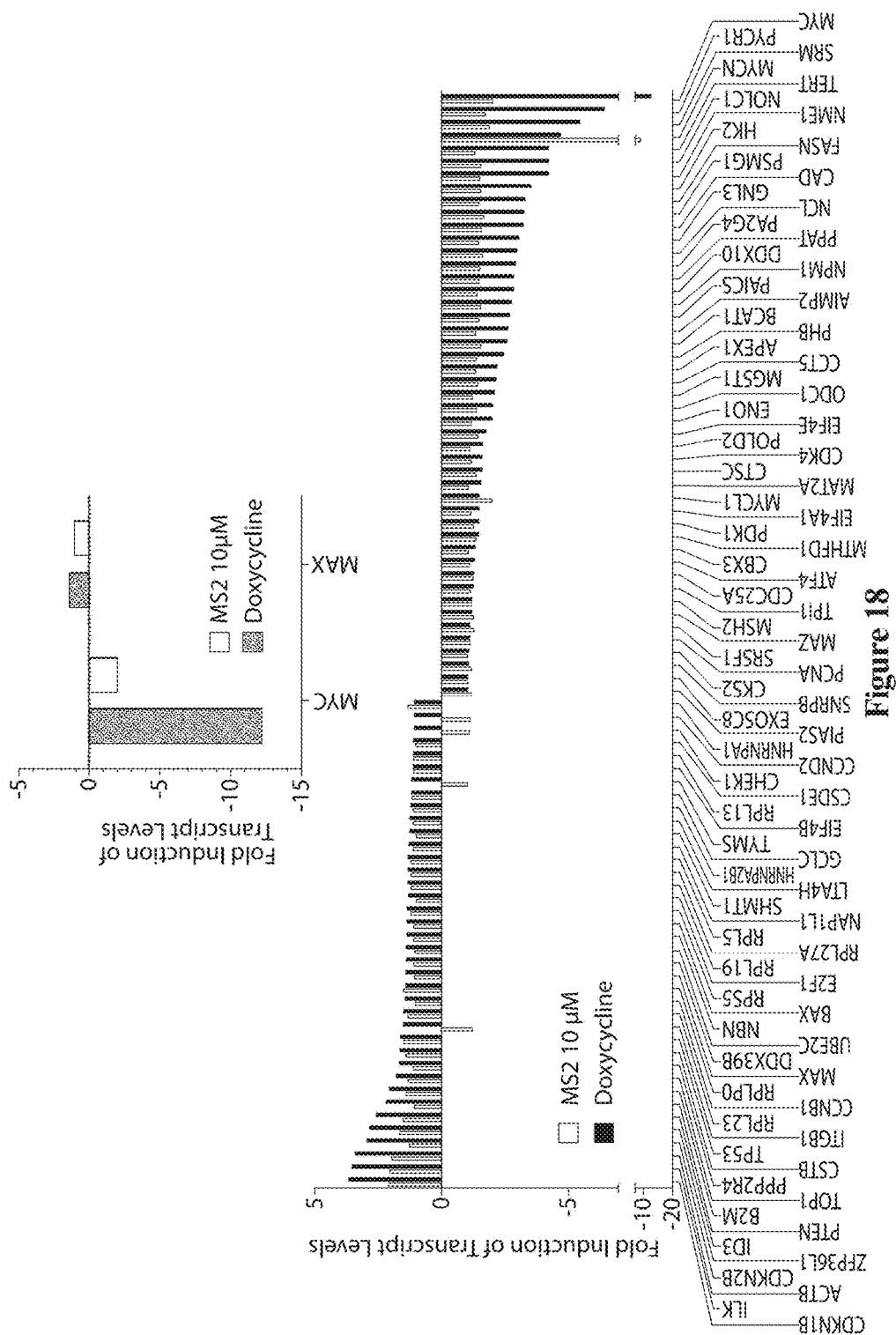

FIG. 18 shows qPCR data, which indicates that KI-MS2-008 decreases Myc transcript levels.

Figure 19:
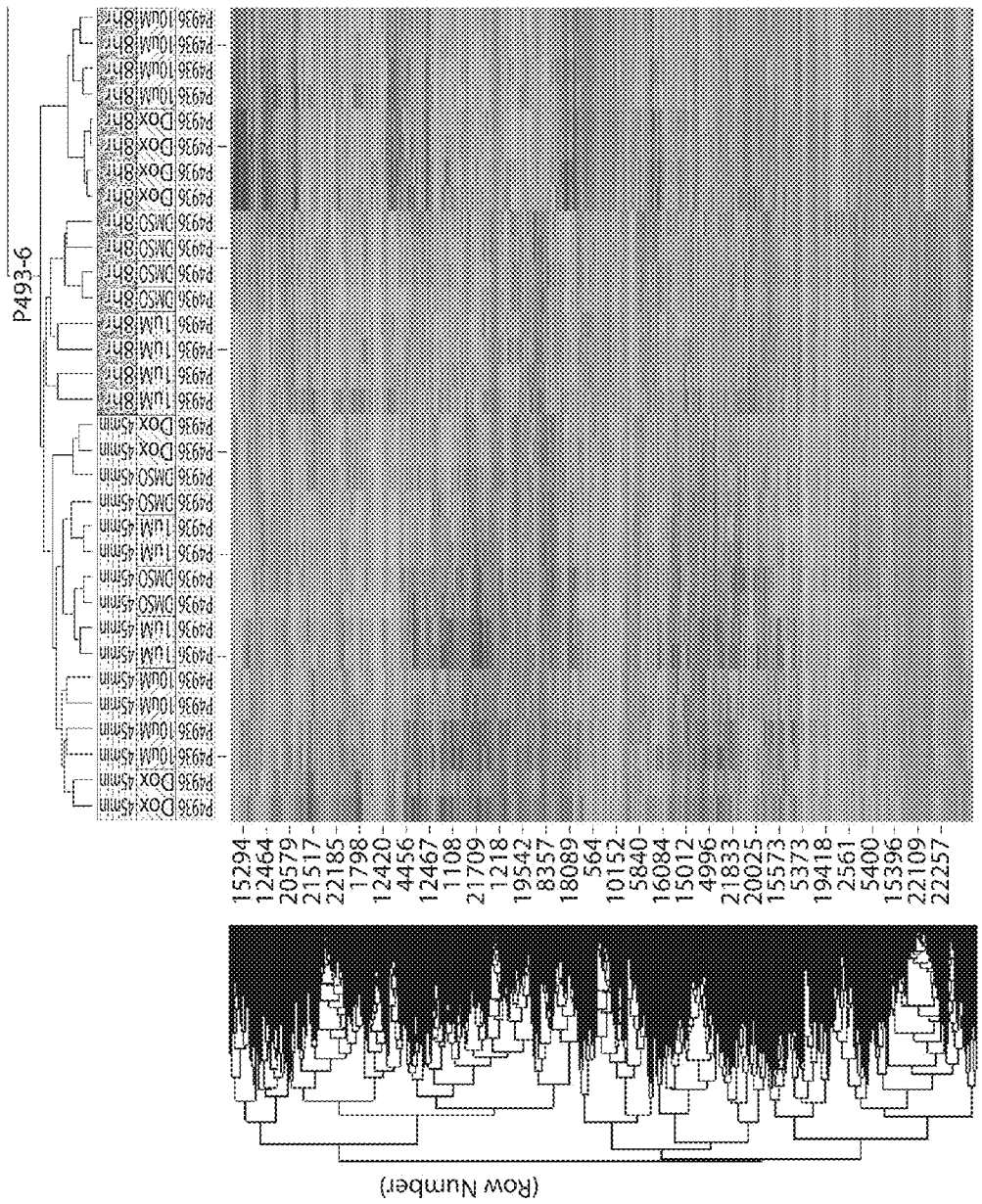
Figure 19:
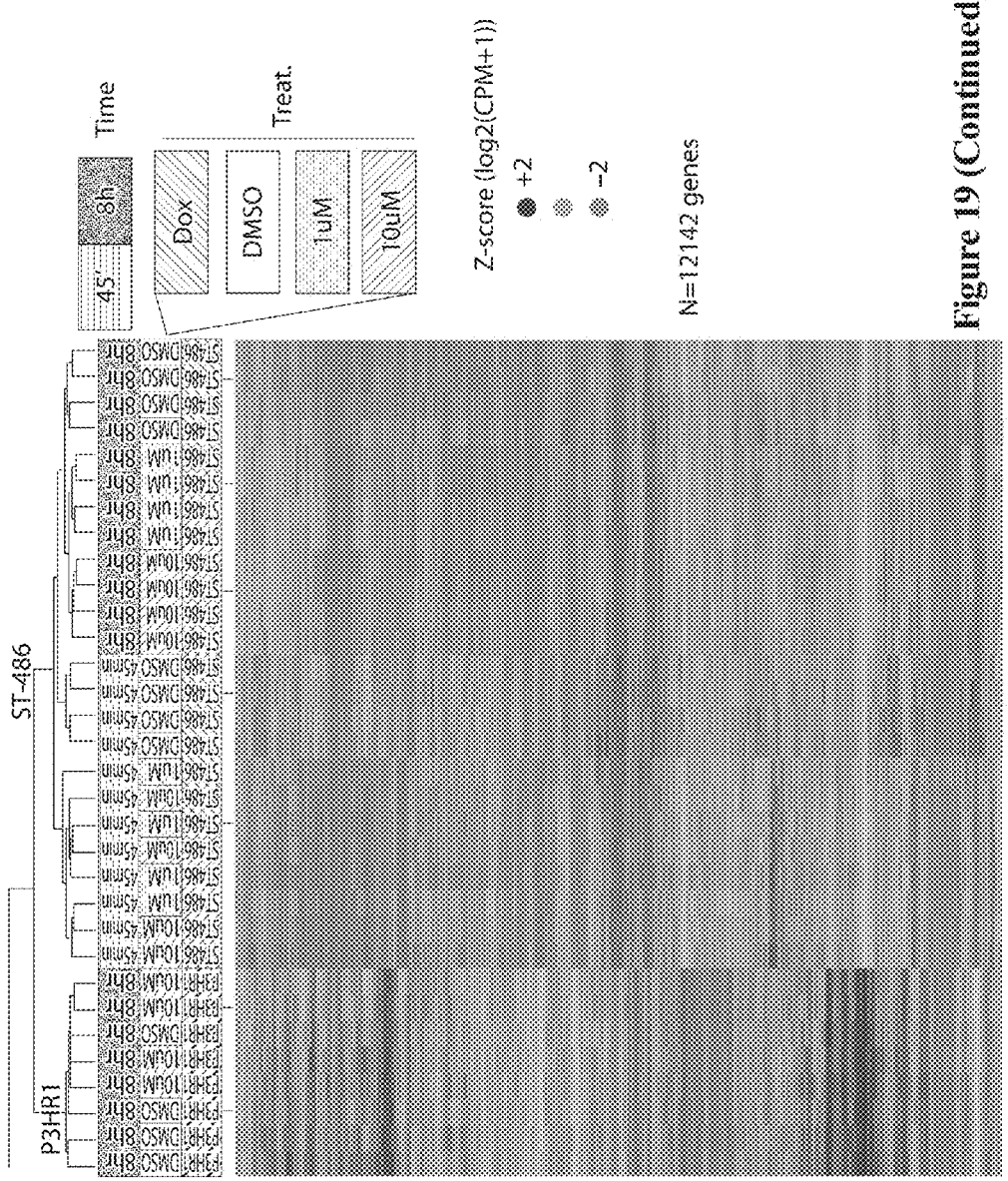

FIG. 19 shows that KI-MS2-008 perturbs transcriptional programs. In particular, RNA-seq shows a strong clustering of cell lines and time points with decent clustering of conditions. P493-6 shows relatively sensitive engineered cell line in viability assay. 10 μM treatment clustered closely with doxycycline treatment, especially at the 8 hour time point. P3HR1 shows relatively insensitive (IC50 51.15 μM) non-engineered cell line in viability assay. Minimal perturbations to the transcriptome. ST-486: relatively sensitive (IC50 18.71 μM) non-engineered cell line in viability assay. Clear perturbations to transcriptome at 45 min.

Figure 20A:
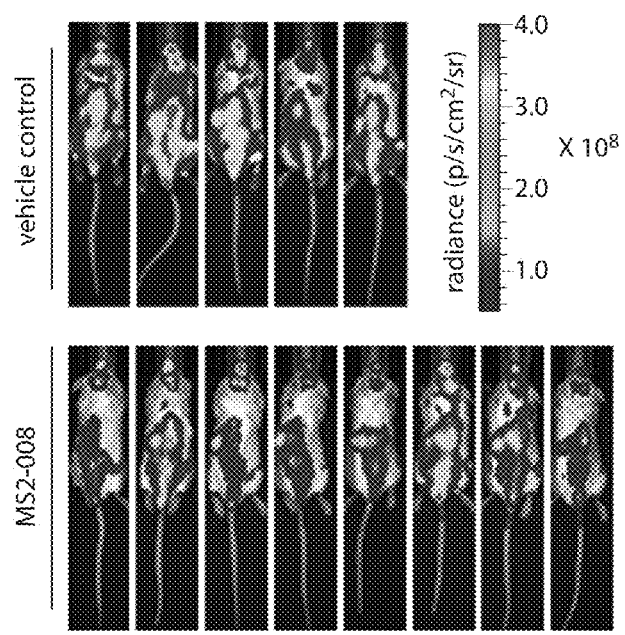
Figure 20B:
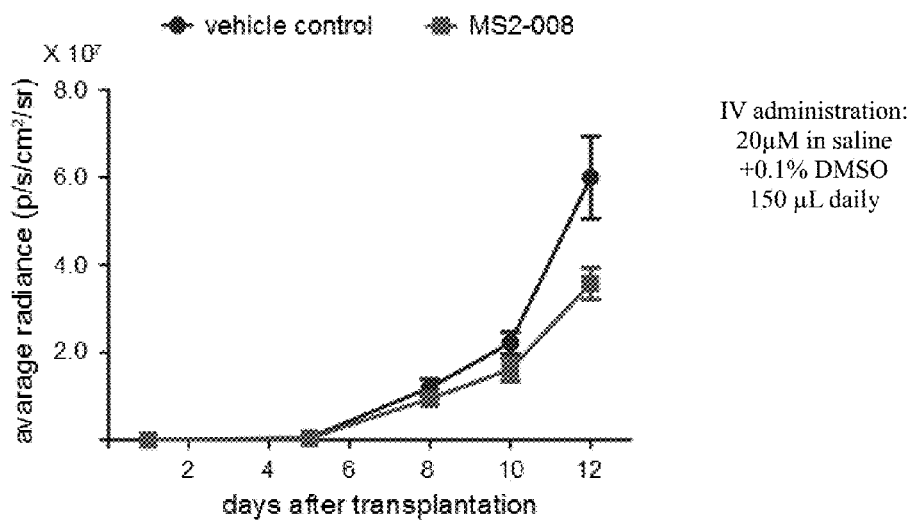
Figure 20C:
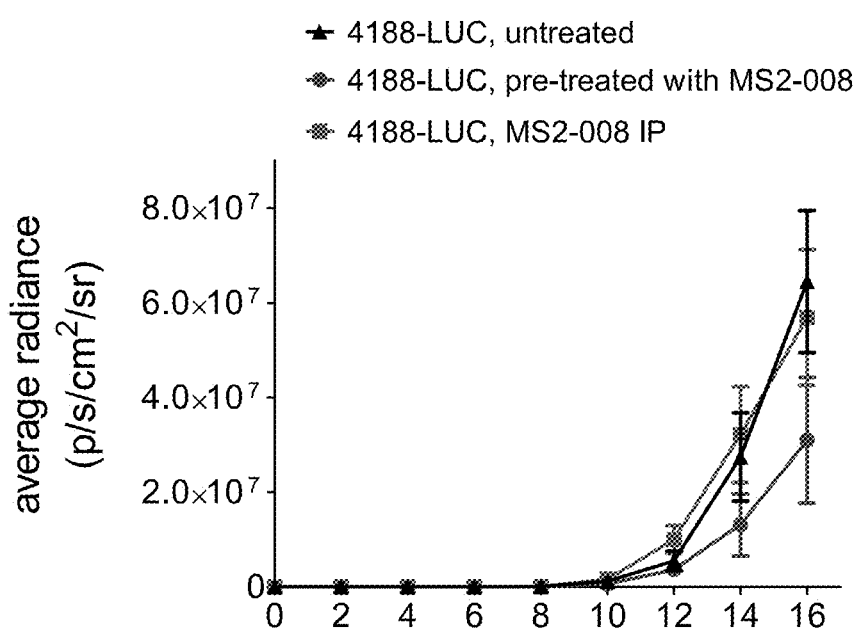

FIGS. 20A to 20C show transplanted Luc-labeled cells from MYC-driven lymphoma model into immune-compromised NSG mice. FIG. 20B shows IV administration of 20 μM in saline+0.1% DMSO, 150 μL daily dose. FIG. 20C shows IP administration of 10 mg/mL in corn oil, 100 μL IP, dosed every other day (d2-16); pre-treatment of 4188-Luc cells with 20 μM in PBS+0.1% DMSO for 24 hours. The data demonstrates that KI-MS2-008 impacts tumor volume in MYC-driven T-ALL model.

Figure 21:
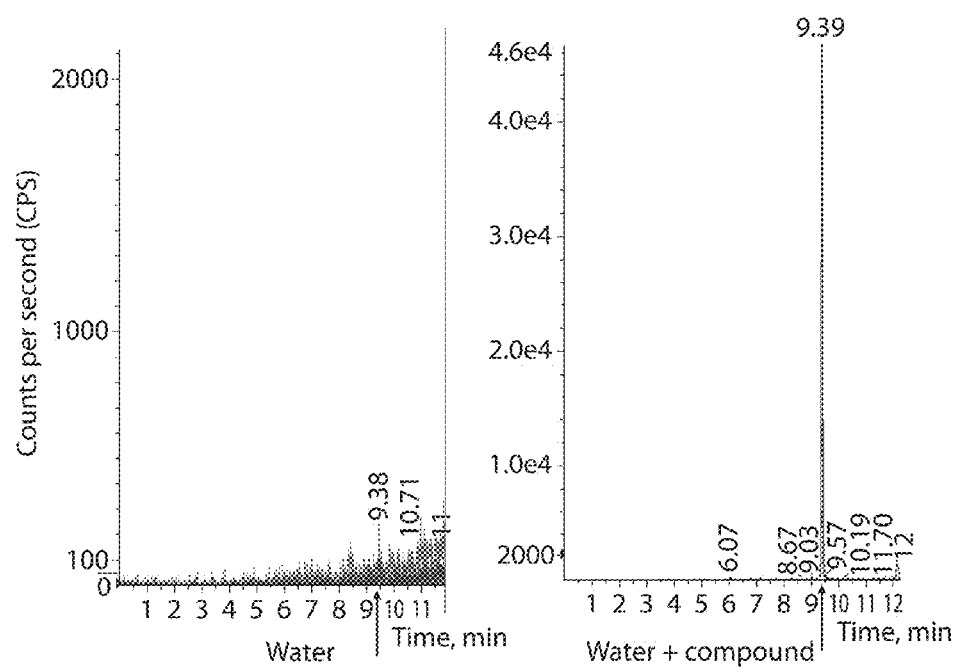

FIG. 21 shows the results of a LC/MS detection method for MS2-008. The compound peak was detected at ~9 minutes.

Figure 22:
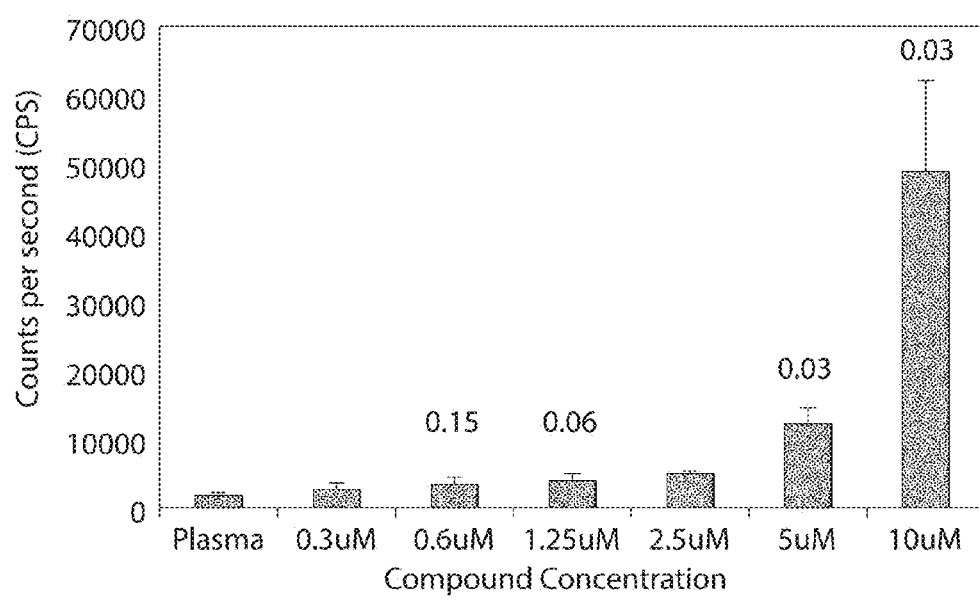

FIG. 22 shows the results of a serial dilution-lowest detection limit test. The data demonstrates that MS2-008 is detectable in processed plasma. n=3 mice for each group. Paired t-test between control plasma and other sample sets: *p<0.001.

Figure 23:
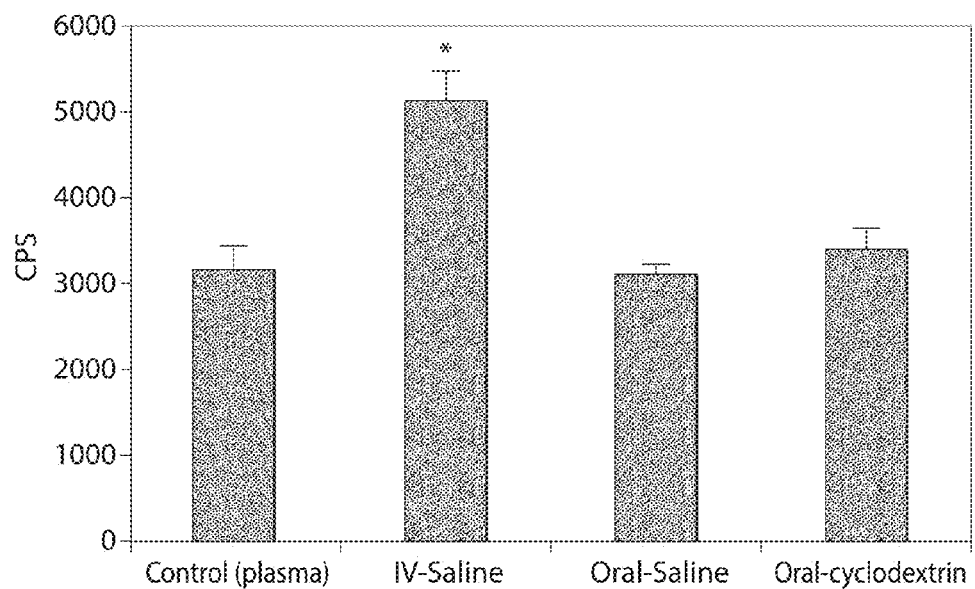

FIG. 23 shows LC/MS analysis for compound IV and oral administration comparison. The data indicates that there is a demonstrable level of compound with IV and no significant change in oral saline or cyclodextrin as compared to control plasma. n=3 animals for each group; paired t-test between control plasma and other sample sets: *p<0.001.

Figure 24:
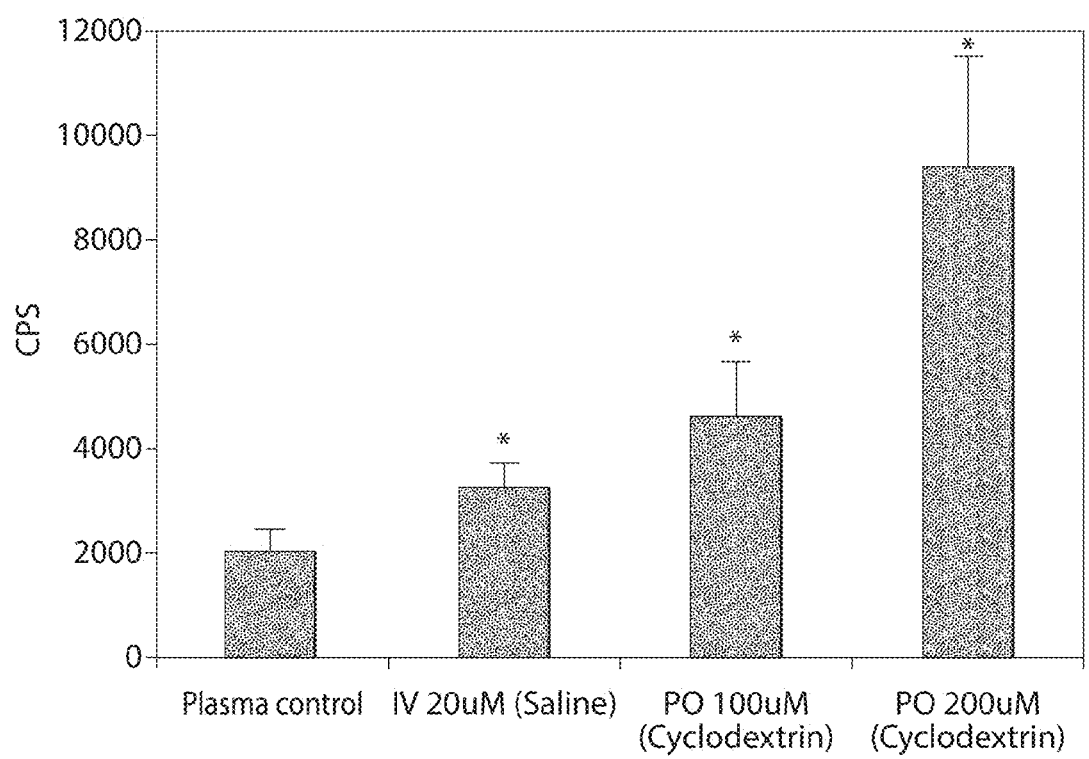

FIG. 24 shows LC/MS analysis which indicates that MS2-008 can be observed in plasma following oral administration at 100 and 200 uM in cyclodextrin. As shown in the graph, there is a demonstrable level of compound with IV dosing. Oral delivery using cyclodextrin vehicle can provide detectable blood levels of the compound. n=3 animals per group; paired t-test between control plasma and other sample sets: *p<0.006.

Figure 25:
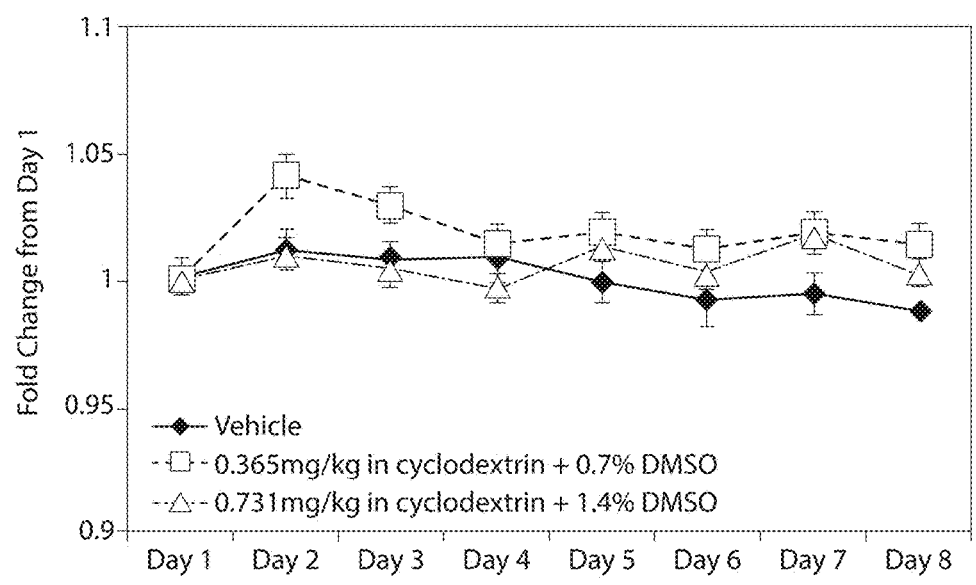

FIG. 25 shows animal weight during a treatment wherein healthy mice were dosed orally with cyclodextrin vehicle or MS2-008 compound, for 7 days. Results indicate that there was no significant change in body weight during the course of compound treatment. n=5 per group.

Figure 26A:
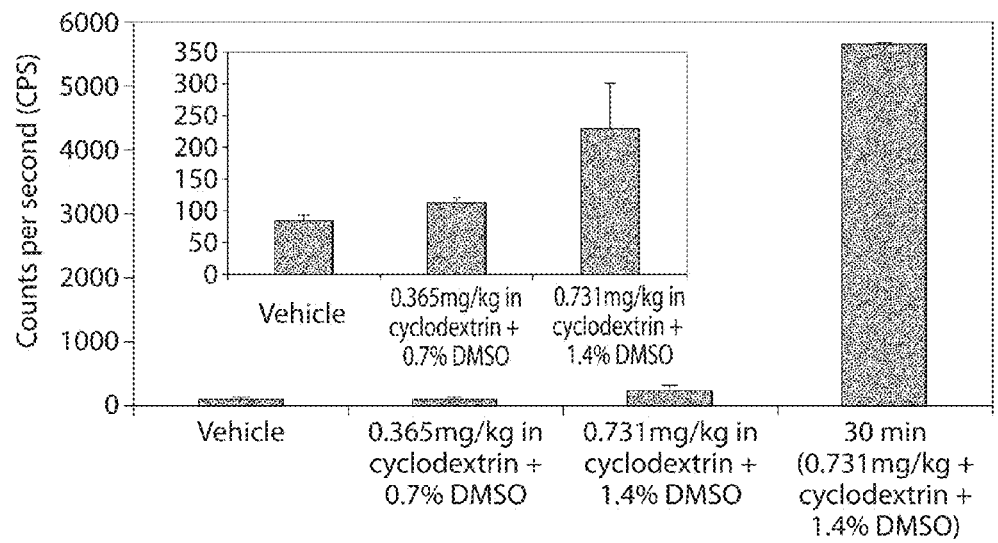
Figure 26B:
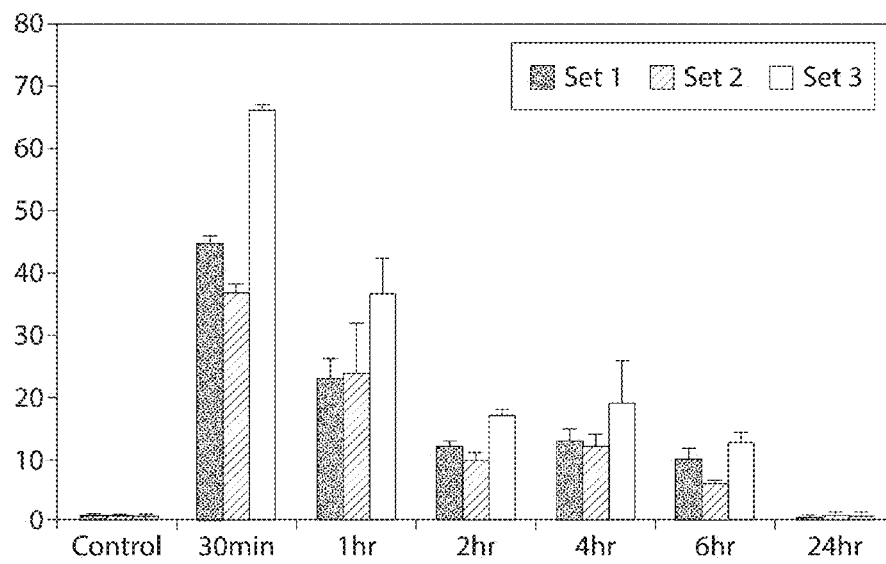

FIG. 26A shows a graph, which indicates that plasma levels of MS2-008 increase slightly following repeated oral dosing. A positive control of plasma collected at 30 minutes of 0.731 mg/kg (200 mM) dosed mice was used. n=5 per group. The inset chart shows data without the positive control sample. FIG. 26B shows pharmacodynamics results following oral delivery of 200 μM of compound MS2-008 in cyclodextrin. Compound MS2-008 was administered PO at 150 ul of 200 μM MS2-008 in 20% cyclodextrin+1.4% DMSO, where blood samples were collected from three animals for vehicle control, 30 min, 1, 2, 4, 6 and 24 hours post compound administration. Animals were euthanized and tissues (liver, kidney, spleen, heart and muscle) were collected and snap frozen on dry ice. Plasma was isolated from the blood samples and frozen. Plasma samples were processed and subjected to LC/MS analysis to determine compound levels. n=3 animals per group for each time point. Sets 1-3 are independent sample processing and LC/MS runs of plasma at each time point.

Figure 27A:
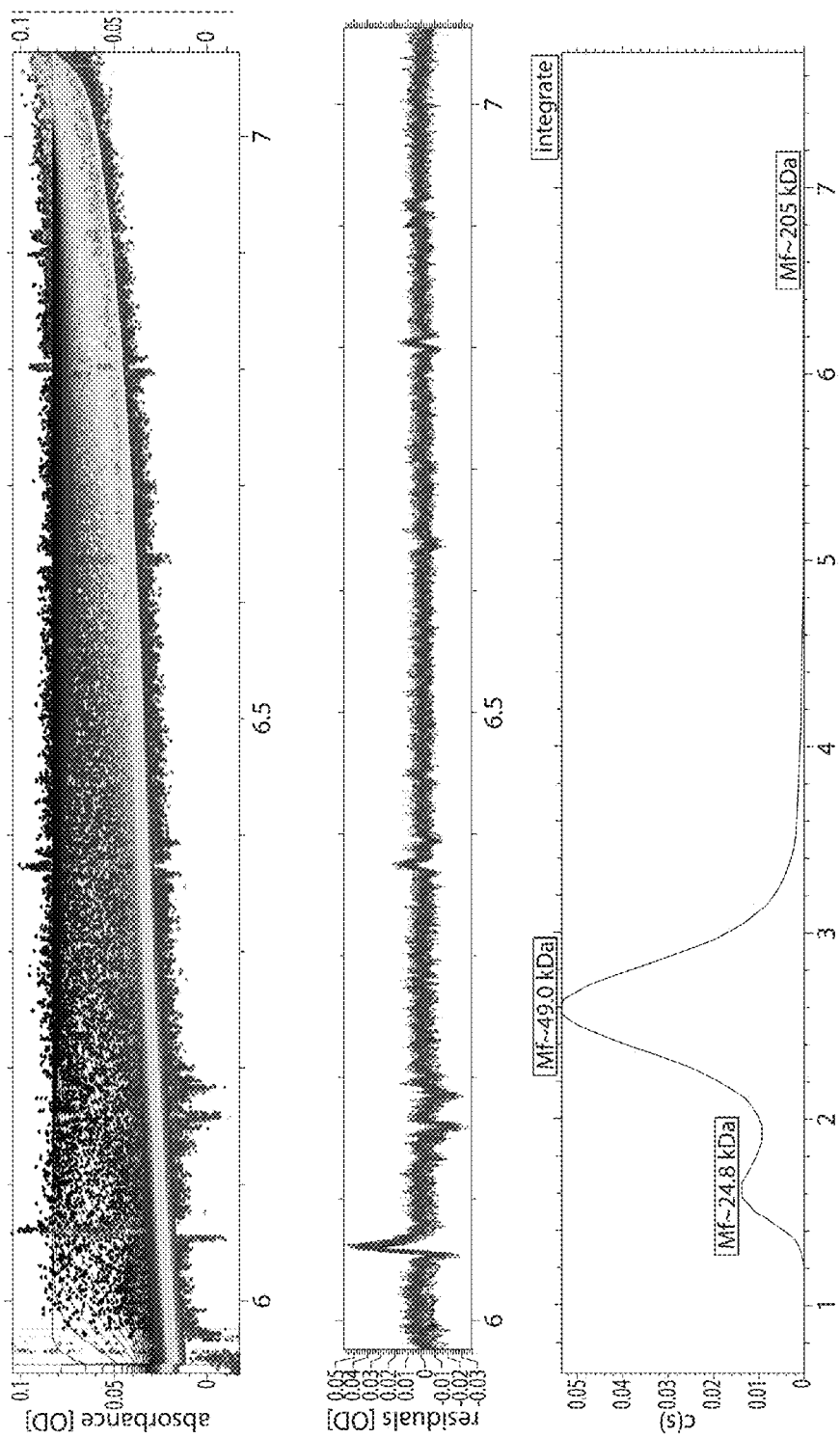

FIG. 27A shows the MAX homodimer induction effect without compound KI-MS2-008 treatment.

Figure 27B:
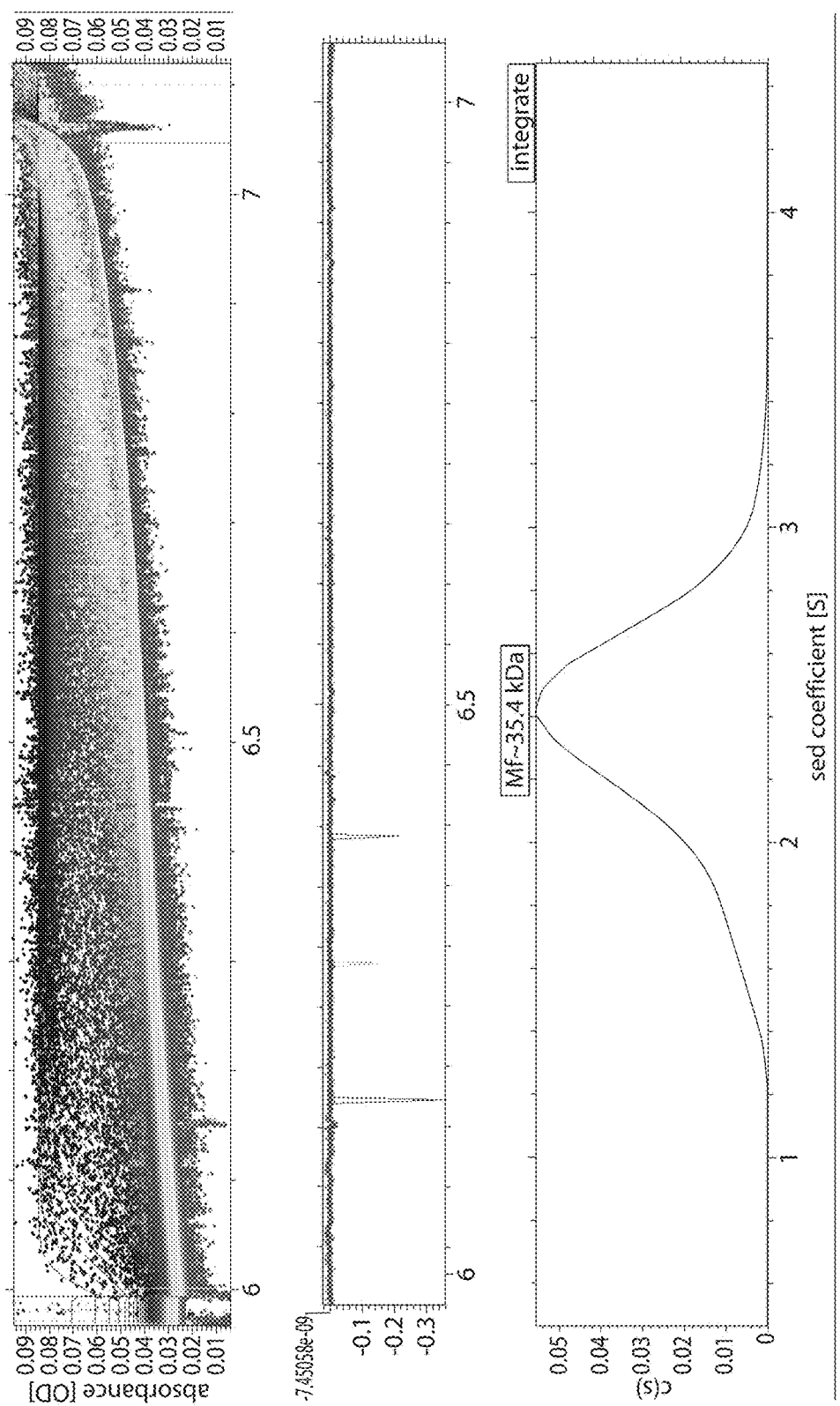

FIG. 27B shows the MAX homodimer induction effect with 10 μM compound KI-MS2-008 treatment. Recombinant human Max protein (ab95309) was dialyzed in 20 mM Tris three times to stabilize the chemical potential of the protein. Two samples were prepared for the experiment. Max protein (0.25 mg/mL) and Max protein pre-incubated one hour with 10 μM MS2-008 were added to the analytical ultracentrifugation (AUC) assembly cells. The assembly cells were positioned into a Beckman XL-I Analytical Ultracentrifuge and centrifuged at 42,000 rpm at 20° C. A sedimentation velocity experiment was started scanning $A_{280}$ every ~1.2 minutes for 18 hours. The data was analyzed with SedFit software by fitting the data with the continuous c(s) distribution model with at a 150 resolution and one sigma confidence level. Untreated Max protein has sedimentation coefficients (c(s)) of 1.574 and 2.593 signifying the monomer and homodimer, respectively, at a 1:6 ratio. Pre-incubating the protein with 10 μM MS2-008 shifted the distribution to predominantly the Max homodimer at a c(s) of 2.345 with a slight shouldering towards 1.5.

DETAILED DESCRIPTION OF CERTAIN EMBODIMENTS OF THE INVENTION

The present disclosure provides, in one aspect, compounds of Formula (I'), Formula (I), Formula (II), Formula (II-A), Formula (III), Formula (IV), and pharmaceutically acceptable salts, solvates, hydrates, polymorphs, co-crystals, tautomers, stereoisomers, isotopically labeled derivatives, and prodrugs thereof. The compounds described herein may be binders of MAX and/or modulators (e.g., inhibitors or activators) of Myc (e.g., c-Myc, L-Myc, and/or N-Myc), Mad, or Mxi1. Therefore, the compounds are useful in modulating transcription and in the treatment and/or prevention of a variety of diseases and conditions, for example, proliferative diseases such as cancer. Also provided are pharmaceutical compositions, kits, methods, and uses including a compound described herein.

Compounds

One aspect of the present disclosure relates to the compounds described herein. The compounds described herein may be MAX binders and/or modulators of Myc (e.g., inhibitors of Myc, Mad, or Mxi1), Mad, or Mxi1. In certain embodiments, a compound described herein is a compound of Formula (I'), Formula (I), or a pharmaceutically acceptable salt, solvate, hydrate, polymorph, co-crystal, tautomer, stereoisomer, isotopically labeled derivative, or prodrug thereof. In certain embodiments, a compound described herein is a compound of Formula (II), or a pharmaceutically acceptable salt, solvate, hydrate, polymorph, co-crystal, tautomer, stereoisomer, isotopically labeled derivative, or prodrug thereof. In certain embodiments, a compound described herein is a compound of Formula (II-A), or a pharmaceutically acceptable salt, solvate, hydrate, polymorph, co-crystal, tautomer, stereoisomer, isotopically labeled derivative, or prodrug thereof. In certain embodiments, a compound described herein is a compound of Formula (III), or a pharmaceutically acceptable salt, solvate, hydrate, polymorph, co-crystal, tautomer, stereoisomer, isotopically labeled derivative, or prodrug thereof. In certain embodiments, a compound described herein is a compound of Formula (IV), or a pharmaceutically acceptable salt, solvate, hydrate, polymorph, co-crystal, tautomer, stereoisomer, isotopically labeled derivative, or prodrug thereof.

Compounds of Formula (I') and (I)

Compounds of Formula (I')

In certain embodiments, the compound of Formula (I') is of the formula:

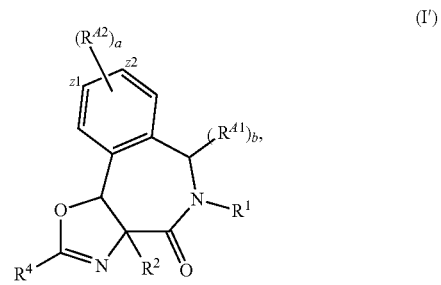

(I')

or a pharmaceutically acceptable salt, solvate, hydrate, polymorph, co-crystal, tautomer, stereoisomer, isotopically labeled derivative, or prodrug thereof, wherein:

$R^1$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or nitrogen protecting group;

$R^2$ is independently hydrogen, halogen, substituted or unsubstituted alkyl, substituted or unsubstituted heterocyclyl, substituted or unsubstituted aryl, or substituted or unsubstituted heteroaryl; and $R^4$ is hydrogen, substituted or unsubstituted alkyl, substituted or unsubstituted carbocyclyl, substituted or unsubstituted heterocyclyl, substituted or unsubstituted aryl, or substituted or unsubstituted heteroaryl;

$R^{41}$ is independently hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR, —N($R^b$)$_2$, —SR, —CN, or —SCN;

$R^{A2}$ is independently hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR, —N($R^b$)$_2$, —SR, —CN, —SCN, —NO$_2$, or optionally two instances of $R^{A2}$ are taken together with the phenyl in Formula (I') to form substituted or unsubstituted carbocyclyl, substituted or unsubstituted heterocyclyl, substituted or unsubstituted aryl, or substituted or unsubstituted heteroaryl;

a is 0, 1, 2, 3, or 4;

b is 0, 1, or 2;

z1 and z2 indicate where two instances of $R^{A2}$ are optionally taken together to form substituted or unsubstituted carbocyclyl, substituted or unsubstituted heterocyclyl, substituted or unsubstituted aryl, or substituted or unsubstituted heteroaryl fused with the phenyl moiety in Formula (I'); and R is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, oxygen protecting group, or sulfur protecting group; and each instance of $R^b$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or nitrogen protecting group, or optionally two $R^b$ are taken together to form substituted or unsubstituted heterocyclyl or substituted or unsubstituted heteroaryl.

In certain embodiments, the compound of Formula (I') is of Formula (I).

Compounds of Formula (I)

In certain embodiments, the compound is of Formula (I):

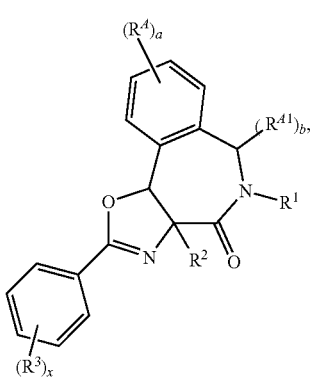

(I)

or a pharmaceutically acceptable salt, solvate, hydrate, polymorph, co-crystal, tautomer, stereoisomer, isotopically labeled derivative, or prodrug thereof, wherein:

x is 1, 2, 3, 4, or 5;

$R^1$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or nitrogen protecting group;

$R^2$ is independently hydrogen, halogen, substituted or unsubstituted alkyl, substituted or unsubstituted heterocyclyl, substituted or unsubstituted aryl, or substituted or unsubstituted heteroaryl; and each instance of $R^3$ is independently hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR, —N($R^b$)$_2$, —SR, —CN, or —SCN;

$R^A$ is independently hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR, —N($R^b$)$_2$, —SR, —CN, or —SCN;

$R^{A1}$ is independently hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR, —N($R^b$)$_2$, —SR, —CN, or —SCN;

a is 0, 1, 2, 3, or 4;

b is 0 1, or 2; and

R is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, oxygen protecting group, or sulfur protecting group; and each instance of $R^b$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, nitrogen protecting group, or optionally two $R^b$ are taken together to form substituted or unsubstituted heterocyclyl or substituted or unsubstituted heteroaryl.

Formulae (I') and (I) include substituent $R^1$. In certain embodiments, $R^1$ is hydrogen. In certain embodiments, $R^1$ is substituted or unsubstituted acyl. In certain embodiments, $R^1$ is —C(=O)R', wherein R' is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl. In certain embodiments, R' is substituted or unsubstituted $C_{1-6}$ alkyl. In certain embodiments, R' is substituted methyl (e.g., —CF$_3$ or —CH$_2$OH). In certain embodiments, R' is methyl. In certain embodiments, R is substituted or unsubstituted aryl (e.g., substituted or unsubstituted, 6- to 10-membered aryl). In certain embodiments, R' is substituted phenyl. In certain embodiments, R' is unsubstituted phenyl. In certain embodiments, R' is of the formula:

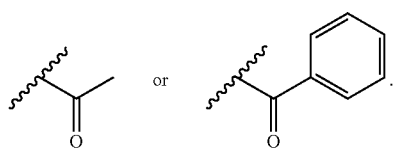

In certain embodiments, R¹ is substituted or unsubstituted C₁₋₆ alkyl. In certain embodiments, R¹ is unsubstituted C₁₋₆ alkyl. In certain embodiments, R¹ is substituted C₁₋₆ alkyl. In certain embodiments, R¹ is of the formula: —(CH₂)ₙRᵃ, wherein: n is 1, 2, 3, 4, 5, or 6; Rᵃ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —ORᵃ², —C(=O)ORᵃ², —C(=O)N(Rᵃᵃ)₂, —N(Rᵃᵃ)₂, —NC(=O)N(Rᵃᵃ)₂, —OC(=O)N(Rᵃᵃ)₂, —OC(=O)ORᵃ², —SRᵃ², or —SO₂Rᵃ²; and each instance of Rᵃ² is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, oxygen protecting group, or sulfur protecting group; and each instance of Rᵃᵃ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, or nitrogen protecting group. In certain embodiments, n is 1. In certain embodiments, n is 2. In certain embodiments, n is 3. In certain embodiments, n is 4. In certain embodiments, n is 5. In certain embodiments, n is 6. In certain embodiments, Rᵃ is substituted or unsubstituted C₁₋₆ alkyl. In certain embodiments, Rᵃ is substituted or unsubstituted alkenyl (e.g., substituted or unsubstituted C₂₋₆ alkenyl). In certain embodiments, Rᵃ is substituted or unsubstituted alkynyl (e.g., substituted or unsubstituted C₂₋₆ alkynyl). In certain embodiments, Rᵃ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, Rᵃ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, Rᵃ is substituted or unsubstituted aryl (e.g., substituted or unsubstituted, 6- to 10-membered aryl). In certain embodiments, Rᵃ is benzyl. In certain embodiments, Rᵃ is substituted or unsubstituted phenyl. In certain embodiments, Rᵃ is substituted or unsubstituted, 5- to 6-membered, monocyclic heteroaryl, wherein one, two, three, or four atoms in the heteroaryl ring system are independently nitrogen, oxygen, or sulfur. In certain embodiments, Rᵃ is —ORᵃ² (e.g., —OH, —O(substituted or unsubstituted C₁₋₆ alkyl) (e.g., —OMe, —OCF₃, —OEt, —OPr, —OBu, or —OBn), or —O(substituted or unsubstituted phenyl) (e.g., —OPh)). In certain embodiments, Rᵃ² is hydrogen. In certain embodiments, Rᵃ² is substituted or unsubstituted C₁₋₆ alkyl. In certain embodiments, Rᵃ² is substituted or unsubstituted alkenyl (e.g., substituted or unsubstituted C₂₋₆ alkenyl). In certain embodiments, Rᵃ² is substituted or unsubstituted alkynyl (e.g., substituted or unsubstituted C₂₋₆ alkynyl). In certain embodiments, Rᵃ² is substituted or unsubstituted aryl (e.g., substituted or unsubstituted, 6- to 10-membered aryl). In certain embodiments, Rᵃ² is substituted or unsubstituted benzyl. In certain embodiments, Rᵃ² is oxygen protecting group. In certain embodiments, Rᵃ² is sulfur protecting group. In certain embodiments, Rᵃ is —C(=O)ORᵃ². In certain embodiments, Rᵃ is —SO₂Rᵃ². In certain embodiments, R¹ is of the formula:

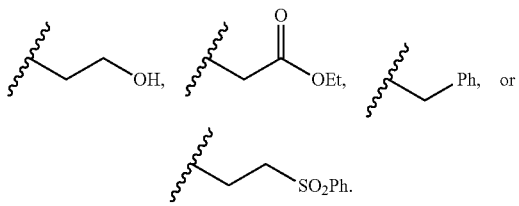

In certain embodiments, R¹ is of the formula:

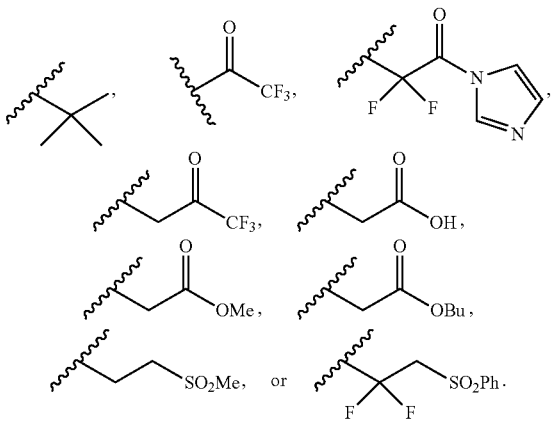

In certain embodiments, Rᵃ is —C(=O)N(Rᵃᵃ)₂. In certain embodiments, n is 1, and Rᵃ is —C(=O)N(Rᵃᵃ)₂. In certain embodiments, R¹ is of the formula:

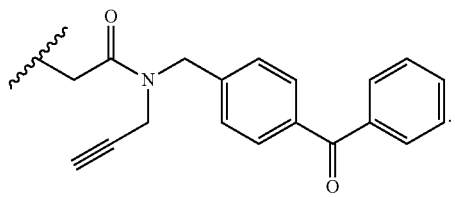 [SMILES: *CC(=O)N(CC#C)Cc1ccc(C(=O)c2ccccc2)cc1]

In certain embodiments, R¹ is of the formula:

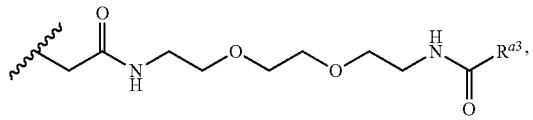

wherein Rᵃ³ is hydrogen, substituted or unsubstituted alkyl, substituted or unsubstituted alkenyl, substituted or unsubstituted alkynyl, substituted or unsubstituted heterocyclyl, substituted or unsubstituted aryl, or substituted or unsubstituted heteroaryl. In certain embodiments, R¹ is of the formula:

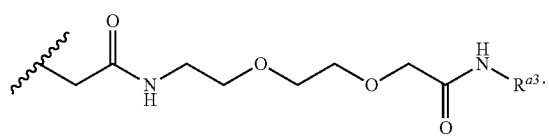

In certain embodiments, $R^1$ is of the formula:

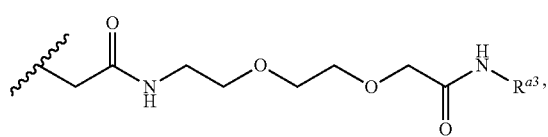

wherein $R^{a3}$ is hydrogen, substituted or unsubstituted alkyl, substituted or unsubstituted alkenyl, substituted or unsubstituted alkynyl, substituted or unsubstituted heterocyclyl, substituted or unsubstituted aryl, or substituted or unsubstituted heteroaryl. In certain embodiments, $R^1$ is of the formula:

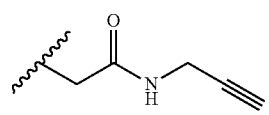 or

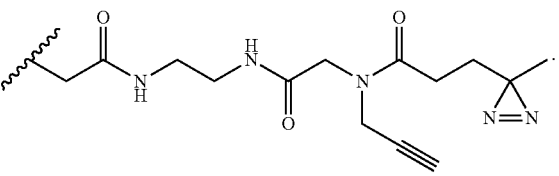

In certain embodiments, $R^1$ is of the formula:

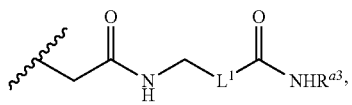

wherein: $L^1$ is a linker of formula:

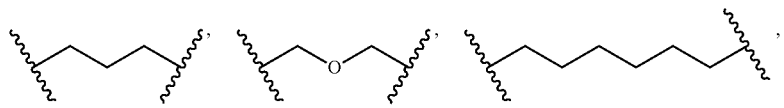

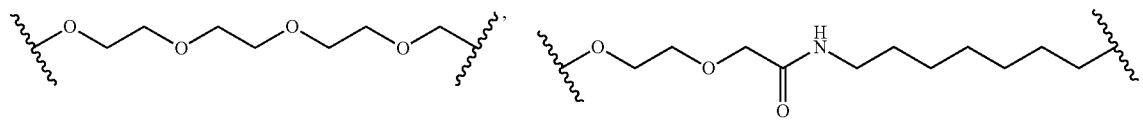

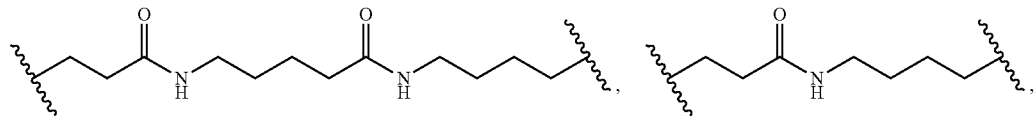

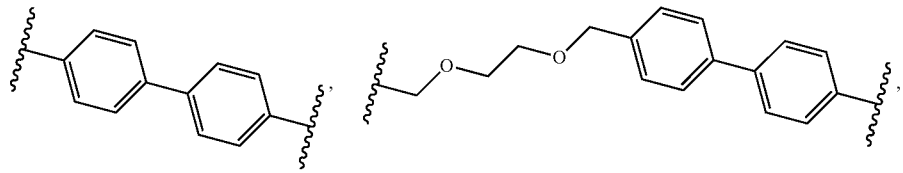

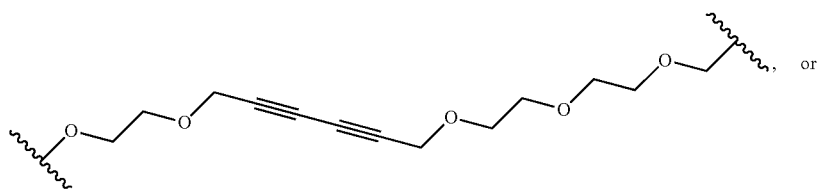

or

-continued

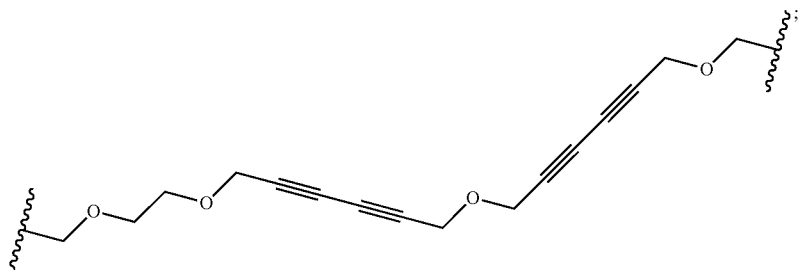

and $R^{a3}$ is hydrogen, substituted or unsubstituted alkyl, substituted or unsubstituted alkenyl, substituted or unsubstituted alkynyl, substituted or unsubstituted heterocyclyl, substituted or unsubstituted aryl, or substituted or unsubstituted heteroaryl. In certain embodiments, $L^1$ is a linker of formula:

In certain embodiments, $R^{a3}$ is hydrogen. In certain embodiments, $R^{a3}$ is substituted or unsubstituted $C_{1-6}$ alkyl. In certain embodiments, $R^{a3}$ is of the formula: $-(CH_2)_c R^{a4}$, wherein: c is 1, 2, 3, 4, or 5; and $R^{a4}$ is substituted or unsubstituted carbocyclyl, substituted or unsubstituted heterocyclyl, substituted or unsubstituted aryl, or substituted or unsubstituted heteroaryl. In certain embodiments, c is 1. In

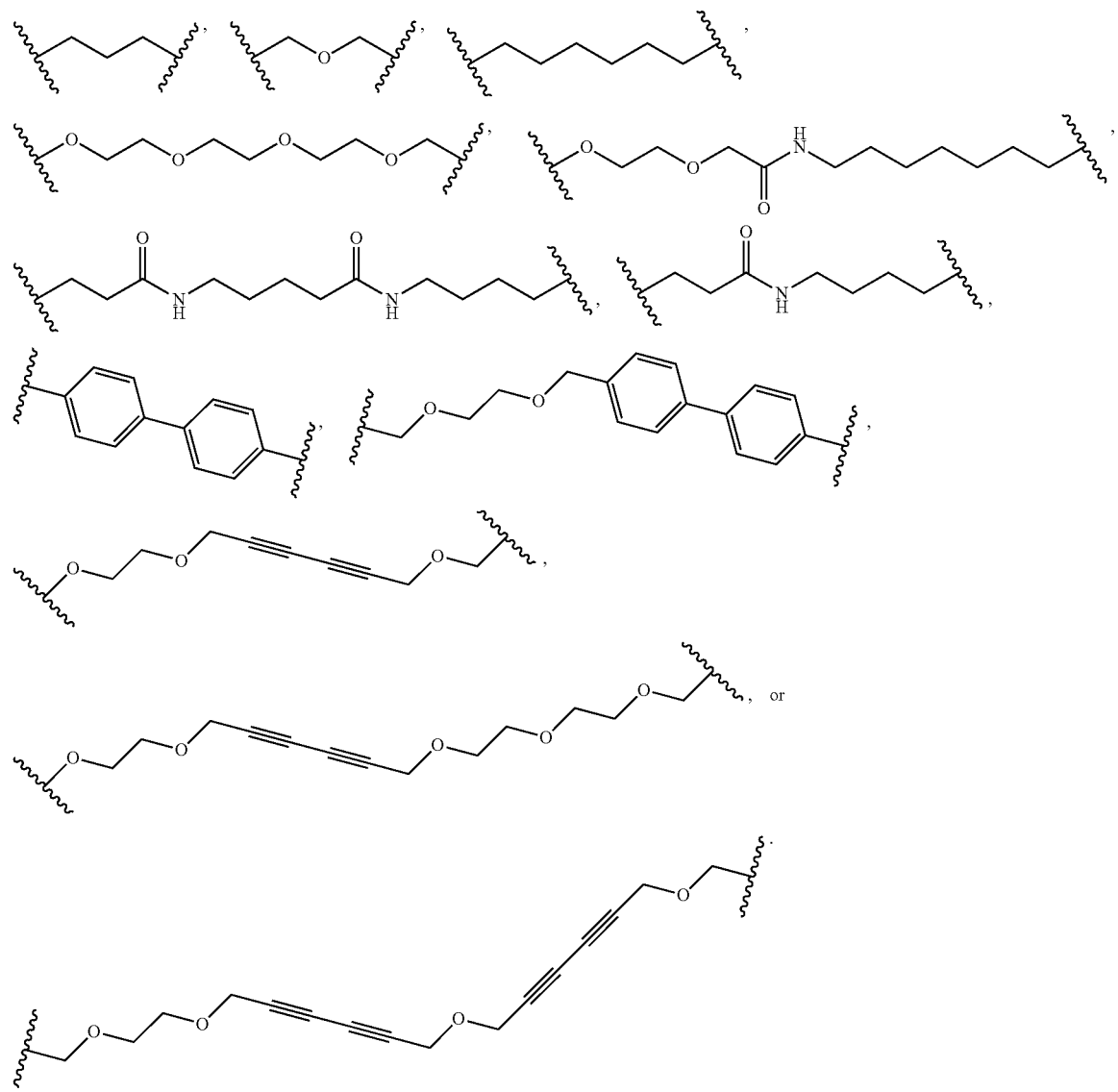

certain embodiments, c is 2. In certain embodiments, c is 3. In certain embodiments, c is 4. In certain embodiments, c is 5. In certain embodiments, $R^{a3}$ is substituted or unsubstituted alkenyl (e.g., substituted or unsubstituted $C_{2-6}$ alkenyl). In certain embodiments, $R^a$ is substituted or unsubstituted alkynyl (e.g., substituted or unsubstituted $C_{2-6}$ alkynyl). In certain embodiments, $R^{a3}$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^{a3}$ is a substituted or unsubstituted bicyclic heterocycle. In certain embodiments, $R^{a3}$ is substituted or unsubstituted aryl (e.g., substituted or unsubstituted, 6- to 10-membered aryl). In certain embodiments, $R^{a4}$ is substituted or unsubstituted heteroaryl. In certain embodiments, $R^{a4}$ is substituted or unsubstituted, 5- to 6-membered, monocyclic heteroaryl, wherein one, two, three, or four atoms in the heteroaryl ring system are independently nitrogen, oxygen, or sulfur. In certain embodiments, $R^{a4}$ is substituted or unsubstituted, 9- to 10-membered, bicyclic heteroaryl, wherein one, two, three, or four atoms in the heteroaryl ring system are independently nitrogen, oxygen, or sulfur.

In certain embodiments, $R^{a3}$ is of the formula:

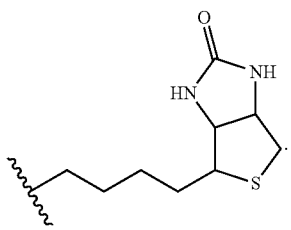 [SMILES: *CCCCC1SCC2NC(=O)NC21]

In certain embodiments, $R^{a3}$ is of the formula:

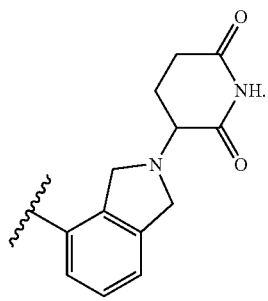 [SMILES: *c1cccc2c1CN(C1CCC(=O)NC1=O)C2]

In certain embodiments, $R^1$ is

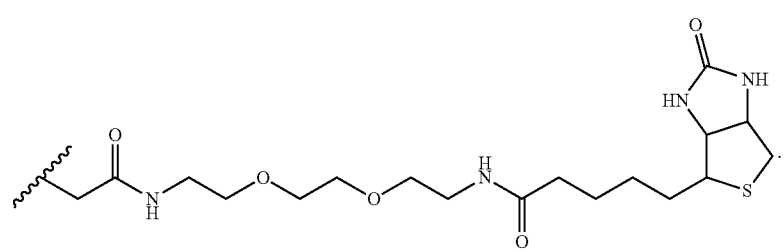 [SMILES: *CC(=O)NCCOCCOCCNC(=O)CCCCC1SCC2NC(=O)NC21]

In certain embodiments, $R^1$ is H

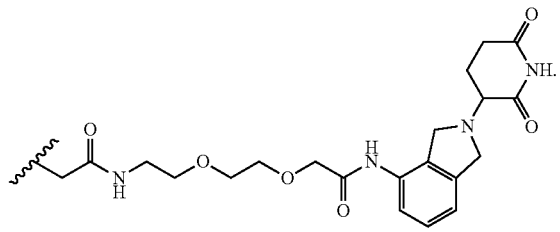 [SMILES: *CC(=O)NCCOCCOCC(=O)Nc1cccc2c1CN(C1CCC(=O)NC1=O)C2]

In certain embodiments, $R^1$ is of the formula:

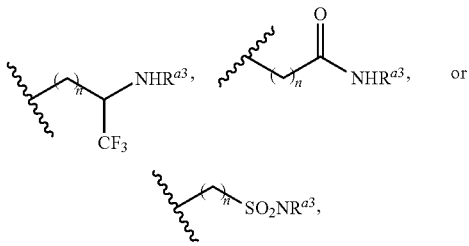

wherein $R^{a3}$ is hydrogen, substituted or unsubstituted alkyl, substituted or unsubstituted alkenyl, substituted or unsubstituted alkynyl, substituted or unsubstituted heterocyclyl, substituted or unsubstituted aryl, or substituted or unsubstituted heteroaryl; and n is 0, 1, 2, 3, 4, 5, or 6. In certain embodiments, n is 0. In certain embodiments, n is 1. In certain embodiments, n is 2. In certain embodiments, n is 3. In certain embodiments, n is 4. In certain embodiments, n is 5. In certain embodiments, n is 6. In certain embodiments, $R^1$ is of the formula:

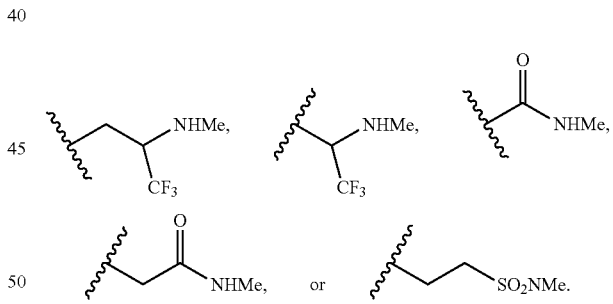

In certain embodiments, $R^1$ is of the formula:

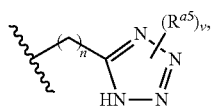

wherein: v is 0 or 1; and $R^{a5}$ is substituted or unsubstituted alkyl. In certain embodiments, v is 0. In certain embodiments, v is 1. In certain embodiments, $R^{a5}$ is substituted or unsubstituted $C_{1-6}$ alkyl (e.g., methyl, ethyl, or propyl). In certain embodiments, $R^1$ is of the formula:

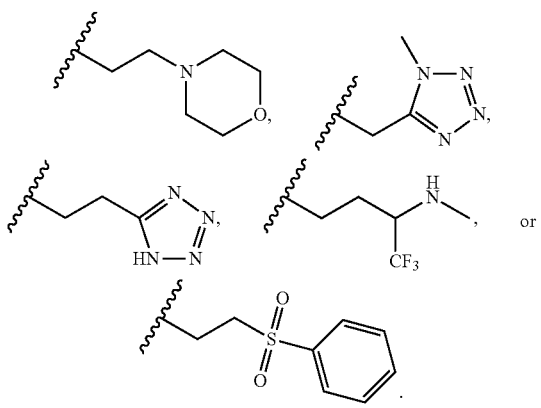

In certain embodiments, $R^1$ is substituted or unsubstituted alkenyl (e.g., substituted or unsubstituted $C_{2-6}$ alkenyl). In certain embodiments, $R^1$ is of the formula:

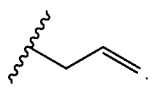 [SMILES: *CC=C]

In certain embodiments, $R^1$ is substituted or unsubstituted alkynyl (e.g., substituted or unsubstituted $C_{2-6}$ alkynyl). In certain embodiments, $R^1$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, $R^1$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^1$ is substituted or unsubstituted aryl (e.g., substituted or unsubstituted, 6- to 10-membered aryl). In certain embodiments, $R^1$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, $R^1$ is a nitrogen protecting group (e.g., benzyl (Bn), t-butyl carbonate (BOC or Boc), benzyl carbamate (Cbz), 9-fluorenylmethyl carbonate (Fmoc), trifluoroacetyl, triphenylmethyl, acetyl, or p-toluenesulfonamide (Ts)).

Formulae (I') and (I) also include substituent $R^2$. In certain embodiments, $R^2$ is hydrogen. In certain embodiments, $R^2$ is halogen (e.g., F, Cl, Br, or I). In certain embodiments, $R^2$ is substituted or unsubstituted $C_{1-6}$ alkyl.

In certain embodiments, $R^2$ is of the formula: $-CH_2(R^{2b})$, wherein: $R^{2b}$ is: 5 to 8-membered substituted or unsubstituted cycloalkyl, 5 to 10-membered substituted or unsubstituted heterocyclyl, 6 to 14-membered substituted or unsubstituted aryl, or 5 to 10-membered substituted or unsubstituted heteroaryl. In certain embodiments, $R^{2b}$ is 5 to 8-membered substituted or unsubstituted cycloalkyl (e.g., cyclohexyl). In certain embodiments, $R^{2b}$ is 5 to 10-membered substituted or unsubstituted heterocyclyl. In certain embodiments, $R^{2b}$ is substituted or unsubstituted oxetane, substituted or unsubstituted tetrahydropyran, or substituted or unsubstituted morpholine. In certain embodiments, $R^{2b}$ is 6 to 14-membered substituted or unsubstituted aryl (e.g., substituted or unsubstituted napthyl). In certain embodiments, $R^{2b}$ is 5 to 10-membered substituted or unsubstituted heteroaryl. In certain embodiments, $R^{2b}$ is substituted or unsubstituted imidazole, substituted or unsubstituted triazole, substituted or unsubstituted tetrazole, substituted or unsubstituted oxazole, substituted or unsubstituted furan, substituted or unsubstituted thiophene, substituted or unsubstituted thiozole, substituted or unsubstituted oxadiazole, substituted or unsubstituted pyridyl, or substituted or unsubstituted pyrimidine. In certain embodiments, $R^2$ is of the formula:

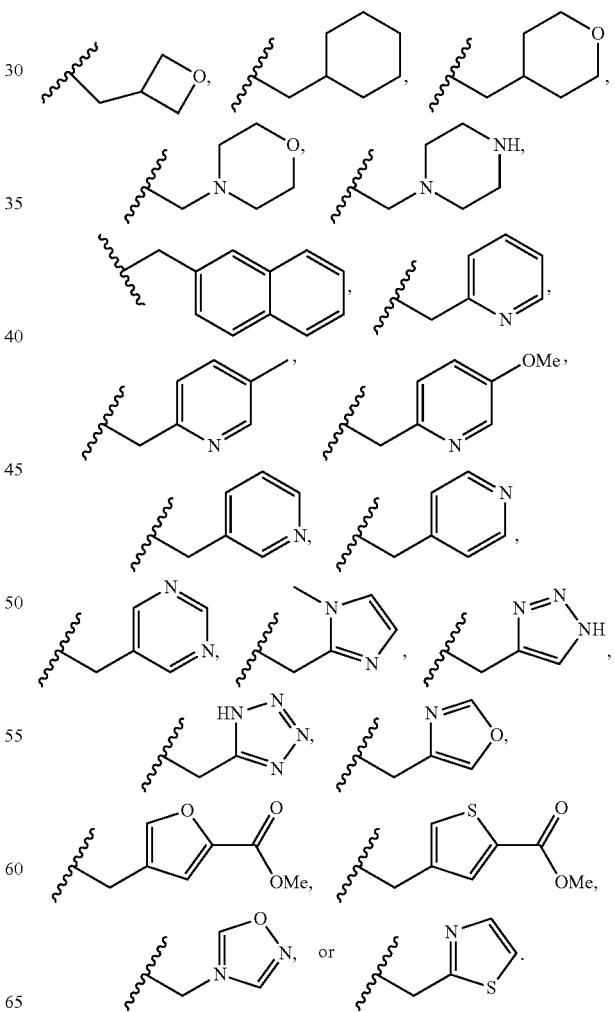

In certain embodiments, $R^2$ is of the formula:

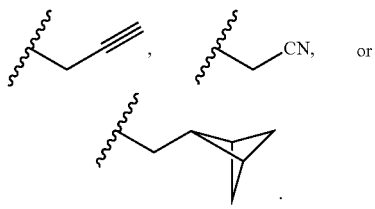

In certain embodiments, $R^2$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^2$ is substituted or unsubstituted aryl (e.g., substituted or unsubstituted, 6- to 10-membered aryl). In certain embodiments, $R^2$ is substituted benzyl. In certain embodiments, $R^2$ is unsubstituted benzyl.

In certain embodiments, $R^2$ is of the formula:

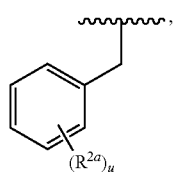

or a pharmaceutically acceptable salt thereof, wherein: u is 1, 2, 3, 4, or 5; and each instance of $R^{2a}$ is independently hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR, —N(R$^b$)$_2$, —NO$_2$, —SR, or —CN. In certain embodiments, u is 1. In certain embodiments, u is 2. In certain embodiments, u is 3. In certain embodiments, u is 4. In certain embodiments, u is 5. In certain embodiments, at least one instance of $R^{2a}$ is hydrogen. In certain embodiments, at least one instance of $R^{2a}$ is halogen (e.g., Cl or F). In certain embodiments, at least one instance of $R^{2a}$ is substituted or unsubstituted acyl (e.g., —C(=O)Me or —C(=O)ONHS). In certain embodiments, at least one instance of $R^{2a}$ is substituted or unsubstituted alkyl (e.g., methyl, ethyl, isopropyl, or butyl). In certain embodiments, at least one instance of $R^{2a}$ is —CF$_3$. In certain embodiments, at least one instance of $R^{2a}$ is isopropyl. In certain embodiments, at least one instance of $R^{2a}$ is substituted or unsubstituted alkenyl. In certain embodiments, at least one instance of $R^{2a}$ is substituted or unsubstituted alkynyl. In certain embodiments, at least one instance of $R^{2a}$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, at least one instance of $R^{2a}$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, at least one instance of $R^{2a}$ is

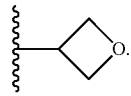

In certain embodiments, at least one instance of $R^{2a}$ is substituted or unsubstituted aryl (e.g., substituted or unsubstituted, 6- to 10-membered aryl). In certain embodiments, at least one instance of $R^{2a}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, at least one instance of $R^{2a}$ is —OR (e.g., —OH or —OMe). In certain embodiments, at least one instance of $R^{2a}$ is —N(R$^b$)$_2$ (e.g., —NMe$_2$). In certain embodiments, at least one instance of $R^{2a}$ is —NO$_2$. In certain embodiments, at least one instance of $R^{2a}$ is —SR. In certain embodiments, at least one instance of $R^{2a}$ is —CN.

In certain embodiments, $R^2$ is substituted phenyl. In certain embodiments, $R^2$ is unsubstituted phenyl. In certain embodiments, $R^2$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur).

Formula (I) also includes one or more instances of substituent $R^3$. In certain embodiments, x is 1. In certain embodiments, x is 2. In certain embodiments, x is 3. In certain embodiments, x is 4. In certain embodiments, x is 5. In certain embodiments, at least one instance of $R^3$ is hydrogen. In certain embodiments, at least one instance of $R^3$ is halogen (e.g., F, Cl, Br, or I). In certain embodiments, at least one instance of $R^3$ is F. In certain embodiments, at least one instance of $R^3$ is Cl. In certain embodiments, at least one instance of $R^3$ is substituted or unsubstituted acyl. In certain embodiments, at least one instance of $R^3$ is substituted or unsubstituted C$_{1-6}$ alkyl. In certain embodiments, at least one instance of $R^3$ is Me. In certain embodiments, at least one instance of $R^3$ is —CF$_3$. In certain embodiments, at least one instance of $R^3$ is substituted or unsubstituted alkenyl (e.g., substituted or unsubstituted C$_{2-6}$ alkenyl). In certain embodiments, at least one instance of $R^3$ is substituted or unsubstituted alkynyl (e.g., substituted or unsubstituted C$_{2-6}$ alkynyl). In certain embodiments, at least one instance of $R^3$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, at least one instance of $R^3$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, at least one instance of $R^3$ is of the formula:

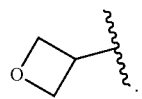

In certain embodiments, at least one instance of $R^3$ is substituted or unsubstituted aryl (e.g., substituted or unsubstituted, 6- to 10-membered aryl). In certain embodiments, at least one instance of $R^3$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, at least one instance of $R^3$ is —OR (e.g., —OH, —O(substituted or unsubstituted $C_{1-6}$ alkyl) (e.g., —OMe, —OCF$_3$, —OEt, —OPr, —OBu, or —OBn), or —O(substituted or unsubstituted phenyl) (e.g., —OPh)). In certain embodiments, at least one instance of $R^3$ is —OH.

In certain embodiments, at least one instance of $R^3$ is of the formula:

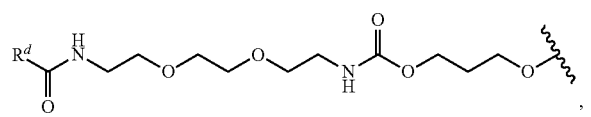

wherein $R^d$ is independently substituted or unsubstituted alkyl, substituted or unsubstituted carbocyclyl, substituted or unsubstituted heterocyclyl, substituted or unsubstituted aryl, or substituted or unsubstituted heteroaryl. In certain embodiments, $R^d$ is substituted or unsubstituted $C_{1-6}$ alkyl. In certain embodiments, $R^d$ is of the formula:

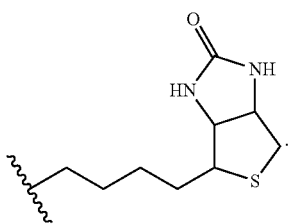 [SMILES: *CCCCC1SCC2NC(=O)NC21]

In certain embodiments, at least one instance of $R^3$ is of the formula: —O(CH$_2$)$_e$OR$^{c1}$, wherein e is independently 1, 2, 3, or 4; and $R^{c1}$ is independently hydrogen, substituted or unsubstituted acyl, substituted or unsubstituted alkyl, substituted or unsubstituted carbocyclyl, substituted or unsubstituted heterocyclyl, substituted or unsubstituted aryl, or substituted or unsubstituted heteroaryl. In certain embodiments, e is 1. In certain embodiments, e is 2. In certain embodiments, e is 3. In certain embodiments, e is 4. In certain embodiments, $R^{c1}$ is hydrogen. In certain embodiments, $R^{c1}$ is substituted or unsubstituted $C_{1-6}$ alkyl. In certain embodiments, $R^{c1}$ is acyl (e.g., acetyl). In certain embodiments, at least one instance of $R^3$ is:

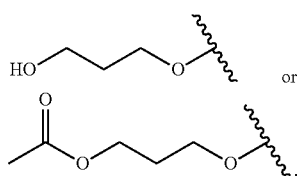

In certain embodiments, $R^{c1}$ is carbocyclyl (e.g., substituted or unsubstituted, 3- to 7-membered, monocyclic carbocyclyl comprising zero, one, or two double bonds in the carbocyclic ring system). In certain embodiments, $R^{c1}$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^{c1}$ is substituted or unsubstituted aryl (e.g., substituted or unsubstituted, 6- to 10-membered aryl). In certain embodiments, $R^{c1}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, at least one instance of $R^3$ is —N(R$^b$)$_2$, wherein each instance of $R^b$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, nitrogen protecting group, or optionally two $R^b$ are taken together to form substituted or unsubstituted heterocyclyl or substituted or unsubstituted heteroaryl. In certain embodiments, at least one instance of $R^3$ is —NH$_2$. In certain embodiments, at least one instance of $R^3$ is —SR (e.g., —SMe). In certain embodiments, at least one instance of $R^3$ is —CN. In certain embodiments, at least one instance of $R^3$ is —SCN.

Formula (I) also includes zero or more instances of substituent $R^A$. In certain embodiments, at least one instance of $R^A$ is hydrogen. In certain embodiments, at least one instance of $R^A$ is halogen (e.g., F, Cl, Br, or I). In certain embodiments, at least one instance of $R^A$ is F. In certain embodiments, at least one instance of $R^A$ is Cl. In certain embodiments, at least one instance of $R^A$ is substituted or unsubstituted acyl. In certain embodiments, at least one instance of $R^A$ is substituted or unsubstituted $C_{1-6}$ alkyl. In certain embodiments, at least one instance of $R^A$ is substituted or unsubstituted alkenyl (e.g., substituted or unsubstituted $C_{2-6}$ alkenyl). In certain embodiments, at least one instance of $R^A$ is substituted or unsubstituted alkynyl (e.g., substituted or unsubstituted $C_{2-6}$ alkynyl). In certain embodiments, at least one instance of $R^A$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, at least one instance of $R^A$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, at least one instance of $R^A$ is substituted or unsubstituted aryl (e.g., substituted or unsubstituted, 6- to 10-membered aryl). In certain embodiments, at least one instance of $R^A$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, at least one instance of $R^A$ is —OR (e.g., —OH, —O(substituted or unsubstituted $C_{1-6}$ alkyl) (e.g., —OMe, —OCF$_3$, —OEt, —OPr, —OBu, or —OBn), or —O(substituted or unsubstituted phenyl) (e.g., —OPh)). In certain embodiments, at least one instance of $R^A$ is —OH. In certain embodiments, at least one instance of $R^A$ is —N($R^b$)$_2$ (e.g., —NH$_2$, —NH (substituted or unsubstituted $C_{1-6}$ alkyl) (e.g., —NHMe), or —NMe$_2$). In certain embodiments, at least one instance of $R^A$ is —NH$_2$. In certain embodiments, at least one instance of $R^A$ is —SR (e.g., —SH, —S(substituted or unsubstituted $C_{1-6}$ alkyl) (e.g., —SMe, —SEt, —SPr, —SBu, or —SBn), or —S(substituted or unsubstituted phenyl) (e.g., —SPh)). In certain embodiments, at least one instance of $R^A$ is —CN. In certain embodiments, at least one instance of $R^A$ is —SCN.

Formula (I') also includes substituent $R^4$. In certain embodiments, $R^4$ is hydrogen. In certain embodiments, $R^4$ is substituted or unsubstituted alkyl (e.g., substituted or unsubstituted $C_{1-6}$ alkyl). In certain embodiments, $R^4$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, $R^4$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^4$ is methyl. In certain embodiments, $R^4$ is substituted or unsubstituted aryl (e.g., substituted or unsubstituted, 6- to 10-membered aryl). In certain embodiments, $R^4$ is substituted or unsubstituted phenyl. In certain embodiments, $R^4$ is of the formula:

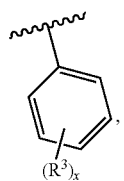

or a pharmaceutically acceptable salt thereof, wherein: x is 1, 2, 3, 4, or 5; and each instance of $R^3$ is independently hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR, —N($R^b$)$_2$, —SR, —CN, or —SCN. In certain embodiments, $R^4$ is

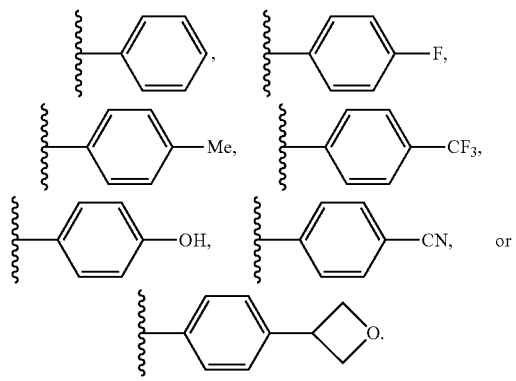

In certain embodiments, $R^4$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, $R^4$ is substituted or unsubstituted 5 membered heteroaryl. In certain embodiments, $R^4$ is substituted or unsubstituted 6-membered heteroaryl. In certain embodiments, $R^4$ is of the formula:

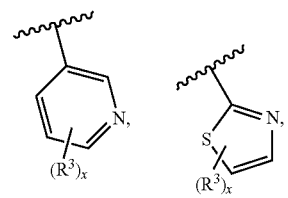

or a pharmaceutically acceptable salt thereof, wherein: x is 1, 2, 3, 4, or 5; and each instance of $R^3$ is independently hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR, —N($R^b$)$_2$, —SR, —CN, or —SCN. In certain embodiments, $R^4$ is of the formula:

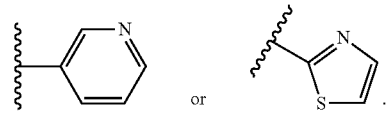 [SMILES: *c1cccnc1 ; *c1nccs1]

In certain embodiments, $R^4$ is —OR$^{4a}$, wherein $R^{4a}$ is hydrogen or substituted or unsubstituted alkyl. In certain embodiments, $R^4$ is

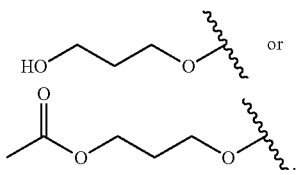

In certain embodiments, the compound of Formula (I') is of the formula:

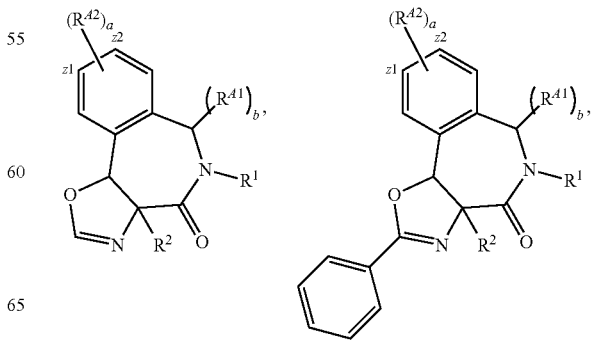

-continued
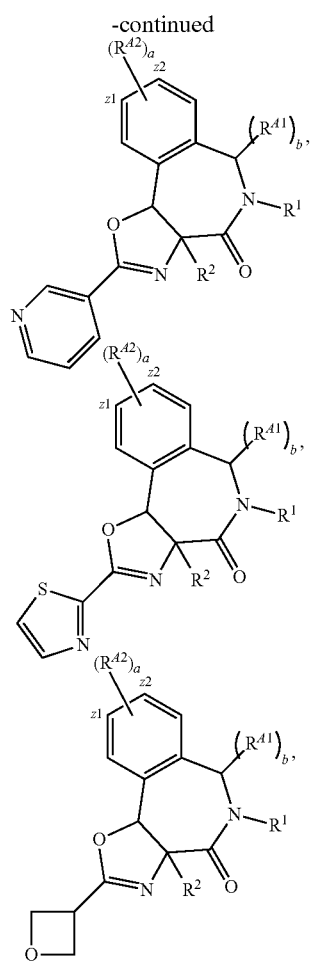
or a pharmaceutically acceptable salt thereof,
In certain embodiments, the compound of Formula (I') is of the formula:
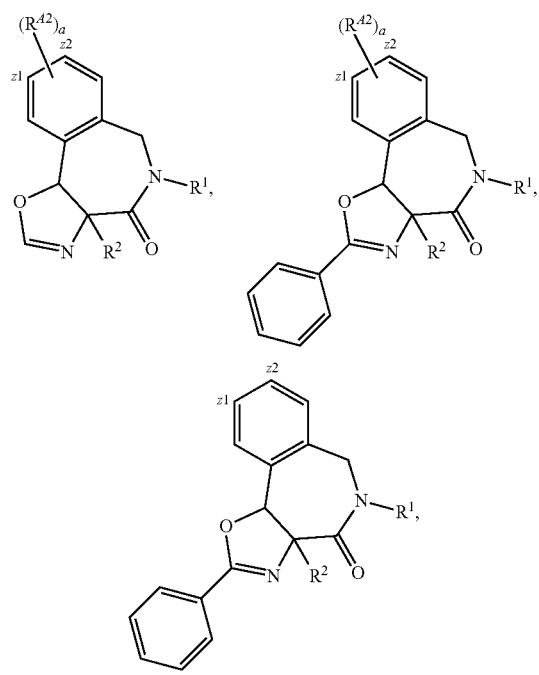
-continued
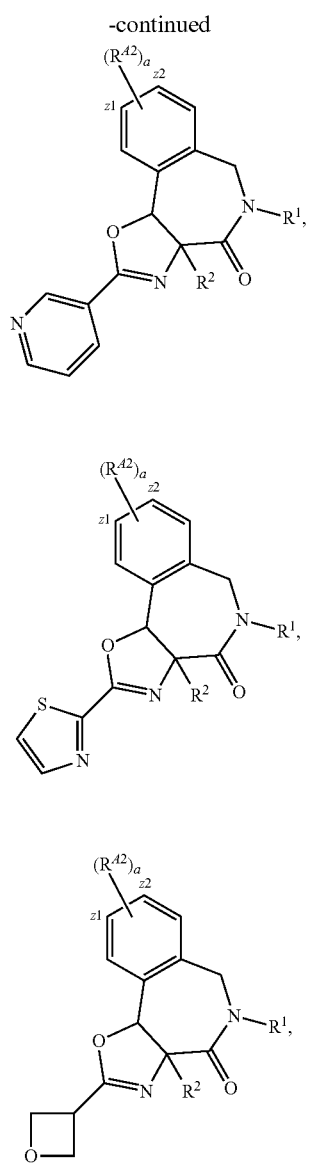
or a pharmaceutically acceptable salt thereof,
In certain embodiments, the compound of Formula (I) is of the formula:
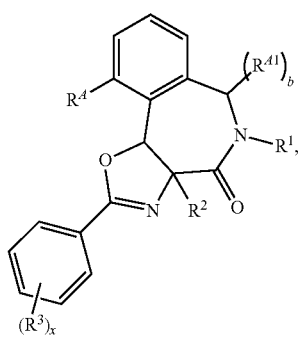

-continued
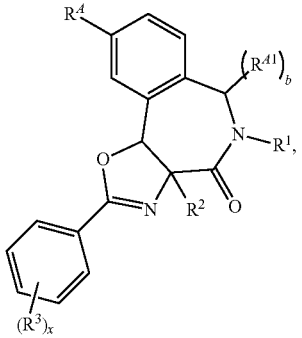
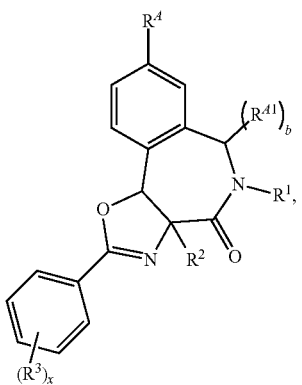
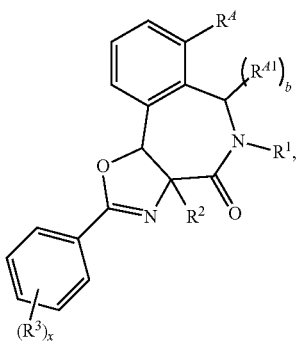
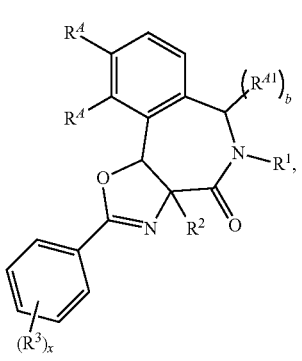
-continued
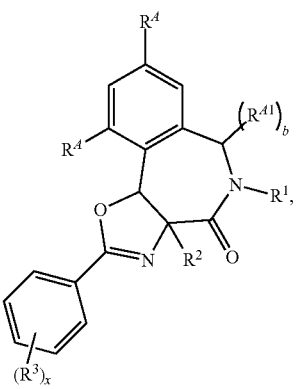
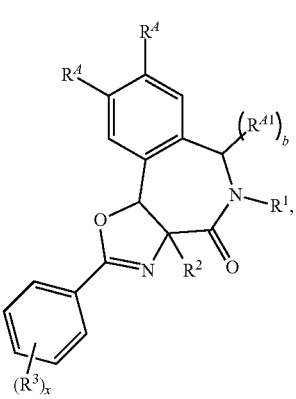
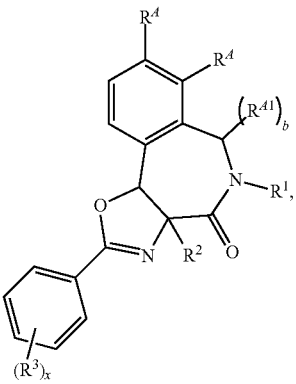
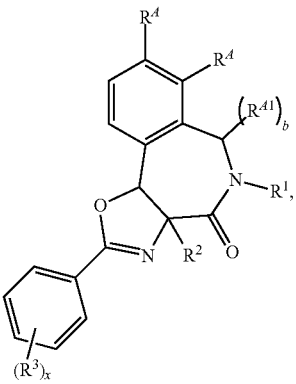

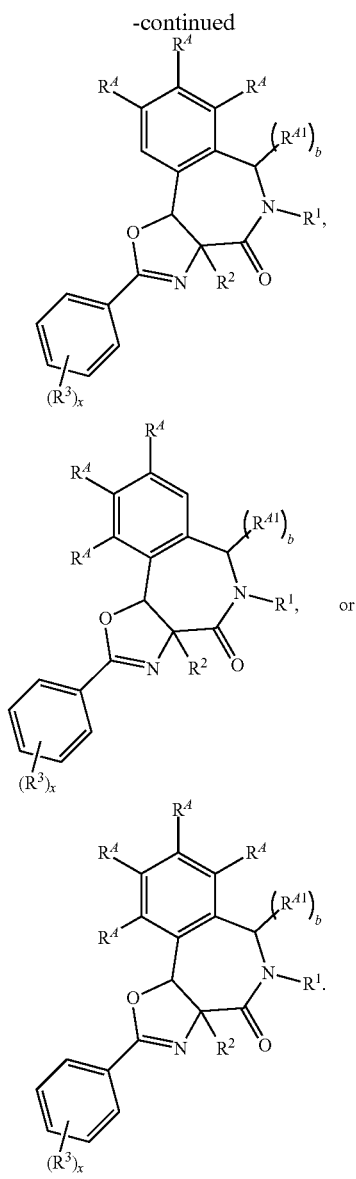

In certain embodiments, a is 0. In certain embodiments, a is 1. In certain embodiments, a is 2. In certain embodiments, a is 3. In certain embodiments, a is 4.

Formulae (I') and (I) include zero or more instances of substituent $R^{A1}$. In certain embodiments, at least one instance of $R^{A1}$ is hydrogen. In certain embodiments, at least one instance of $R^{A1}$ is halogen (e.g., F, Cl, Br, or I). In certain embodiments, at least one instance of $R^{A1}$ is substituted or unsubstituted acyl. In certain embodiments, at least one instance of $R^{A1}$ is substituted or unsubstituted $C_{1-6}$ alkyl. In certain embodiments, at least one instance of $R^{A1}$ is substituted or unsubstituted alkenyl (e.g., substituted or unsubstituted $C_{2-6}$ alkenyl). In certain embodiments, at least one instance of $R^{A1}$ is substituted or unsubstituted alkynyl (e.g., substituted or unsubstituted $C_{2-6}$ alkynyl). In certain embodiments, at least one instance of $R^{A1}$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, at least one instance of $R^{A1}$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, at least one instance of $R^{A1}$ is substituted or unsubstituted aryl (e.g., substituted or unsubstituted, 6- to 10-membered aryl). In certain embodiments, at least one instance of $R^{A1}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, at least one instance of $R^{A1}$ is —OR (e.g., —OH, —O(substituted or unsubstituted $C_{1-6}$ alkyl) (e.g., —OMe, —OCF$_3$, —OEt, —OPr, —OBu, or —OBn), or —O(substituted or unsubstituted phenyl) (e.g., —OPh)). In certain embodiments, $R^{A1}$ is —N(R$^b$)$_2$ (e.g., —NH$_2$, —NH(substituted or unsubstituted $C_{1-6}$ alkyl) (e.g., —NHMe)), or —NMe$_2$). In certain embodiments, at least one instance of $R^{A1}$ is —SR (e.g., —SH, —S(substituted or unsubstituted $C_{1-6}$ alkyl) (e.g., —SMe, —SEt, —SPr, —SBu, or —SBn), or —S(substituted or unsubstituted phenyl) (e.g., —SPh)). In certain embodiments, at least one instance of $R^{A1}$ is —CN. In certain embodiments, at least one instance of $R^{A1}$ is —SCN.

In certain embodiments, b is 0. In certain embodiments, b is 1. In certain embodiments, b is 2. In certain embodiments, one instance of $R^{A1}$ is hydrogen, and the other instance is a non-hydrogen substituent. In certain embodiments, both instances of $R^{A1}$ are hydrogen. In certain embodiments, both instances of $R^{A1}$ are non-hydrogen substituents.

Formula (I') includes zero or more instances of substituent $R^{A2}$. In certain embodiments, at least one instance of $R^{A2}$ is hydrogen. In certain embodiments, at least one instance of $R^{A2}$ is halogen (e.g., F, Cl, Br, or I). In certain embodiments, at least one instance of $R^{A2}$ is substituted or unsubstituted acyl. In certain embodiments, at least one instance of $R^{A2}$ is substituted or unsubstituted alkyl (e.g., substituted or unsubstituted $C_{1-6}$ alkyl). In certain embodiments, at least one instance of $R^{A2}$ is substituted or unsubstituted alkenyl (e.g., substituted or unsubstituted $C_{2-6}$ alkenyl). In certain embodiments, at least one instance of $R^{A2}$ is substituted or unsubstituted alkynyl (e.g., substituted or unsubstituted $C_{2-6}$ alkynyl). In certain embodiments, at least one instance of $R^{A2}$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, at least one instance of $R^{A2}$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, at least one instance of $R^{A2}$ is substituted or unsubstituted aryl (e.g., substituted or unsubstituted, 6- to 10-membered aryl). In certain embodiments, at least one instance of $R^{A2}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, at least one instance of $R^{A2}$ is —OR (e.g., —OH, —O(substituted or unsubstituted $C_{1-6}$ alkyl) (e.g., —OMe, —OCF$_3$, —OEt, —OPr, —OBu, or —OBn), or —O(substituted or unsubstituted phenyl) (e.g., —OPh)). In certain embodiments, at least one instance of $R^{A2}$ is —N(R$^b$)$_2$ (e.g., —NH$_2$, —NH(substituted or unsubstituted C$_{1-6}$ alkyl) (e.g., —NHMe)), or —NMe$_2$). In certain embodiments, at least one instance of $R^{A2}$ is —SR (e.g., —SH, —S(substituted or unsubstituted C$_{1-6}$ alkyl) (e.g., —SMe, —SEt, —SPr, —SBu, or —SBn), or —S(substituted or unsubstituted phenyl) (e.g., —SPh)). In certain embodiments, at least one instance of $R^{A2}$ is —CN. In certain embodiments, at least one instance of $R^{A2}$ is —SCN. In certain embodiments, at least one instance of $R^{A2}$ is —NO$_2$. In certain embodiments, two instances of $R^{A2}$ are taken together with the phenyl in Formula (I') to form substituted or unsubstituted carbocyclyl, substituted or unsubstituted heterocyclyl, substituted or unsubstituted aryl, or substituted or unsubstituted heteroaryl. Z1 and z2 indicate where two instances of $R^{A2}$ are optionally taken together to form substituted or unsubstituted carbocyclyl, substituted or unsubstituted heterocyclyl, substituted or unsubstituted aryl, or substituted or unsubstituted heteroaryl fused with the phenyl moiety in Formula (I'). In certain embodiments, one instance of $R^{A2}$ is hydrogen, and the other instance is a non-hydrogen substituent. In certain embodiments, both instances of $R^{A2}$ are hydrogen. In certain embodiments, both instances of $R^{A2}$ are non-hydrogen substituents.

In certain embodiments, two instances of $R^{A2}$ are taken together to form substituted or unsubstituted carbocyclyl, substituted or unsubstituted heterocyclyl, substituted or unsubstituted aryl, or substituted or unsubstituted heteroaryl fused with the phenyl moiety in Formula (I'), of the formula:

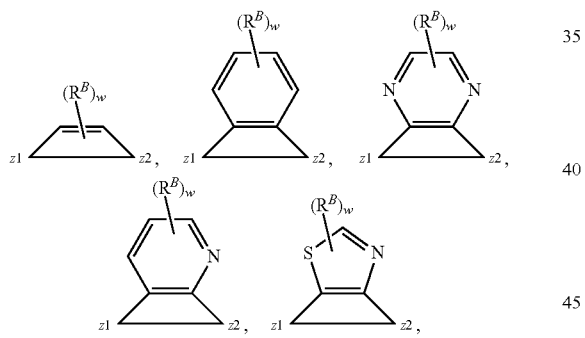

or a pharmaceutically acceptable salt thereof, wherein: w is 0, 1, 2, 3, or 4; and each instance of $R^B$ is independently hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR, —N(R$^b$)$_2$, —NO$_2$, —SR, —CN, or —SCN. In certain embodiments, w is 0. In certain embodiments, w is 1. In certain embodiments, w is 2. In certain embodiments, w is 3. In certain embodiments, w is 4. In certain embodiments, at least one instance of $R^B$ is hydrogen. In certain embodiments, at least one instance of $R^B$ is hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR, —N(R$^b$)$_2$, —NO$_2$, —SR, —CN, or —SCN. In certain embodiments, at least one instance of $R^B$ is hydrogen, F, —NO$_2$, CN, or —CO$_2$H.

In certain embodiments, two instances of $R^{A2}$ are taken together with the phenyl in Formula (I') to form a compound of the formula:

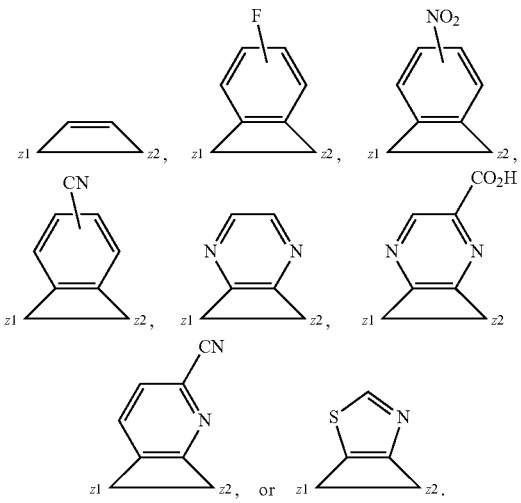

In certain embodiments, the compound of Formula (I') is of the following formula:

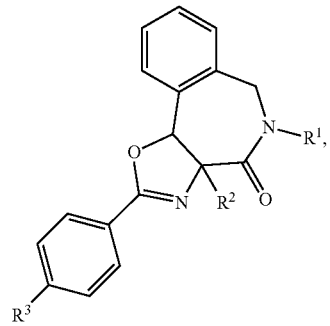

or a pharmaceutically acceptable salt thereof.

In certain embodiments, the compound of Formula (I') is of the following formula:

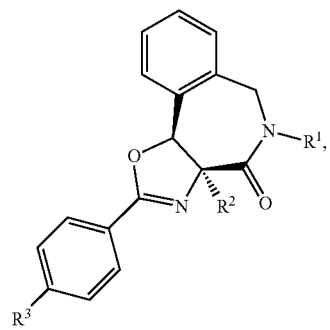

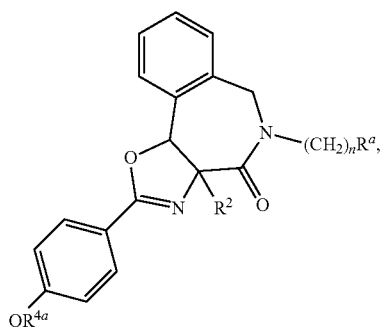
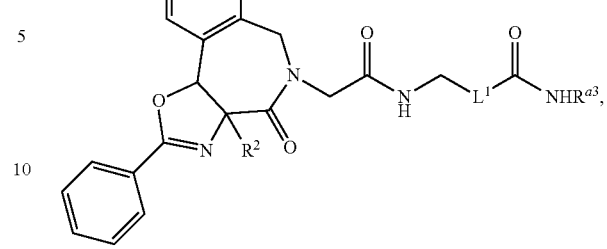
or a pharmaceutically acceptable salt thereof.
In certain embodiments, the compound of Formula (I) is of the following formula:
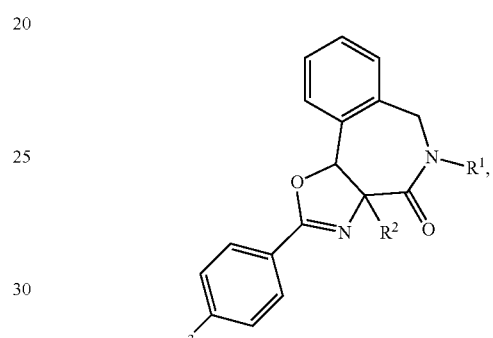
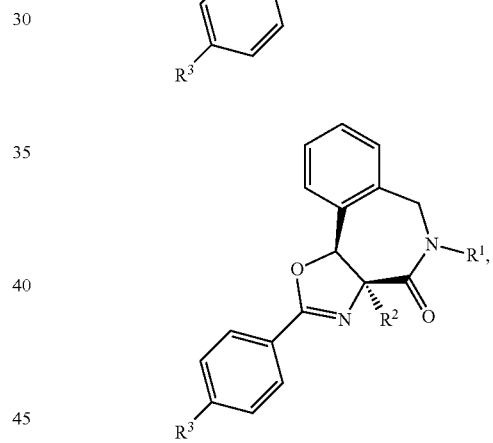
or a pharmaceutically acceptable salt thereof.
In certain embodiments, the compound of Formula (I) is of the following formula:
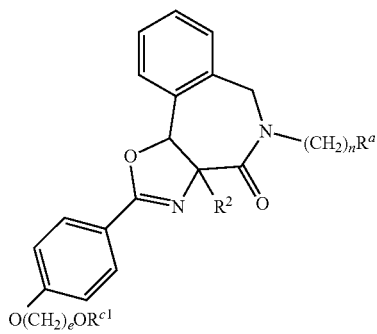 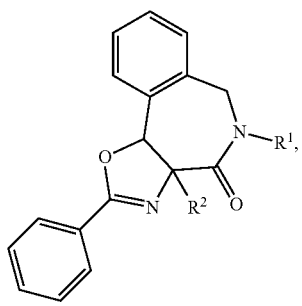 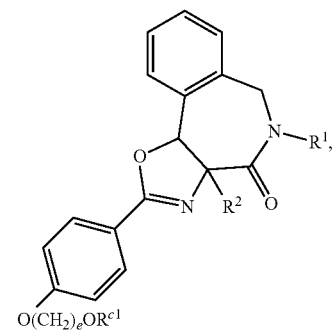

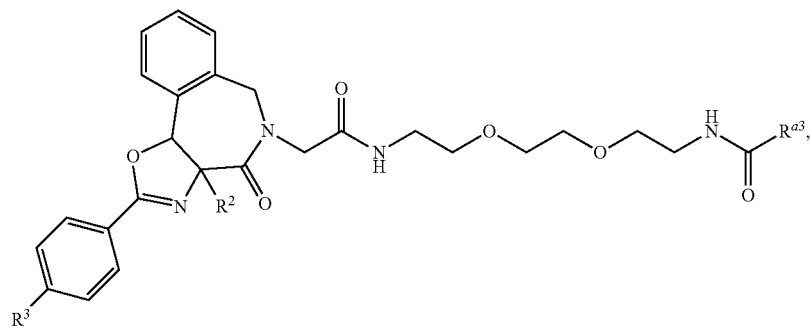
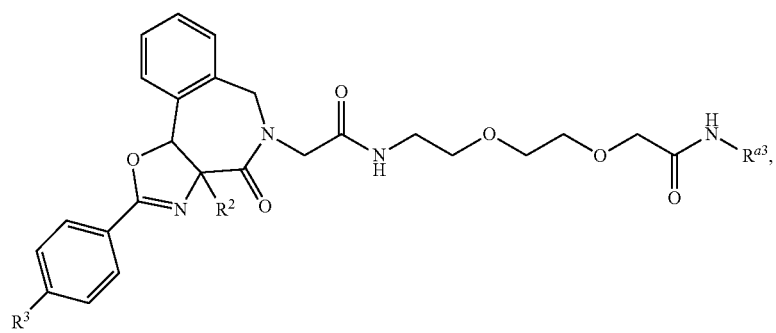
or a pharmaceutically acceptable salt thereof.
In certain embodiments, the compound of Formulae (I') or (I) is of the formula:
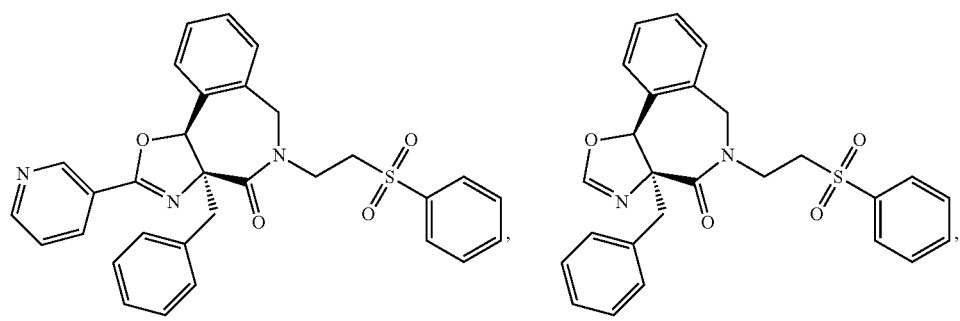
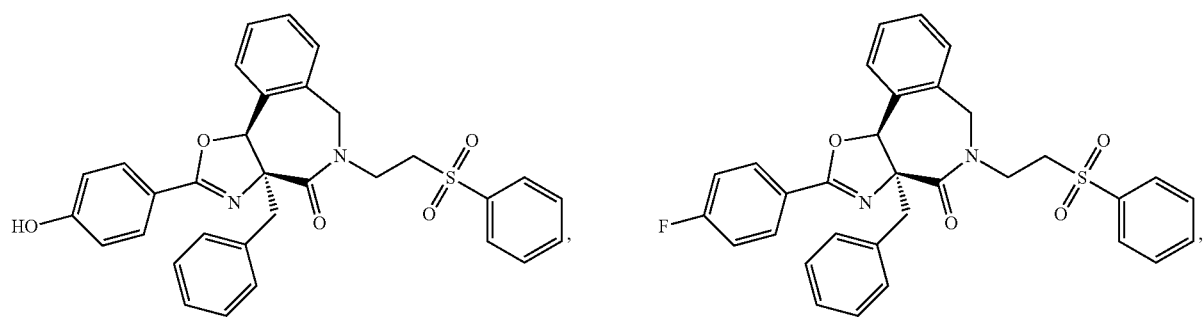

83
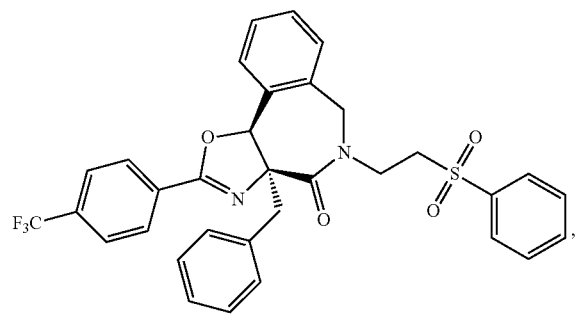
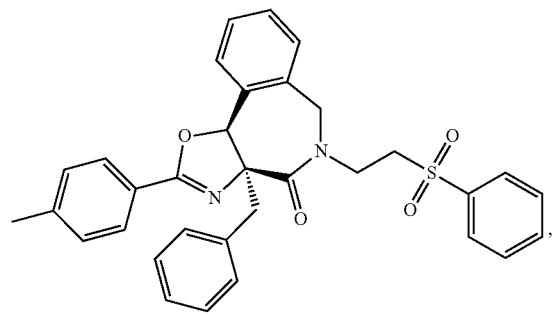
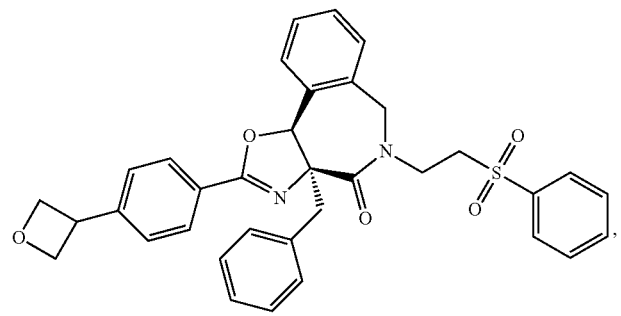
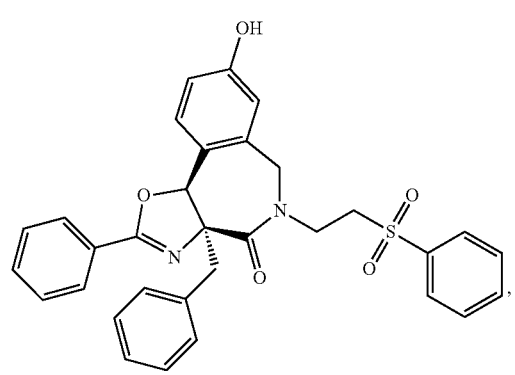
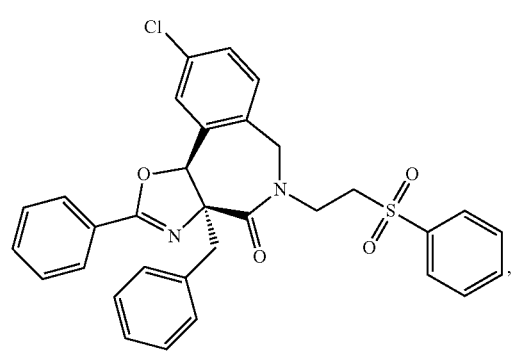
84
-continued
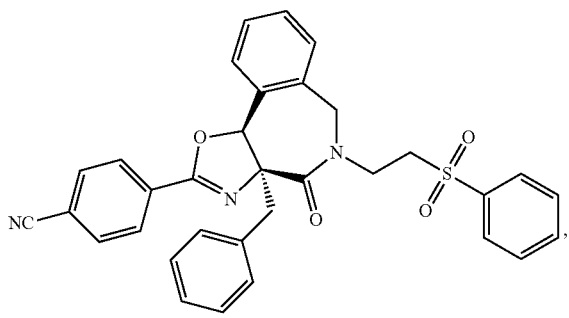
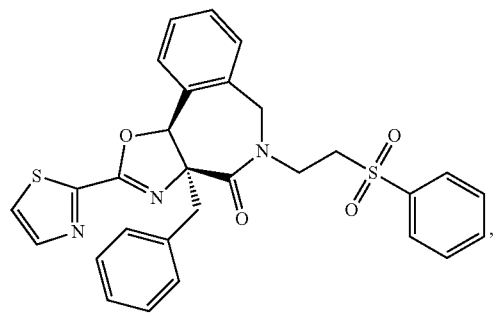
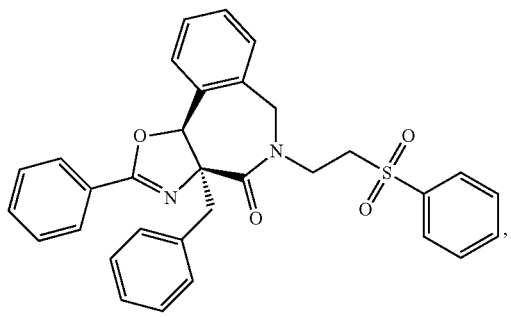
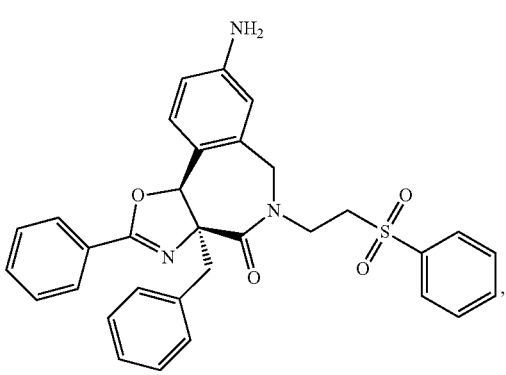
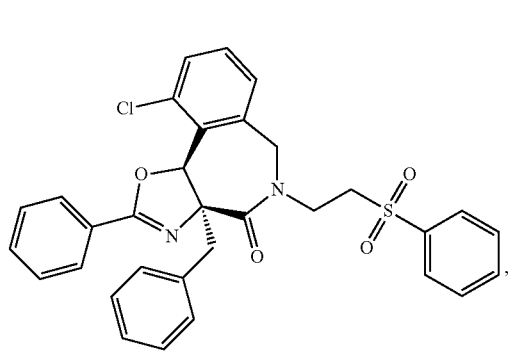

-continued
85
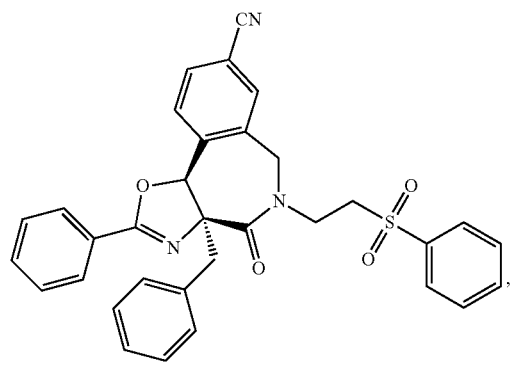
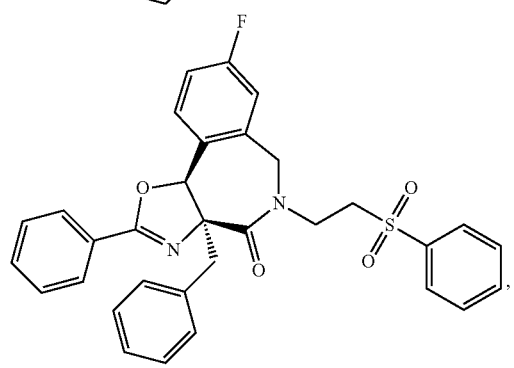
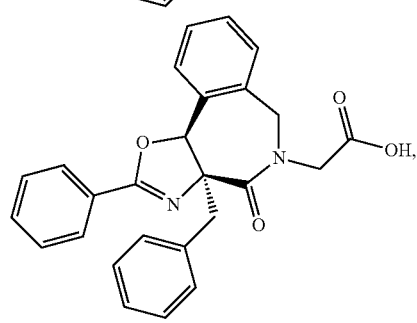
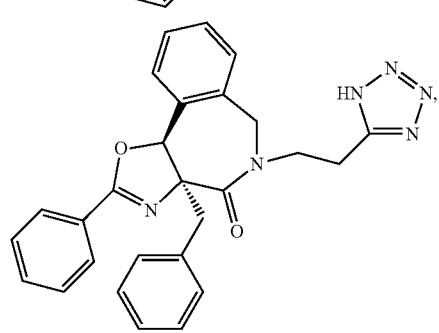
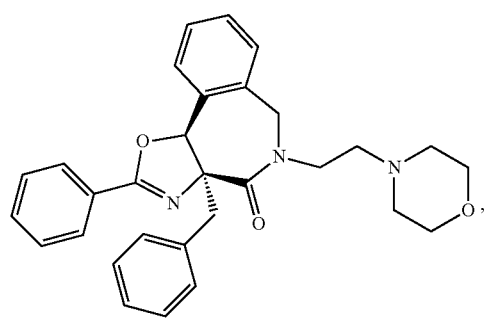
86
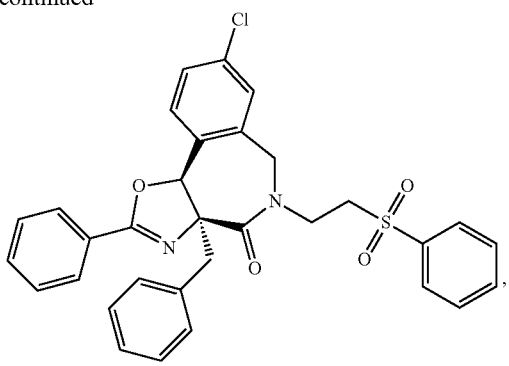
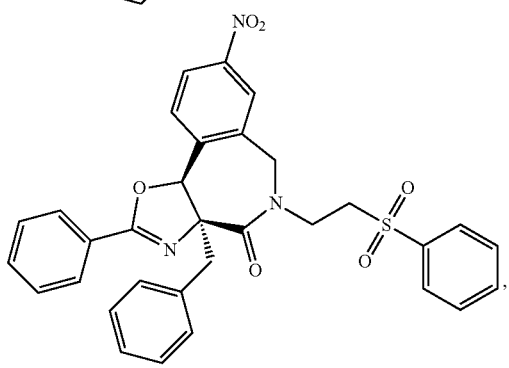
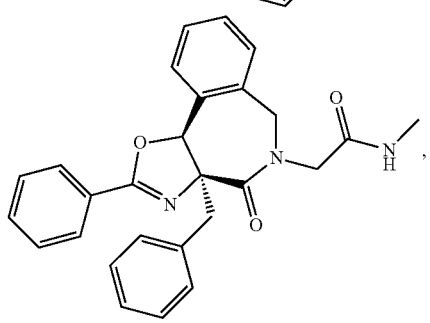
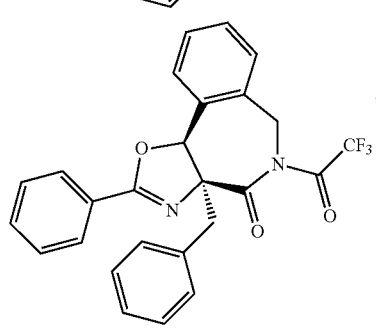
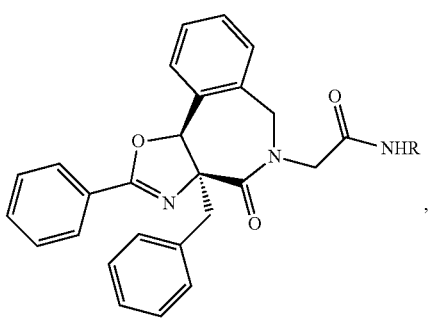

-continued
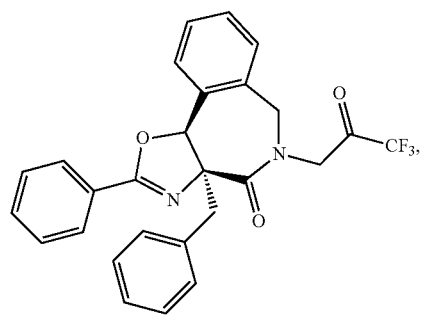
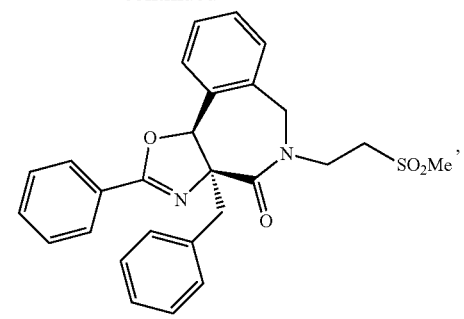
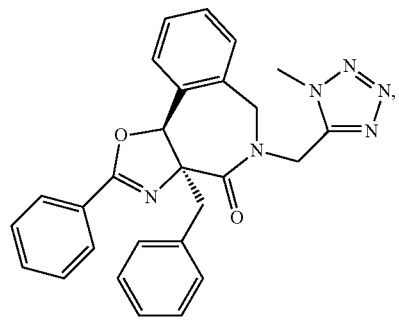
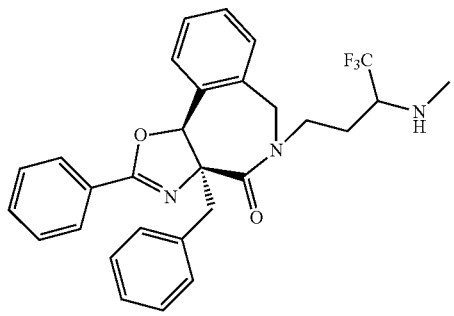
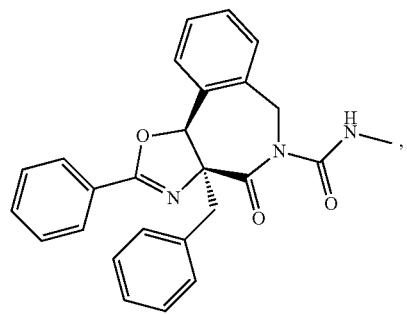
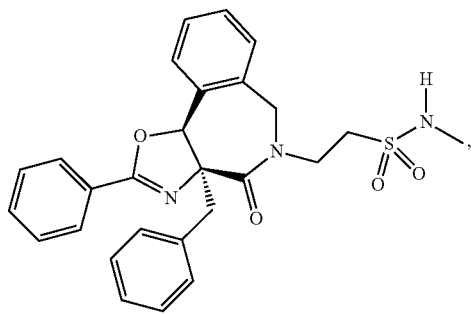
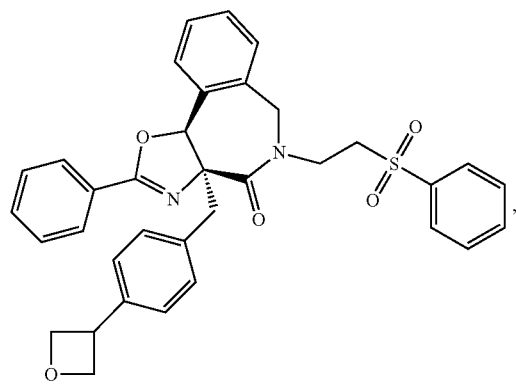
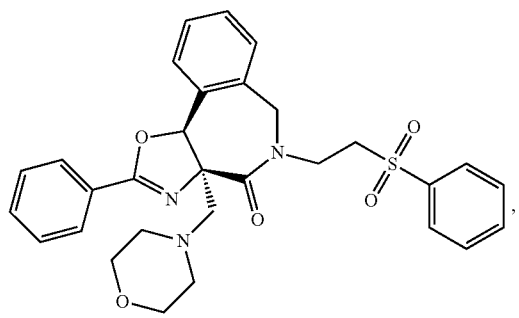
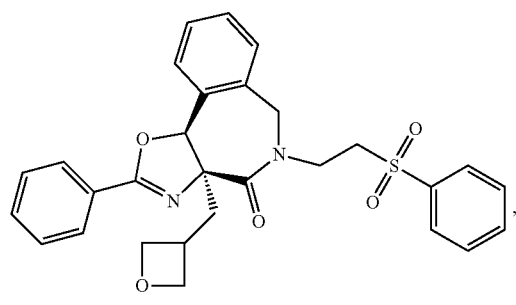
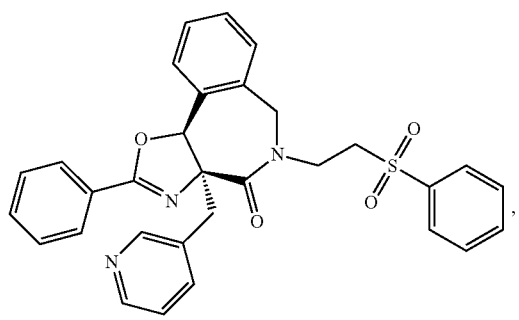

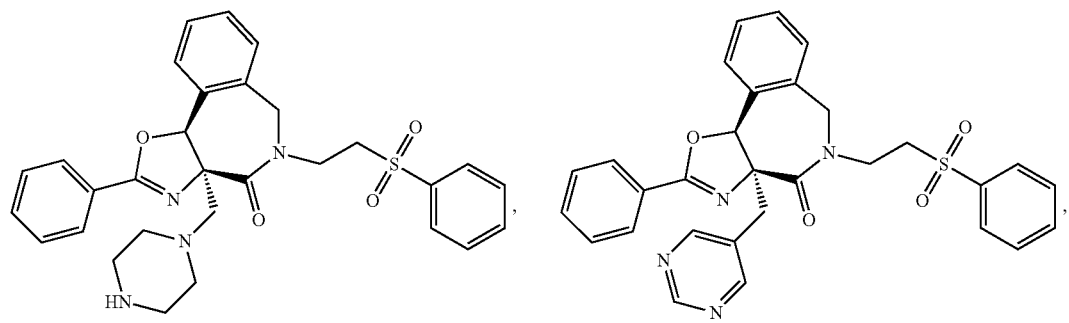
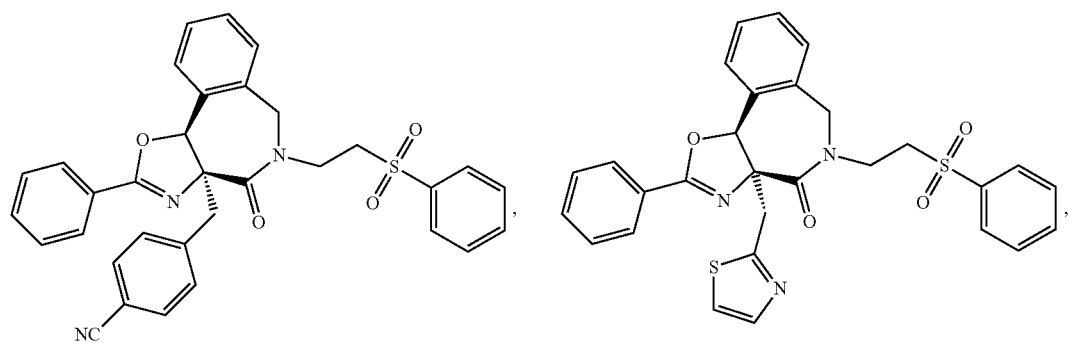
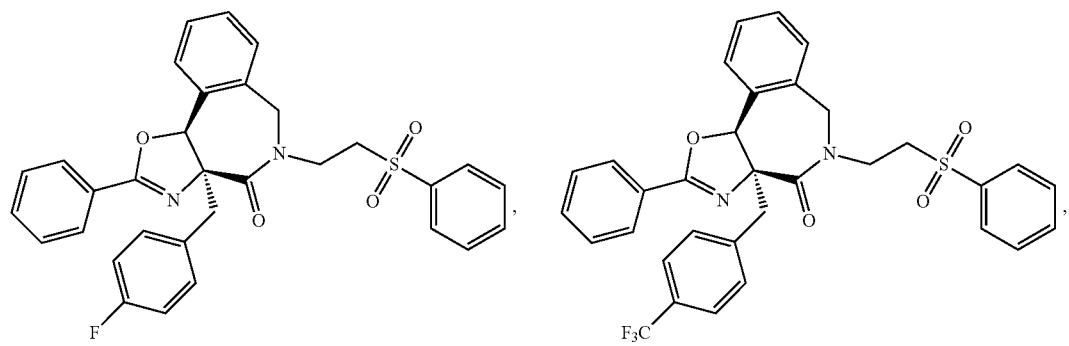
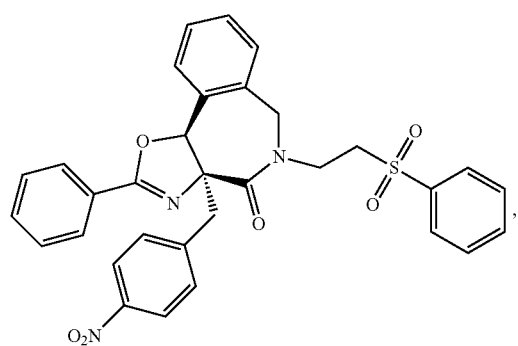

(MS2-090)
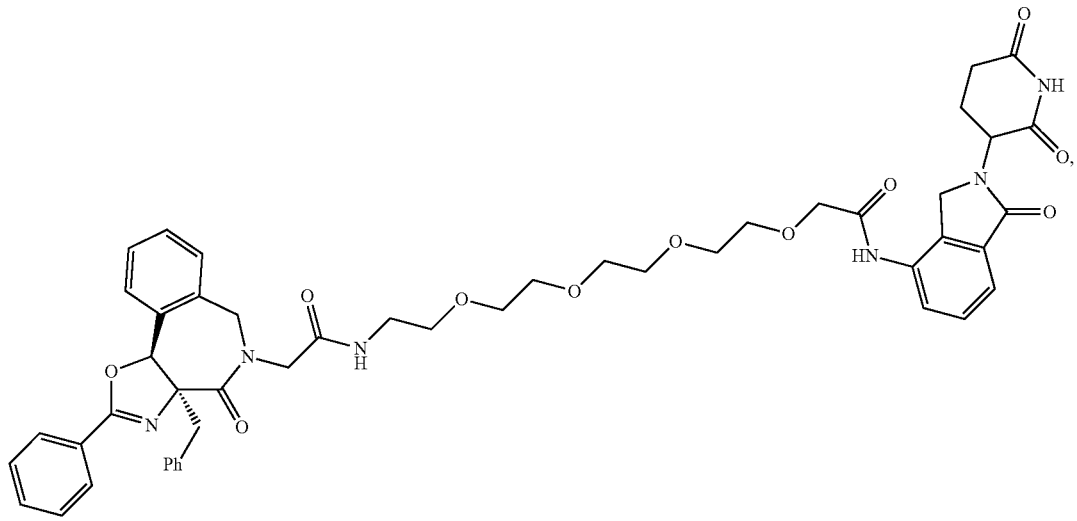
(MS2-078)
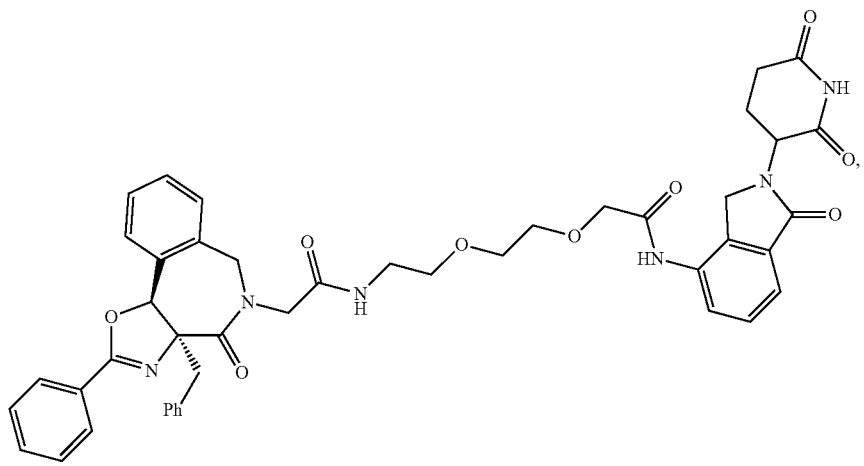
(MS2-089)
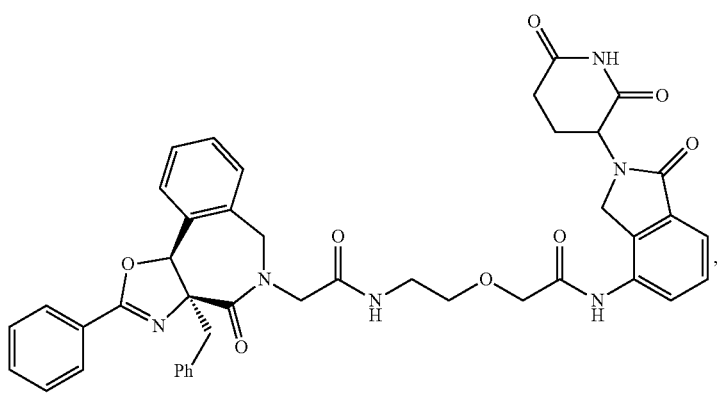

(MS2-096)
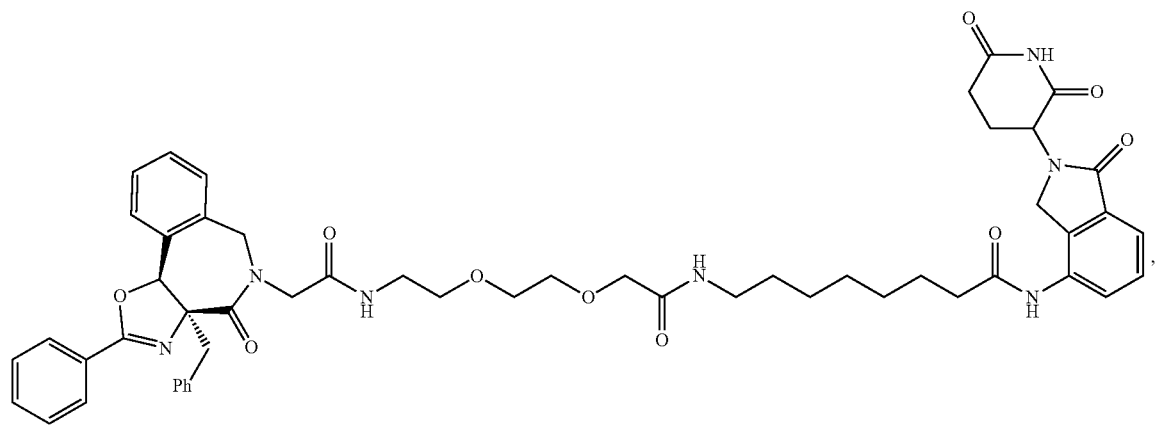
(MS2-095)
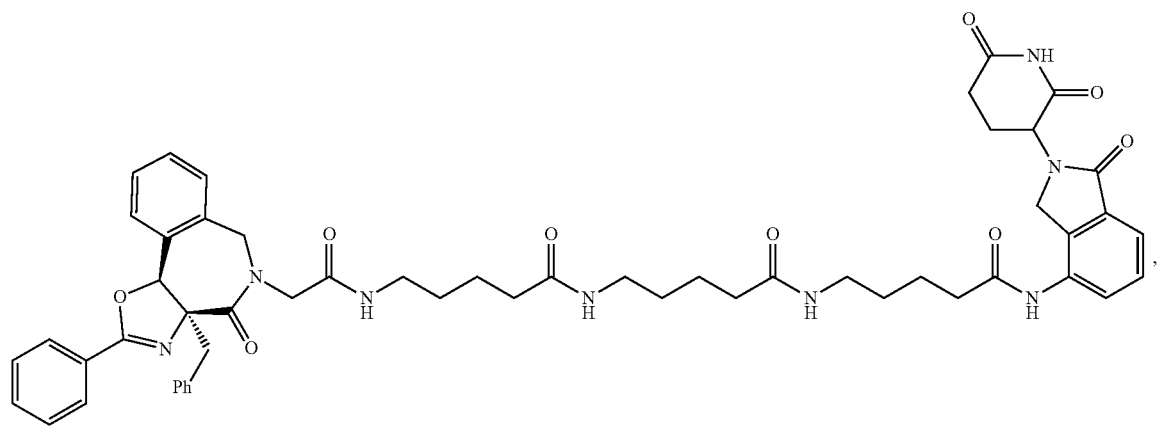
(MS2-094)
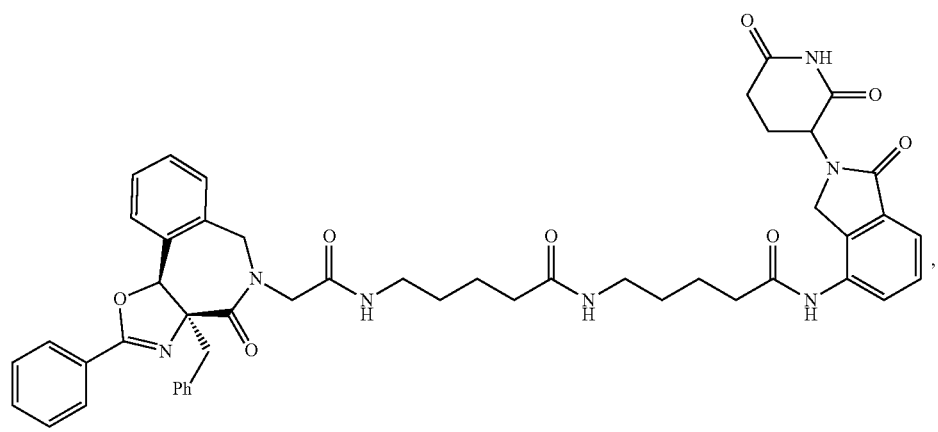

-continued
(MS2-093)
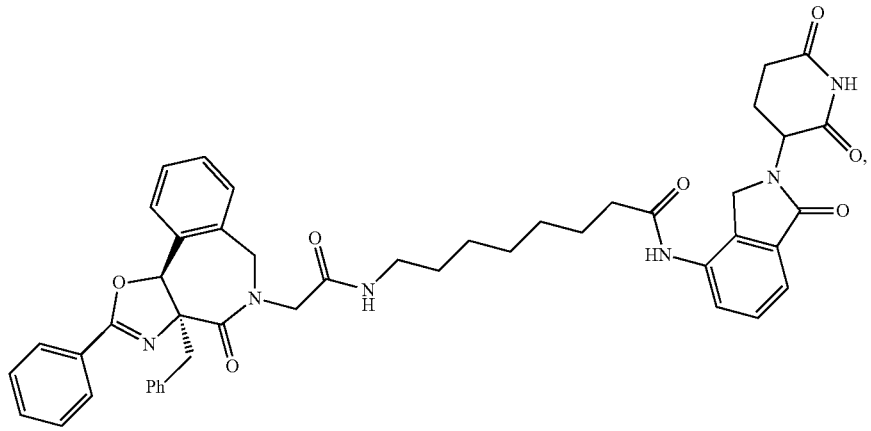
(MS2-092)
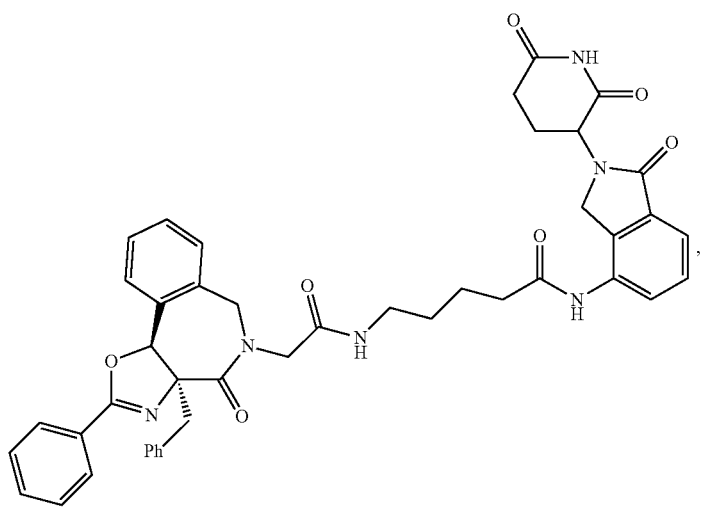
(MS2-090-Me)
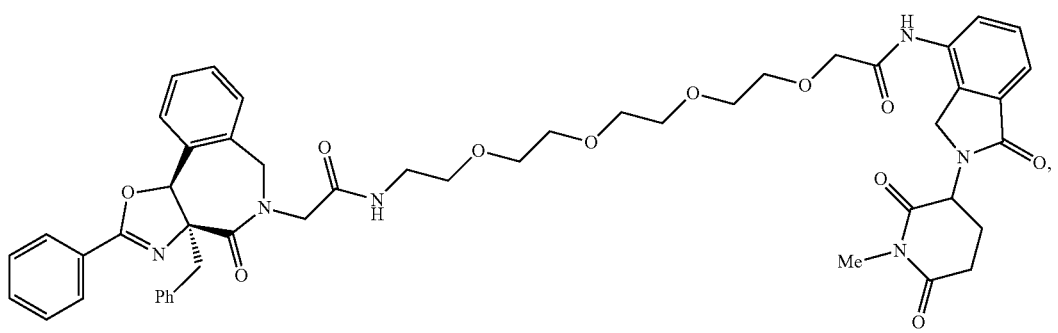
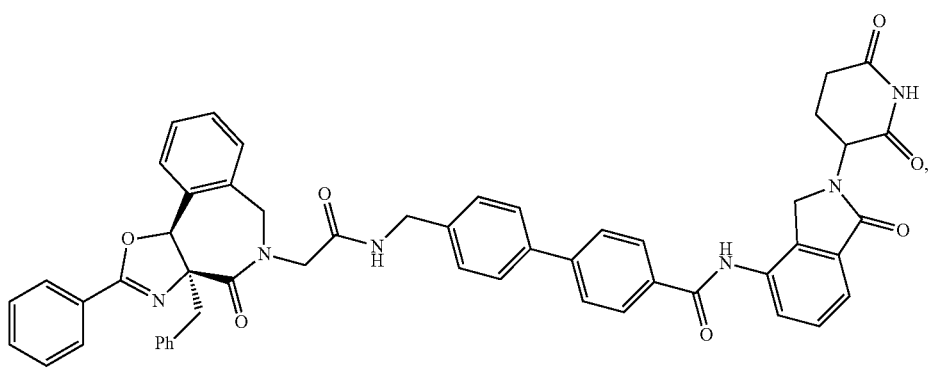

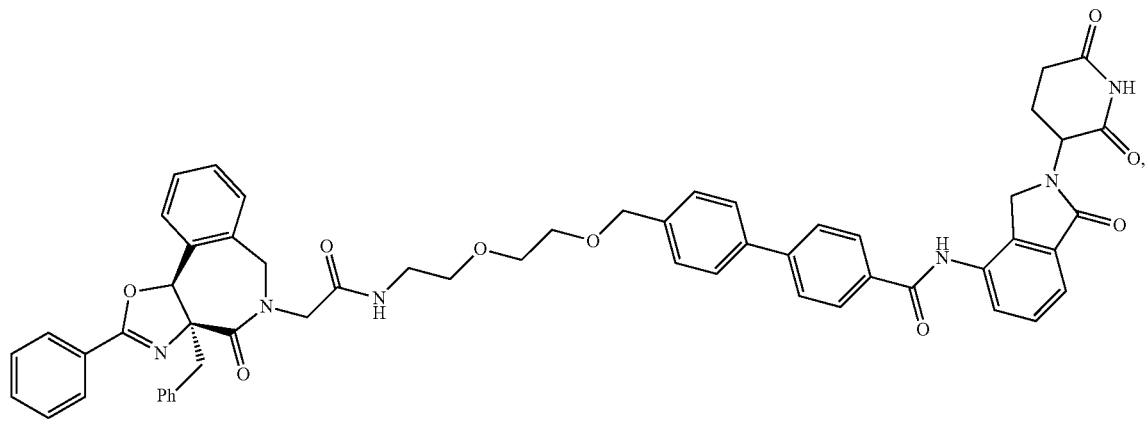
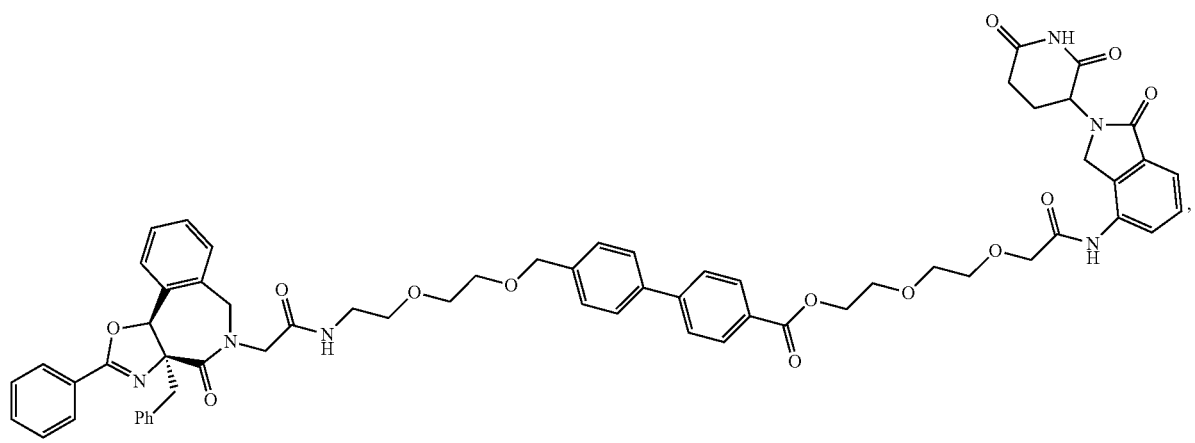
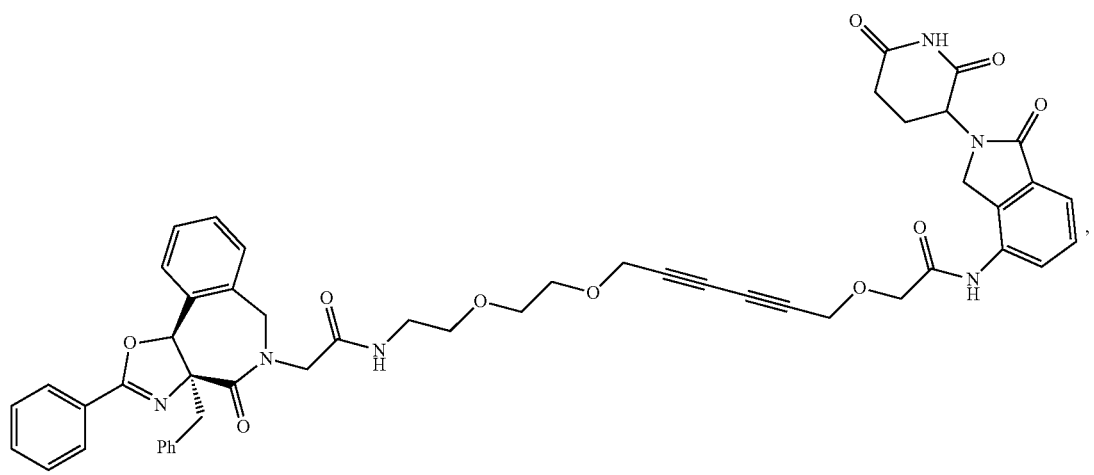

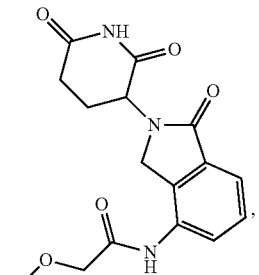
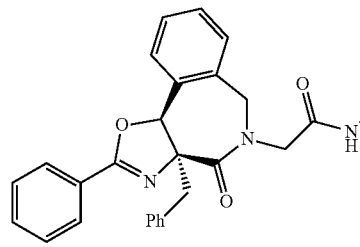
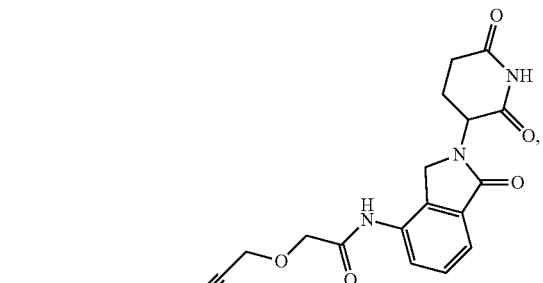
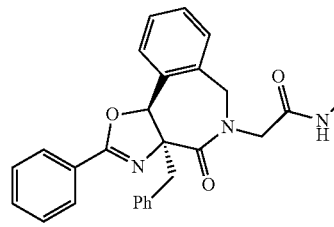
or a pharmaceutically acceptable salt thereof.
In certain embodiments, the compound of Formula (I) is of the formula:
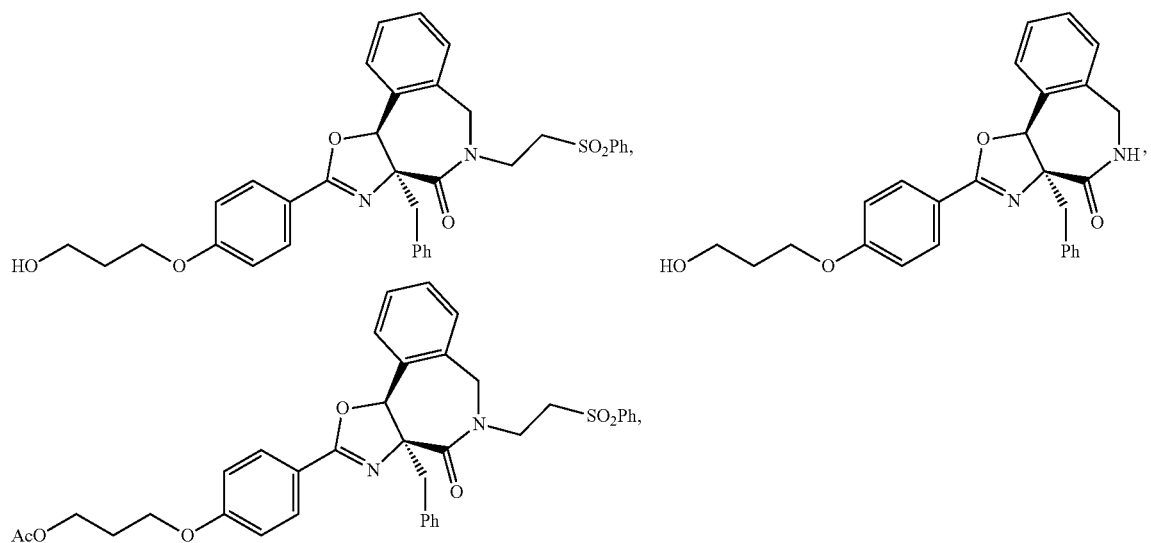

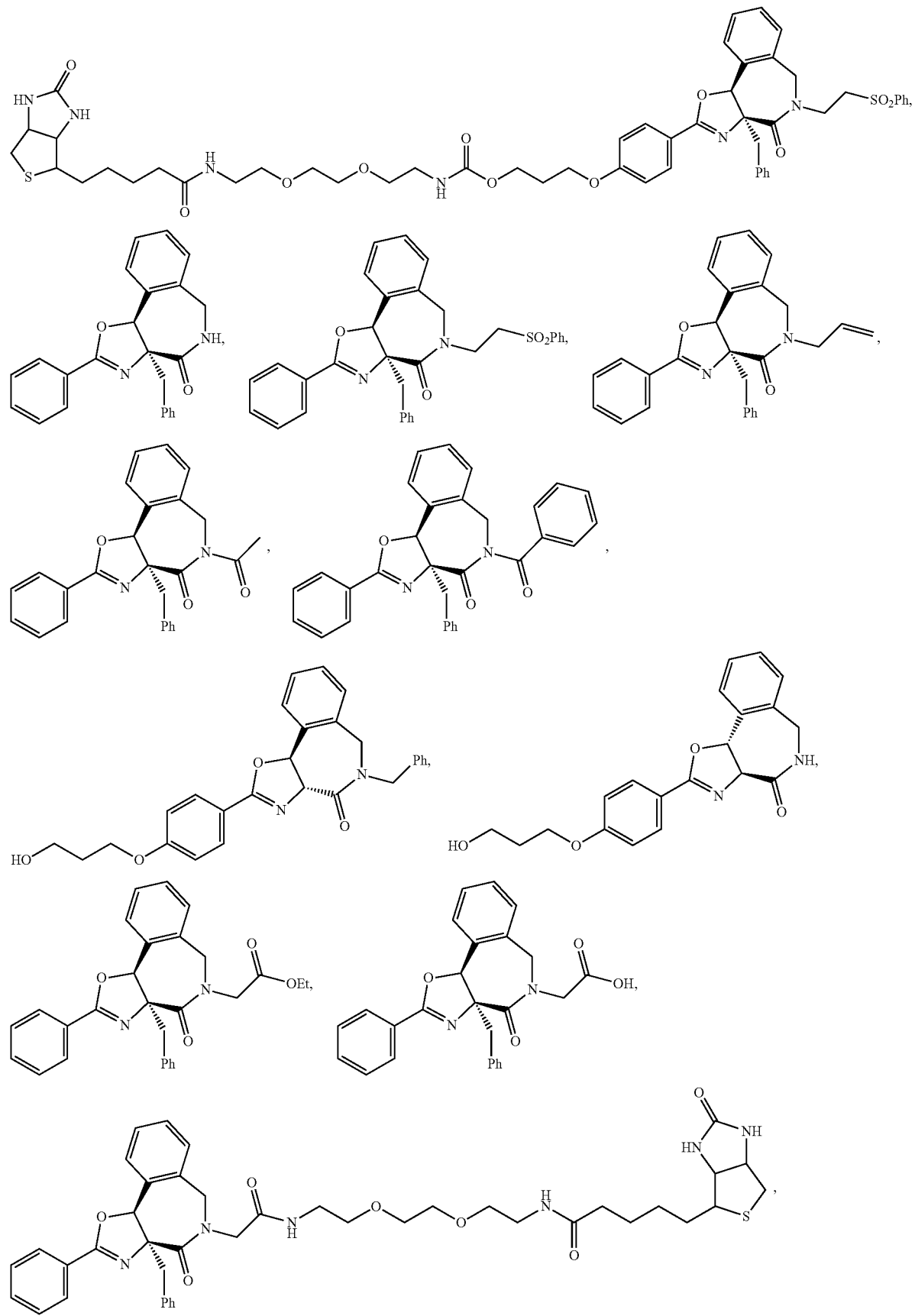

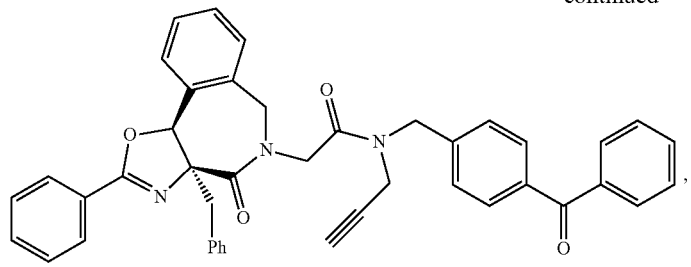

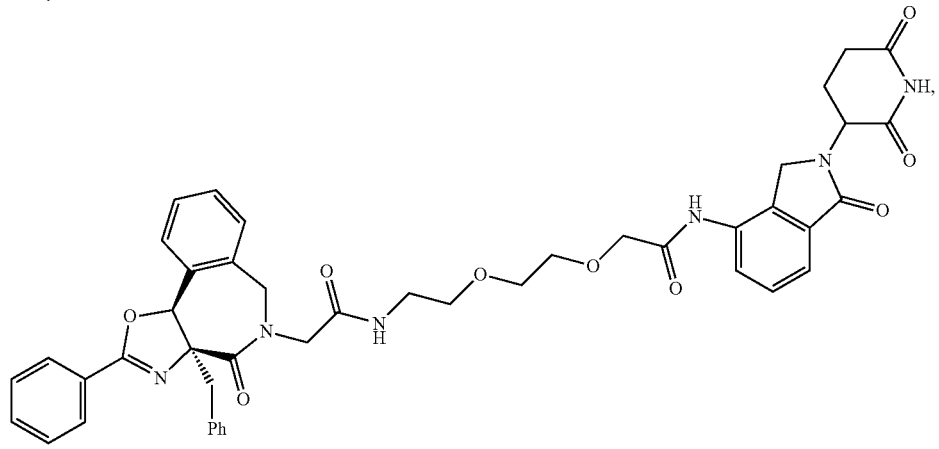

or a pharmaceutically acceptable salt thereof.

Compounds of Formula (II)

In certain embodiments, the compound is of Formula (II):

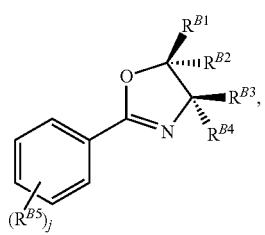

(II)

or a pharmaceutically acceptable salt, solvate, hydrate, polymorph, co-crystal, tautomer, stereoisomer, isotopically labeled derivative, or prodrug thereof, wherein:

j is 1, 2, 3, 4, or 5;

$R^{B1}$ is independently hydrogen, halogen, substituted or unsubstituted alkyl, substituted or unsubstituted carbocyclyl, substituted or unsubstituted heterocyclyl, substituted or unsubstituted aryl, substituted or unsubstituted heteroaryl, —$OR^{d1}$, —$N(R^{zz})_2$, —$SR^{d1}$, —CN, —SCN, or —$SO_2R^{d1}$;

$R^{B2}$ is independently hydrogen, halogen, substituted or unsubstituted alkyl, substituted or unsubstituted carbocyclyl, substituted or unsubstituted heterocyclyl, substituted or unsubstituted aryl, substituted or unsubstituted heteroaryl, —$OR^{d1}$, —$N(R^{zz})_2$, —$SR^{d1}$, —CN, —SCN, or —$SO_2R^{d1}$;

or $R^{B1}$ and $R^{B2}$ are taken together to form =O, a spiro-linked, substituted or unsubstituted carbocyclyl, or a spiro-linked, substituted or unsubstituted heterocyclyl;

$R^{B3}$ is independently hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{d1}$, —$N(R^{zz})_2$, —$SR^{d1}$, —CN, —SCN;

$R^{d1}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, oxygen protecting group, sulfur protecting group, or —$SO_2R''$; and each instance of $R^{zz}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, nitrogen protecting group, or optionally two $R^{zz}$ are taken together to form substituted or unsubstituted heterocyclyl or substituted or unsubstituted heteroaryl;

each instance of $R''$ is independently hydrogen, substituted or unsubstituted alkyl, or substituted or unsubstituted aryl;

$R^{B4}$ is independently hydrogen, halogen, substituted or unsubstituted acyl, substituted or unsubstituted alkyl, substituted or unsubstituted carbocyclyl, substituted or unsubstituted heterocyclyl, substituted or unsubstituted aryl, substituted or unsubstituted heteroaryl, —$OR^{d1}$, —$N(R^{zz})_2$, —$SR^{d1}$, —CN, —SCN;

or $R^{B3}$ and $R^{B4}$ are taken together to form =O, a spiro-linked, substituted or unsubstituted carbocyclyl, or a spiro-linked, substituted or unsubstituted heterocyclyl; and each instance of $R^{B5}$ is independently hydrogen, halogen, substituted or unsubstituted acyl, substituted or unsubstituted alkyl, substituted or unsubstituted aryl, substituted or unsubstituted heteroaryl, —$OR^{d1}$, —$N(R^{zz})_2$, —$SR^{d1}$, —CN, or —SCN.

Formula (II) includes substituent $R^{B1}$. In certain embodiments, $R^{B1}$ is hydrogen. In certain embodiments, $R^{B1}$ is halogen (e.g., F, Cl, Br, or I). In certain embodiments, $R^{B1}$ is F. In certain embodiments, $R^{B1}$ is Cl. In certain embodiments, $R^{B1}$ is substituted or unsubstituted $C_{1-6}$ alkyl. In certain embodiments, $R^{B1}$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, $R^{B1}$ is cyclopropyl. In certain embodiments, $R^{B1}$ is cyclobutyl. In certain embodiments, $R^{B1}$ is cyclopentyl. In certain embodiments, $R^{B1}$ is of the formula:

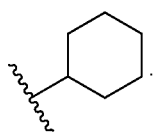

In certain embodiments, $R^{B1}$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^{B1}$ is substituted or unsubstituted aryl (e.g., substituted or unsubstituted, 6- to 10-membered aryl). In certain embodiments, $R^{B1}$ is substituted phenyl. In certain embodiments, $R^{B1}$ is unsubstituted phenyl. In certain embodiments, $R^{B1}$ is of the formula:

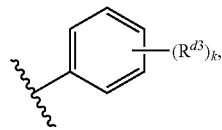

wherein: k is 0, 1, 2, 3, 4, or 5; $R^{d3}$ is independently substituted or unsubstituted alkyl, halogen, —$OR^{d4}$, —$N_3$, —$N(R^{d10})_2$, —$SR^{d4}$, —CN, —SCN, —$SO_2R^{d4}$, —C(=O)$R^{d4}$, —C(=O)$OR^{d4}$, —C(=O)N($R^{d10}$)$_2$, or —$NO_2$; and $R^{d4}$ is independently hydrogen, or substituted or unsubstituted $C_{1-6}$ alkyl, oxygen protecting group, or sulfur protecting group; and $R^{d10}$ is independently hydrogen, substituted or unsubstituted $C_{1-6}$ alkyl, or nitrogen protecting group, or optionally two $R^{d10}$ are taken together to form substituted or unsubstituted heterocyclyl or substituted or unsubstituted heteroaryl. In certain embodiments, k is 0. In certain embodiments, k is 1. In certain embodiments, k is 2. In certain embodiments, k is 3. In certain embodiments, k is 4. In certain embodiments, k is 5. In certain embodiments, $R^{d3}$ is substituted or unsubstituted $C_{1-6}$ alkyl. In certain embodiments, $R^{d3}$ is:

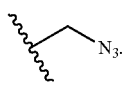 [SMILES: *CN=[N+]=[N-]]

In certain embodiments, $R^{d3}$ is halogen (e.g., F, Cl, Br, or I). In certain embodiments, $R^{d3}$ is —$OR^{d4}$ (e.g., —OH, —O(substituted or unsubstituted $C_{1-6}$ alkyl) (e.g., —OMe, —$OCF_3$, —OEt, —OPr, —OBu, or —OBn), or —O(substituted or unsubstituted phenyl) (e.g., —OPh)). In certain embodiments, $R^{d4}$ is substituted or unsubstituted $C_{1-6}$ alkyl.

In certain embodiments, $R^{d4}$ is substituted methyl. In certain embodiments, $R^{d4}$ is unsubstituted methyl. In certain embodiments, $R^{d3}$ is —OMe. In certain embodiments, $R^{d3}$ is —$N_3$. In certain embodiments, $R^{d3}$ is —$N(R^{d10})_2$ (e.g., —$NH_2$, —NH(substituted or unsubstituted $C_{1-6}$ alkyl) (e.g., —NHMe), or —$NMe_2$). In certain embodiments, $R^{d3}$ is —$SR^{d4}$ (e.g., —SH, —S(substituted or unsubstituted $C_{1-6}$ alkyl) (e.g., —SMe, —SEt, —SPr, —SBu, or —SBn), or —S(substituted or unsubstituted phenyl) (e.g., —SPh)). In certain embodiments, $R^{d3}$ is —CN. In certain embodiments, $R^{d3}$ is —SCN. In certain embodiments, $R^{d3}$ is —$SO_2R^{d4}$. In certain embodiments, $R^{d3}$ is —$SO_2$Me. In certain embodiments, $R^{d3}$ is —C(=O)$R^{d4}$. In certain embodiments, $R^{d3}$ is —C(=O)$OR^{d4}$. In certain embodiments, $R^{d3}$ is —C(=O)N($R^{d1}$)$_2$. In certain embodiments, $R^{B1}$ is of the formula:

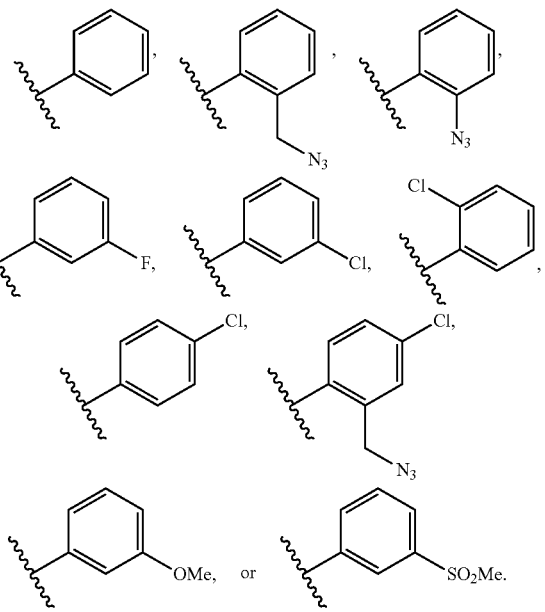

In certain embodiments, $R^{B1}$ is of the formula:

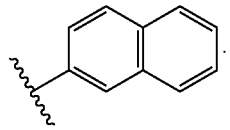 [SMILES: *c1ccc2ccccc2c1]

In certain embodiments, $R^{B1}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, $R^{B1}$ is of the formula:

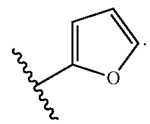

In certain embodiments, $R^{B1}$ is thiophenyl. In certain embodiments, $R^{B1}$ is pyrrole. In certain embodiments, $R^{B1}$ is —$OR^{d1}$, wherein $R^{d1}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, oxygen protecting group, or sulfur protecting group. In certain embodiments, $R^{B1}$ is —$OR^{d1}$ (e.g., —OMe). In certain embodiments, $R^{B1}$ is —$N(R^{zz})_2$, wherein each instance of $R^{zz}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, nitrogen protecting group, or optionally two $R^{zz}$ are taken together to form substituted or unsubstituted heterocyclyl or substituted or unsubstituted heteroaryl (e.g., —NMe₂). In certain embodiments, $R^{B1}$ is —$SR^{d1}$ (e.g., —SMe). In certain embodiments, $R^{B1}$ is —CN. In certain embodiments, $R^{B1}$ is —SCN. In certain embodiments, $R^{B1}$ is —$SO_2R''$.

Formula (II) also includes substituent $R^{B2}$. In certain embodiments, $R^{B2}$ is hydrogen. In certain embodiments, $R^{B2}$ is halogen (e.g., F, Cl, Br, or I). In certain embodiments, $R^{B1}$ is F. In certain embodiments, $R^{B2}$ is Cl. In certain embodiments, $R^{B2}$ is substituted or unsubstituted $C_{1-6}$ alkyl. In certain embodiments, $R^{B2}$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, $R^{B2}$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^{B2}$ is substituted or unsubstituted aryl (e.g., substituted or unsubstituted, 6- to 10-membered aryl). In certain embodiments, $R^{B2}$ is substituted phenyl. In certain embodiments, $R^{B2}$ is unsubstituted phenyl. In certain embodiments, $R^{B2}$ is of the formula:

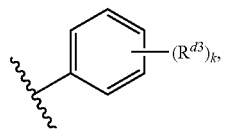

wherein k is 0, 1, 2, 3, 4, or 5; $R^{d3}$ is independently substituted or unsubstituted alkyl, halogen, —$OR^{d4}$, —$N_3$, —$N(R^{d10})_2$, —$SR^{d4}$, —CN, —SCN, —$SO_2R^{d4}$, —$C(=O)R^{d4}$, —$C(=O)OR^{d4}$, —$C(=O)N(R^{d10})_2$, or —$NO_2$; and $R^{d4}$ is independently hydrogen, or substituted or unsubstituted $C_{1-6}$ alkyl, oxygen protecting group, or sulfur protecting group; and $R^{d10}$ is independently hydrogen, substituted or unsubstituted $C_{1-6}$ alkyl, or nitrogen protecting group, or optionally two $R^{d10}$ are taken together to form substituted or unsubstituted heterocyclyl or substituted or unsubstituted heteroaryl.

In certain embodiments, k is 0. In certain embodiments, k is 1. In certain embodiments, k is 2. In certain embodiments, k is 3. In certain embodiments, k is 4. In certain embodiments, k is 5. In certain embodiments, $R^{d3}$ is substituted or unsubstituted $C_{1-6}$ alkyl. In certain embodiments, $R^{d3}$ is:

In certain embodiments, $R^{d3}$ is halogen (e.g., F, Cl, Br, or I). In certain embodiments, $R^{d3}$ is —$N_3$. In certain embodiments, $R^{B2}$ is of the formula:

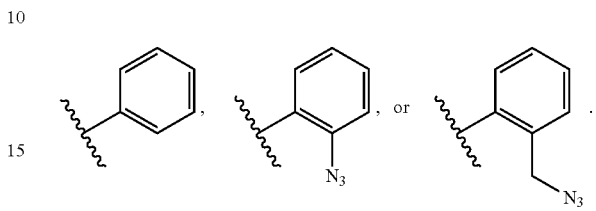

In certain embodiments, $R^{d3}$ is —$N(R^{d10})_2$ (e.g., —$NH_2$). In certain embodiments, $R^{d3}$ is —$SR^{d4}$. In certain embodiments, $R^{d3}$ is —CN. In certain embodiments, $R^{d3}$ is —SCN. In certain embodiments, $R^{d3}$ is —$SO_2R^{d4}$. In certain embodiments, $R^{d3}$ is —$C(=O)R^{d4}$. In certain embodiments, $R^{d3}$ is —$C(=O)OR^{d4}$. In certain embodiments, $R^{d3}$ is —$C(=O)N(R^{d10})_2$. In certain embodiments, $R^{d3}$ is —$NO_2$. In certain embodiments, $R^{B2}$ is —$OR^{d1}$ (e.g., —OMe). In certain embodiments, $R^{B2}$ is —$N(R^{zz})_2$ (e.g., —NMe₂). In certain embodiments, $R^{B2}$ is —$SR^{d1}$ (e.g., —SMe). In certain embodiments, $R^{B2}$ is —CN. In certain embodiments, $R^{B2}$ is —SCN. In certain embodiments, $R^{B2}$ is —$SO_2R^{d1}$.

In certain embodiments, substituents $R^{B1}$ and $R^{B2}$ are taken together to form =O. In certain embodiments, substituents $R^{B1}$ and $R^{B2}$ are taken together to form a spiro-linked, substituted or unsubstituted carbocyclyl (e.g., substituted or unsubstituted, 3- to 7-membered carbocyclyl comprising zero, one, or two double bonds in the carbocyclic ring system). In certain embodiments, substituents $R^{B1}$ and $R^{B2}$ are taken together to form spiro-linked, substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, substituents $R^{B1}$ and $R^{B2}$ are taken together to form:

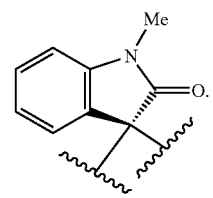

Formula (II) may include substituent $R^{B3}$. In certain embodiments, $R^{B3}$ is hydrogen. In certain embodiments, $R^{B3}$ is halogen (e.g., F, Cl, Br, or I). In certain embodiments, $R^{B3}$ is substituted or unsubstituted acyl. In certain embodiments, $R^{B3}$ is of the formula: —$C(=O)OR^{d1}$, wherein $R^{d1}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, oxygen protecting group, sulfur protecting group, or —$SO_2R''$; and each instance of $R''$ is independently hydrogen, substituted or unsubstituted alkyl, or substituted or unsubstituted aryl. In certain embodiments, $R^{B3}$ is —C(=O)OH or —C(=O)OMe. In certain embodiments, $R^{B3}$ is —C(=O)$R^{d1}$ (e.g., —C(=O)Me).

In certain embodiments, $R^{B3}$ is of the formula: —C(=O)N($R^{d2}$)$_2$; and each occurrence of $R^{d2}$ is independently hydrogen, substituted or unsubstituted alkyl, substituted or unsubstituted carbocyclyl, substituted or unsubstituted heterocyclyl, substituted or unsubstituted aryl, substituted or unsubstituted heteroaryl, nitrogen protecting group, or two instances of $R^{d2}$ are taken together to form a substituted or unsubstituted, heterocyclic ring. In certain embodiments, at least one instance of $R^{d2}$ is hydrogen. In certain embodiments, at least one instance of $R^{d2}$ is substituted or unsubstituted $C_{1-6}$ alkyl. In certain embodiments, at least one instance of $R^{d2}$ is of the formula: —(CH$_2$)$_p$O$R^{d5}$, or —(CH$_2$)$_p$C(=O)O$R^{d5}$, wherein: p is 1, 2, 3, 4, 5, or 6; and $R^{d5}$ is independently hydrogen, or substituted or unsubstituted $C_{1-6}$ alkyl. In certain embodiments, p is 1. In certain embodiments, p is 2. In certain embodiments, p is 3. In certain embodiments, at least one instance of $R^{d2}$ is —(CH$_2$)$_2$OH or —(CH$_2$)OMe. In certain embodiments, at least one instance of $R^{d2}$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, at least one instance of $R^{d2}$ is substituted or unsubstituted, 3- to 9-membered, monocyclic heterocyclic ring comprising zero, one, or two double bonds in the heterocyclic ring system, wherein one, two, or three atoms of the heterocyclic ring system are independently nitrogen, oxygen, or sulfur. In certain embodiments, at least one instance of $R^{d2}$ is substituted or unsubstituted aryl (e.g., substituted or unsubstituted, 6- to 10-membered aryl). In certain embodiments, at least one instance of $R^{d2}$ is substituted phenyl. In certain embodiments, at least one instance of $R^{d2}$ is unsubstituted phenyl. In certain embodiments, two instances of $R^{d2}$ are taken together to form a substituted or unsubstituted, 3- to 9-membered, monocyclic heterocyclic ring comprising zero, one, or two double bonds in the heterocyclic ring system, wherein one, two, or three atoms of the heterocyclic ring system are independently nitrogen, oxygen, or sulfur. In certain embodiments, two instances of $R^{d2}$ are taken together to form a ring of formula:

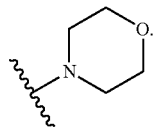

In certain embodiments, $R^{B3}$ is substituted or unsubstituted $C_{1-6}$ alkyl. In certain embodiments, $R^{B3}$ is of the formula: —CH$_2$O$R^d$1. In certain embodiments, $R^{d1}$ is hydrogen. In certain embodiments, $R^{d1}$ is substituted or unsubstituted $C_{1-6}$ alkyl. In certain embodiments, $R^{d1}$ is substituted or unsubstituted aryl (e.g., substituted or unsubstituted, 6- to 10-membered aryl). In certain embodiments, $R^{d1}$ is substituted phenyl. In certain embodiments, $R^{d1}$ is unsubstituted phenyl. In certain embodiments, $R^{B3}$ is: —CH$_2$OH. In certain embodiments, $R^{B3}$ is substituted or unsubstituted alkenyl (e.g., substituted or unsubstituted $C_{2-6}$ alkenyl). In certain embodiments, $R^{B3}$ is substituted or unsubstituted alkynyl (e.g., substituted or unsubstituted $C_{2-6}$ alkynyl). In certain embodiments, $R^{B3}$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, $R^{B3}$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^{B3}$ is substituted or unsubstituted aryl (e.g., substituted or unsubstituted, 6- to 10-membered aryl). In certain embodiments, $R^{B3}$ is substituted benzyl. In certain embodiments, $R^{B3}$ is unsubstituted benzyl. In certain embodiments, $R^{B3}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, $R^{B3}$ is —O$R^{d1}$ (e.g., —OMe). In certain embodiments, $R^{B3}$ is —N($R^{zz}$)$_2$ (e.g., —NMe$_2$). In certain embodiments, $R^{B3}$ is —S$R^{d1}$ (e.g., —SMe). In certain embodiments, $R^{B3}$ is —CN. In certain embodiments, $R^{B3}$ is —SCN.

Formula (II) includes substituent $R^{B4}$. In certain embodiments, $R^{B4}$ is hydrogen. In certain embodiments, $R^{B4}$ is halogen (e.g., F, Cl, Br, or I). In certain embodiments, $R^{B4}$ is substituted or unsubstituted acyl. In certain embodiments, $R^{B4}$ is of the formula: —C(=O)O$R^{d1}$, wherein $R^{d1}$ is substituted or unsubstituted $C_{1-6}$ alkyl. In certain embodiments, $R^{B4}$ is —C(=O)$R^{d1}$. In certain embodiments, $R^{B4}$ is of the formula: —C(=O)N($R^{d2}$)$_2$ (e.g., —C(=O)NHMe). In certain embodiments, $R^{B4}$ is substituted or unsubstituted $C_{1-6}$ alkyl. In certain embodiments, $R^{B4}$ is of the formula: —(CH$_2$)$_m$$R^{d1}$, —(CH$_2$)$_m$O$R^{d1}$, or —C(=O)O$R^{d1}$, wherein m is 1, 2, or 3. In certain embodiments, m is 1. In certain embodiments, m is 2. In certain embodiments, m is 3. In certain embodiments, $R^{d1}$ is hydrogen. In certain embodiments, $R^{d1}$ is substituted or unsubstituted $C_{1-6}$ alkyl. In certain embodiments, $R^{d1}$ is substituted or unsubstituted alkenyl (e.g., substituted or unsubstituted $C_{2-6}$ alkenyl). In certain embodiments, $R^{d1}$ is substituted or unsubstituted alkynyl (e.g., substituted or unsubstituted $C_{2-6}$ alkynyl). In certain embodiments, $R^{d1}$ is —SO$_2$Ph. In certain embodiments, $R^{B4}$ is

or —C(=O)OMe. In certain embodiments, $R^{B4}$ is substituted or unsubstituted alkenyl (e.g., substituted or unsubstituted $C_{2-6}$ alkenyl). In certain embodiments, $R^{B4}$ is substituted or unsubstituted alkynyl (e.g., substituted or unsubstituted $C_{2-6}$ alkynyl). In certain embodiments, $R^{B4}$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, $R^{B4}$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^{B4}$ is substituted or unsubstituted aryl (e.g., substituted or unsubstituted, 6- to 10-membered aryl). In certain embodiments, $R^{B4}$ is substituted benzyl. In certain embodiments, $R^{B4}$ is unsubstituted benzyl. In certain embodiments, $R^{B4}$ is substituted phenyl. In certain embodiments, $R^{B4}$ is unsubstituted phenyl. In certain embodiments, $R^{B4}$ is substituted napthyl. In certain embodiments, $R^{B4}$ is unsubstituted napthyl. In certain embodiments, $R^{B4}$ is of the formula:

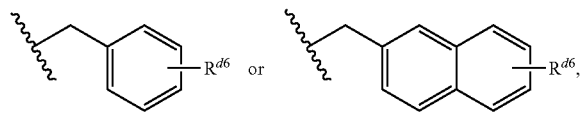

wherein $R^{d6}$ is independently hydrogen, halogen, substituted or unsubstituted alkyl, $-N(R^{d7})_2$, $-S(R^{d7})$, or $-OR^{d7}$, wherein $R^{d7}$ is independently hydrogen or substituted or unsubstituted alkyl. In certain embodiments, $R^{d6}$ is hydrogen. In certain embodiments, $R^{d6}$ is halogen (e.g., F, Cl, Br, or I). In certain embodiments, $R^{d6}$ is substituted or unsubstituted $C_{1-6}$ alkyl. In certain embodiments, $R^{d6}$ is

$N_3$. In certain embodiments, $R^{d6}$ is isopropyl. In certain embodiments, $R^{d6}$ is $-N(R^{d7})_2$ (e.g., $-NH_2$, $-NH$(substituted or unsubstituted $C_{1-6}$ alkyl) (e.g., $-NHMe$), or $-NMe_2$). In certain embodiments, $R^{d6}$ is $-S(R^{d7})$ (e.g., $-SH$, $-S$(substituted or unsubstituted $C_{1-6}$ alkyl) (e.g., $-SMe$, $-SEt$, $-SPr$, $-SBu$, or $-SBn$), or $-S$(substituted or unsubstituted phenyl) (e.g., $-SPh$)). In certain embodiments, $R^{d6}$ is $-OR^{d7}$ (e.g., $-OH$, $-O$(substituted or unsubstituted $C_{1-6}$ alkyl) (e.g., $-OMe$, $-OCF_3$, $-OEt$, $-OPr$, $-OBu$, or $-OBn$), or $-O$(substituted or unsubstituted phenyl) (e.g., $-OPh$)). In certain embodiments, $R^{d7}$ is substituted or unsubstituted $C_{1-6}$ alkyl. In certain embodiments, $R^{d6}$ is $-OMe$. In certain embodiments, $R^{B4}$ is of the formula:

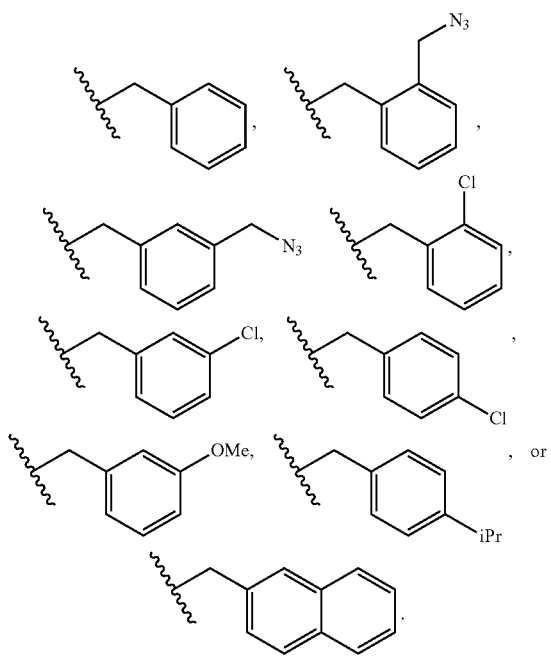

In certain embodiments, $R^{B4}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, $R^{B4}$ is $-OR^{d1}$ (e.g., $-OMe$). In certain embodiments, $R^{B4}$ is $-N(R^{zz})_2$ (e.g., $-NMe_2$). In certain embodiments, $R^{B4}$ is $-SR^{d1}$ (e.g., $-SMe$). In certain embodiments, $R^{B4}$ is $-CN$. In certain embodiments, $R^{B4}$ is $-SCN$. In certain embodiments, substituents $R^{B3}$ and $R^{B4}$ are taken together to form $=O$. In certain embodiments, substituents $R^{B3}$ and $R^{B4}$ are taken together to form a spiro-linked, substituted or unsubstituted carbocyclyl (e.g., substituted or unsubstituted, 3- to 7-membered carbocyclyl comprising zero, one, or two double bonds in the carbocyclic ring system). In certain embodiments, substituents $R^{B3}$ and $R^{B4}$ are taken together to form a spiro-linked, substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur).

Formula (II) includes one or more instances of substituent $R^{B5}$. In certain embodiments, j is 1. In certain embodiments, j is 2. In certain embodiments, j is 3. In certain embodiments, j is 4. In certain embodiments, j is 5. In certain embodiments, at least one instance of $R^{B5}$ is hydrogen. In certain embodiments, at least one instance of $R^{B5}$ is halogen (e.g., F, Cl, Br, or I). In certain embodiments, at least one instance of $R^{B5}$ is substituted or unsubstituted acyl. In certain embodiments, $R^{B5}$ is substituted or unsubstituted $C_{1-6}$ alkyl. In certain embodiments, at least one instance of $R^{B5}$ is substituted or unsubstituted aryl (e.g., substituted or unsubstituted, 6- to 10-membered aryl). In certain embodiments, at least one instance of $R^{B5}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, at least one instance of $R^{B5}$ is $-OR$ (e.g., $-OH$, $-O$(substituted or unsubstituted $C_{1-6}$ alkyl) (e.g., $-OMe$, $-OCF_3$, $-OEt$, $-OPr$, $-OBu$, or $-OBn$), or $-O$(substituted or unsubstituted phenyl) (e.g., $-OPh$)). In certain embodiments, at least one instance of $R^{B5}$ is of the formula: $-O(CH_2)_fOR^{d8}$, wherein: f is 1, 2, 3, 4, 5, or 6; and $R^{d8}$ is independently hydrogen or substituted or unsubstituted $C_{1-6}$ alkyl. In certain embodiments, f is 1. In certain embodiments, f is 2. In certain embodiments, f is 3. In certain embodiments, f is 4. In certain embodiments, f is 5. In certain embodiments, f is 6. In certain embodiments, $R^{d8}$ is substituted or unsubstituted $C_{1-6}$ alkyl. In certain embodiments, at least one instance of $R^{B5}$ is of the formula:

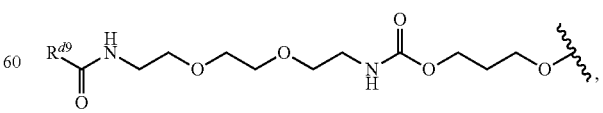

wherein $R^{d9}$ is substituted or unsubstituted alkyl, substituted or unsubstituted aryl, or substituted or unsubstituted heteroaryl. In certain embodiments, at least one instance of $R^{B5}$ is of the formula:

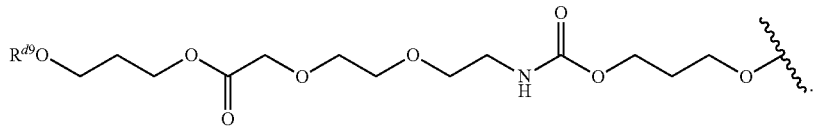

In certain embodiments $R^{d9}$ is substituted or unsubstituted $C_{1-6}$ alkyl. In certain embodiments, $R^{d9}$ is

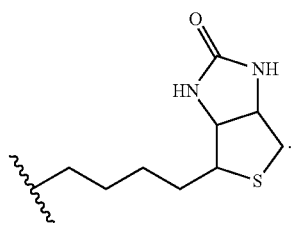 [SMILES: *CCCCC1SCC2NC(=O)NC21]

In certain embodiments, at least one instance of $R^{B5}$ is of the formula:

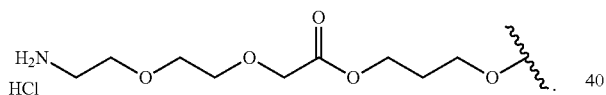

In certain embodiments, $R^{d9}$ is substituted or unsubstituted aryl (e.g., substituted or unsubstituted, 6- to 10-membered aryl). In certain embodiments, $R^{d9}$ is substituted phenyl. In certain embodiments, $R^{d9}$ is unsubstituted phenyl. In certain embodiments, $R^{d9}$ is of the formula:

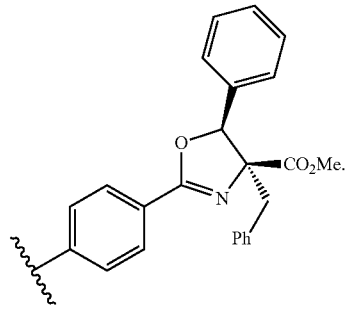 [SMILES: *c1ccc(C2=N[C@](Cc3ccccc3)(C(=O)OC)[C@H](c3ccccc3)O2)cc1]

In certain embodiments, $R^{d9}$ is substituted or unsubstituted heteroaryl. In certain embodiments, at least one instance of $R^{B5}$ is —$OR^{d1}$ (e.g., —OMe). In certain embodiments, at least one instance of $R^{B5}$ is —$N(R^{zz})_2$ (e.g., —$NMe_2$). In certain embodiments, at least one instance of $R^{B5}$ is —$SR^{d1}$ (e.g., —SMe). In certain embodiments, at least one instance of $R^{B5}$ is —CN. In certain embodiments, at least one instance of $R^{B5}$ is —SCN.

In certain embodiments, the compound of Formula (II) is of the following formula:

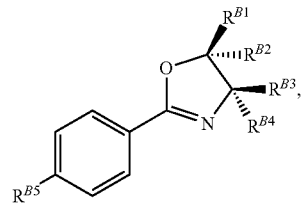

or a pharmaceutically acceptable salt thereof.

In certain embodiments, the compound of Formula (II) is of the formula:

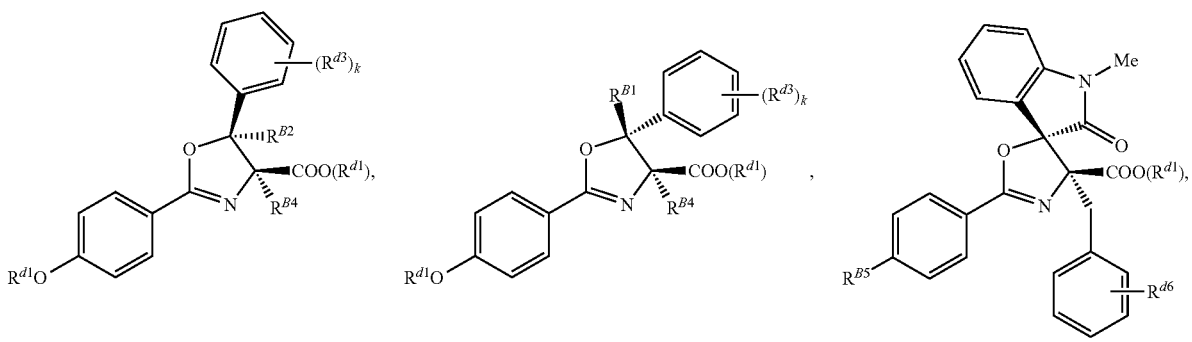

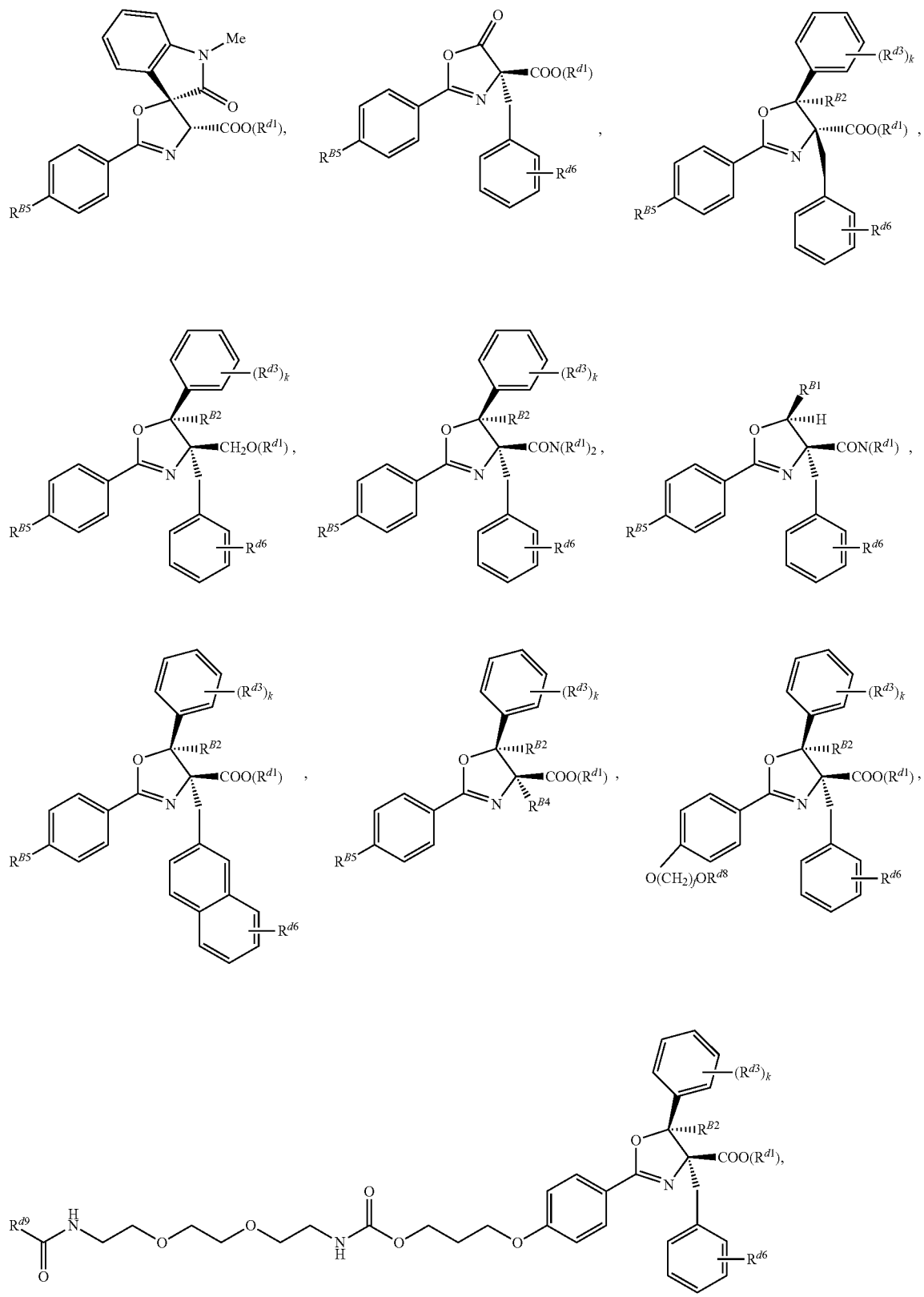

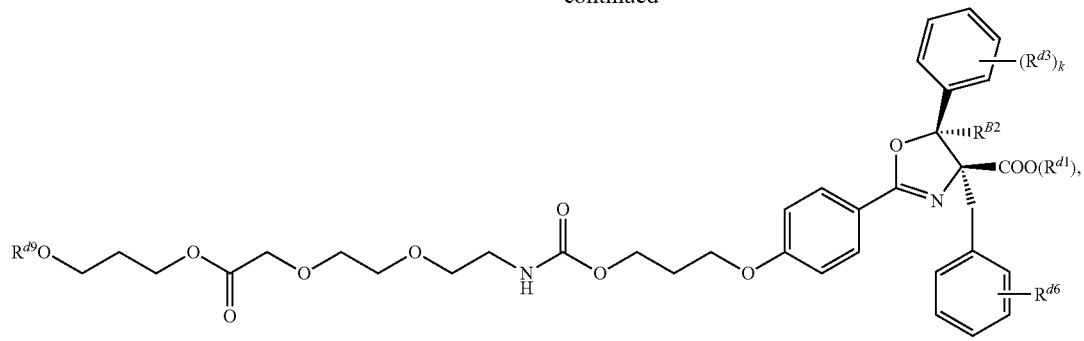
or a pharmaceutically acceptable salt thereof.
In certain embodiments, the compound of Formula (II) is of the formula:
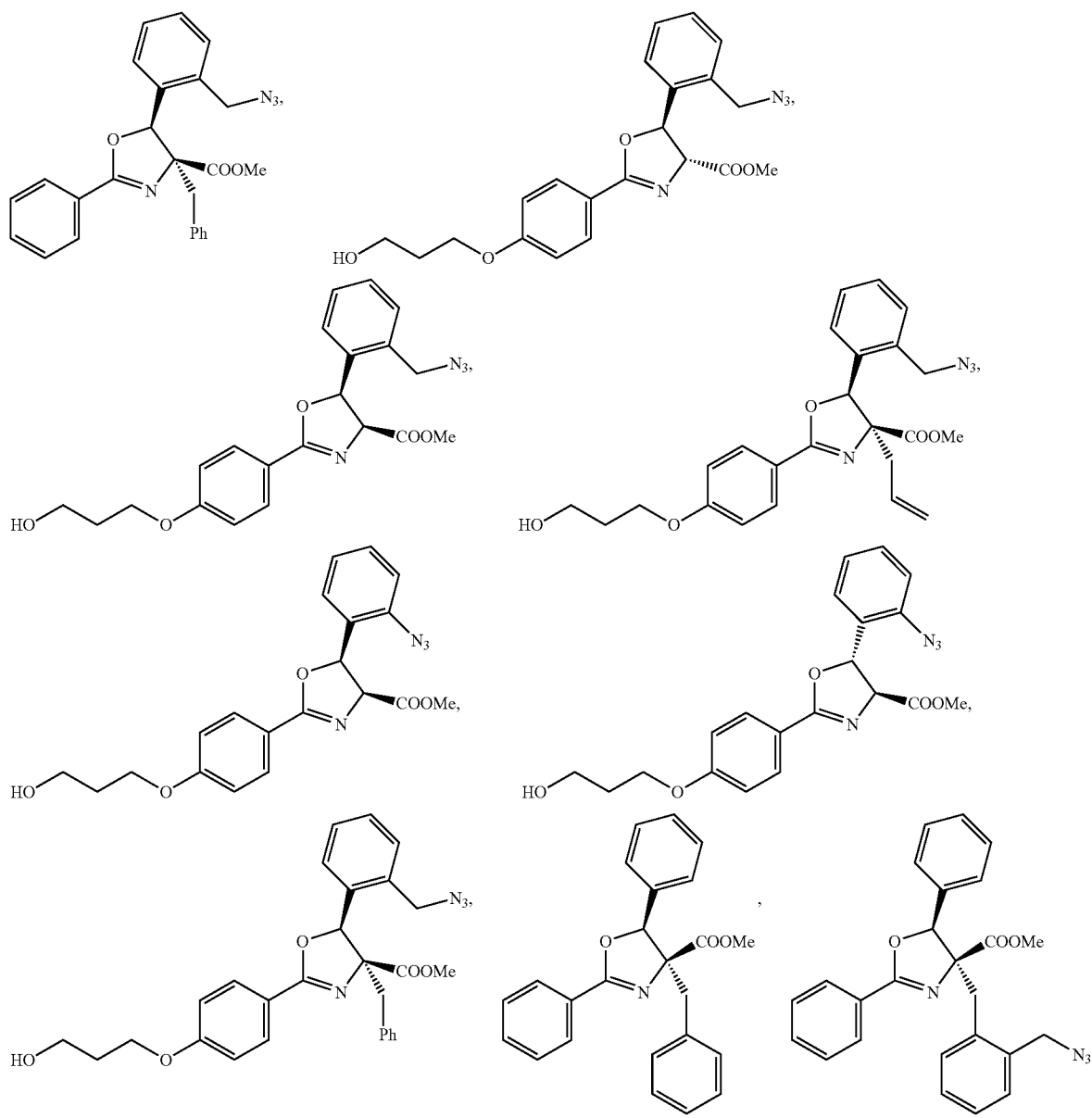

-continued
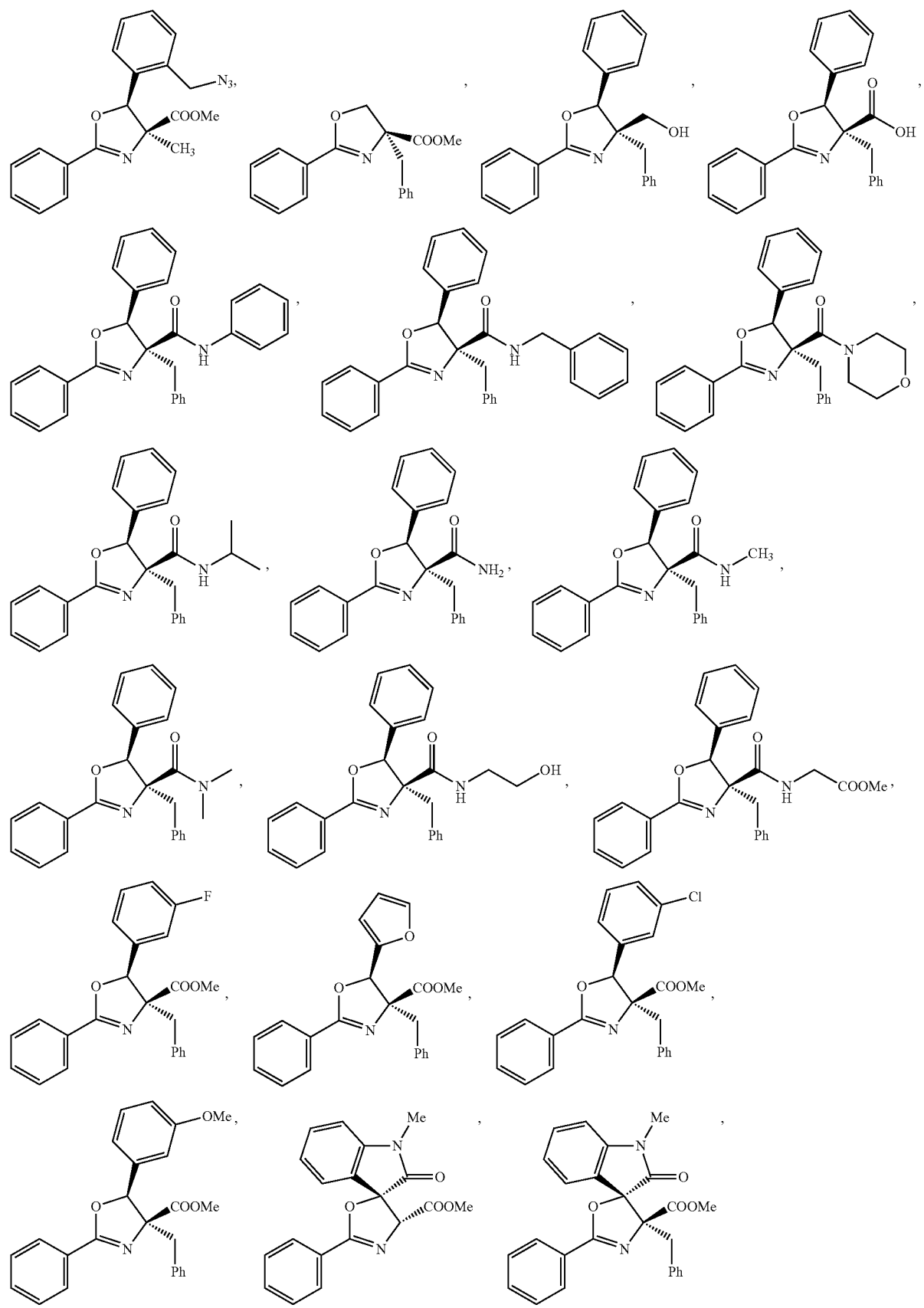

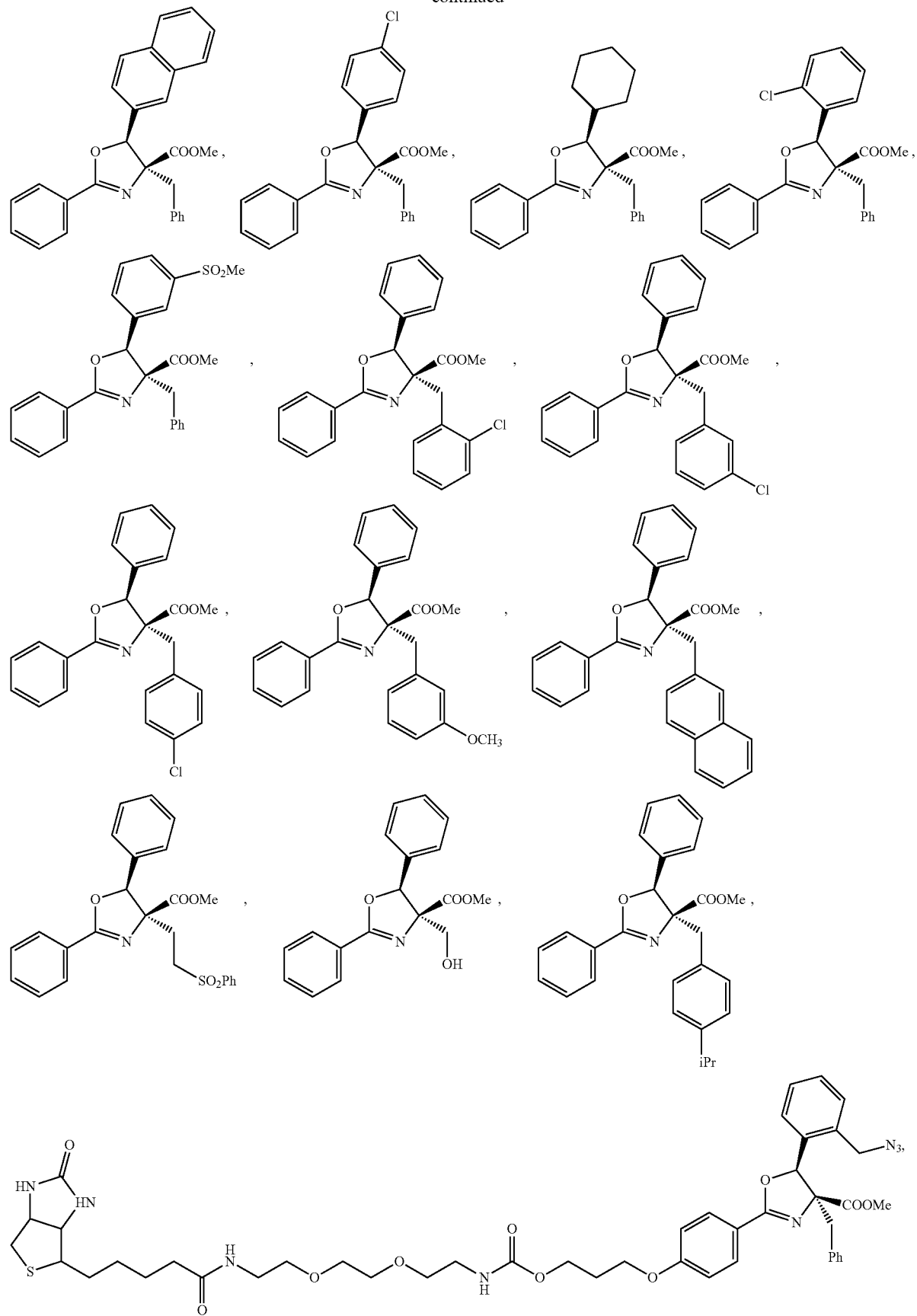

-continued
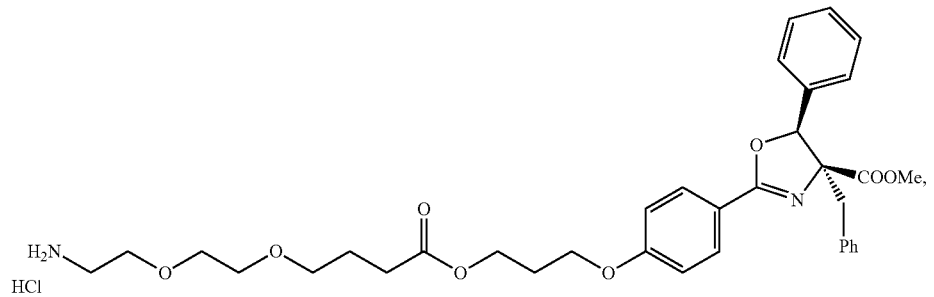
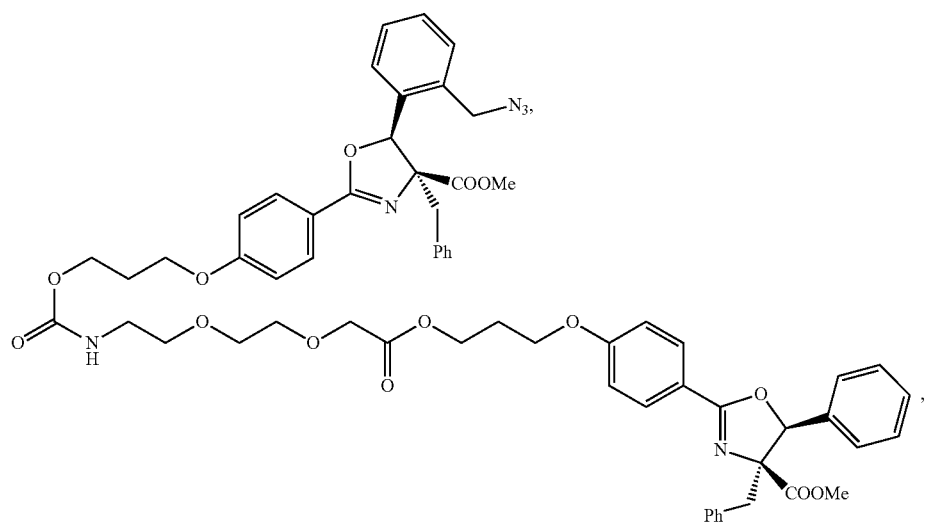
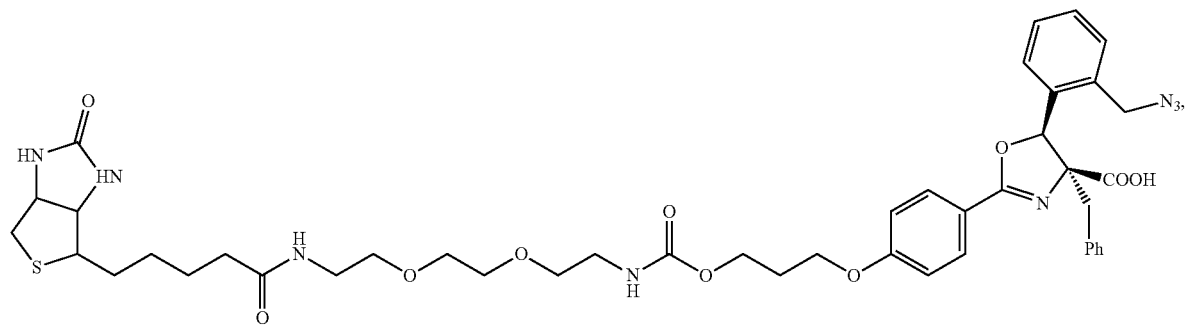
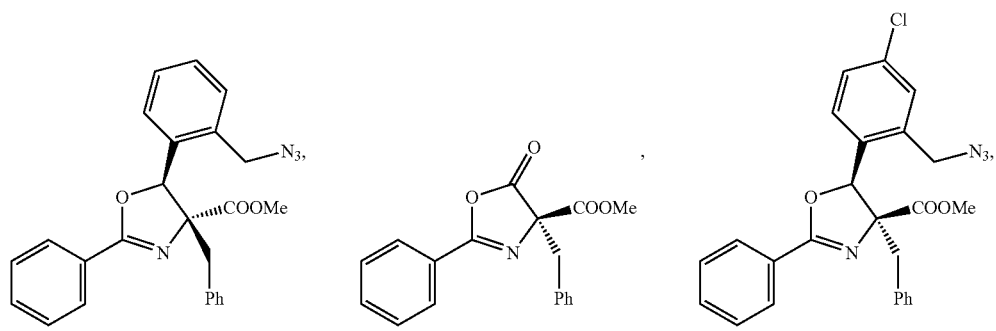
or a pharmaceutically acceptable salt thereof.

Compounds of Formula (II-A)

In certain embodiments, the compound is of Formula (II-A):

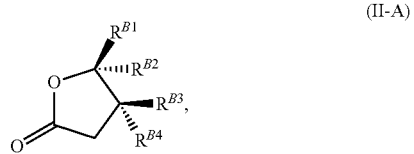

(II-A)

or a pharmaceutically acceptable salt, solvate, hydrate, polymorph, co-crystal, tautomer, stereoisomer, isotopically labeled derivative, or prodrug thereof, wherein:

$R^{B1}$ is independently hydrogen, halogen, substituted or unsubstituted alkyl, substituted or unsubstituted carbocyclyl, substituted or unsubstituted heterocyclyl, substituted or unsubstituted aryl, or substituted or unsubstituted heteroaryl, —$OR^{d1}$, —$N(R^{zz})_2$, —$SR^{d1}$, —CN, —SCN, or —$SO_2R^{d1}$;

$R^{B2}$ is independently hydrogen, halogen, substituted or unsubstituted alkyl, substituted or unsubstituted carbocyclyl, substituted or unsubstituted heterocyclyl, substituted or unsubstituted aryl, or substituted or unsubstituted heteroaryl, —$OR^{d1}$, —$N(R^{zz})_2$, —$SR^{d1}$, —CN, —SCN, or —$SO_2R^{d1}$;

or $R^{B1}$ and $R^{B2}$ are taken together to form =O, a spiro-linked, substituted or unsubstituted carbocyclyl, or a spiro-linked, substituted or unsubstituted heterocyclyl;

$R^{B3}$ is independently hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{d1}$, —$N(R^{zz})_2$, —$SR^{d1}$, —CN, or —SCN;

$R^{d1}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, oxygen protecting group, sulfur protecting group, or —$SO_2R"$;

each instance of $R^{zz}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, nitrogen protecting group, or optionally two $R^{zz}$ are taken together to form substituted or unsubstituted heterocyclyl or substituted or unsubstituted heteroaryl;

each instance of $R"$ is independently hydrogen, substituted or unsubstituted alkyl, or substituted or unsubstituted aryl; and $R^{B4}$ is independently hydrogen, halogen, substituted or unsubstituted acyl, substituted or unsubstituted alkyl, substituted or unsubstituted carbocyclyl, substituted or unsubstituted heterocyclyl, substituted or unsubstituted aryl, substituted or unsubstituted heteroaryl, —$OR^{d1}$, —$N(R^{zz})_2$, —$SR^{d1}$, —CN, —SCN;

or $R^{B3}$ and $R^{B4}$ are taken together to form =O, a spiro-linked, substituted or unsubstituted carbocyclyl, or a spiro-linked, substituted or unsubstituted heterocyclyl.

Formula (II-A) includes substituent $R^B$. In certain embodiments, $R^{B1}$ is hydrogen. In certain embodiments, $R^{B1}$ is halogen (e.g., F, Cl, Br, or I). In certain embodiments, $R^{B1}$ is substituted or unsubstituted $C_{1-6}$ alkyl. In certain embodiments, $R^{B1}$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, $R^{B1}$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^{B1}$ is substituted or unsubstituted aryl (e.g., substituted or unsubstituted, 6- to 10-membered aryl). In certain embodiments, $R^{B1}$ is substituted phenyl. In certain embodiments, $R^{B1}$ is unsubstituted phenyl. In certain embodiments, $R^{B1}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, $R^{B1}$ is —$OR^{d1}$ (e.g., —OMe). In certain embodiments, $R^{B1}$ is —$N(R^{zz})_2$ (e.g., —$NMe_2$). In certain embodiments, $R^{B1}$ is —$SR^{d1}$ (e.g., —SMe). In certain embodiments, $R^{B1}$ is —CN. In certain embodiments, $R^{B1}$ is —SCN. In certain embodiments, $R^{B1}$ is —$SO_2R^{d1}$.

Formula (II-A) may include substituent $R^{B2}$. In certain embodiments, $R^{B2}$ is hydrogen. In certain embodiments, $R^{B2}$ is halogen (e.g., F, Cl, Br, or I). In certain embodiments, $R^{B2}$ is substituted or unsubstituted $C_{1-6}$ alkyl. In certain embodiments, $R^{B2}$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, $R^{B2}$ s substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^{B2}$ is substituted or unsubstituted aryl (e.g., substituted or unsubstituted, 6- to 10-membered aryl). In certain embodiments, $R^{B2}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, $R^{B2}$ is —$OR^{d1}$ (e.g., —OMe). In certain embodiments, $R^{B2}$ is —$N(R^{zz})_2$ (e.g., —$NMe_2$). In certain embodiments, $R^{B2}$ is —$SR^{d1}$ (e.g., —SMe). In certain embodiments, $R^{B2}$ is —CN. In certain embodiments, $R^{B2}$ is —SCN. In certain embodiments, $R^{B2}$ is —$SO_2R^{d1}$.

In certain embodiments, substituents $R^{B1}$ and $R^{B2}$ are taken together to form =O. In certain embodiments, substituents $R^{B1}$ and $R^{B2}$ are taken together to form a spiro-linked, substituted or unsubstituted carbocyclyl (e.g., substituted or unsubstituted, 3- to 7-membered carbocyclyl comprising zero, one, or two double bonds in the carbocyclic ring system). In certain embodiments, substituents $R^{B1}$ and $R^{B2}$ are taken together to form a spiro-linked, substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur).

Formula (II-A) includes substituent $R^{B3}$. In certain embodiments, $R^{B3}$ is hydrogen. In certain embodiments, $R^{B3}$ is halogen (e.g., F, Cl, Br, or I). In certain embodiments, $R^{B3}$ is substituted or unsubstituted acyl. In certain embodiments, $R^{B3}$ is —C(=O)O$R^{d1}$. In certain embodiments, $R^{d1}$ is substituted or unsubstituted $C_{1-6}$ alkyl. In certain embodiments, $R^{B3}$ is substituted or unsubstituted $C_{1-6}$ alkyl. In certain embodiments, $R^{B3}$ is substituted or unsubstituted alkenyl (e.g., substituted or unsubstituted $C_{2-6}$ alkenyl). In certain embodiments, $R^{B3}$ is substituted or unsubstituted alkynyl (e.g., substituted or unsubstituted $C_{2-6}$ alkynyl). In certain embodiments, $R^{B3}$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, $R^{B3}$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^{B3}$ is substituted or unsubstituted aryl (e.g., substituted or unsubstituted, 6- to 10-membered aryl). In certain embodiments, $R^{B3}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, $R^{B3}$ is —O$R^{d1}$ (e.g., —OH, —O(substituted or unsubstituted $C_{1-6}$ alkyl) (e.g., —OMe, —OCF$_3$, —OEt, —OPr, —OBu, or —OBn), or —O(substituted or unsubstituted phenyl) (e.g., —OPh)). In certain embodiments, $R^{B3}$ is —N($R^{zz}$)$_2$ (e.g., —NH$_2$, —NH(substituted or unsubstituted $C_{1-6}$ alkyl) (e.g., —NHMe), or —NMe$_2$). In certain embodiments, $R^{B3}$ is —S$R^{d1}$ (e.g., —SH, —S(substituted or unsubstituted $C_{1-6}$ alkyl) (e.g., —SMe, —SEt, —SPr, —SBu, or —SBn), or —S(substituted or unsubstituted phenyl) (e.g., —SPh)). In certain embodiments, $R^{B3}$ is —CN. In certain embodiments, $R^{B3}$ is —SCN.

Formula (II-A) may include substituent $R^{B4}$. In certain embodiments, $R^{B4}$ is hydrogen. In certain embodiments, $R^{B4}$ is halogen (e.g., F, Cl, Br, or I). In certain embodiments, $R^{B4}$ is substituted or unsubstituted acyl. In certain embodiments, $R^{B4}$ is substituted or unsubstituted $C_{1-6}$ alkyl. In certain embodiments, $R^{B4}$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, $R^{B4}$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^{B4}$ is substituted or unsubstituted aryl (e.g., substituted or unsubstituted, 6- to 10-membered aryl). In certain embodiments, $R^{B4}$ is substituted benzyl. In certain embodiments, $R^{B4}$ is unsubstituted benzyl. In certain embodiments, $R^{B4}$ is of the formula:

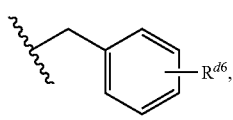

wherein $R^{d6}$ is independently hydrogen, halogen, substituted or unsubstituted alkyl, —N($R^{d7}$)$_2$, —S($R^{d7}$), or —O$R^{d7}$, wherein $R^{d7}$ is independently hydrogen or substituted or unsubstituted alkyl. In certain embodiments, $R^{B4}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, $R^{d6}$ is substituted or unsubstituted $C_{1-6}$ alkyl. In certain embodiments, $R^{d6}$ is —N($R^{d7}$)$_2$ (e.g., —NH$_2$, —NH(substituted or unsubstituted $C_{1-6}$ alkyl) (e.g., —NHMe), or —NMe$_2$). In certain embodiments, $R^{d6}$ is —S($R^{d7}$) (e.g., —SH, —S(substituted or unsubstituted $C_{1-6}$ alkyl) (e.g., —SMe, —SEt, —SPr, —SBu, or —SBn), or —S(substituted or unsubstituted phenyl) (e.g., —SPh)). In certain embodiments, $R^{d6}$ is —O$R^{d7}$ (e.g., —OH, —O(substituted or unsubstituted $C_{1-6}$ alkyl) (e.g., —OMe, —OCF$_3$, —OEt, —OPr, —OBu, or —OBn), or —O(substituted or unsubstituted phenyl) (e.g., —OPh)). In certain embodiments, $R^{B4}$ is —O$R^{d1}$ (e.g., —OMe). In certain embodiments, $R^{B4}$ is —N($R^{zz}$)$_2$ (e.g., —NMe$_2$). In certain embodiments, $R^{B4}$ is —S$R^{d1}$ (e.g., —SMe). In certain embodiments, $R^{B4}$ is —CN. In certain embodiments, $R^{B4}$ is —SCN. In certain embodiments, $R^{B4}$ is —SO$_2R^{d1}$.

In certain embodiments, substituents $R^{B3}$ and $R^{B4}$ are taken together to form =O. In certain embodiments, substituents $R^{B3}$ and $R^{B4}$ are taken together to form a spiro-linked, substituted or unsubstituted carbocyclyl (e.g., substituted or unsubstituted, 3- to 7-membered carbocyclyl comprising zero, one, or two double bonds in the carbocyclic ring system). In certain embodiments, substituents $R^{B3}$ and $R^{B4}$ are taken together to form a spiro-linked, substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur).

In certain embodiments, the compound of Formula (II-A) is of the formula:

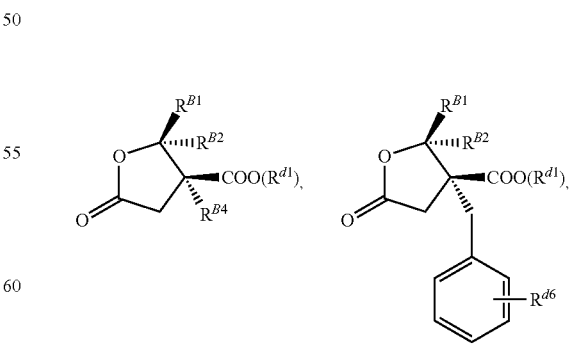

or a pharmaceutically acceptable salt thereof.

In certain embodiments, the compound of Formula (II-A) is of the following formula:

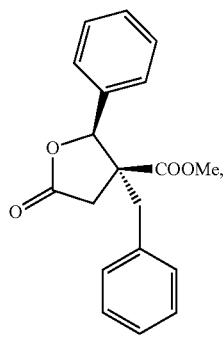 [SMILES: COC(=O)[C@@]1(Cc2ccccc2)CC(=O)O[C@H]1c1ccccc1]

or a pharmaceutically acceptable salt thereof.

Compounds of Formula (III)

In certain embodiments, the compound is of Formula (III):

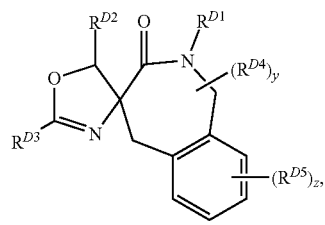
(III)

or a pharmaceutically acceptable salt, solvate, hydrate, polymorph, co-crystal, tautomer, stereoisomer, isotopically labeled derivative, or prodrug thereof, wherein:

y is 1, 2, 3, or 4;

z is 1, 2, 3, or 4;

$R^{D1}$ is independently hydrogen, substituted or unsubstituted acyl, substituted or unsubstituted alkyl, substituted or unsubstituted alkenyl, substituted or unsubstituted alkynyl, substituted or unsubstituted heterocyclyl, or substituted or unsubstituted aryl, substituted or unsubstituted heteroaryl, or nitrogen protecting group;

$R^{D2}$ is independently hydrogen, halogen, substituted or unsubstituted acyl, substituted or unsubstituted alkyl, substituted or unsubstituted heterocyclyl, substituted or unsubstituted aryl, or substituted or unsubstituted heteroaryl; and $R^{D3}$ is independently hydrogen, halogen, substituted or unsubstituted acyl, substituted or unsubstituted alkyl, substituted or unsubstituted heterocyclyl, substituted or unsubstituted aryl, or substituted or unsubstituted heteroaryl;

$R^{D4}$ is independently hydrogen, halogen, substituted or unsubstituted acyl, substituted or unsubstituted alkyl, substituted or unsubstituted heterocyclyl, substituted or unsubstituted aryl, or substituted or unsubstituted heteroaryl; and $R^{D5}$ is independently hydrogen, halogen, substituted or unsubstituted acyl, substituted or unsubstituted alkyl, substituted or unsubstituted heterocyclyl, substituted or unsubstituted aryl, or substituted or unsubstituted heteroaryl.

Formula (III) includes substituent $R^{D1}$. In certain embodiments, $R^{D1}$ is hydrogen. In certain embodiments, $R^{D1}$ is substituted or unsubstituted acyl (e.g., acetyl). In certain embodiments, $R^{D1}$ is —C(=O)$R^{f1}$; and $R^{f1}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl. In certain embodiments, $R^{f1}$ is hydrogen. In certain embodiments, $R^{f1}$ is substituted or unsubstituted $C_{1-6}$ alkyl. In certain embodiments, $R^{f1}$ is substituted or unsubstituted methyl. In certain embodiments, $R^{D1}$ is substituted or unsubstituted $C_{1-6}$ alkyl. In certain embodiments, $R^{D1}$ is

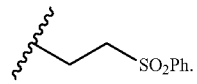

In certain embodiments, $R^{D1}$ is substituted or unsubstituted alkenyl (e.g., substituted or unsubstituted $C_{2-6}$ alkenyl). In certain embodiments, $R^{D1}$ is substituted or unsubstituted alkynyl (e.g., substituted or unsubstituted $C_{2-6}$ alkynyl). In certain embodiments, $R^{D1}$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^{D1}$ is substituted or unsubstituted aryl (e.g., substituted or unsubstituted, 6- to 10-membered aryl). In certain embodiments, $R^{D1}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, $R^{D1}$ is a nitrogen protecting group (e.g., benzyl (Bn), t-butyl carbonate (BOC or Boc), benzyl carbamate (Cbz), 9-fluorenylmethyl carbonate (Fmoc), trifluoroacetyl, triphenylmethyl, acetyl, or p-toluenesulfonamide (Ts)).

Formula (III) includes substituent $R^{D2}$. In certain embodiments, $R^{D2}$ is hydrogen. In certain embodiments, $R^{D2}$ is halogen (e.g., F, Cl, Br, or I). In certain embodiments, $R^{D2}$ is substituted or unsubstituted acyl. In certain embodiments, $R^{D2}$ is substituted or unsubstituted $C_{1-6}$ alkyl. In certain embodiments, $R^{D2}$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^{D2}$ is substituted or unsubstituted aryl (e.g., substituted or unsubstituted, 6- to 10-membered aryl). In certain embodiments, $R^{D2}$ is substituted phenyl. In certain embodiments, $R^{D2}$ is unsubstituted phenyl. In certain embodiments, $R^{D2}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur).

Formula (III) includes substituent $R^{D3}$. In certain embodiments, $R^{D3}$ is hydrogen. In certain embodiments, $R^{D3}$ is halogen (e.g., F, Cl, Br, or I). In certain embodiments, $R^{D3}$ is substituted or unsubstituted acyl. In certain embodiments, $R^{D3}$ is substituted or unsubstituted $C_{1-6}$ alkyl. In certain embodiments, $R^{D3}$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^{D3}$ is substituted or unsubstituted aryl (e.g., substituted or unsubstituted, 6- to 10-membered aryl). In certain embodiments, $R^{D3}$ is substituted phenyl. In certain embodiments, $R^{D3}$ is unsubstituted phenyl. In certain embodiments, $R^{D3}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur).

Formula (III) includes one or more instances of substituent $R^{D4}$. In certain embodiments, y is 1. In certain embodiments, y is 2. In certain embodiments, y is 3. In certain embodiments, y is 4. In certain embodiments, at least one instance of $R^{D4}$ is hydrogen. In certain embodiments, at least one instance of $R^{D4}$ is halogen (e.g., F, Cl, Br, or I). In certain embodiments, at least one instance of $R^{D4}$ is substituted or unsubstituted acyl. In certain embodiments, at least one instance of $R^{D4}$ is substituted or unsubstituted $C_{1-6}$ alkyl. In certain embodiments, at least one instance of $R^{D4}$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, at least one instance of $R^{D4}$ is substituted or unsubstituted aryl (e.g., substituted or unsubstituted, 6- to 10-membered aryl). In certain embodiments, at least one instance of $R^{D4}$ is substituted phenyl. In certain embodiments, at least one instance of $R^{D4}$ is unsubstituted phenyl. In certain embodiments, at least one instance of $R^{D4}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur).

Formula (III) includes one or more instances of substituent $R^{D5}$. In certain embodiments, z is 1. In certain embodiments, z is 2. In certain embodiments, z is 3. In certain embodiments, z is 4. In certain embodiments, at least one instance of $R^{D5}$ is hydrogen. In certain embodiments, at least one instance of $R^{D5}$ is halogen (e.g., F, Cl, Br, or I). In certain embodiments, at least one instance of $R^{D5}$ is substituted or unsubstituted acyl. In certain embodiments, at least one instance of $R^{D5}$ is substituted or unsubstituted $C_{1-6}$ alkyl. In certain embodiments, at least one instance of $R^{D5}$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, at least one instance of $R^{D5}$ is substituted or unsubstituted aryl (e.g., substituted or unsubstituted, 6- to 10-membered aryl). In certain embodiments, at least one instance of $R^{D5}$ is substituted phenyl. In certain embodiments, at least one instance of $R^{D5}$ is unsubstituted phenyl. In certain embodiments, at least one instance of $R^{D5}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur).

In certain embodiments, the compound of Formula (III) is of the following formulae:

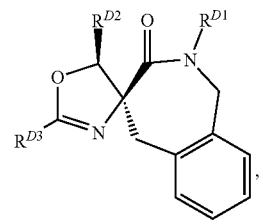

or a pharmaceutically acceptable salt thereof.

In certain embodiments, the compound of Formula (III) is of the formula:

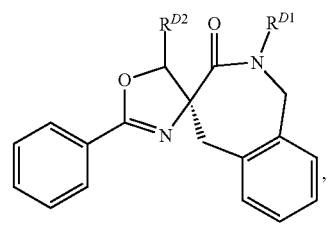

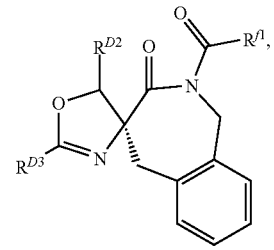

or a pharmaceutically acceptable salt thereof.

In certain embodiments, the compound of Formula (III) is of the formula:

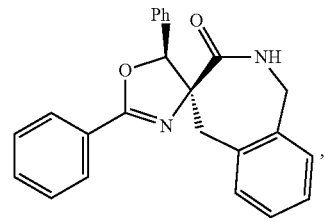

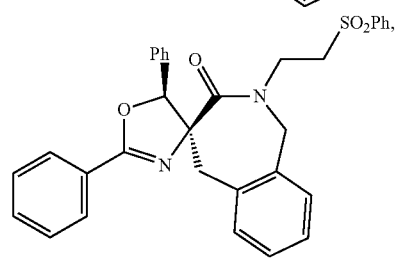

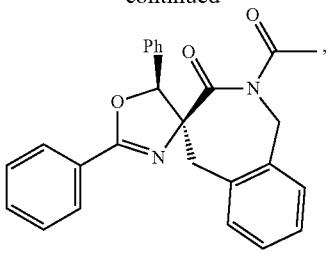

or a pharmaceutically acceptable salt thereof.

Compounds of Formula (IV)

In certain embodiments, the compound is of Formula (IV):

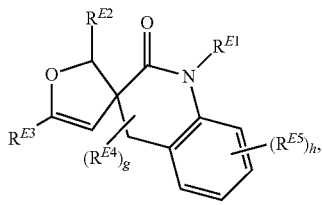

(IV)

or a pharmaceutically acceptable salt, solvate, hydrate, polymorph, co-crystal, tautomer, stereoisomer, isotopically labeled derivative, or prodrug thereof, wherein:

g is 1 or 2;

h is 1, 2, 3, or 4;

$R^{E1}$ is independently hydrogen, substituted or unsubstituted acyl, substituted or unsubstituted alkyl, substituted or unsubstituted alkenyl, substituted or unsubstituted alkynyl, substituted or unsubstituted heterocyclyl, substituted or unsubstituted aryl, or substituted or unsubstituted heteroaryl, or nitrogen protecting group;

$R^{E2}$ is independently hydrogen, halogen, substituted or unsubstituted acyl, substituted or unsubstituted alkyl, substituted or unsubstituted heterocyclyl, substituted or unsubstituted aryl, or substituted or unsubstituted heteroaryl;

$R^{E3}$ is independently hydrogen, halogen, substituted or unsubstituted acyl, substituted or unsubstituted alkyl, substituted or unsubstituted heterocyclyl, substituted or unsubstituted aryl, or substituted or unsubstituted heteroaryl; and $R^{E}$ is independently hydrogen, halogen, substituted or unsubstituted acyl, substituted or unsubstituted alkyl, substituted or unsubstituted heterocyclyl, substituted or unsubstituted aryl, or substituted or unsubstituted heteroaryl; and $R^{E5}$ is independently hydrogen, halogen, substituted or unsubstituted acyl, substituted or unsubstituted alkyl, substituted or unsubstituted heterocyclyl, substituted or unsubstituted aryl, or substituted or unsubstituted heteroaryl.

Formula (IV) includes substituent $R^{E1}$. In certain embodiments, $R^{E1}$ is hydrogen. In certain embodiments, $R^{E1}$ is halogen (e.g., F, Cl, Br, or I). In certain embodiments, $R^{E1}$ is substituted or unsubstituted acyl (e.g., acetyl). In certain embodiments, $R^{E1}$ is —C(=O)$R^{g1}$, and $R^{g1}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl. In certain embodiments, $R^{E1}$ is —C(=O)O$R^{g1}$. In certain embodiments, $R^{g1}$ is substituted or unsubstituted $C_{1-6}$ alkyl. In certain embodiments, $R^{g1}$ is substituted or unsubstituted methyl. In certain embodiments, $R^{g1}$ is substituted or unsubstituted ethyl. In certain embodiments, $R^{E1}$ is substituted or unsubstituted $C_{1-6}$ alkyl. In certain embodiments, $R^{E1}$ is —CH$_2$C(=O)O$R^{g1}$. In certain embodiments, $R^{E1}$ is of the formula:

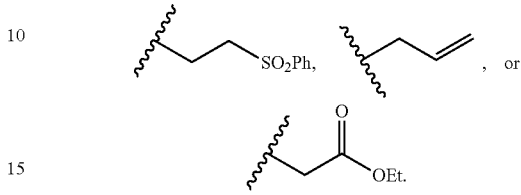

In certain embodiments, $R^{E1}$ is substituted or unsubstituted alkenyl (e.g., substituted or unsubstituted $C_{2-6}$ alkenyl). In certain embodiments, $R^{E1}$ is substituted or unsubstituted alkynyl (e.g., substituted or unsubstituted $C_{2-6}$ alkynyl). In certain embodiments, $R^{E1}$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^{E1}$ is substituted or unsubstituted aryl (e.g., substituted or unsubstituted, 6- to 10-membered aryl). In certain embodiments, $R^{E1}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, $R^{E1}$ is a nitrogen protecting group (e.g., benzyl (Bn), t-butyl carbonate (BOC or Boc), benzyl carbamate (Cbz), 9-fluorenylmethyl carbonate (Fmoc), trifluoroacetyl, triphenylmethyl, acetyl, or p-toluenesulfonamide (Ts)).

Formula (IV) includes substituent $R^{E2}$. In certain embodiments, $R^{E2}$ is hydrogen. In certain embodiments, $R^{E2}$ is halogen (e.g., F, Cl, Br, or I). In certain embodiments, $R^{E2}$ is substituted or unsubstituted acyl (e.g., acetyl). In certain embodiments, $R^{E2}$ is substituted or unsubstituted $C_{1-6}$ alkyl. In certain embodiments, $R^{E2}$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^{E2}$ is substituted or unsubstituted aryl (e.g., substituted or unsubstituted, 6- to 10-membered aryl). In certain embodiments, $R^{E2}$ is substituted phenyl. In certain embodiments, $R^{E2}$ is unsubstituted phenyl. In certain embodiments, $R^{E2}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur).

Formula (IV) includes substituent $R^{E3}$. In certain embodiments, $R^{E3}$ is hydrogen. In certain embodiments, $R^{E3}$ is halogen (e.g., F, Cl, Br, or I). In certain embodiments, $R^{E3}$ is substituted or unsubstituted acyl (e.g., acetyl). In certain embodiments, $R^{E3}$ is substituted or unsubstituted $C_{1-6}$ alkyl. In certain embodiments, $R^{E3}$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^{E3}$ is substituted or unsubstituted aryl (e.g., substituted or unsubstituted, 6- to 10-membered aryl). In certain embodiments, $R^{E3}$ is substituted phenyl. In certain embodiments, $R^{E3}$ is unsubstituted phenyl. In certain embodiments, $R^{E3}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur).

Formula (IV) includes one or more instances of substituent $R^{E4}$. In certain embodiments, g is 1. In certain embodiments, g is 2. In certain embodiments, at least one instance of $R^{E4}$ is hydrogen. In certain embodiments, at least one instance of $R^{E4}$ is halogen (e.g., F, Cl, Br, or I). In certain embodiments, at least one instance of $R^{E4}$ is substituted or unsubstituted acyl (e.g., acetyl). In certain embodiments, at least one instance of $R^{E4}$ is substituted or unsubstituted $C_{1-6}$ alkyl. In certain embodiments, at least one instance of $R^{E4}$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, at least one instance of $R^{E4}$ is substituted or unsubstituted aryl (e.g., substituted or unsubstituted, 6- to 10-membered aryl). In certain embodiments, at least one instance of $R^{E4}$ is substituted phenyl. In certain embodiments, at least one instance of $R^{E4}$ is unsubstituted phenyl. In certain embodiments, at least one instance of $R^{E4}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur).

Formula (IV) includes one or more instances of substituent $R^{E5}$. In certain embodiments, h is 1. In certain embodiments, h is 2. In certain embodiments, h is 3. In certain embodiments, h is 4. In certain embodiments, at least one instance of $R^{E5}$ is hydrogen. In certain embodiments, at least one instance of $R^{E5}$ is halogen (e.g., F, Cl, Br, or I). In certain embodiments, at least one instance of $R^{E5}$ is substituted or unsubstituted acyl (e.g., acetyl). In certain embodiments, at least one instance of $R^{E5}$ is substituted or unsubstituted $C_{1-6}$ alkyl. In certain embodiments, at least one instance of $R^{E5}$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, at least one instance of $R^{E5}$ is substituted or unsubstituted aryl (e.g., substituted or unsubstituted, 6- to 10-membered aryl). In certain embodiments, at least one instance of $R^{E5}$ is substituted phenyl. In certain embodiments, at least one instance of $R^{E5}$ is unsubstituted phenyl. In certain embodiments, at least one instance of $R^{E5}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur).

In certain embodiments, the compound of Formula (IV) is of the formula:

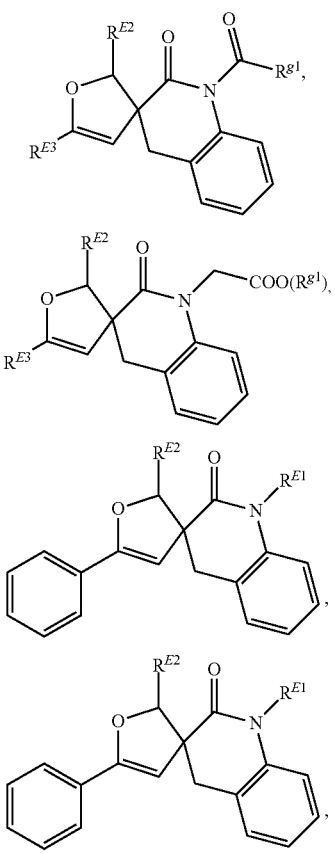

or a pharmaceutically acceptable salt thereof.

In certain embodiments, the compound of Formula (IV) is of the formula:

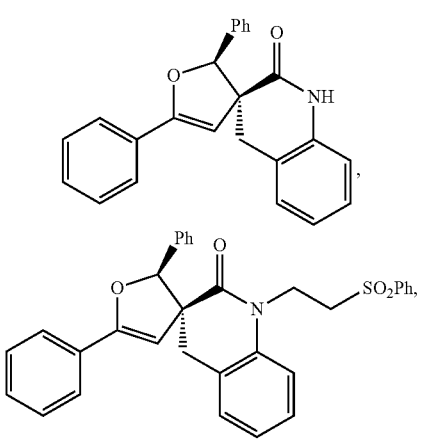

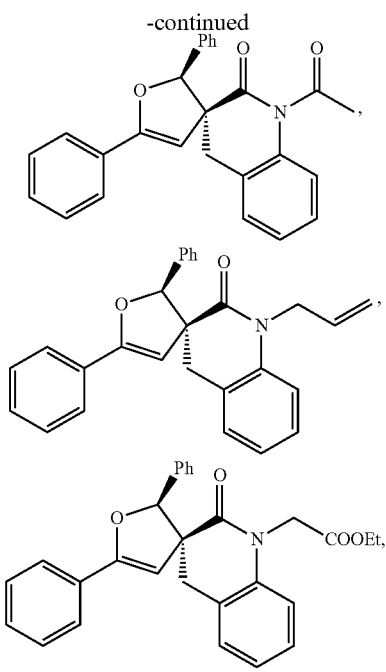

or a pharmaceutically acceptable salt thereof.

The compounds described herein may bind (e.g., reversibly binding or irreversibly binding, through covalent and/or non-covalent interactions) MAX. The compounds described herein may also prevent or reduce the interaction or binding of MAX with another molecule (e.g., peptide or protein). The compounds described herein may be useful in modulating (e.g., inhibiting) the activity of Myc, Mad, or Mxi1 in a subject in need thereof, treating diseases associated with Myc (e.g., diseases associated with aberrant activity (e.g., increased activity) of Myc) in a subject in need thereof, treating diseases in a subject in need thereof (e.g., proliferative diseases), preventing diseases associated with Myc (e.g., diseases associated with aberrant activity (e.g., increased activity) of Myc) in a subject in need thereof, and/or preventing diseases in a subject in need thereof (e.g., proliferative diseases), and/or as research tools (e.g., for studying Myc (e.g., studying the activity of Myc, studying the role of Myc in transcription or gene regulation) in a subject, biological sample, tissue, or cell).

Pharmaceutical Compositions, Kits, and Administration

The present disclosure also provides pharmaceutical compositions comprising a compound described herein and optionally a pharmaceutically acceptable excipient. The pharmaceutical compositions may be useful in binding MAX, modulating (e.g., inhibiting) the activity of Myc, Mad, or Mxi1 in a subject in need thereof, treating diseases associated with Myc (e.g., diseases associated with aberrant activity (e.g., increased activity) of Myc) in a subject in need thereof, treating diseases in a subject in need thereof (e.g., proliferative diseases), preventing diseases associated with Myc (e.g., diseases associated with aberrant activity (e.g., increased activity) of Myc) in a subject in need thereof, and/or preventing diseases (e.g., proliferative diseases) in a subject in need thereof. The pharmaceutical compositions described herein may be useful for modulating (e.g., inhibiting) the transcription of genes controlled by Myc (e.g., c-Myc, L-Myc, or N-Myc), Mad, or Mxi1 in a subject in need thereof. The pharmaceutical compositions described herein may also be useful as research tools, e.g., for studying Myc (e.g., studying the role of Myc in transcription or gene regulation) in a subject, biological sample, tissue, or cell.

In certain embodiments, the Myc is c-Myc. In certain embodiments, the Myc is L-Myc or N-Myc. In certain embodiments, the compositions may bind Mad. In certain embodiments, the compositions may bind Mxi1.

In certain embodiments, the subject being treated is an animal. The animal may be of either sex and may be at any stage of development. In certain embodiments, the subject described herein is a human. In certain embodiments, the subject is a non-human animal. In certain embodiments, the subject is a mammal. In certain embodiments, the subject is a non-human mammal. In certain embodiments, the subject is a domesticated animal, such as a dog, cat, cow, pig, horse, sheep, or goat. In certain embodiments, the subject is a companion animal, such as a dog or cat. In certain embodiments, the subject is a livestock animal, such as a cow, pig, horse, sheep, or goat. In certain embodiments, the subject is a zoo animal. In another embodiment, the subject is a research animal, such as a rodent (e.g., mouse, rat), dog, pig, or non-human primate. In certain embodiments, the animal is a genetically engineered animal. In certain embodiments, the animal is a transgenic animal (e.g., transgenic mice and transgenic pigs). In certain embodiments, the subject is a fish or reptile.

In certain embodiments, the cell contacted with an effective amount of a compound or pharmaceutical composition described herein is in vitro. In certain embodiments, the contacted cell is ex vivo. In certain embodiments, the contacted cell described herein is in vivo.

In certain embodiments, the compound described herein is provided in an effective amount in the pharmaceutical composition. In certain embodiments, the effective amount is a therapeutically effective amount. In certain embodiments, the effective amount is a prophylactically effective amount. In certain embodiments, a therapeutically effective amount is an amount effective for binding MAX. In certain embodiments, a therapeutically effective amount is an amount effective for modulating (e.g., inhibiting) the activity of Myc. In certain embodiments, a therapeutically effective amount is an amount effective for treating a disease disease (e.g., proliferative disease). In certain embodiments, a therapeutically effective amount is an amount effective for modulating (e.g., inhibiting) the activity of Myc, Mad, or Mxi1 and treating a disease (e.g., proliferative disease). In certain embodiments, a prophylactically effective amount is an amount effective for modulating (e.g., inhibiting) the activity of Myc, Mad, or Mxi1. In certain embodiments, a prophylactically effective amount is an amount effective for modulating (e.g., inhibiting) the transcription of genes controlled by Myc (e.g., c-Myc, L-Myc, or N-Myc), Mad, or Mxi1 in a subject in need thereof. In certain embodiments, a prophylactically effective amount is an amount effective for preventing a disease (e.g., proliferative disease). In certain embodiments, a prophylactically effective amount is an amount effective for modulating (e.g., inhibiting) the activity of Myc, Mad, or Mxi1 and preventing a disease (e.g., proliferative disease).

In certain embodiments, the effective amount is an amount effective for modulating (e.g., inhibiting) the activity of Myc by at least 10%, at least 20%, at least 30%, at least 40%, at least 50%, at least 60%, at least 70%, at least 80%, at least 90%, at least 95%, or at least 98%. In certain embodiments, the effective amount is an amount effective for modulating (e.g., inhibiting) the activity of Myc by not more than 10%, not more than 20%, not more than 30%, not more than 40%, not more than 50%, not more than 60%, not more than 70%, not more than 80%, not more than 90%, not more than 95%, or not more than 98%.

Pharmaceutical compositions described herein can be prepared by any method known in the art of pharmacology. In general, such preparatory methods include bringing the compound described herein (i.e., the "active ingredient") into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as one-half or one-third of such a dosage.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween® 20), polyoxyethylene sorbitan (Tween® 60), polyoxyethylene sorbitan monooleate (Tween® 80), sorbitan monopalmitate (Span® 40), sorbitan monostearate (Span® 60), sorbitan tristearate (Span® 65), glyceryl monooleate, sorbitan monooleate (Span® 80), polyoxyethylene esters (e.g., polyoxyethylene monostearate (Myrj® 45), polyoxyethylene hydrogenated castor oil, polyethoxylated castor oil, polyoxymethylene stearate, and Solutol®), sucrose fatty acid esters, polyethylene glycol fatty acid esters (e.g., Cremophor®), polyoxyethylene ethers, (e.g., polyoxyethylene lauryl ether (Brij® 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F-68, poloxamer P-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant® Plus, Phenonip®, methylparaben, Germall® 115, Germaben® II, Neolone®, Kathon®, and Euxyl®.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates described herein are mixed with solubilizing agents such as Cremophor®, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Compositions for rectal or vaginal administration are typically suppositories which can be prepared by mixing the conjugates described herein with suitable non-irritating excipients or carriers such as cocoa butter, polyethylene glycol, or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Dosage forms for topical and/or transdermal administration of a compound described herein may include ointments, pastes, creams, lotions, gels, powders, solutions, sprays, inhalants, and/or patches. Generally, the active ingredient is admixed under sterile conditions with a pharmaceutically acceptable carrier or excipient and/or any needed preservatives and/or buffers as can be required. Additionally, the present disclosure contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices. Intradermal compositions can be administered by devices which limit the effective penetration length of a needle into the skin. Alternatively or additionally, conventional syringes can be used in the classical mantoux method of intradermal administration. Jet injection devices which deliver liquid formulations to the dermis via a liquid jet injector and/or via a needle which pierces the stratum corneum and produces a jet which reaches the dermis are suitable. Ballistic powder/particle delivery devices which use compressed gas to accelerate the compound in powder form through the outer layers of the skin to the dermis are suitable.

Formulations suitable for topical administration include, but are not limited to, liquid and/or semi-liquid preparations such as liniments, lotions, oil-in-water and/or water-in-oil emulsions such as creams, ointments, and/or pastes, and/or solutions and/or suspensions. Topically administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition described herein can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions described herein formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition described herein. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein. A pharmaceutical composition described herein can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition described herein can be prepared, packaged, and/or sold in a formulation for ophthalmic administration. Such formulations may, for example, be in the form of eye drops including, for example, a 0.1-1.0% (w/w) solution and/or suspension of the active ingredient in an aqueous or oily liquid carrier or excipient. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are also contemplated as being within the scope of this disclosure.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily usage of the compositions described herein will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the compound or pharmaceutical composition described herein is suitable for topical administration to the eye of a subject.

The exact amount of a compound required to achieve an effective amount will vary from subject to subject, depending, for example, on species, age, and general condition of a subject, severity of the side effects or disorder, identity of the particular compound, mode of administration, and the like. An effective amount may be included in a single dose (e.g., single oral dose) or multiple doses (e.g., multiple oral doses). In certain embodiments, when multiple doses are administered to a subject or applied to a biological sample, tissue, or cell, any two doses of the multiple doses include different or substantially the same amounts of a compound described herein. In certain embodiments, when multiple doses are administered to a subject or applied to a biological sample, tissue, or cell, the frequency of administering the multiple doses to the subject or applying the multiple doses to the biological sample, tissue, or cell is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the biological sample, tissue, or cell is one dose per day. In certain embodiments, the frequency of administering the multiple doses to the subject or applying the multiple doses to the biological sample, tissue, or cell is two doses per day. In certain embodiments, the frequency of administering the multiple doses to the subject or applying the multiple doses to the biological sample, tissue, or cell is three doses per day. In certain embodiments, when multiple doses are administered to a subject or applied to a biological sample, tissue, or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, tissue, or cell. In certain embodiments, the duration between the first dose and last dose of the multiple doses is three months, six months, or one year. In certain embodiments, the duration between the first dose and last dose of the multiple doses is the lifetime of the subject, tissue, or cell. In certain embodiments, a dose (e.g., a single dose, or any dose of multiple doses) described herein includes independently between 0.1 µg and 1 µg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of a compound described herein. In certain embodiments, a dose described herein includes independently between 1 mg and 3 mg, inclusive, of a compound described herein. In certain embodiments, a dose described herein includes independently between 3 mg and 10 mg, inclusive, of a compound described herein. In certain embodiments, a dose described herein includes independently between 10 mg and 30 mg, inclusive, of a compound described herein. In certain embodiments, a dose described herein includes independently between 30 mg and 100 mg, inclusive, of a compound described herein.

Dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

A compound or composition, as described herein, can be administered in combination with one or more additional pharmaceutical agents (e.g., therapeutically and/or prophylactically active agents). The compounds or compositions can be administered in combination with additional pharmaceutical agents that improve their activity (e.g., activity (e.g., potency and/or efficacy) in treating a disease (e.g., proliferative disease) in a subject in need thereof, in preventing a disease in a subject in need thereof, in binding MAX and/or modulating (e.g., inhibiting) the activity of Myc in a subject, biological sample, tissue, or cell, or to improve bioavailability, improve safety, reduce drug resistance, reduce and/or modify metabolism, inhibit excretion, and/or modify distribution in a subject, biological sample, tissue, or cell. It will also be appreciated that the therapy employed may achieve a desired effect for the same disorder, and/or it may achieve different effects. In certain embodiments, a pharmaceutical composition described herein including a compound described herein and an additional pharmaceutical agent shows a synergistic effect that is absent in a pharmaceutical composition including one of the compound and the additional pharmaceutical agent, but not both.

The compound or composition can be administered concurrently with, prior to, or subsequent to one or more additional pharmaceutical agents, which may be useful as, e.g., combination therapies. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the compound described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

The additional pharmaceutical agents include, but are not limited to, anti-proliferative agents, anti-cancer agents, anti-angiogenesis agents, anti-inflammatory agents, immunosuppressants, anti-bacterial agents, anti-viral agents, cardiovascular agents, cholesterol-lowering agents, anti-diabetic agents, anti-allergic agents, contraceptive agents, pain-relieving agents, and combinations thereof. In certain embodiments, the additional pharmaceutical agent is an anti-proliferative agent (e.g., anti-cancer agent). In certain embodiments, the additional pharmaceutical agent is ABITREXATE (methotrexate), ADE, Adriamycin RDF (doxorubicin hydrochloride), Ambochlorin (chlorambucil), ARRANON (nelarabine), ARZERRA (ofatumumab), BOSULIF (bosutinib), BUSULFEX (busulfan), CAMPATH (alemtuzumab), CERUBIDINE (daunorubicin hydrochloride), CLAFEN (cyclophosphamide), CLOFAREX (clofarabine), CLOLAR (clofarabine), CVP, CYTOSAR-U (cytarabine), CYTOXAN (cyclophosphamide), ERWINAZE (Asparaginase Erwinia Chrysanthemi), FLUDARA (fludarabine phosphate), FOLEX (methotrexate), FOLEX PFS (methotrexate), GAZYVA (obinutuzumab), GLEEVEC (imatinib mesylate), Hyper-CVAD, ICLUSIG (ponatinib hydrochloride), IMBRUVICA (ibrutinib), LEUKERAN (chlorambucil), LINFOLIZIN (chlorambucil), MARQIBO (vincristine sulfate liposome), METHOTREXATE LPF (methorexate), MEXATE (methotrexate), MEXATE-AQ (methotrexate), mitoxantrone hydrochloride, MUSTARGEN (mechlorethamine hydrochloride), MYLERAN (busulfan), NEOSAR (cyclophosphamide), ONCASPAR (Pegaspargase), PURINETHOL (mercaptopurine), PURIXAN (mercaptopurine), Rubidomycin (daunorubicin hydrochloride), SPRYCEL (dasatinib), SYNRIBO (omacetaxine mepesuccinate), TARABINE PFS (cytarabine), TASIGNA (nilotinib), TREANDA (bendamustine hydrochloride), TRISENOX (arsenic trioxide), VINCASAR PFS (vincristine sulfate), ZYDELIG (idelalisib), or a combination thereof. In certain embodiments, the additional pharmaceutical agent is an anti-lymphoma agent. In certain embodiments, the additional pharmaceutical agent is ABITREXATE (methotrexate), ABVD, ABVE, ABVE-PC, ADCETRIS (brentuximab vedotin), ADRIAMYCIN PFS (doxorubicin hydrochloride), ADRIAMYCIN RDF (doxorubicin hydrochloride), AMBOCHLORIN (chlorambucil), AMBOCLORIN (chlorambucil), ARRANON (nelarabine), BEACOPP, BECENUM (carmustine), BELEODAQ (belinostat), BEXXAR (tositumomab and iodine I 131 tositumomab), BICNU (carmustine), BLENOXANE (bleomycin), CARMUBRIS (carmustine), CHOP, CLAFEN (cyclophosphamide), COPP, COPP-ABV, CVP, CYTOXAN (cyclophosphamide), DEPOCYT (liposomal cytarabine), DTIC-DOME (dacarbazine), EPOCH, FOLEX (methotrexate), FOLEX PFS (methotrexate), FOLOTYN (pralatrexate), HYPER-CVAD, ICE, IMBRUVICA (ibrutinib), INTRON A (recombinant interferon alfa-2b), ISTODAX (romidepsin), LEUKERAN (chlorambucil), LINFOLIZIN (chlorambucil), Lomustine, MATULANE (procarbazine hydrochloride), METHOTREXATE LPF (methotrexate), MEXATE (methotrexate), MEXATE-AQ (methotrexate), MOPP, MOZOBIL (plerixafor), MUSTARGEN (mechlorethamine hydrochloride), NEOSAR (cyclophosphamide), OEPA, ONTAK (denileukin diftitox), OPPA, R-CHOP, REVLIMID (lenalidomide), RITUXAN (rituximab), STANFORD V, TREANDA (bendamustine hydrochloride), VAMP, VELBAN (vinblastine sulfate), VELCADE (bortezomib), VELSAR (vinblastine sulfate), VINCASAR PFS (vincristine sulfate), ZEVALIN (ibritumomab tiuxetan), ZOLINZA (vorinostat), ZYDELIG (idelalisib), or a combination thereof. In certain embodiments, the additional pharmaceutical agent is REVLIMID (lenalidomide), DACOGEN (decitabine), VIDAZA (azacitidine), CYTOSAR-U (cytarabine), IDAMYCIN (idarubicin), CERUBIDINE (daunorubicin), LEUKERAN (chlorambucil), NEOSAR (cyclophosphamide), FLUDARA (fludarabine), LEUSTATIN (cladribine), or a combination thereof. In certain embodiments, the additional pharmaceutical agent is ABITREXATE (methotrexate), ABRAXANE (paclitaxel albumin-stabilized nanoparticle formulation), AC, AC-T, ADE, ADRIAMYCIN PFS (doxorubicin hydrochloride), ADRUCIL (fluorouracil), AFINITOR (everolimus), AFINITOR DISPERZ (everolimus), ALDARA (imiquimod), ALIMTA (pemetrexed disodium), AREDIA (pamidronate disodium), ARIMIDEX (anastrozole), AROMASIN (exemestane), AVASTIN (bevacizumab), BECENUM (carmustine), BEP, BICNU (carmustine), BLENOXANE (bleomycin), CAF, CAMPTOSAR (irinotecan hydrochloride), CAPOX, CAPRELSA (vandetanib), CARBOPLATIN-TAXOL, CARMUBRIS (carmustine), CASODEX (bicalutamide), CEENU (lomustine), CERUBIDINE (daunorubicin hydrochloride), CERVARIX (recombinant HPV bivalent vaccine), CLAFEN (cyclophosphamide), CMF, COMETRIQ (cabozantinib-s-malate), COSMEGEN (dactinomycin), CYFOS (ifosfamide), CYRAMZA (ramucirumab), CYTOSAR-U (cytarabine), CYTOXAN (cyclophosphamide), DACOGEN (decitabine), DEGARELIX, DOXIL (doxorubicin hydrochloride liposome), DOXORUBICIN HYDROCHLORIDE, DOX-SL (doxorubicin hydrochloride liposome), DTIC-DOME (dacarbazine), EFUDEX (fluorouracil), ELLENCE (epirubicin hydrochloride), ELOXATIN (oxaliplatin), ERBITUX (cetuximab), ERIVEDGE (vismodegib), ETOPOPHOS (etoposide phosphate), EVACET (doxorubicin hydrochloride liposome), FARESTON (toremifene), FASLODEX (fulvestrant), FEC, FEMARA (letrozole), FLUOROPLEX (fluorouracil), FOLEX (methotrexate), FOLEX PFS (methotrexate), FOLFIRI, FOLFIRI-BEVACIZUMAB, FOLFIRI-CETUXIMAB, FOLFIRINOX, FOLFOX, FU-LV, GARDASIL (recombinant human papillomavirus (HPV) quadrivalent vaccine), GEMCITABINE-CISPLATIN, GEMCITABINE-OXALIPLATIN, GEMZAR (gemcitabine hydrochloride), GILOTRIF (afatinib dimaleate), GLEEVEC (imatinib mesylate), GLIADEL (carmustine implant), GLIADEL WAFER (carmustine implant), HERCEPTIN (trastuzumab), HYCAMTIN (topotecan hydrochloride), IFEX (ifosfamide), IFOSFAMIDUM (ifosfamide), INLYTA (axitinib), INTRON A (recombinant interferon alfa-2b), IRESSA (gefitinib), IXEMPRA (ixabepilone), JAKAFI (ruxolitinib phosphate), JEVTANA (cabazitaxel), KADCYLA (ado-trastuzumab emtansine), KEYTRUDA (pembrolizumab), KYPROLIS (carfilzomib), LIPODOX (doxorubicin hydrochloride liposome), LUPRON (leuprolide acetate), LUPRON DEPOT (leuprolide acetate), LUPRON DEPOT-3 MONTH (leuprolide acetate), LUPRON DEPOT-4 MONTH (leuprolide acetate), LUPRON DEPOT-PED (leuprolide acetate), MEGACE (megestrol acetate), MEKINIST (trametinib), METHAZOLASTONE (temozolomide), METHOTREXATE LPF (methotrexate), MEXATE (methotrexate), MEXATE-AQ (methotrexate), MITOXANTRONE HYDROCHLORIDE, MITOZYTREX (mitomycin c), MOZOBIL (plerixafor), MUSTARGEN (mechlorethamine hydrochloride), MUTAMYCIN (mitomycin c), MYLOSAR (azacitidine), NAVELBINE (vinorelbine tartrate), NEOSAR (cyclophosphamide), NEXAVAR (sorafenib tosylate), NOLVADEX (tamoxifen citrate), NOVALDEX (tamoxifen citrate), OFF, PAD, PARAPLAT (carboplatin), PARAPLATIN (carboplatin), PEG-INTRON (peginterferon alfa-2b), PEMETREXED DISODIUM, PERJETA (pertuzumab), PLATINOL (cisplatin), PLATINOL-AQ (cisplatin), POMALYST (pomalidomide), prednisone, PROLEUKIN (aldesleukin), PROLIA (denosumab), PROVENGE (sipuleucel-t), REVLIMID (lenalidomide), RUBIDOMYCIN (daunorubicin hydrochloride), SPRYCEL (dasatinib), STIVARGA (regorafenib), SUTENT (sunitinib malate), SYLATRON (peginterferon alfa-2b), SYLVANT (siltuximab), SYNOVIR (thalidomide), TAC, TAFINLAR (dabrafenib), TARABINE PFS (cytarabine), TARCEVA (erlotinib hydrochloride), TASIGNA (nilotinib), TAXOL (paclitaxel), TAXOTERE (docetaxel), TEMODAR (temozolomide), THALOMID (thalidomide), TOPOSAR (etoposide), TORISEL (temsirolimus), TPF, TRISENOX (arsenic trioxide), TYKERB (lapatinib ditosylate), VECTIBIX (panitumumab), VEIP, VELBAN (vinblastine sulfate), VELCADE (bortezomib), VELSAR (vinblastine sulfate), VEPESID (etoposide), VIADUR (leuprolide acetate), VIDAZA (azacitidine), VINCASAR PFS (vincristine sulfate), VOTRIENT (pazopanib hydrochloride), WELLCOVORIN (leucovorin calcium), XALKORI (crizotinib), XELODA (capecitabine), XELOX, XGEVA (denosumab), XOFIGO (radium 223 dichloride), XTANDI (enzalutamide), YERVOY (ipilimumab), ZALTRAP (ziv-aflibercept), ZELBORAF (vemurafenib), ZOLADEX (goserelin acetate), ZOMETA (zoledronic acid), ZYKADIA (ceritinib), ZYTIGA (abiraterone acetate), ENMD-2076, PCI-32765, AC220, dovitinib lactate (TKI258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (VELCADE)), mTOR inhibitors (e.g., rapamycin, temsirolimus (CCI-779), everolimus (RAD-001), ridaforolimus, AP23573 (Ariad), AZD8055 (AstraZeneca), BEZ235 (Novartis), BGT226 (Norvartis), XL765 (Sanofi Aventis), PF-4691502 (Pfizer), GDC0980 (Genetech), SF1126 (Semafoe) and OSI-027 (OSI)), oblimersen, gemcitabine, carminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin, aminopterin, and hexamethyl melamine, or a combination thereof. In certain embodiments, the additional pharmaceutical agent is a binder or modulator (e.g., inhibitor or activator) of Myc, Mad, or Mxi1. In certain embodiments, the additional pharmaceutical agent is a protein kinase inhibitor (e.g., tyrosine protein kinase inhibitor). In certain embodiments, the additional pharmaceutical agent is selected from the group consisting of epigenetic or transcriptional modulators (e.g., DNA methyltransferase inhibitors, histone deacetylase inhibitors (HDAC inhibitors), lysine methyltransferase inhibitors), antimitotic drugs (e.g., taxanes and vinca alkaloids), hormone receptor modulators (e.g., estrogen receptor modulators and androgen receptor modulators), cell signaling pathway inhibitors (e.g., tyrosine protein kinase inhibitors), modulators of protein stability (e.g., proteasome inhibitors), Hsp90 inhibitors, glucocorticoids, all-trans retinoic acids, and other agents that promote differentiation. In certain embodiments, the compounds described herein or pharmaceutical compositions can be administered in combination with an anti-cancer therapy including, but not limited to, surgery, radiation therapy, transplantation (e.g., stem cell transplantation, bone marrow transplantation), immunotherapy, and chemotherapy.

Also encompassed by the disclosure are kits (e.g., pharmaceutical packs). The kits provided may comprise a pharmaceutical composition or compound described herein and a container (e.g., a vial, ampule, bottle, syringe, and/or dispenser package, or other suitable container). In some embodiments, provided kits may optionally further include a second container comprising a pharmaceutical excipient for dilution or suspension of a pharmaceutical composition or compound described herein. In some embodiments, the pharmaceutical composition or compound described herein provided in the first container and the second container are combined to form one unit dosage form. In some embodiments, the pharmaceutical composition or compound described herein provided in the first container and the second container are combined to form multiple unit dosages.

Thus, in one aspect, provided are kits including a first container comprising a compound or pharmaceutical composition as described herein. The compounds in the kits described herein may be useful in binding MAX in a subject in need thereof, modulating (e.g., inhibiting) the activity of Myc, Mad, or Mxi1 in a subject in need thereof, treating diseases associated with Myc (e.g., diseases associated with aberrant activity (e.g., increased activity) of Myc) in a subject in need thereof, treating diseases (e.g., proliferative diseases) in a subject in need thereof, preventing diseases associated with Myc (e.g., diseases associated with aberrant activity (e.g., increased activity) of Myc) in a subject in need thereof, preventing diseases (e.g., proliferative diseases) in a subject in need thereof, and/or regulate transcription of Myc in a subject, biological sample, or tissue. The kits described herein may also be useful as research tools, e.g., for studying Myc (e.g., studying the role of Myc in transcription or gene regulation) in a subject, biological sample, tissue, or cell.

In certain embodiments, a kit described herein further includes instructions for using the compound or pharmaceutical composition included in the kit. A kit described herein may also include information as required by a regulatory agency such as the U.S. Food and Drug Administration (FDA). In certain embodiments, the information included in the kits is prescribing information. In certain embodiments, the kits and instructions provide for treating a disease (e.g., proliferative disease) in a subject in need thereof. In certain embodiments, the kits and instructions provide for preventing a disease (e.g., proliferative disease) in a subject in need thereof. In certain embodiments, the kits and instructions provide for binding MAX in a subject in need thereof. In certain embodiments, the kits and instructions provide for modulating (e.g., inhibiting) the activity of Myc, Mad, or Mxi1 in a subject, biological sample, tissue, or cell. A kit described herein may include one or more additional pharmaceutical agents described herein as a separate composition.

Methods of Treatment and Uses

Myc is associated with a wide range of diseases (e.g., proliferative disease). The compounds described herein may bind (e.g., reversibly bind or irreversibly bind) MAX and/or modulating (e.g., inhibiting or increasing) the activity (e.g., aberrant activity, such as increased or decreased activity) of Myc, Mad, or Mxi1. In certain embodiments, aberrant activity of Myc is increased activity of Myc. Modulation of Myc using the compounds described herein may be an effective approach to treat and/or prevent the disease (e.g., proliferative disease). Compounds described herein that include a small-molecule label may also be useful in identifying the association of Myc with a disease (e.g., proliferative disease). The present disclosure thus provides methods of binding MAX in a subject, biological sample, tissue, or cell; methods of modulating (e.g., inhibiting or increasing) the activity of Myc, Mad, or Mxi1 in a subject, biological sample, tissue, or cell; and methods of treating and/or preventing diseases (e.g., proliferative diseases, inflammatory diseases, or autoimmune diseases) in a subject in need thereof.

In another aspect, the present disclosure provides methods of modulating (e.g., inhibiting) the transcription of genes controlled by Myc (e.g., c-Myc, L-Myc, or N-Myc) in a subject in need thereof, the methods comprising administering to the subject an effective amount of a compound or pharmaceutical composition described herein.

In another aspect, the present disclosure provides methods of modulating (e.g., inhibiting) the activity of Myc (e.g., c-Myc, L-Myc, or N-Myc), Mad, or Mxi1 in a biological sample, tissue, or cell, the methods comprising contacting the biological sample, tissue, or cell with an effective amount of a compound, or pharmaceutical composition thereof, as described herein.

In certain embodiments, the activity of Myc in a subject, biological sample, tissue, or cell is inhibited by a compound described herein by at least 1%, at least 3%, at least 10%, at least 20%, at least 30%, at least 40%, at least 50%, at least 60%, at least 70%, at least 80%, at least 90%, at least 95%, at least 98%, at least 99%, and at least 99.9%. In certain embodiments, the activity of Myc in a subject, biological sample, tissue, or cell is inhibited by a compound described herein by not more than 1%, not more than 3%, not more than 10%, not more than 20%, not more than 30%, not more than 40%, not more than 50%, not more than 60%, not more than 70%, not more than 80%, or not more than 90%. In some embodiments, the activity of Myc in a subject, biological sample, tissue, or cell is selectively inhibited by the compound, pharmaceutical composition, kit, use, or method. In some embodiments, the activity of Myc in a subject, biological sample, tissue, or cell is selectively inhibited by the compound, pharmaceutical composition, kit, use, or method, compared to a different transcription factor (e.g., SP1, AP-1, C/EBP, heat shock factor, ATF/CREB, Oct-1, NF-1). In some embodiments, the activity of c-Myc in a subject, biological sample, tissue, or cell is selectively inhibited by the compound, pharmaceutical composition, kit, use, or method, compared to a different Myc (e.g., L-Myc, N-Myc) and/or a different transcription factor (e.g., SP1, AP-1, C/EBP, heat shock factor, ATF/CREB, Oct-1, NF-1). In some embodiments, the activity of Myc in a subject, biological sample, tissue, or cell is reversibly inhibited by the compound, pharmaceutical composition, kit, use, or method. In some embodiments, the activity of Myc in a subject, biological sample, tissue, or cell is irreversibly inhibited by the compound, pharmaceutical composition, kit, use, or method. In certain embodiments, the compound, inhibits the activity of a mutant (e.g., Myc with a point mutantation) form of Myc (e.g., MYC, MYCL, and/or MYCN). In certain embodiments, the compound, pharmaceutical composition, kit, use, or method modulates (e.g., inhibits) somatic amplification of Myc (e.g., MYC, MYCL, and/or MYCN). In certain embodiments, the compound, pharmaceutical composition, kit, use, or method regulates (e.g., down-regulates) the transcription of genes controlled by Myc (e.g., MYC, MYCL, and/or MYCN). In certain embodiments, the compound, pharmaceutical composition, kit, use, or method modulates (e.g., inhibits) the transcription of genes controlled by Myc (e.g., c-Myc, L-Myc, or N-Myc) in In certain embodiments, the compound, pharmaceutical composition, kit, use, or method modulates (e.g., decreases) the stability of a protein that encodes Myc (e.g., MYC, MYCL, and/or MYCN). In certain embodiments, the compound, pharmaceutical composition, kit, use, or method modulates (e.g., decreases) the stability of Myc.

In some embodiments, the compounds or pharmaceutical compositions described herein selectively inhibit the activity of cells expressing Myc, compared to the inhibition of the activity of cells not expressing Myc. In certain embodiments, the selectivity is at least 2-fold, at least 3-fold, at least 5-fold, or at least 10-fold. In certain embodiments, the selectivity is not more than 10-fold, not more than 5-fold, not more than 3-fold, or not more than 2-fold. Combinations of the above-referenced ranges (e.g., at least 2-fold and not more than 10-fold) are also within the scope of the disclosure.

Another aspect of the present disclosure relates to methods of treating a disease (e.g., a disease associated with Myc (e.g., a disease associated with aberrant activity (e.g., increased activity) of Myc) in a subject in need thereof), the methods comprising administering to the subject an effective amount (e.g., therapeutically effective amount) of a compound or pharmaceutical composition described herein.

In certain embodiments, a disease described herein is associated with Myc. In certain embodiments, a disease described herein is associated with aberrant activity (e.g., increased or decreased activity) of Myc. In certain embodiments, a disease described herein is associated with increased activity of Myc. In certain embodiments, a disease described herein is associated with the increased stability of Myc (e.g., MYC, MYCL, and/or MYCN). In certain embodiments, a disease described herein is associated with increased stability of Myc. In certain embodiments, a disease being treated is a proliferative disease. In certain embodiments, the disease is cancer. In certain embodiments, the cancer is lung cancer (e.g., bronchogenic carcinoma, small cell lung cancer (SCLC), non-small cell lung cancer (NSCLC), adenocarcinoma of the lung). In certain embodiments, the cancer is brain cancer (e.g., meningioma, glioblastomas, glioma (e.g., astrocytoma, oligodendroglioma), medulloblastoma). In certain embodiments, a disease described herein is lymphoma (e.g., Hodgkin lymphoma, non-Hodgkin lymphoma (e.g., Burkitt's lymphoma)). In certain embodiments, a disease described herein is a benign neoplasm. In certain embodiments, the disease is associated with pathological angiogenesis.

In still another aspect, the present disclosure provides the pharmaceutical compositions described herein for use in binding MAX, modulating (e.g., inhibiting) the activity of Myc, Mad, or Mxi1, treating a disease associated with Myc (e.g., disease associated with aberrant activity (e.g., increased activity) of Myc), treating and/or preventing a disease (e.g., proliferative disease), preventing a disease associated with Myc (e.g., disease associated with aberrant activity (e.g., increased activity) of Myc).

EXAMPLES

In order that the present disclosure may be more fully understood, the following examples are set forth. The synthetic and biological examples described in this application are offered to illustrate the compounds, pharmaceutical compositions, and methods provided herein and are not to be construed in any way as limiting their scope.

Preparation and Characterization of the Compounds Described Herein

Preparation of the Compounds

The compounds provided herein can be prepared from readily available starting materials using methods known in the art, such as the methods described in Shaw et al., *Angew. Chem. Int. Ed.*, 2006, 45, 1722-1726. Where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvents used, but such conditions can be determined by those skilled in the art by routine experimentation.

An overview of an exemplary synthesis of compound KI-MS2-008 (compound 8) is shown in FIGS. 5A to 5B.

Example 1. Preparation of Compound 8

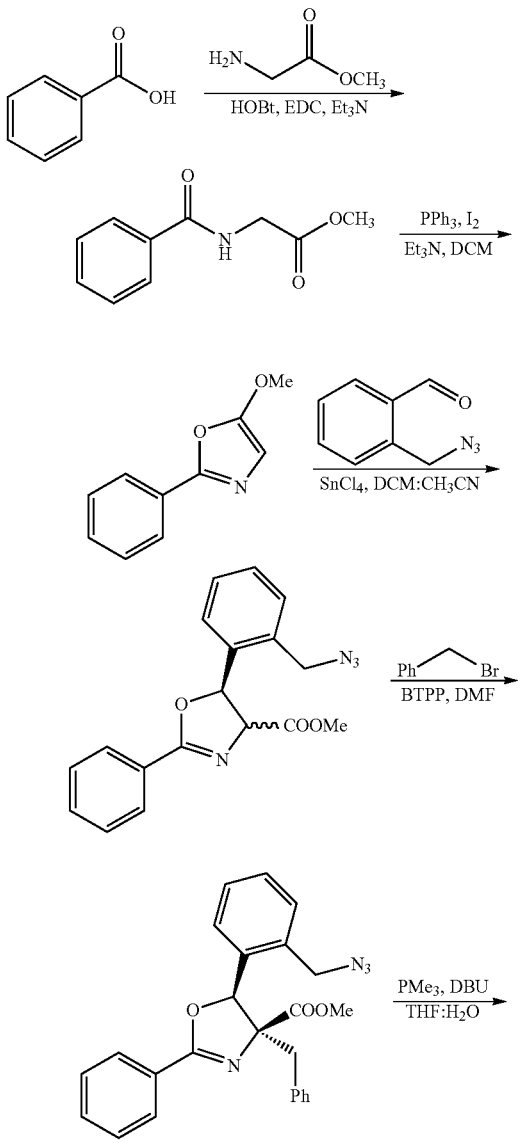

-continued

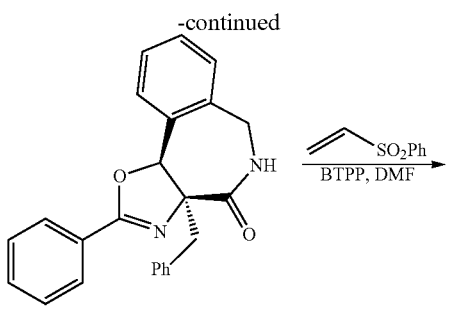

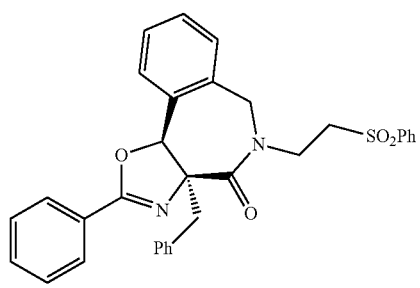

Methyl 2-benzamidoacetate

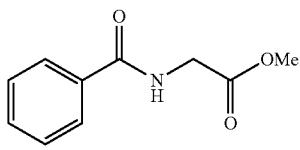 [SMILES: COC(=O)CNC(=O)c1ccccc1]

To a solution of benzoic acid (4.35 g, 35.31 mmol) and glycine methyl ester hydrochloride (4.03 g, 32.10 mmol) in DMF (50 ml) was added EDC hydrochloride (6.77 g, 35.31 mmol), HOBt (4.77 g, 35.31 mmol) and DIPEA (12.30 ml, 70.62 mmol) at room temperature. The mixture was stirred overnight, prior to be quenched with sat. NaHCO$_3$ (150 ml). The aqueous layer was extracted with AcOEt (3×30 ml), and the combined organic layers washed with sat. NaHCO$_3$ (1×20 ml), brine (2×30 ml), dried over MgSO$_4$, filtered and concentrated to furnish methyl 2-benzamidoacetate (6.07 g, 98% yield) in good purity.

5-methoxy-2-phenyloxazole

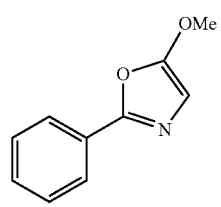 [SMILES: COc1cnc(-c2ccccc2)o1]

A solution of methyl 2-benzamidoacetate (4.25 g, 22.00 mmol) and Et$_3$N (14.7 ml, 104.5 mmol) in DCM (10 ml) was added dropwise to a solution of iodine (12.56 g, 49.48 mmol) and triphenylphosphine (12.98 g, 49.48 mmol) at room temperature. After 5 h, the mixture was concentrated and purified by short plug on silica gel (15 to 40% AcOEt in hexanes) to provide 5-methoxy-2-phenyloxazole (3.8 g, 98% yield).

Methyl 5-(2-(azidomethyl)phenyl)-2-phenyl-4,5-dihydrooxazole-4-carboxylate

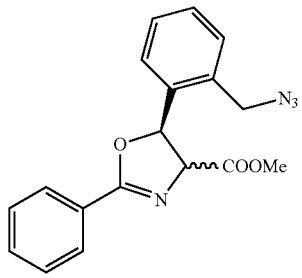 [SMILES: COC(=O)C1N=C(c2ccccc2)O[C@H]1c1ccccc1CN=[N+]=[N-]]

An oven-dried flask was charged with 5-methoxy-2-phenyloxazole (2.54 g, 14.51 mmol), 2-(azidomethyl)benzaldehyde (2.58 g, 15.96 mmol) and dry 1:1 DCM:CH$_3$CN (100 ml). The flask was purged with argon, cooled to 0° C. followed by the addition of SnCl$_4$ (17.6 ml, 1.0M in DCM). The reaction was stirred overnight, then cooled to 0° C., diluted with sat. NaHCO$_3$ (100 ml) and DCM (75 ml) and vigorously stirred for 3 h. The aqueous layer was extracted with AcOEt (4×30 ml). The combined organic layers were dried over MgSO$_4$, filtered, concentrated and purified by column chromatography (10 to 45% AcOEt in hexanes) to afford methyl 5-(2-(azidomethyl)phenyl)-2-phenyl-4,5-dihydrooxazole-4-carboxylate (4.49 g, 92% yield) as a 4:1 mixture of diastereomers.

Methyl (4S,5S)-5-(2-(azidomethyl)phenyl)-4-benzyl-2-phenyl-4,5-dihydrooxazole-4-carboxylate
(Compound 6)

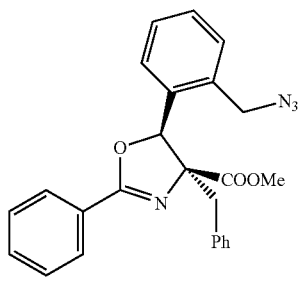 [SMILES: COC(=O)[C@@]1(Cc2ccccc2)N=C(c2ccccc2)O[C@H]1c1ccccc1CN=[N+]=[N-]]

A cis/trans mixture of methyl 5-(2-(azidomethyl)phenyl)-2-phenyl-4,5-dihydrooxazole-4-carboxylate (4.49 g, 13.35 mmol) was diluted in DMF (50 ml). BTPP (5.40 ml, 17.35 mmol) was then added at room temperature followed by benzyl bromide (6.40 ml, 53.40 mmol), K$_2$CO$_3$ (3.69 g, 26.70 mmol) and TBAI (2.46 g, 6.67 mmol). After 16 h, the reacting mixture was concentrated and purified by column chromatography on silica gel (5 to 40% AcOEt in hexanes) to afford compound 6 (5.28 g, 93% yield) as a 95:5 dr. The other diastereomer (lower Rf) can also be isolated.

(3aS,10bS)-3a-benzyl-2-phenyl-3a,5,6,10b-tetra-hydro-4H-benzo[c]furo[2,3-e]azepin-4-one (Compound 7)

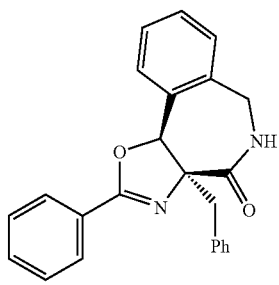 [SMILES: O=C1NCc2ccccc2[C@@H]2OC(c3ccccc3)=N[C@]12Cc1ccccc1]

Compound 6 (1.73 g, 4.06 mmol) was diluted in THF: $H_2O$ (10:1, 100 ml) followed by the addition of DBU (0.64 ml, 4.26 mmol) and $PMe_3$ (4.50 ml, 1.0M in THF) at room temperature. After 16 h, water was added and the aqueous layer extracted with DCM (3×). The combined organic layers were dried over $MgSO_4$, filtered, concentrated and purified by column chromatography on silica gel (0 to 15% MeOH in DCM) providing Compound 7 (1.21 g, 81% yield).

(3aS,10bS)-3a-benzyl-2-phenyl-5-(2-(phenylsulfonyl)ethyl)-3a,5,6,10b-tetrahydro-4H-benzo[c]furo[2,3-e]azepin-4-one (Compound 8)

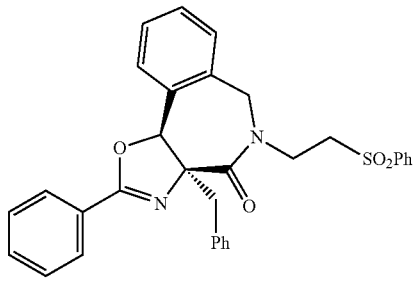

To a solution of Compound 7 (1.10 g, 2.99 mmol) in DMF (15 ml) were successively added BTPP (1.20 ml, 3.86 mmol) and phenyl vinyl sulfone (1.00 g, 5.97 mmol) at room temperature. The reacting mixture was stirred overnight then diluted with water (50 ml). The aqueous layer was extracted with AcOEt (3×15 ml). The combined organic layers were dried over $MgSO_4$, filtered, concentrated and purified by column chromatography (20 to 60% AcOEt in hexanes) to afford Compound 8 (1.55 g, 97% yield).

Characterization of the Compounds

Example 1. Solubility and Half-Life of Compound 1

Exemplary solubility and half-life of compound 1 are shown in Table 1.

TABLE 1

Solubility and half-life of compound 1

| | Solubility at 25° C. (µM) | Half-life (minute) |
|---|---|---|
| Aqueous solubility (simulated intestinal fluid) | 200 | |
| Aqueous solubility (PBS, pH 7.4) | 9.2 | |
| Aqueous solubility (simulated gastric fluid) | 51.2 | |
| Intrinsic clearance (liver microsomes, human) | | 21 |

Compound Screening

An small-molecule microarray (SMM)-based approach was applied to identify small molecule MAX binders. More than 20,000 compounds were screened from the Broad Institute's diversity-oriented synthesis (DOS) and natural product and commercial (NPC) libraries using previously described protocols [7], for binding to purified full-length Max with a 6× His epitope tag at the N-terminus. Hits from this screen were identified by reading out a fluorescent signal (Alexa-647-labeled antibody). Z-scores were computed for each compound according to published methods [8]. Analysis of the composite Z-scores corresponding to the SMM screen revealed several assay positives.

Biological Assays of the Compounds Described Herein

Example 1. c-Myc Reporter Gene Assay of Exemplary Compounds Described Herein

Figure 1A:
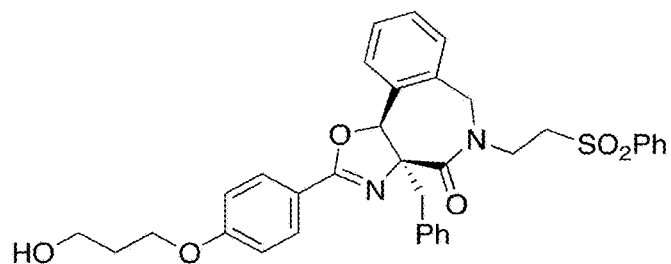
FIG. 1A shows the chemical structure of Compound 1.
Figure 1B:
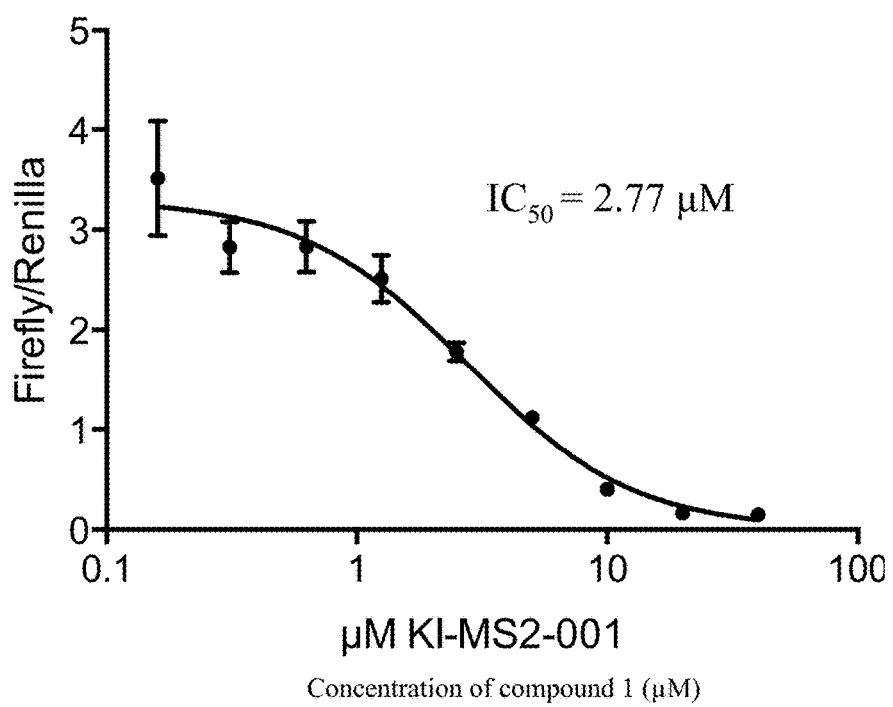
FIG. 1B shows exemplary results of Compound 1 in an initial reporter assay. The activity of Compound 1 against Myc was measured as a Firefly/Renilla ratio, using the Myc reporter assay (Qiagen) in HEK293T cells after treatment with Compound 1 for 16 hours. Results are expressed as a mean+/−SD (n=3). SD: standard deviation.

Select compounds described herein that were SMM assay positives were evaluated in several versions of a c-Myc reporter gene assay, including a commercial assay from Qiagen. The compounds' activities against c-Myc were measured as a Firefly/*Renilla* ratio, using the Myc reporter assay (Qiagen) in HEK293T cells after treatment with the compounds for 16 hours. Exemplary results are shown in Table 2. Compound 1 was a potent inhibitor with an $IC_{50}$ value of 2.77 µM (FIG. 1B and Table 2).

TABLE 2

$IC_{50}$ values of exemplary compounds described herein in the c-Myc reporter assay and viability data in select cell lines. Viability was assessed by CELL TITER GLO assay (Promega). Results expressed as a mean +/− SEM (n = 3).

| Compound # | c-Myc reporter assay $IC_{50}$ (µM) | P493-6 Myc ON Viability in cells (µM) | P493-6 Myc OFF Viability in cells (µM) | cLogP |
|---|---|---|---|---|
| 1 | 1.99 | 6.8 | 58.1 | — |
| 2 | 9.34 | — | — | — |
| 3 | 4.7 | — | — | — |
| 5 | 5.38 | — | — | — |
| 6 | 4.67 | — | — | 6.9 |
| 7 | 11.34 | — | — | — |
| 8 | 1.25 | — | — | — |
| 9 | 2.74 | — | — | — |
| 10 | 1.62 | — | — | — |
| 11 | 4.29 | — | — | — |
| 13 | 7.88 | — | — | — |
| 14trans | 22.8 | — | — | — |
| 14cis | 32.63 | — | — | — |
| 15 | 4.28 | — | — | — |
| 18 | inactive | — | — | — |

TABLE 2-continued

IC$_{50}$ values of exemplary compounds described herein in the c-Myc reporter assay and viability data in select cell lines. Viability was assessed by CELL TITER GLO assay (Promega). Results expressed as a mean +/− SEM (n = 3).

| Compound # | c-Myc reporter assay IC$_{50}$ (µM) | P493-6 Myc ON Viability in cells (µM) | P493-6 Myc OFF Viability in cells (µM) | cLogP |
|---|---|---|---|---|
| 19 | 35.97 | — | — | — |
| 20cis | 19.75 | — | — | — |
| 20cis | 42.01 | — | — | — |
| 21 | 2.54 | — | — | — |
| 22 | inactive | — | — | — |
| 23 | 5.49 | — | — | 5.8 |
| 24 | 1.97 | — | — | 6.9 |
| 25 | 5.67 | — | — | — |
| 26 | 2.41 | — | — | — |
| 27 | 1.99 | — | — | — |
| 28 | 2.51 | — | — | — |
| 29 | 2.15 | — | — | — |
| 30 | 14.13 | — | — | — |
| 31 | 45.1 | — | — | 4.3 |
| 32 | not tested | — | — | — |
| 33 | 4.6 | 8.8 | 19.7 | — |
| 34 | not tested | not tested | not tested | — |
| 35 | not tested | not tested | not tested | — |
| 36 | not tested | not tested | not tested | — |
| 37 | 12.5 | 34.3 | 135 | 5.1 |
| 38 | 54.7 | inactive | inactive | 5.4 |
| 39 | 13.4 | 16.9 | high | 6.9 |
| 40 | 7 | 6.8 | 37 | 7 |
| 41 | 16.5 | 20.1 | 151 | 6 |
| 42 | 14.9 | 15.8 | 75.3 | 6.1 |
| 43 | 19.4 | 49 | 145 | 4.8 |
| 44 | 17.8 | 33.1 | 87.9 | 5.3 |
| 45 | 18.2 | 4 | 262.2 | 5.8 |
| 46 | 45.7 | 56 | inactive | 5 |
| 47 | 20.5 | 22 | 314 | 5.6 |
| 48 | 15.5 | 8.8 | 14.2 | 6 |
| 49 | 12.8 | 9.1 | 56.7 | 5 |
| 50 | 7.2 | 10.9 | 30.8 | 6.5 |
| 51 | 13.5 | 10 | 31.5 | 5.8 |
| 52 | 96.2 | 114.4 | 90.2 | — |
| 53 | 34.8 | 38.9 | 117.3 | — |
| 54 | 13.3 | 27.9 | 51.1 | 7 |
| 55 | 30.5 | 56.6 | 409.5 | 6.5 |
| 56 | 19.2 | 14.2 | 843.2 | 6.8 |
| 58 | 17.3 | 6.8 | 51.4 | 6.5 |
| 59 | 26.2 | 7.1 | 19.3 | 4.2 |
| 60 | 8 | 17 | inactive | 6.6 |
| 61 | 14.9 | 16.2 | inactive | 6.6 |
| 62 | 11.9 | 23.9 | high | 6.6 |
| 63 | 12.5 | 9.8 | inactive | 5.8 |
| 64 | 7.2 | 20.3 | 36.5 | 7 |
| 65 | 6.8 | 6.5 | high | 4.2 |
| 66 | 182.3 | 149.7 | inactive | 3.1 |
| 67 | not tested | not tested | not tested | 7.3 |
| 68 | 21.1 | 39.9 | inactive | 3.4 |
| 69 | not tested | not tested | not tested | — |
| 70 | not tested | not tested | not tested | — |
| 71 | not tested | not tested | not tested | — |
| 72 | not tested | not tested | not tested | — |
| 73 | — | — | — | — |
| 74 | — | — | — | — |
| 75 | — | — | — | — |
| 76 | — | — | — | — |
| 77 | — | — | — | — |
| 78 | — | — | — | — |

TABLE 3

IC$_{50}$ values of exemplary compounds described herein in the c-Myc reporter assay and viability data in select cell lines.

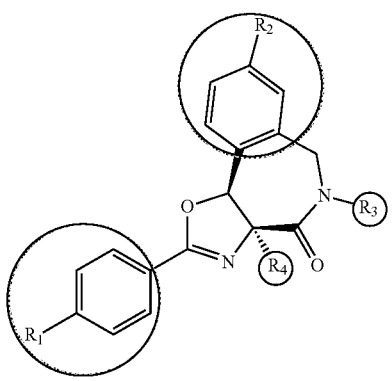

| Compound | R$_1$ | R$_2$ | R$_3$ | R$_4$ | IC$_{50}$ (µM) Reporter assay | IC$_{50}$ (µM) Myc ON | IC$_{50}$ (µM) Myc OFF |
|---|---|---|---|---|---|---|---|
| 1a | H | H | H | H | >50 | | |
| 2a | H | H | H | 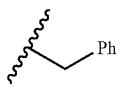 | 16.76 | >50 | >50 |

TABLE 3-continued
IC$_{50}$ values of exemplary compounds described herein in the c-Myc reporter assay and viability data in select cell lines.
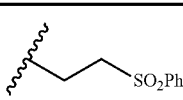
| Compound | R$_1$ | R$_2$ | R$_3$ | R$_4$ | IC$_{50}$ (μM) Reporter assay | IC$_{50}$ (μM) Myc ON | IC$_{50}$ (μM) Myc OFF |
|---|---|---|---|---|---|---|---|
| 3a | H | H | 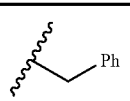 SO$_2$Ph | 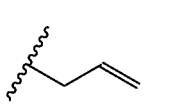 [SMILES: *CC=C] Ph | 6.19 | 11.44 | >50 |
| 4a | H | H | 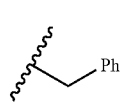 | 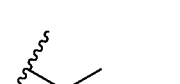 Ph | 7.67 | 31.78 | >50 |
| 5a | H | H | 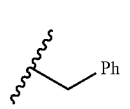 | 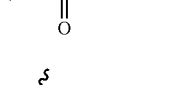 Ph | 4.81 | 19.34 | >50 |
| 6a | H | H |  Ph | 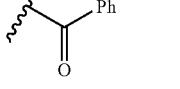 Ph | 17.20 | >50 | >50 |
| 7a | H | H | 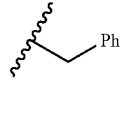 OEt | 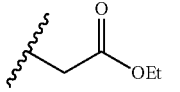 Ph | 3.38 | 39.27 | >50 |
| 8a | H | H | 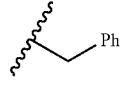 OH | 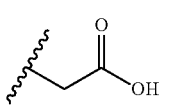 Ph | >50 | >50 | >50 |
| 9a | H | H | 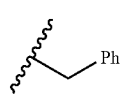 OtBu | 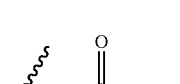 Ph | | | |
| 10a | H | H | 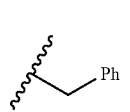 OH | 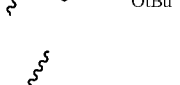 Ph | 2.15 | | |
| 11a | H | H |  | Ph | 10.14 | | |

TABLE 3-continued

IC$_{50}$ values of exemplary compounds described herein in the c-Myc reporter
assay and viability data in select cell lines.

| Compound | R$_1$ | R$_2$ | R$_3$ | R$_4$ | IC$_{50}$ (μM) Reporter assay | IC$_{50}$ (μM) Myc ON | IC$_{50}$ (μM) Myc OFF |
|---|---|---|---|---|---|---|---|
| 12a | H | H | ~C(O)NHCH$_2$CH$_2$NHC(O)CH$_2$N(CH$_2$C≡CH)C(O)CH$_2$CH$_2$C(CH$_3$)(N=N) | ~CH$_2$Ph | 18.73 | | |
| 13a | H | Cl | ~CH$_2$CH$_2$SO$_2$Ph | ~CH$_2$Ph | 5.94 | 25.80 | >50 |
| 14a | ~OCH$_2$CH$_2$CH$_2$OH | H | H | ~CH$_2$Ph | 9.34 | | |
| 15$^a$ | ~OCH$_2$CH$_2$CH$_2$OH | H | ~CH$_2$CH$_2$SO$_2$Ph | ~CH$_2$Ph | 11.70 | 14.50 | >50 |
| 15$^b$ | ~OCH$_2$CH$_2$CH$_2$OH | H | ~CH$_2$CH$_2$SO$_2$Ph | ~CH$_2$Ph | 4.74 | 8.49 | >50 |
| 15$^c$ | ~OCH$_2$CH$_2$CH$_2$OH | H | ~CH$_2$CH$_2$SO$_2$Ph | ~CH$_2$Ph | 4.77 | 16.58 | >50 |
| 16a | ~OCH$_2$CH$_2$CH$_2$OH | H | ~CH$_2$Ph | ~CH$_2$Ph | 7.88 | | |
| 17a | ~OCH$_2$CH$_2$CH$_2$OAc | H | ~CH$_2$CH$_2$SO$_2$Ph | ~CH$_2$Ph | 4.7 | | |

$^a$Racemic mixture.
$^{b,c}$Enantiopure

TABLE 4

Predicted CLogP values of exemplary compounds described herein.

| Compound | R₁ | R₂ | R₃ | R₄ | Predicted CLogP |
|---|---|---|---|---|---|
| 1' | Ph | H | ~~~SO₂Ph | ~~~Ph | 6.38 |
| 2' | Ph | H | ~~~SO₂Ph | ~~~C₆H₄-F | 6.53 |
| 3' | Ph | H | ~~~SO₂Ph | ~~~C₆H₄-CN | 5.82 |
| 4' | Ph | H | ~~~SO₂Ph | ~~~C₆H₄-C(O)ONHS | 6.35 |
| 5' | Ph | H | ~~~SO₂Ph | ~~~CH₂-piperazine-NH | 4.09 |
| 6' | Ph | H | ~~~SO₂Ph | ~~~CH₂-morpholine | 4.49 |
| 7' | Ph | H | ~~~SO₂Ph | ~~~C₆H₄-oxetanyl | 5.64 |
| 8' | Ph | H | ~~~SO₂Ph | ~~~CH₂-(2-pyridyl) | 4.88 |
| 9' | Ph | H | ~~~SO₂Ph | ~~~CH₂-(5-pyrimidyl) | 3.93 |

TABLE 4-continued

Predicted CLogP values of exemplary compounds described herein.

| Compound | R₁ | R₂ | R₃ | R₄ | Predicted CLogP |
|---|---|---|---|---|---|
| 10' | Ph | H | ~~~CH₂CH₂CH₂SO₂Ph | ~~~CH₂-(N-methylimidazol-2-yl) | 3.99 |
| 11' | Ph | H | ~~~CH₂CH₂CH₂SO₂Ph | ~~~CH₂-(1H-1,2,3-triazol-4-yl) | 3.82 |
| 12' | Ph | H | ~~~CH₂CH₂CH₂SO₂Ph | ~~~CH₂-(1H-tetrazol-5-yl) | 3.55 |
| 13' | Ph | H | ~~~CH₂CH₂CH₂SO₂Ph | ~~~CH₂-(oxazol-4-yl) | 3.83 |
| 14' | Ph | H | ~~~CH₂CH₂CH₂SO₂Ph | ~~~CH₂-(thiazol-2-yl) | 4.73 |
| 15' | Ph | H | ~~~CH₂CH₂CH₂SO₂Ph | ~~~CH₂C≡CH | 5.01 |
| 16' | Ph | H | ~~~CH₂CH₂CH₂SO₂Ph | ~~~CH₂C≡N | 4.02 |
| 17' | Ph | H | ~~~CH₂CH₂CH₂SO₂Ph | ~~~CH₂-(bicyclo[1.1.1]) | 6.77 |
| 18' | Ph | H | ~~~CH₂CH₂-(1H-tetrazol-5-yl) | ~~~CH₂CH₂Ph | 4.68 |
| 19' | Ph | H | ~~~CH₂CH₂CH₂-(morpholin-4-yl) | ~~~CH₂CH₂Ph | 5.65 |

TABLE 4-continued
Predicted CLogP values of exemplary compounds described herein.
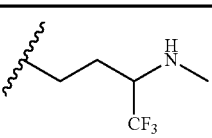
| Compound | R₁ | R₂ | R₃ | R₄ | Predicted CLogP |
|---|---|---|---|---|---|
| 20' | Ph | H | 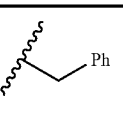 | 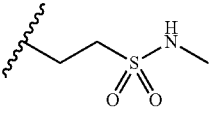 [SMILES: *CCS(=O)(=O)NC] Ph | 6.06 |
| 21' | Ph | H | 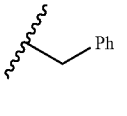 | 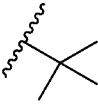 [SMILES: *C(C)(C)C] Ph | 5.09 |
| 22' | Ph | H | 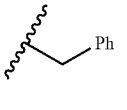 | 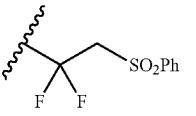 Ph | 6.66 |
| 23' | Ph | H | 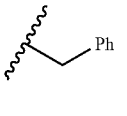 SO₂Ph | 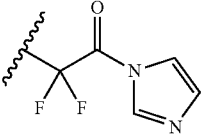 [SMILES: *C(F)(F)C(=O)n1ccnc1] Ph | 7.73 |
| 24' | Ph | H | 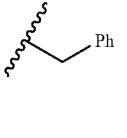 |  Ph | 6.63 |
| 25' | Ph | 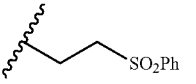 | 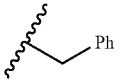 SO₂Ph | 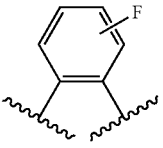 Ph | 5.34 |
| 26' | Ph | 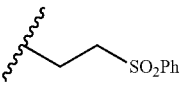 | 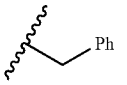 SO₂Ph | 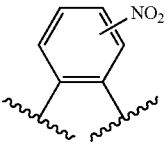 Ph | 6.53 |
| 28' | Ph | 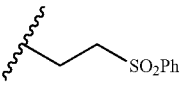 | 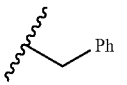 SO₂Ph | 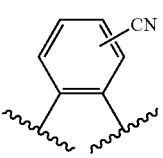 Ph | 6.13 |
| 29' | Ph | 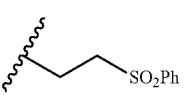 | 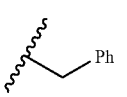 SO₂Ph | Ph | 5.82 |

TABLE 4-continued

Predicted CLogP values of exemplary compounds described herein.

| Compound | R₁ | R₂ | R₃ | R₄ | Predicted CLogP |
|---|---|---|---|---|---|
| 30' | Ph | pyrazine-2,3-diyl | ~(CH₂)₂SO₂Ph | ~CH₂Ph | 3.93 |
| 31' | Ph | 2-CN-pyridine-5,6-diyl | ~(CH₂)₂SO₂Ph | ~CH₂Ph | 4.71 |
| 32' | Ph | thiazole-4,5-diyl | ~(CH₂)₂SO₂Ph | ~CH₂Ph | 4.73 |
| 33' | Ph | 2-COOH-pyrazine-5,6-diyl | ~(CH₂)₂SO₂Ph | ~CH₂Ph | 4.34 |
| 34' | Me | H | ~(CH₂)₂SO₂Ph | ~CH₂Ph | 4.76 |
| 35' | 3-pyridyl | H | ~(CH₂)₂SO₂Ph | ~CH₂Ph | 4.89 |
| 36' | 4-F-C₆H₄ | H | ~(CH₂)₂SO₂Ph | ~CH₂Ph | 6.53 |

TABLE 5

Predicted CLogP values and molecular weights of exemplary compounds described herein.

| Compound | Predicted CLogP | Molecular Weight |
|---|---|---|
| *(structure 1: pyridinyl-oxazole fused benzazepine with benzyl and phenylsulfonylethyl substituents)* | 4.8851 | |
| *(structure 2: oxazole fused benzazepine with benzyl and phenylsulfonylethyl substituents)* | 3.91325 | |
| *(structure 3: 4-hydroxyphenyl-oxazole fused benzazepine with benzyl and phenylsulfonylethyl substituents)* | 5.7151 | |
| *(structure 4: 4-fluorophenyl-oxazole fused benzazepine with benzyl and phenylsulfonylethyl substituents)* | 6.5251 | |

TABLE 5-continued
Predicted CLogP values and molecular weights of exemplary compounds described herein.
| Compound | Predicted CLogP | Molecular Weight |
|---|---|---|
| 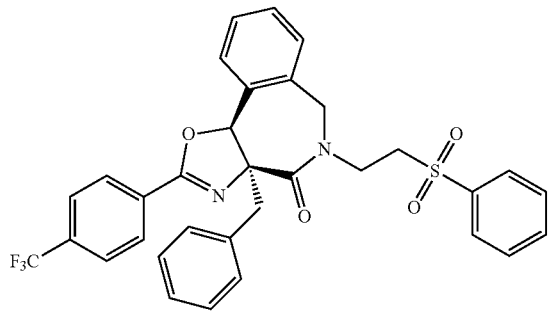 [SMILES: O=C1N(CCS(=O)(=O)c2ccccc2)Cc2ccccc2[C@@H]2OC(c3ccc(O)cc3)=N[C@]12Cc1ccccc1] | 7.2651 | |
| 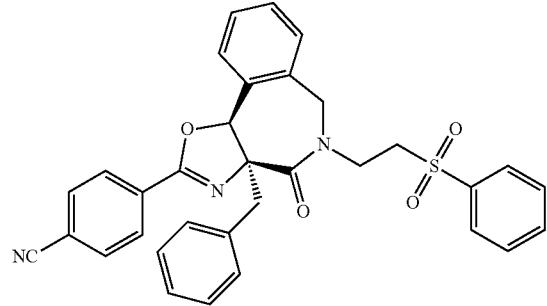 [SMILES: N#Cc1ccc(C2=N[C@]3(Cc4ccccc4)C(=O)N(CCS(=O)(=O)c4ccccc4)Cc4ccccc4[C@@H]3O2)cc1] | 5.8151 | |
| 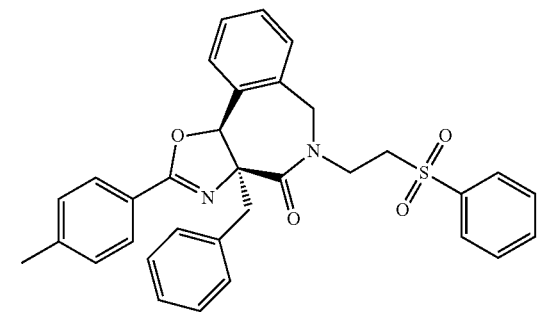 [SMILES: Cc1ccc(C2=N[C@]3(Cc4ccccc4)C(=O)N(CCS(=O)(=O)c4ccccc4)Cc4ccccc4[C@@H]3O2)cc1] | 6.8811 | |
| 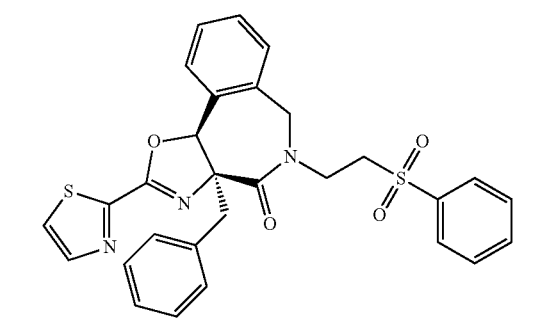 [SMILES: O=C1N(CCS(=O)(=O)c2ccccc2)Cc2ccccc2[C@@H]2OC(c3nccs3)=N[C@]12Cc1ccccc1] | 4.7261 | |

TABLE 5-continued
Predicted CLogP values and molecular weights of exemplary compounds described herein.
| Compound | Predicted CLogP | Molecular Weight |
|---|---|---|
| 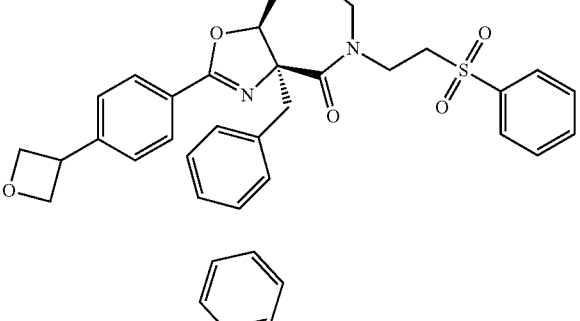 | 5.6351 | |
| 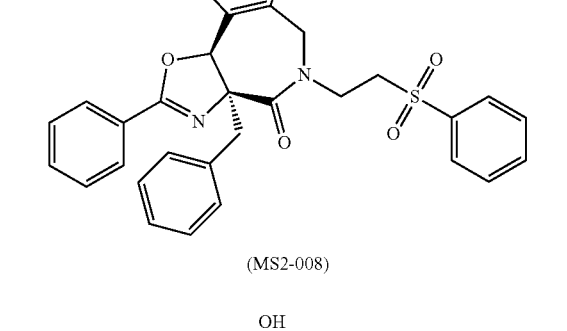 (MS2-008) | 6.3821 | |
| 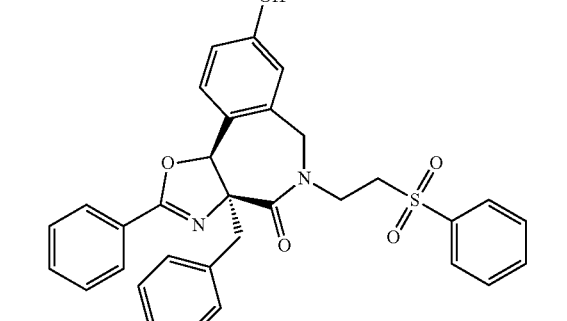 | 5.7151 | |
| 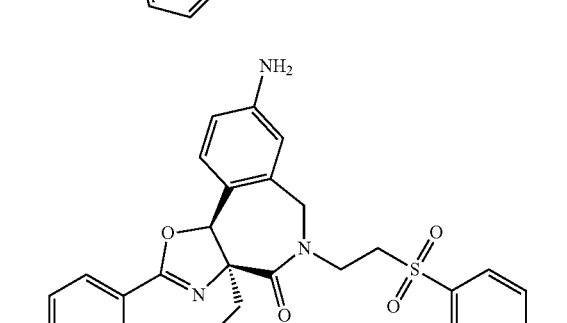 | 5.1551 | |

TABLE 5-continued

Predicted CLogP values and molecular weights of exemplary compounds described herein.

| Compound | Predicted CLogP | Molecular Weight |
|---|---|---|
| *(structure: chloro-substituted benzazepine fused oxazoline with benzyl and phenylsulfonylethyl substituents)* | 7.0951 | |
| *(structure: chloro-substituted benzazepine fused oxazoline with benzyl and phenylsulfonylethyl substituents)* | 7.0951 | |
| *(structure: CN-substituted benzazepine fused oxazoline with benzyl and phenylsulfonylethyl substituents)* | 5.8151 | |
| *(structure: chloro-substituted benzazepine fused oxazoline with benzyl and phenylsulfonylethyl substituents)* | 7.0951 | |

TABLE 5-continued

Predicted CLogP values and molecular weights of exemplary compounds described herein.

| Compound | Predicted CLogP | Molecular Weight |
|---|---|---|
| *(structure with F-substituted aryl, oxazole, benzyl, phenylsulfonylethyl)* | 6.5 | 251 |
| *(structure with NO₂-substituted aryl, oxazole, benzyl, phenylsulfonylethyl)* | 6.1 | 251 |
| *(structure with unsubstituted aryl, oxazole, benzyl, phenylsulfonylethyl)* | 6.38 | |
| *(structure with unsubstituted aryl, oxazole, benzyl, carboxymethyl)* | 5.45 | |

TABLE 5-continued

Predicted CLogP values and molecular weights of exemplary compounds described herein.

| Compound | Predicted CLogP | Molecular Weight |
|---|---|---|
| | 4.8996 | |
| | 4.37 | |
| | 6.168 | |
| | 5.65 | |

TABLE 5-continued

Predicted CLogP values and molecular weights of exemplary compounds described herein.

| Compound | Predicted CLogP | Molecular Weight |
|---|---|---|
| (structure: benzoxazepine with phenyl-oxazoline, benzyl, N-CH2-C(O)-CF3 substituent) | 6.050 | |
| (structure: benzoxazepine with phenyl-oxazoline, benzyl, N-CH2CH2-SO2Me substituent) | 4.6039 | |
| (structure: benzoxazepine with phenyl-oxazoline, benzyl, N-CH2-(1-methyltetrazol-5-yl) substituent) | 4.3213 | |
| (structure: benzoxazepine with phenyl-oxazoline, benzyl, N-CH2CH2-CH(CF3)-NHMe substituent) | 6.0597 | |

TABLE 5-continued

Predicted CLogP values and molecular weights of exemplary compounds described herein.

| Compound | Predicted CLogP | Molecular Weight |
|---|---|---|
| (structure) | 5.3652 | |
| (structure) | 5.089 | |
| (structure) | 5.6351 | |
| (structure) | 4.4901 | |

TABLE 5-continued

Predicted CLogP values and molecular weights of exemplary compounds described herein.

| Compound | Predicted CLogP | Molecular Weight |
|---|---|---|
| [structure] | 4.0971 | |
| [structure] | 4.8851 | |
| [structure] | 5.6351 | |
| [structure] | 4.0851 | |

TABLE 5-continued

Predicted CLogP values and molecular weights of exemplary compounds described herein.

| Compound | Predicted CLogP | Molecular Weight |
|---|---|---|
| (structure) | 3.9281 | |
| (structure) | 5.8151 | |
| (structure) | 4.7261 | |
| (structure) | 6.5251 | |

TABLE 5-continued

Predicted CLogP values and molecular weights of exemplary compounds described herein.

| Compound | Predicted CLogP | Molecular Weight |
|---|---|---|
| [chemical structure] | 6.1251 | |
| [chemical structure] | 7.2651 | |
| [chemical structure] | 7.8 | 877 |
| [chemical structure] | 8.0 | 965 |

TABLE 5-continued

Predicted CLogP values and molecular weights of exemplary compounds described herein.

| Compound | Predicted CLogP | Molecular Weight |
|---|---|---|
| | 8.0 | 1111 |
| | 4.1 | 904 |
| | 3.8 | 993 |

TABLE 5-continued
Predicted CLogP values and molecular weights of exemplary compounds described herein.
| Compound | Predicted CLogP | Molecular Weight |
|---|---|---|
| 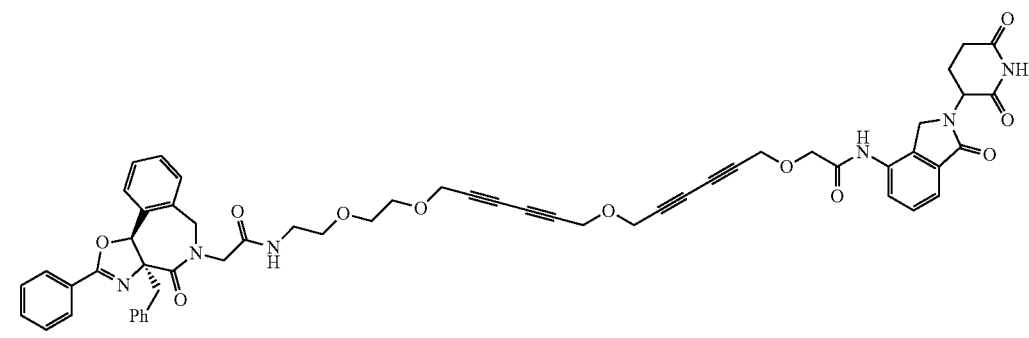 [SMILES: O=C(CN1Cc2ccccc2[C@@H]2OC(c3ccccc3)=N[C@]2(Cc2ccccc2)C1=O)NCCOCCOCC#CC#CCOCC#CC#CCOCC(=O)Nc1cccc2c1CN(C1CCC(=O)NC1=O)C2=O] | 3.5 | 997 |
TABLE 6
Predicted CLogP values and molecular weights of exemplary compounds described herein.
| Generic Formula of Compound | 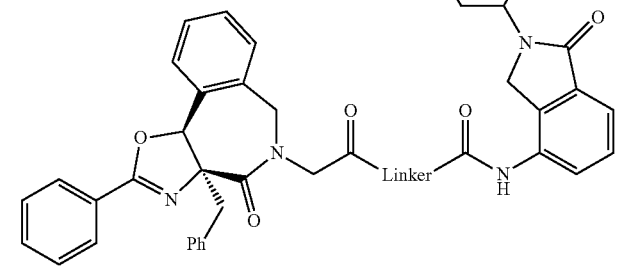 | | |
|---|---|---|---|
| Compound Number | Linker | Molecular Weight | CLogP |
| MS2-090 | 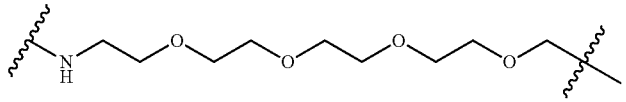 [SMILES: *COCCOCCOCCOCCN*] | 900 | 4.4 |
| MS2-078 | 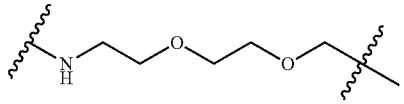 [SMILES: *COCCOCCN*] | 812 | 4.7 |
| MS2-089 | 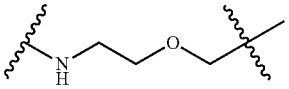 [SMILES: *COCCN*] | 768 | 4.8 |
| MS2-096 | 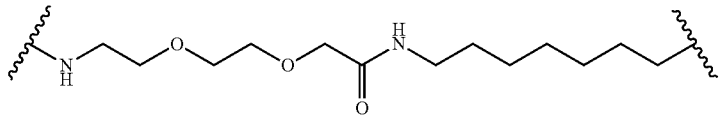 [SMILES: *CCCCCCCNC(=O)COCCOCCN*] | 954 | 5.9 |

TABLE 6-continued

Predicted CLogP values and molecular weights of exemplary compounds described herein.

| Generic Formula of Compound | 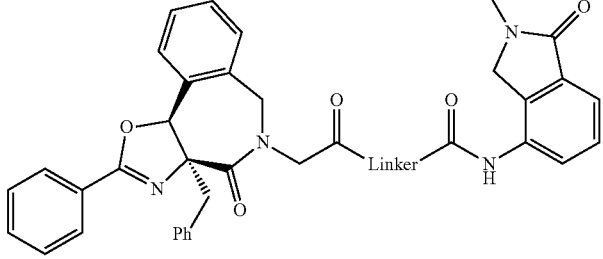 | | |
|---|---|---|---|
| Compound Number | Linker | Molecular Weight | CLogP |
| MS2-095 | 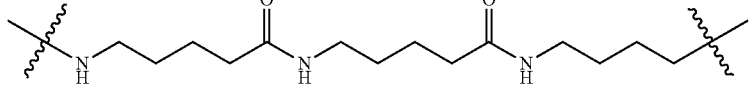 | 965 | 3.6 |
| MS2-094 | 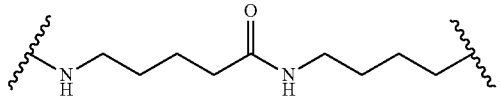 [SMILES: *CCCCNC(=O)CCCCN*] | 865 | 4.3 |
| MS2-093 | 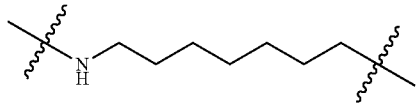 [SMILES: *CCCCCCCN*] | 808 | 6.6 |
| MS2-092 | 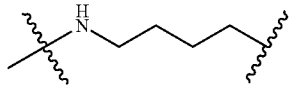 [SMILES: *CCCCN*] | 768 | 5.1 |

Example 2. Cell Viability Assay of Exemplary Compounds Described Herein

The effect of Compound 1 on cell viability in several cancer cell lines and normal human astrocytes (NHA) was determined. The cancer cell lines employed in the assay included those corresponding to Burkitt's lymphoma (ST486 and CA46), small cell lung cancer (NCI-H1963), and glioblastoma (GBM4). The cell viability of normal human astrocytes (NHA) was also assayed. Exemplary results are shown in FIG. 2, where viability was assessed by CELL TITER GLO assay (Promega). Compound 1 demonstrated an effect in cell viability in a variety of cancer cell lines, consistent with the notion that Myc is a key oncoprotein in a broad range of cancers. The effects of other compounds described herein on cell viability in several cancer cell lines were also determined, and exemplary results are shown in Table 2, where viability was assessed by CELL TITER GLO assay (Promega).

Example 3. Selectivity of Exemplary Compounds Described Herein for Cells Expressing Myc The selectivity of Compound 1 for cells expressing Myc over non-Myc expressing cells in cancer cell line P493-6 (engineered cell line derived from human B-cells) was determined. Adding doxycycline to P493-6 growth media shuts off Myc transcription [9]. Exemplary results are shown in FIGS. 3A to 3B, where cell viability was assessed by CELL TITER GLO assay (Promega). FIG. 3A depicts the assay results for cells expressing Myc, and FIG. 3B depicts the assay results for non-Myc expressing cells. Compound 1 demonstrated a selectivity for cells expressing Myc and exhibited decreased cell viability, compared to non-Myc expressing cells in cancer cell lines. The selectivity of other compounds described herein in cancer cell line cancer cell line P493-6 was also determined, and exemplary results are shown in Table 2, where viability was assessed by CELL TITER GLO assay (Promega).

Example 4. Target Identification Experiments of Exemplary Compounds Described Herein In order to explore the mechanism of action of Compound 1, preliminary target identification experiments involving affinity-based pull downs were carried out. Compound 1 was modified to include a biotinylated probe, which had been shown to be tolerated during an evaluation of select compounds (Table 2). Compound 5 contains a biotinylated probe, and was found to have an $IC_{50}$ value of 5.4 µM in Myc reporter assay. The structure of Compound 5 allowed for linking Compound 1 to beads (streptavidin agarose, Pierce, Thermo Fisher after Scientific). After incubating the loaded beads with pure MAX protein and Compound 1, which was unbound to the beads and acted a soluble competitor, followed by a pull down of the beads and subsequent analysis by Western blot of c-Myc levels, there was less MAX pulled down in the presence of Compound 1 as a soluble competitor (FIG. 4A). After incubating the loaded beads with nuclear lysate, followed by a pull down of the beads and subsequent analysis by Western blot of c-Myc levels, MAX was pulled down and c-Myc was co-precipitated (FIG. 4B). This suggests that Compound 1 is may bind to MAX in pure protein solution and in cell lysates.

Example 5. Synthesis of KI-MS2 Pulldown Reagent

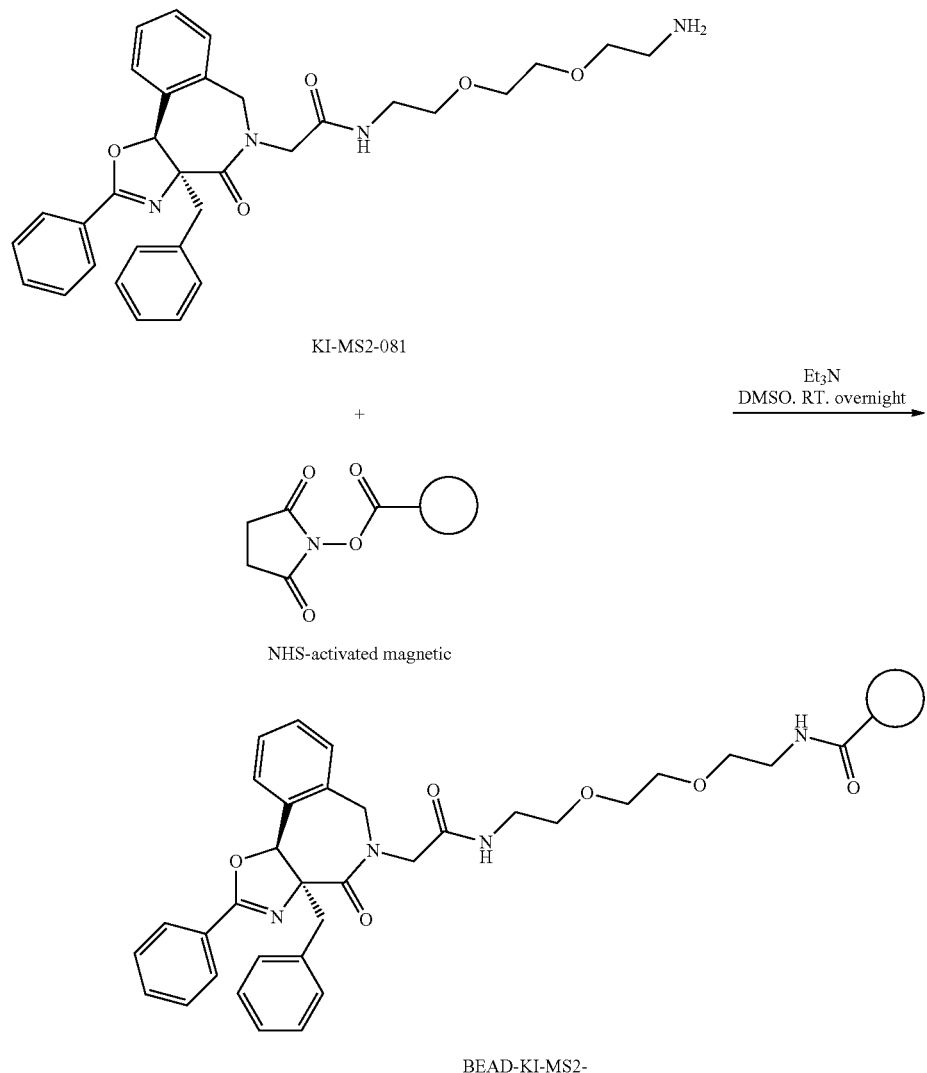

50 µL of Pierce™ NHS-Activated Magnetic Beads (ThermoFisher Scientific) were washed three times with 500 µL DMSO. 100 µL of DMSO was added to the washed beads, along with 0.5 µL of 10 mM KI-MS2-081 or 0.5 µL of DMSO for the empty beads and 0.75 µL triethylamine. This reaction mixture was incubated overnight at room temperature. Next, 2.5 µL of aminoethanol was added to each set of beads to block unreacted NHS groups. The following day, beads were washed three times with 500 µL DMSO, followed by three washes with 500 µL wash buffer (150 mM NaCl, 50 mM Tris, protease inhibitor cocktail, phosphatase inhibitors, pH 7.5).

Example 5—LC/MS Detection Method

Frozen samples were brought to room temperature (RT) then reconstituted in 20 µl methanol and 80 µl water. Samples were aliquoted into LCMS tubes with preslit caps and were run on C18 column with 5% ACN in water+0.1% FA as mobile phase A and 95% ACN in water+0.1% as mobile phase B. A linear gradient was used: 0-0.5 min 0% B; 0.5-10.5 min 0-100% B; 10.5-15.5 min 100% B; 15.5-17.5 min 100-0% B; run stopped at 23 min. Flow rate was 0.4 ml/min and injection volume was 10 µl. The mass spec (Sciex API4000) was operated under multiple reaction monitoring mode scanning for the 4 most prominent fragments of the compound: m/z 105.1, 519.1, 416, 205.1 (blue, red, green, and grey, respectively). The parameters were: curtain gas 25 units; ion source gas 1, 30 units; ion source gas 2, 30 units; temperature 550° C.; ion spray voltage 5500 V; declustering potential 96 V, and collision energy 57 eV. The results are shown in FIG. 21 and demonstrate that LC/MS methods for compound detection were found and developed.

Example 6—Plasma Extraction Method for Non-Polar Compounds

Samples of 10 µl plasma were extracted in eppendorf tubes by quickly adding 500 µl of cold MeOH, followed by 300 µl cold water, and 500 µl cold chloroform. The tubes were mixed by hand for a few seconds, vortexed at max speed for 10 min at 4° C., and then centrifuged for 5 min at max speed at 4° C. The chloroform layer (bottom layer) was transferred to a new tube and evaporated in a SpeedVac. The tubes were frozen at −80° C. until LCMS analysis.

Example 7—MS2-008 is Detectable in Processed Plasma

A plasma protein binding study was conducted to determine if the MS2-008 compound has high or low protein extraction using the above plasma extraction method. Plasma was processed from blood samples. Water and plasma samples were spiked with MS2-008 and subjected to the plasma extraction protocol. Preliminary results showed minimal differences between extraction from water or plasma.

A serial dilution-lowest detection limit test was also conducted. A serial dilution of the MS2-008 compound was made in plasma samples from each animal. Plasma samples were frozen and then the desired compound was extracted from the plasma using the method described above. Approximately 0.6 µM seems to be the lowest reliable detectable concentration. n=3 mice for each group. Paired t-test between control plasma and other sample sets: *p<0.001 (FIG. 22). The results shown in FIG. 22 indicate that MS2-008 is detectable in processed plasma.

In view of the above results, compound extraction from plasma methods was developed. Plasma and blood do not seem to significantly bind compound and compound detection limits from plasma were determined (>0.6 µM).

Example 8—Compound IV and Oral Comparison

Previously, a significant effect on tumor development was observed in animals dosed via I.V. but not oral or IP formulations in corn oil. As such, to the aim was to determine how much compound is present in the blood at 1 hour post administration (IV or PO). The same dose of MS2-008 compound for PO administration with the IV saline vehicle and in 20% cyclodextrin, a common oral vehicle was also used. MS2-008 administered at 150 µl of 20 uM MS2-008 in saline+0.1% DMSO for IV and oral saline; 20 µM MS2-008 in 20% cyclodextrin+0.1% DMSO.

MS2-008 administered at 150 µl of 20 uM MS2-008 in saline+0.1% DMSO for IV and oral saline; 20 µM MS2-008 in 20% cyclodextrin+0.1% DMSO. Blood samples were collected in EDTA tubes 1 hour post administration, spun, and then the plasma was collected and processed for LC/MS analysis. The results, as shown in FIG. 23, indicate a demonstrable level of compound with IV and no significant change in oral saline or cyclodextrin as compared to control plasma. n=3 animals for each group; paired t-test between control plasma and other sample sets: *p<0.001 (see FIG. 23).

Example 9—Pharmacodynamics Following Oral Delivery of 200 µM of MS2-008 in Cyclodextrin Compound MS2-008 was administered PO at 150 ul of 200 µM MS2-008 in 20% cyclodextrin+1.4% DMSO. Blood samples were collected from three animals for vehicle control, 30 min, 1, 2, 4, 6 and 24 hours post compound administration. Animals were euthanized and the tissues (liver, kidney, spleen, heart and muscle) were collected and snap frozen on dry ice. The plasma was isolated from the blood samples and frozen. Plasma samples were processed and subjected to LC/MS analysis to determine compound levels. n=3 animals per group for each time point. Sets 1-3 are independent sample processing and LC/MS runs of plasma at each time point. (See FIG. 26B).

Drug clearance is rapid for the first couple of hours between 30 min and 1 hour the concentration drops 50% and between 1-2 hours it drops another 50%. The compound concentration then remains relatively stable between 2 and 6 hours and drops back to non-detectable by 24 hours.

Example 10—No Toxicity was Observed Following Repeated Dosing of MS2-008

Healthy mice were dosed orally with cyclodextrin vehicle, 0.364 mg/kg (100 mM) or 0.731 mg/kg (200 mM) compound daily for 7 days. Animal weights were acquired each day. On day 8, blood samples were collected to look at plasma concentration of compound. Mice were then euthanized and liver and kidneys were preserved in formalin for H&E staining to look at cellular indicators of toxicity. Histology slides were observed by a certified pathologist. n=5 per group.

Animal weights and behavioral observations indicated that there was no significant change in body weight or behavior were observed during the course of compound treatment (see FIG. 25).

Histology results showed that following an examination of sections of liver and kidney from all study animals, no signs of hepatic or renal organ damage were observed.

Following 7 days of PO dosing, mouse weights did not change and histology results for all treated mice indicate that there was no signs of organ toxicity at the doses used (~5× and 10× concentrations used in earlier efficacy studies).

Plasma samples collected at the time of study termination indicate that following repeated dosing, the compound is almost completely cleared within 24 hours. However there is a slightly higher level of the compound remaining in the plasma in the higher dose at the conclusion of the study (see FIG. 26A).

REFERENCES

1. Vita et al., Semin. Cancer Biol., 16, 318-330, (2006).
2. Dang, Mol. Cell Biol., 19, 1-11 (1999).
3. Eilers et al., Genes Dev., 22, 2755-2766 (2008).
4. van Riggelen et al., Nat. Rev. Cancer, 10, 301-309 (2010).
5. Dang et al., Semin. Cancer Biol., 16, 253-264 (2006).
6. Soucek et al., Genes Dev., 5, 504-513 (2013).
7. Duffner, et al., Curr. Opin. Chem. Biol., 11, 74-82 (2007).
8. Seiler et al., Nucleic Acid Res., 36, 351-359 (2008).
9. Pajic, et al., Int. J. Cancer, 87, 787-793 (2000).

205

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

206

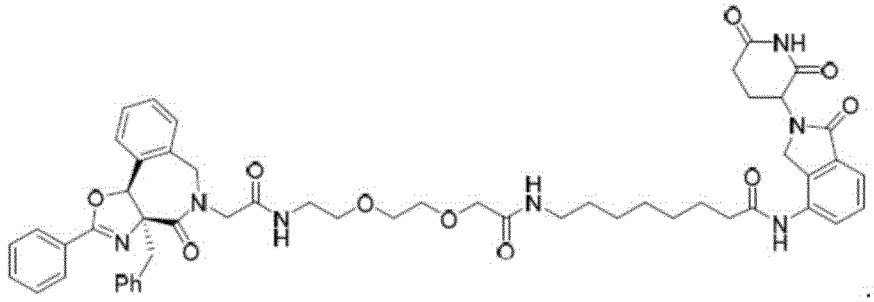

What is claimed is:
1. A compound of Formula (I'):

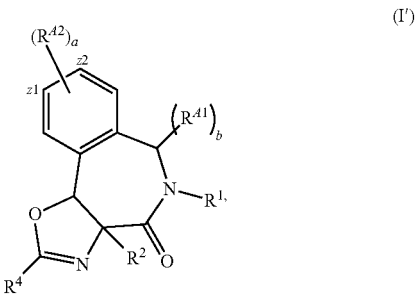

or a pharmaceutically acceptable salt thereof, wherein:
$R^1$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or nitrogen protecting group;
$R^2$ is independently hydrogen, substituted or unsubstituted phenyl, substituted or unsubstituted benzyl, or of the formula: —CH$_2$(R$^{2b}$), wherein:
$R^{2b}$ is 5 to 8-membered substituted or unsubstituted cycloalkyl, 5 to 10-membered substituted or unsubstituted heterocyclyl, 6 to 14-membered substituted or unsubstituted aryl, or 5 to 10-membered substituted or unsubstituted heteroaryl; and
$R^4$ is hydrogen, substituted or unsubstituted alkyl, substituted or unsubstituted carbocyclyl, substituted or unsubstituted heterocyclyl, unsubstituted phenyl, substituted or unsubstituted heteroaryl, or of the formula:

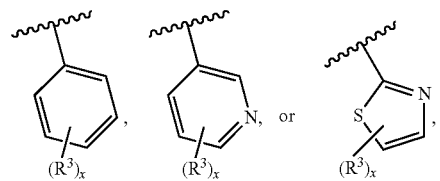

wherein:
x is 1, 2, 3, 4, or 5; and
each instance of $R^3$ is independently hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —N(R$^b$)$_2$, —SR, —CN, —SCN, or of the formula —O(CH$_2$)$_e$OR$^{c1}$, wherein:
e is independently 1, 2, 3, or 4; and
$R^{c1}$ is independently substituted or unsubstituted acyl, substituted or unsubstituted alkyl, substituted or unsubstituted carbocyclyl, substituted or unsubstituted heterocyclyl, substituted or unsubstituted aryl, or substituted or unsubstituted heteroaryl;
$R^{A1}$ is independently hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR, —N(R$^b$)$_2$, —SR, —CN, or —SCN;

R$^{42}$ is independently hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR, —N(R$^b$)$_2$, —SR, —CN, —SCN, —NO$_2$, or optionally two instances of R$^{42}$ are taken together with the phenyl in Formula (I') to form substituted or unsubstituted carbocyclyl, substituted or unsubstituted heterocyclyl, substituted or unsubstituted aryl or substituted or unsubstituted heteroaryl;

a is 0, 1, 2, 3, or 4;

b is 0, 1, or 2;

z1 and z2 indicate where two instances of R$^{42}$ are optionally taken together to form substituted or unsubstituted carbocyclyl, substituted or unsubstituted heterocyclyl, substituted or unsubstituted aryl, or substituted or unsubstituted heteroaryl fused with the phenyl moiety in Formula (I'); and R is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, oxygen protecting group, or sulfur protecting group; and each instance of R$^b$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, nitrogen protecting group, or optionally two R$^b$ are taken together to form substituted or unsubstituted heterocyclyl or substituted or unsubstituted heteroaryl;

wherein acyl is independently —C(=O)R$^{aa}$, —CHO, —CO$_2$R$^{aa}$, —C(=O)N(R$^{bb}$)$_2$, —C(=NR$^{bb}$)R$^{aa}$, —C(=NR$^{bb}$)OR$^{aa}$, or —C(=NR$^{bb}$)N(R$^{bb}$)$_2$;

wherein each acyl, alkyl, alkenyl, alkynyl, carbocyclyl, heterocyclyl, heterocyclic ring, heteroaryl ring, aryl, and heteroaryl referred to above is substituted with one or more substituents at a carbon atom, the one or more substituents at the carbon atom are independently selected from the substituents in Group (i);

when any one of the heterocyclyl, heterocyclic ring, heteroaryl, and heteroaryl ring, referred to above is substituted with one or more substituents at a nitrogen atoms, the one or more substituents at the nitrogen atom are independently selected from the substituents in Group (ii);

Group (i) consists of halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —OP(=O)(R$^{aa}$)$_2$, —OP(=O)(OR$^{cc}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —OP(R$^{cc}$)$_2$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups; or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$; and Group (ii) consists of hydrogen, —OH, —OR$^{aa}$, —N(R$^{cc}$)$_2$, —CN, —C(=O)R$^{aa}$, —C(=O)N(R$^{CC}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups;

wherein:

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of $R^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl and 5-10 membered heteroaryl, or two R$^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3^+$X$^-$, —NH(C$_{1-6}$ alkyl)$_2^+$X$^-$, —NH$_2$(C$_{1-6}$ alkyl)$^+$X$^-$, —NH$_3^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, 5-10 membered heteroaryl; or two geminal R$^{gg}$ substituents can be joined to form =O or =S; and X$^-$ is a counterion, wherein the counterion is a halide ion, NO$_3^-$, ClO$_4^-$, OH$^-$, H$_2$PO$_4^-$, HSO$_4^-$, a sulfonate ion, or a carboxylate ion;

wherein carbocyclyl is a monocyclic, saturated, non-aromatic cyclic hydrocarbon group having from 3 to 10 ring carbon atoms;

wherein heterocyclyl is a non-aromatic, 5- to 10-membered monocyclic or bicyclic ring, wherein one or two atoms in the heterocyclic ring are independently nitrogen, oxygen, or sulfur;

wherein aryl is an aromatic, 6- to 10-membered monocyclic or bicyclic ring; and wherein heteroaryl is an aromatic 5- to 6-membered, monocyclic ring, wherein one, two, three, or four atoms in the heteroaryl ring system are independently nitrogen, oxygen, or sulfur.

2. The compound of claim 1, or a pharmaceutically acceptable salt thereof, wherein R$^4$ is hydrogen, C$_{1-6}$ substituted or unsubstituted alkyl, or substituted or unsubstituted 5 to 6-membered heteroaryl.

3. The compound of claim 1, or a pharmaceutically acceptable salt thereof, wherein two instances of R$^{A2}$ are taken together with the phenyl in Formula (I') to form substituted or unsubstituted carbocyclyl, substituted or unsubstituted heterocyclyl, substituted or unsubstituted aryl or substituted or unsubstituted heteroaryl of the formula:

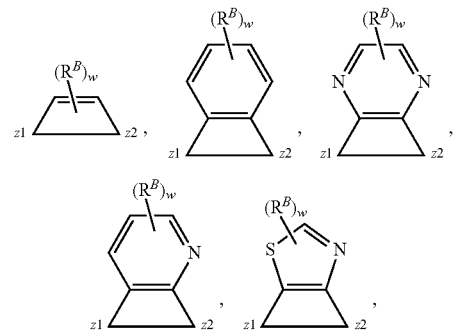

or a pharmaceutically acceptable salt thereof, wherein:

w is 0, 1, 2, 3, or 4; and each instance of R$^B$ is independently hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR, —N(R$^b$)$_2$, —NO$_2$, —SR, —CN, or —SCN.

4. The compound of claim 1, wherein the compound is of the formula:

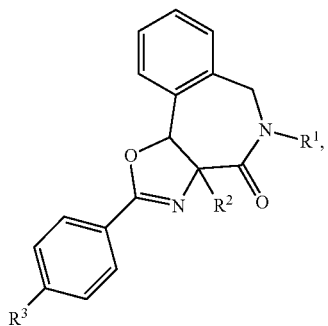

or a pharmaceutically acceptable salt thereof.

5. The compound of claim 1, or a pharmaceutically acceptable salt thereof, wherein $R^1$ is of the formula: —$(CH_2)_nR^a$, wherein:

n is 1, 2, 3, 4, 5, or 6;

$R^a$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{a2}$, —$C(=O)OR^{a2}$, —$C(=O)N(R^{aa})_2$, —$N(R^{aa})_2$, —$NC(=O)N(R^{aa})_2$, —$OC(=O)N(R^{aa})_2$, —$OC(=O)OR^{a2}$, —$SR^{a2}$, or —$SO_2R^{a2}$;

each instance of $R^{a2}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, oxygen protecting group, or sulfur protecting group; and each instance of $R^{aa}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, or nitrogen protecting group.

6. The compound of claim 1, or a pharmaceutically acceptable salt thereof, wherein $R^1$ is:

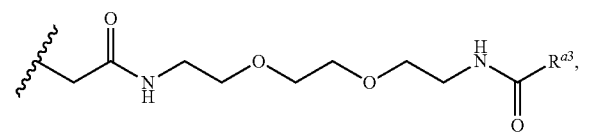

wherein $R^{a3}$ is hydrogen, substituted or unsubstituted alkyl, substituted or unsubstituted alkenyl, substituted or unsubstituted alkynyl, substituted or unsubstituted heterocyclyl, substituted or unsubstituted aryl, or substituted or unsubstituted heteroaryl.

7. The compound of claim 1, or a pharmaceutically acceptable salt thereof, wherein $R^1$ is of the formula:

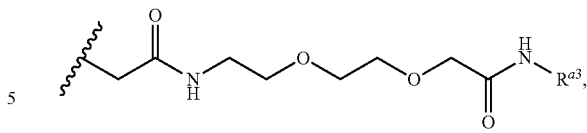

wherein $R^{a3}$ is hydrogen, substituted or unsubstituted alkyl, substituted or unsubstituted alkenyl, substituted or unsubstituted alkynyl, substituted or unsubstituted heterocyclyl, substituted or unsubstituted aryl, or substituted or unsubstituted heteroaryl.

8. The compound of claim 1, or a pharmaceutically acceptable salt thereof, wherein $R^1$ is of the formula:

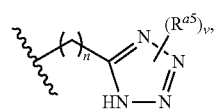

wherein:

v is 0 or 1; and $R^{a5}$ is substituted or unsubstituted alkyl.

9. The compound of claim 1, or a pharmaceutically acceptable salt thereof, wherein $R^2$ is of the formula:

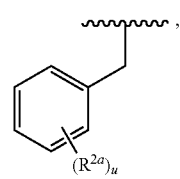

or a pharmaceutically acceptable salt thereof, wherein:

u is 1, 2, 3, 4, or 5; and each instance of $R^{2a}$ is independently hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR, —$N(R^b)_2$, —$NO_2$, —SR, or —CN.

10. The compound of claim 1, or a pharmaceutically acceptable salt thereof, wherein $R^2$ is of the formula: —$CH_2(R^{2b})$, wherein:

$R^{2b}$ is 5 to 8-membered substituted or unsubstituted cycloalkyl, 5 to 10-membered substituted or unsubstituted heterocyclyl, 6 to 14-membered substituted or unsubstituted aryl, or 5 to 10-membered substituted or unsubstituted heteroaryl.

11. The compound of claim 1, wherein the compound is of the formula:

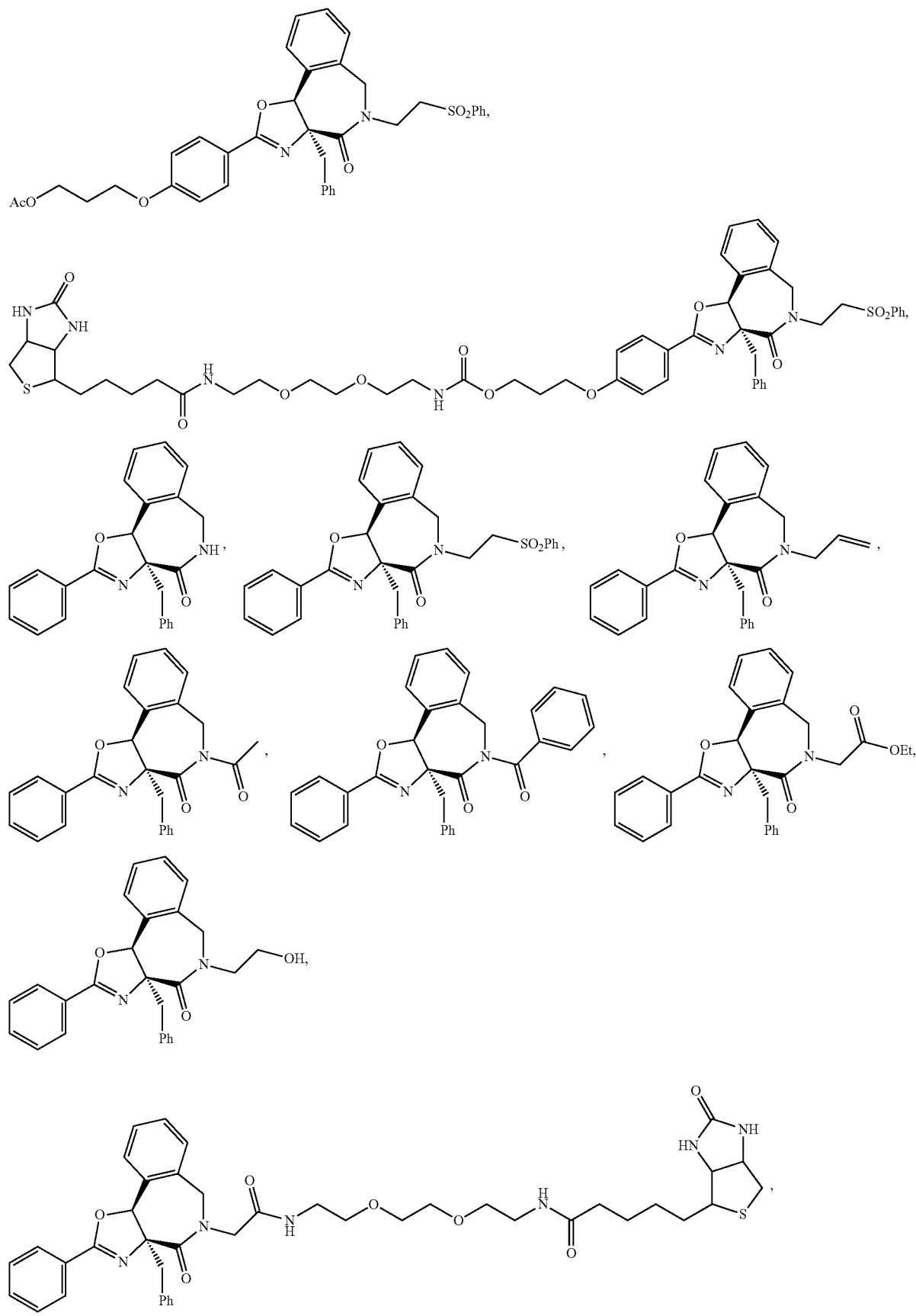

-continued
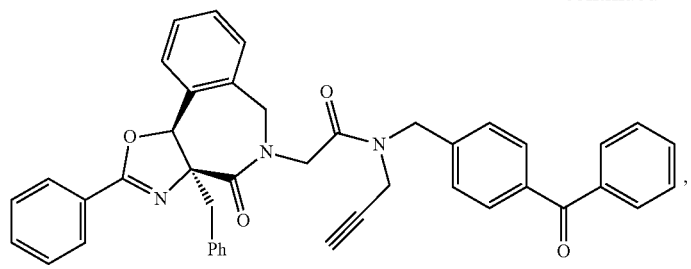
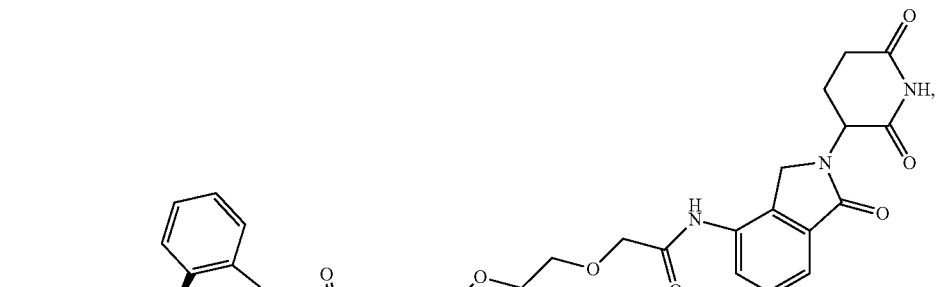
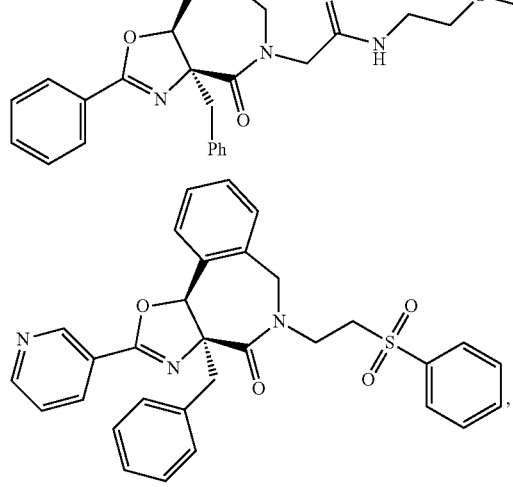
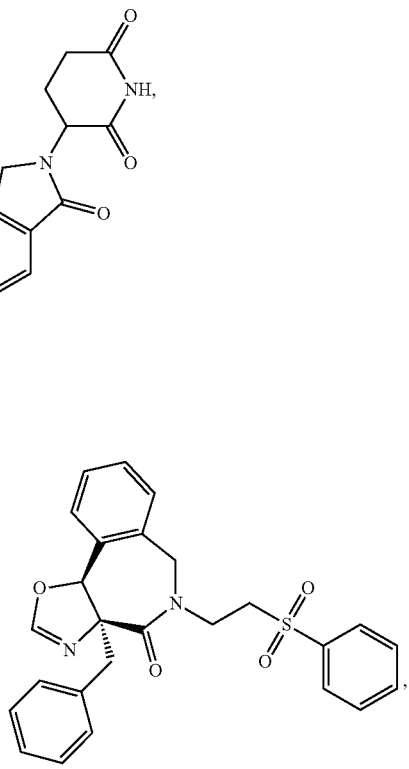
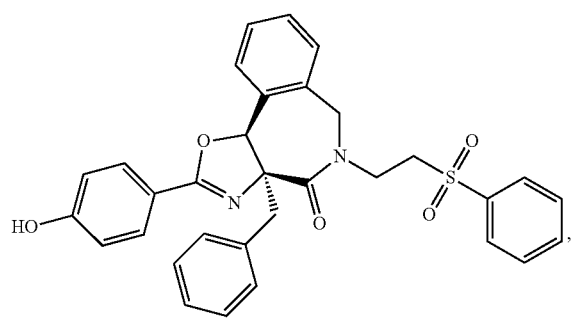
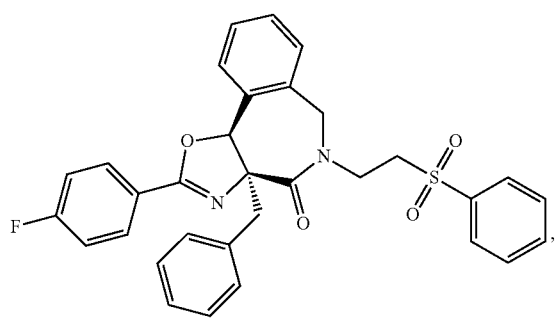
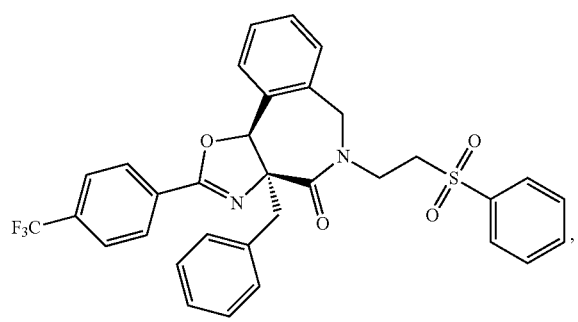
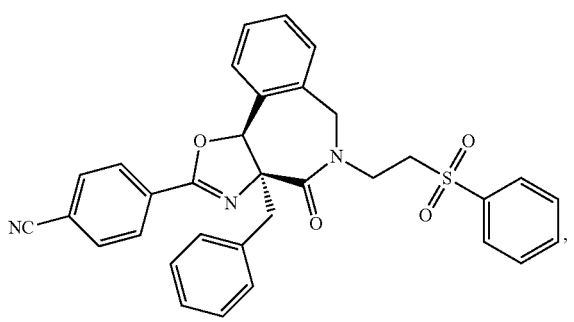

217
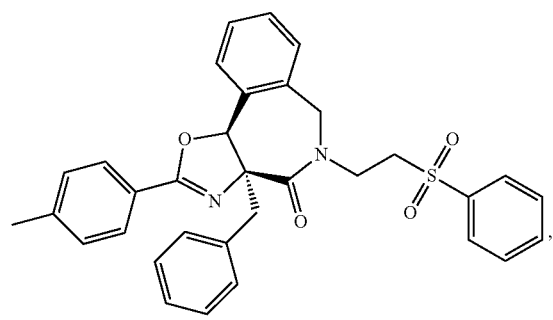
218
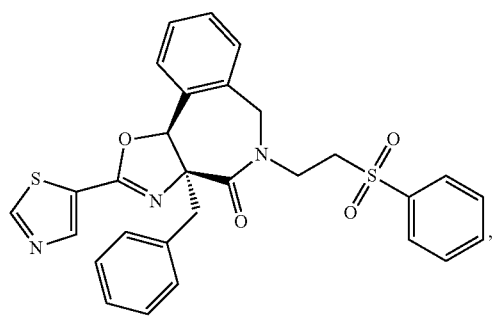
-continued
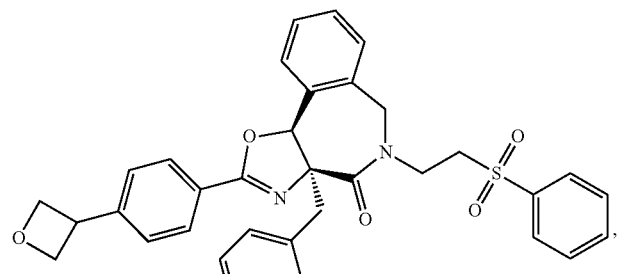
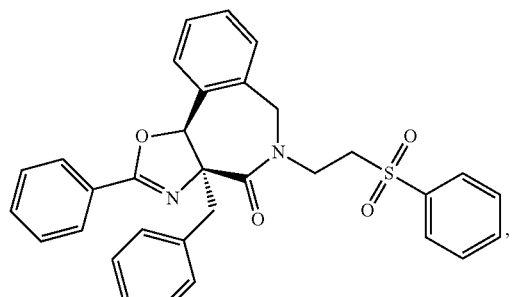
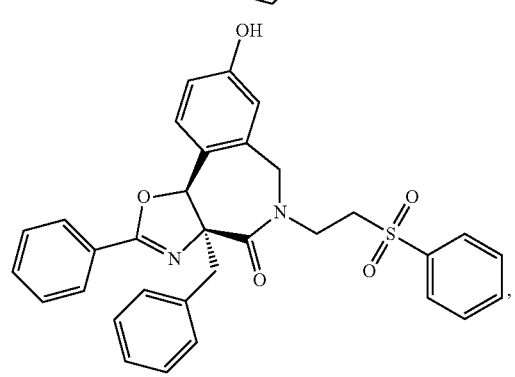
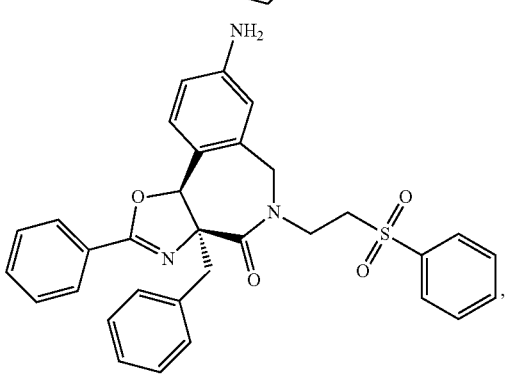
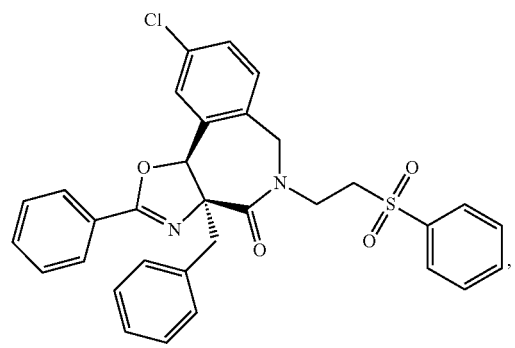
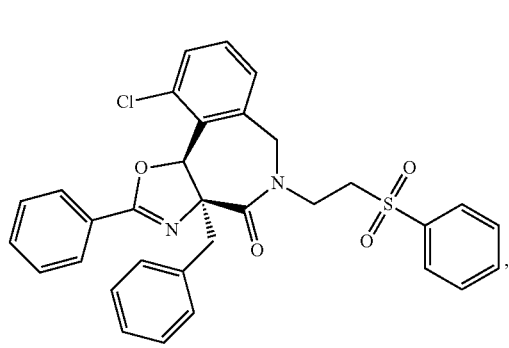
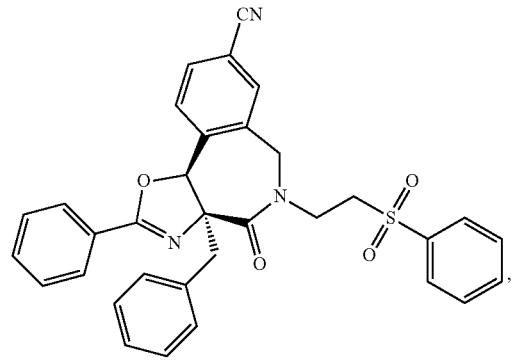
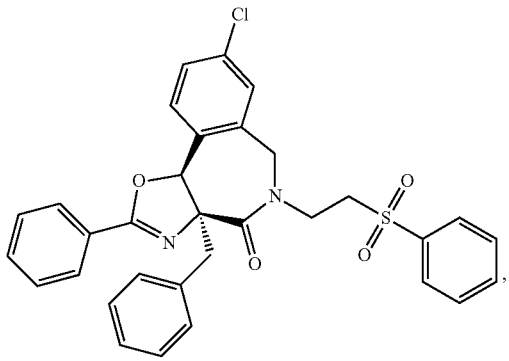

219 220
-continued
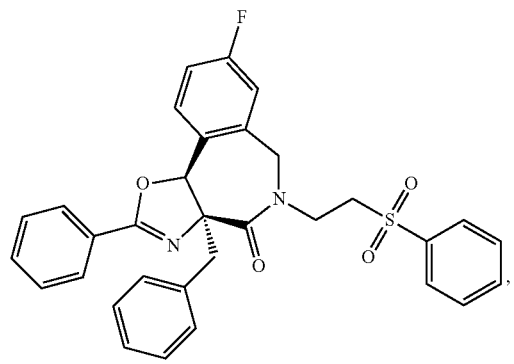
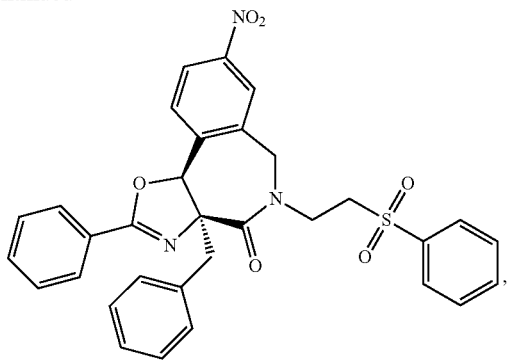
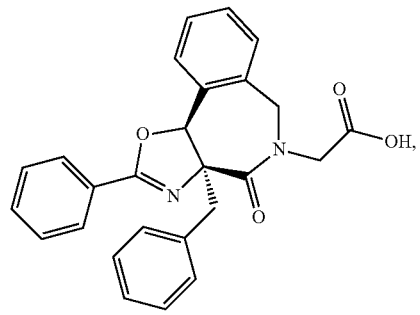
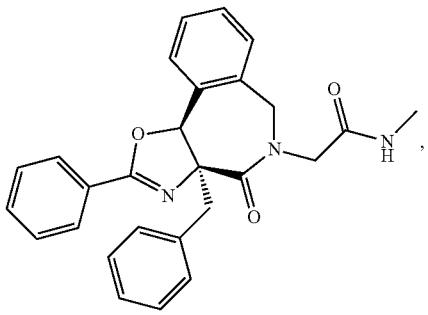
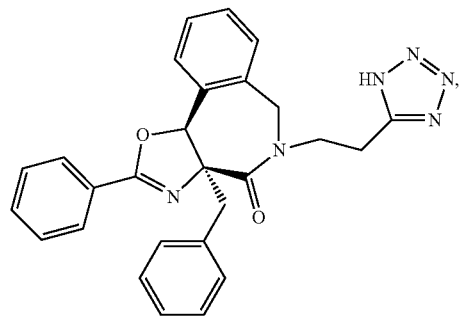
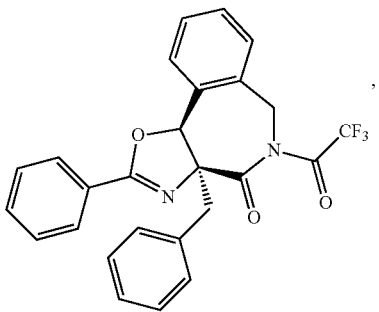
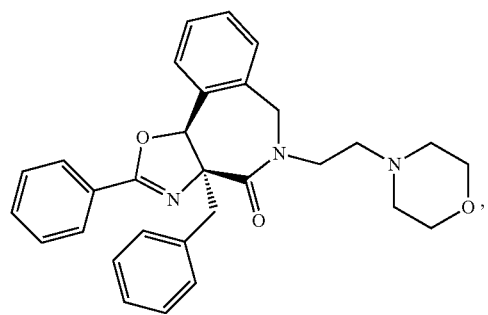
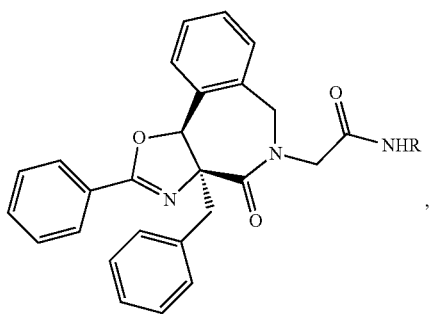
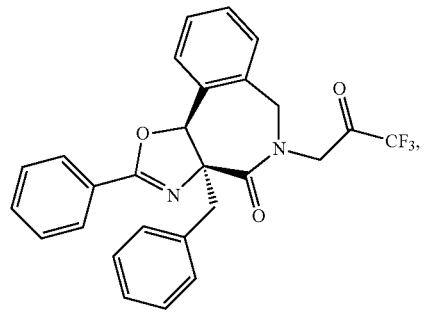
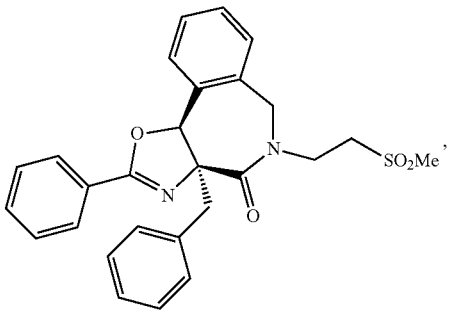

221
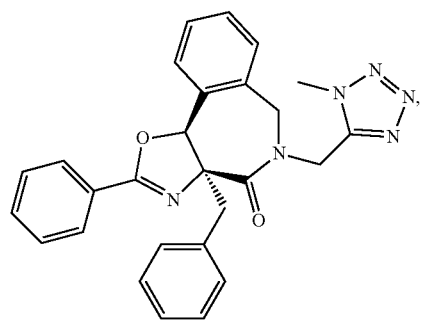
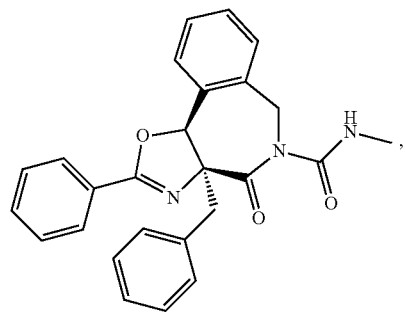
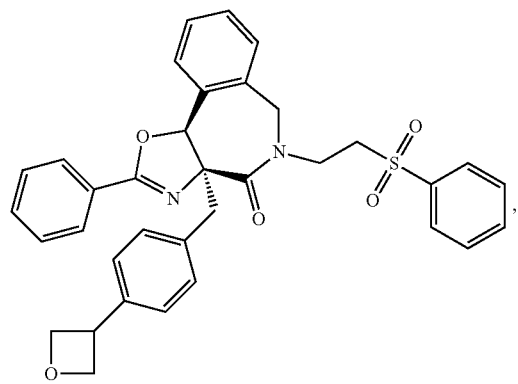
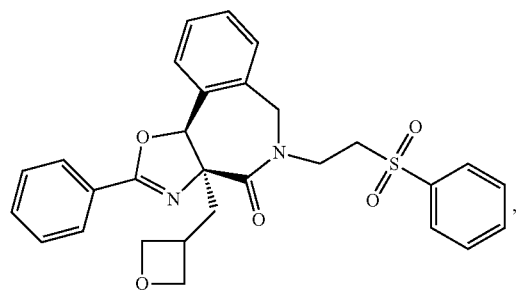
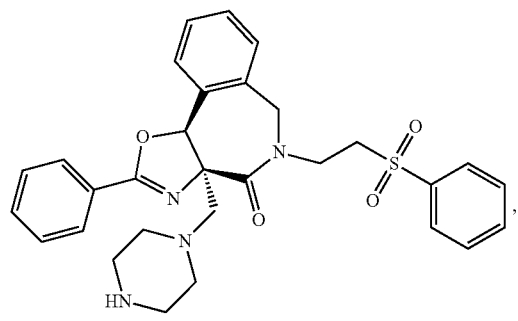
222
-continued
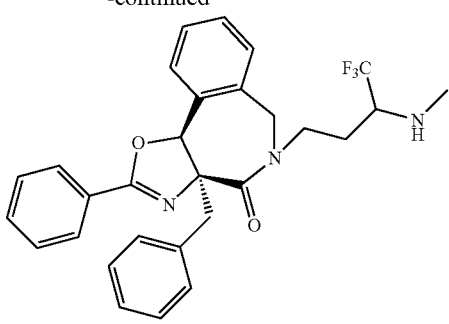
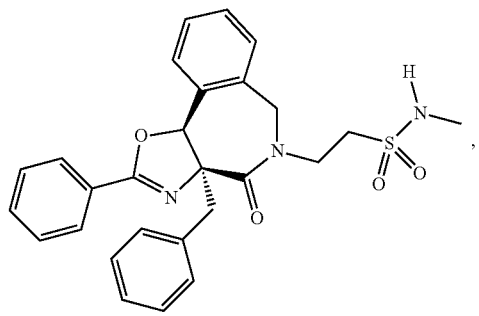
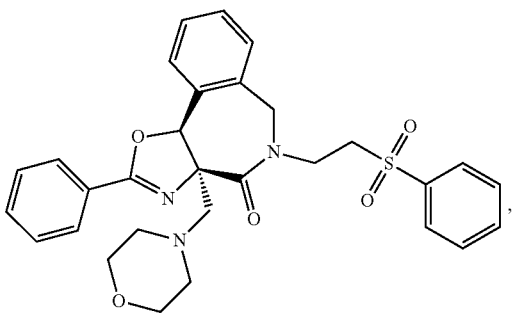
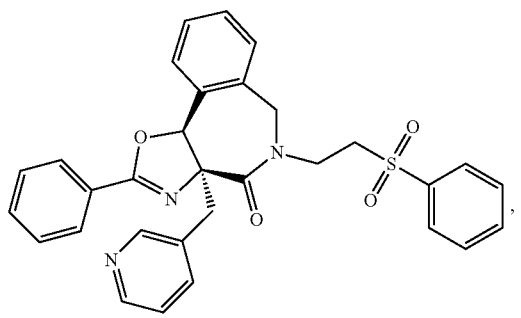
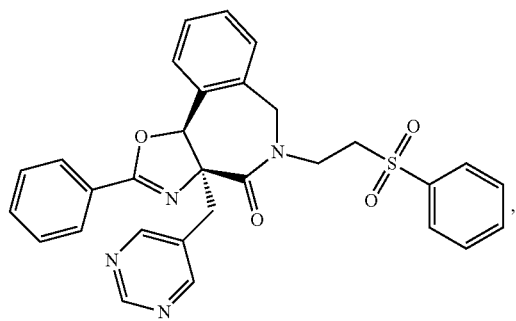

223 224
-continued
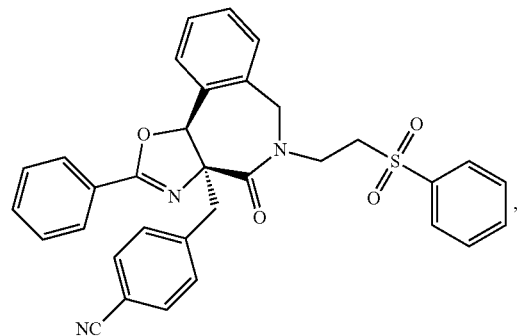,
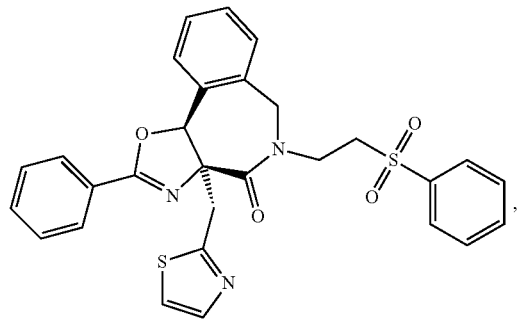,
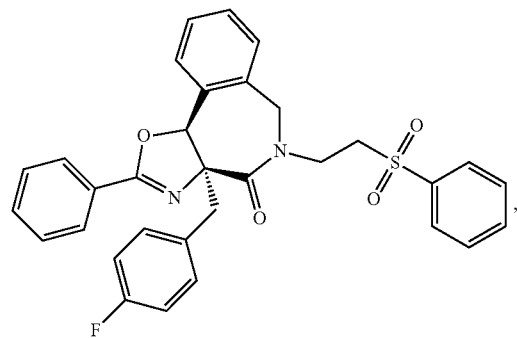,
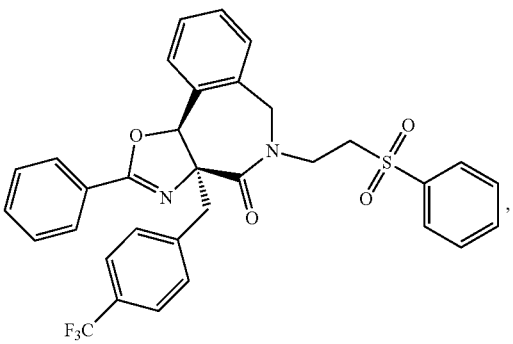,
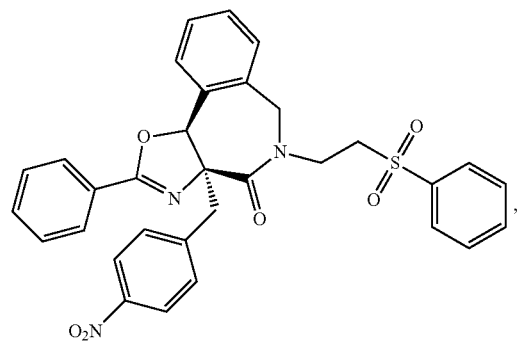,
(MS2-090)
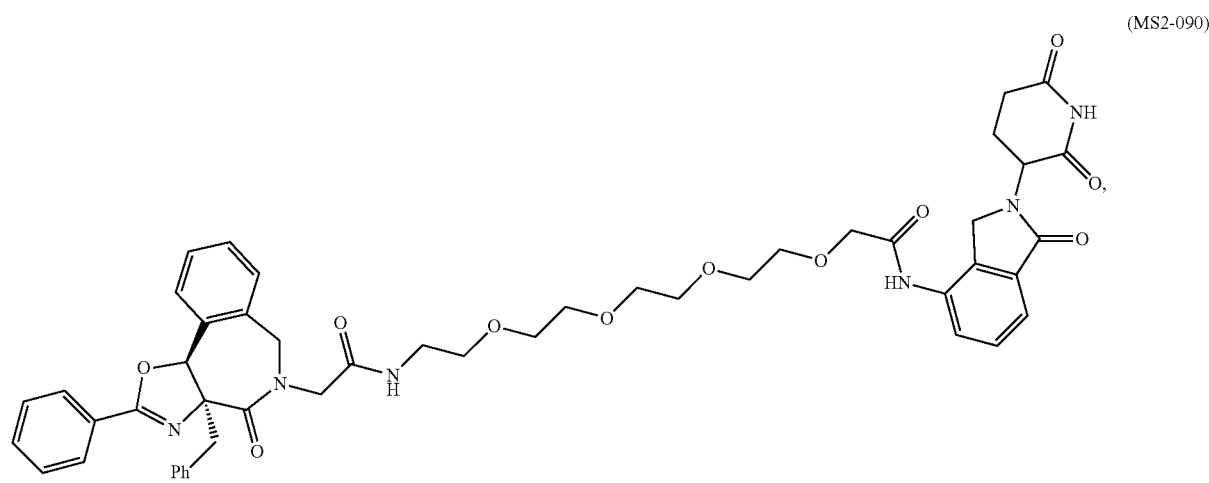

-continued
(MS2-078)
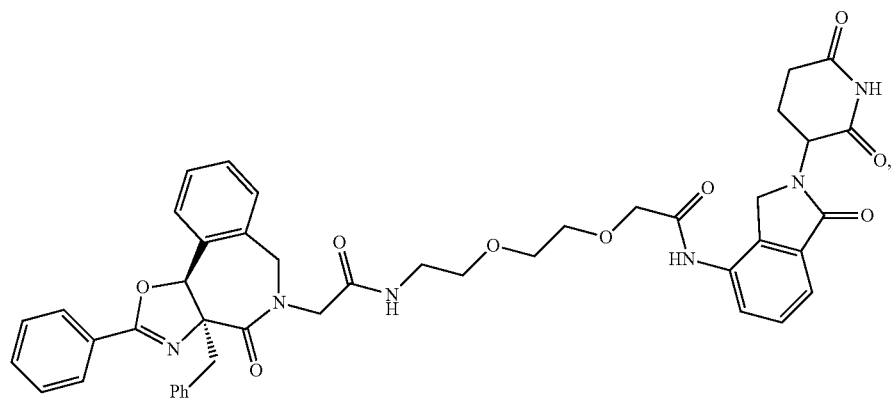
(MS2-089)
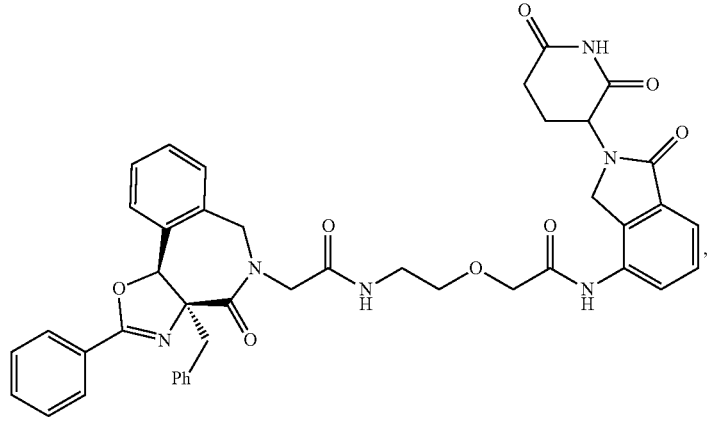
(MS2-096)
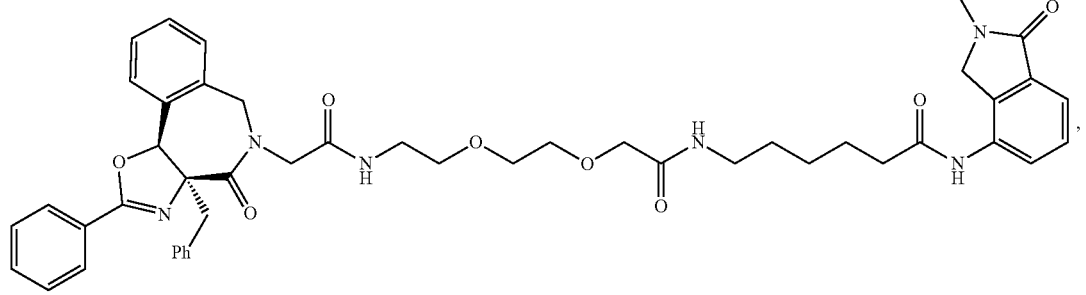
(MS2-095)
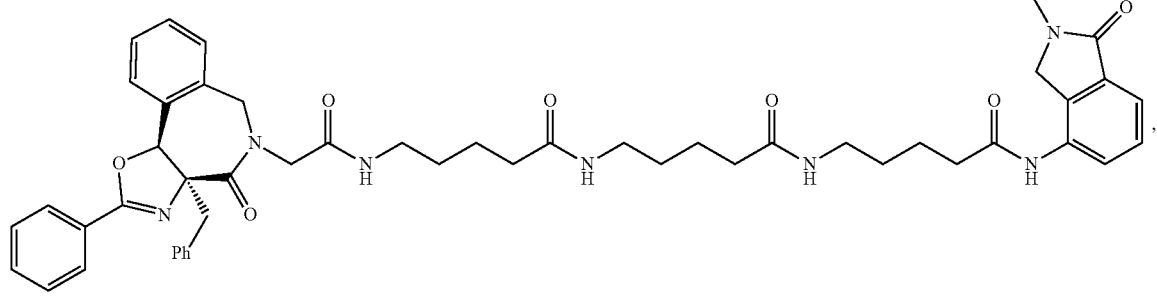

-continued
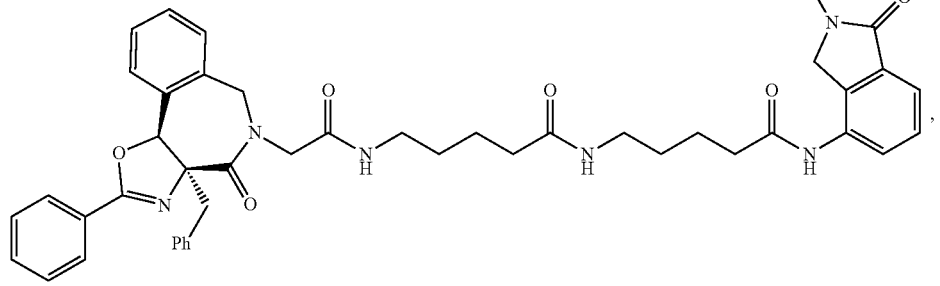
(MS2-094)
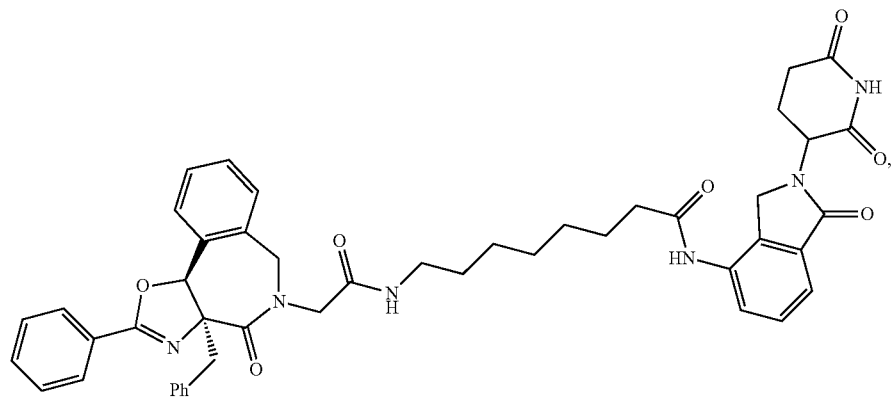
(MS2-093)
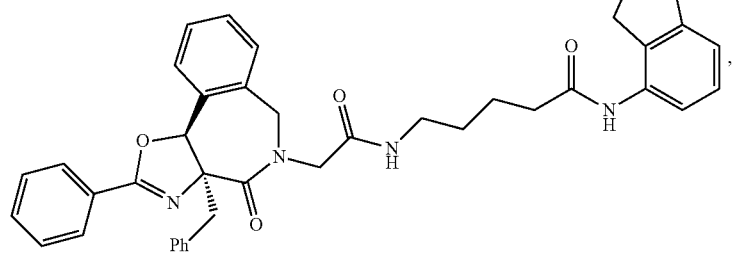
(MS2-092)
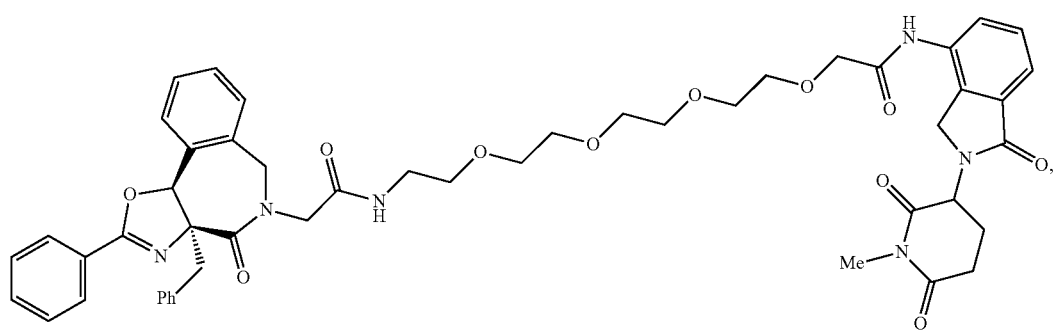
(MS2-090-Me)

-continued
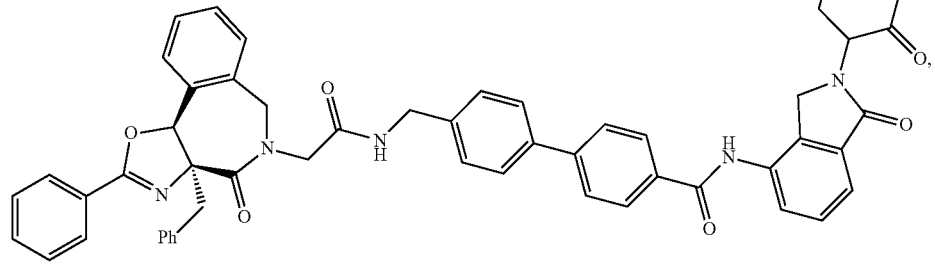
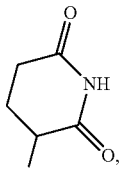
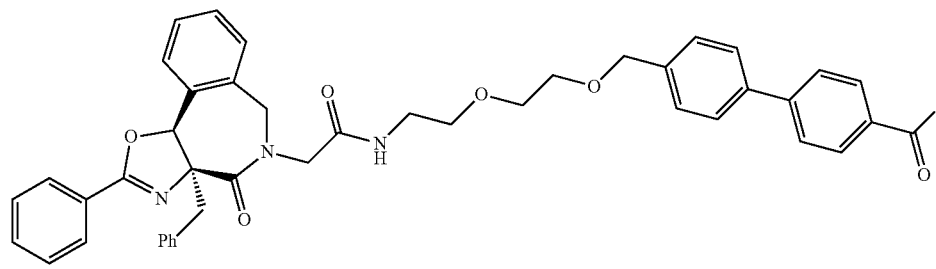
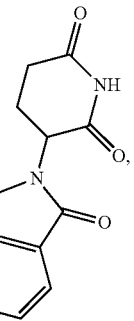
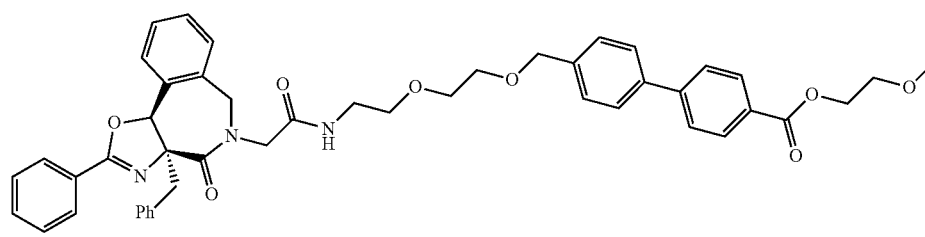
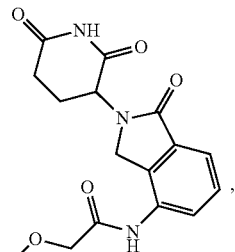
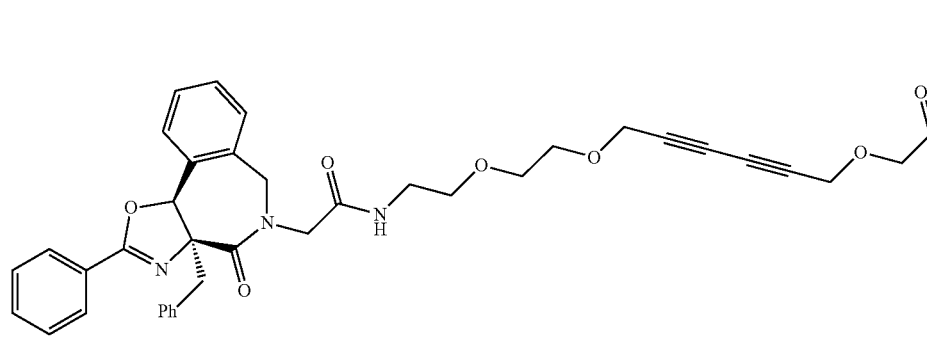
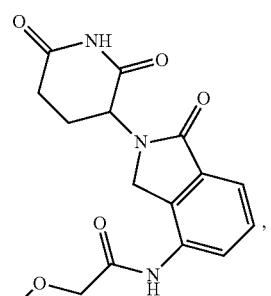

-continued

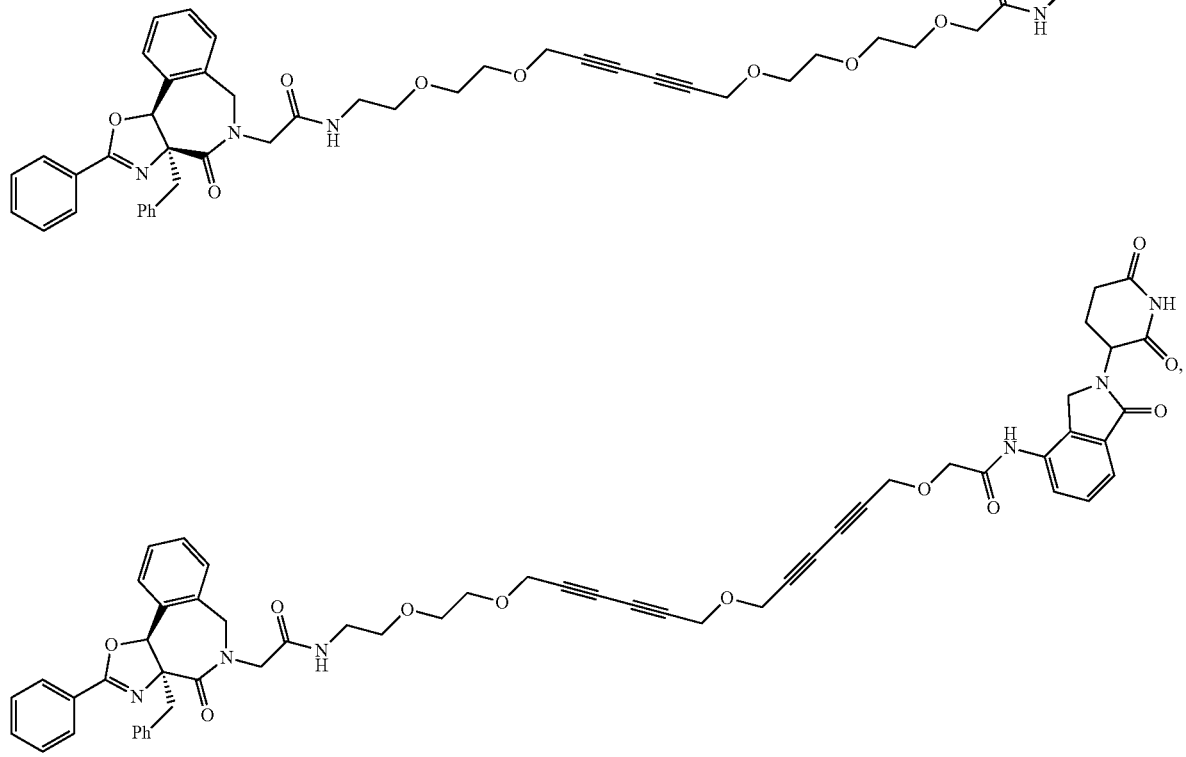

or a pharmaceutically acceptable salt thereof.

12. A pharmaceutical composition comprising a compound of claim 1, or a pharmaceutically acceptable salt thereof, and a pharmaceutically acceptable excipient.

13. The compound of claim 1, wherein $R^4$ is substituted or unsubstituted 5 to 6-membered heteroaryl.

14. The compound of claim 1, wherein $R^4$ is of the formula:

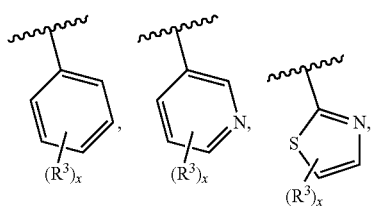

or a pharmaceutically acceptable salt thereof, wherein:
x is 1, 2, 3, 4, or 5; and
each instance of $R^3$ is independently hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR, —N($R^b$)$_2$, —SR, —CN, or —SCN.

15. The compound of claim 14, wherein $R^4$ is of the formula:

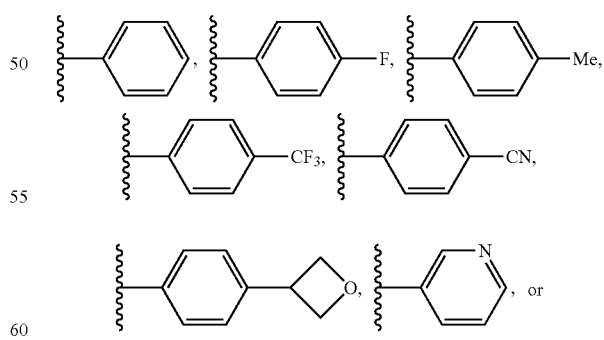

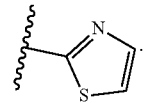

16. The compound of claim 1, wherein $R^1$ is:
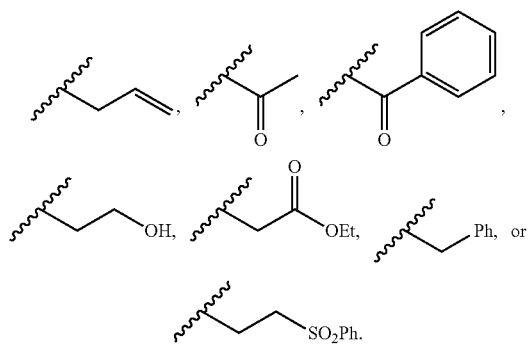
17. The compound of claim 1, wherein $R^1$ is:
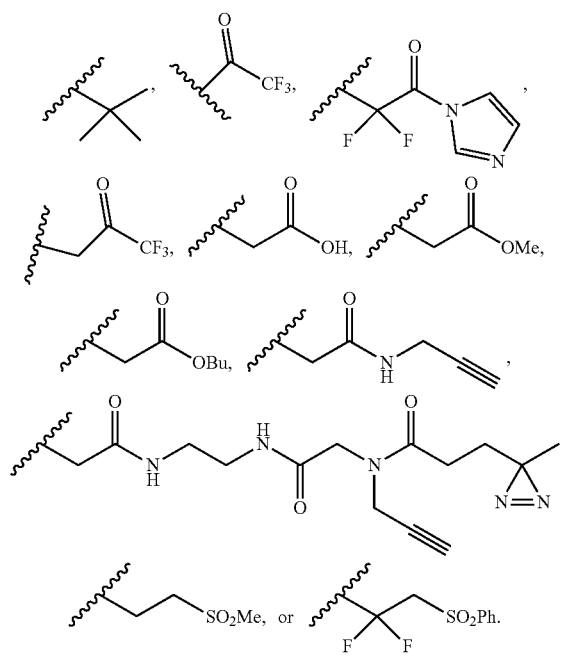
18. The compound of claim 1, wherein $R^1$ is of the formula:
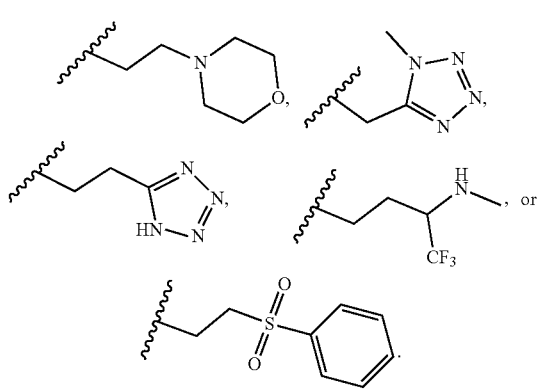
19. The compound of claim 1, wherein $R^2$ is of the formula:
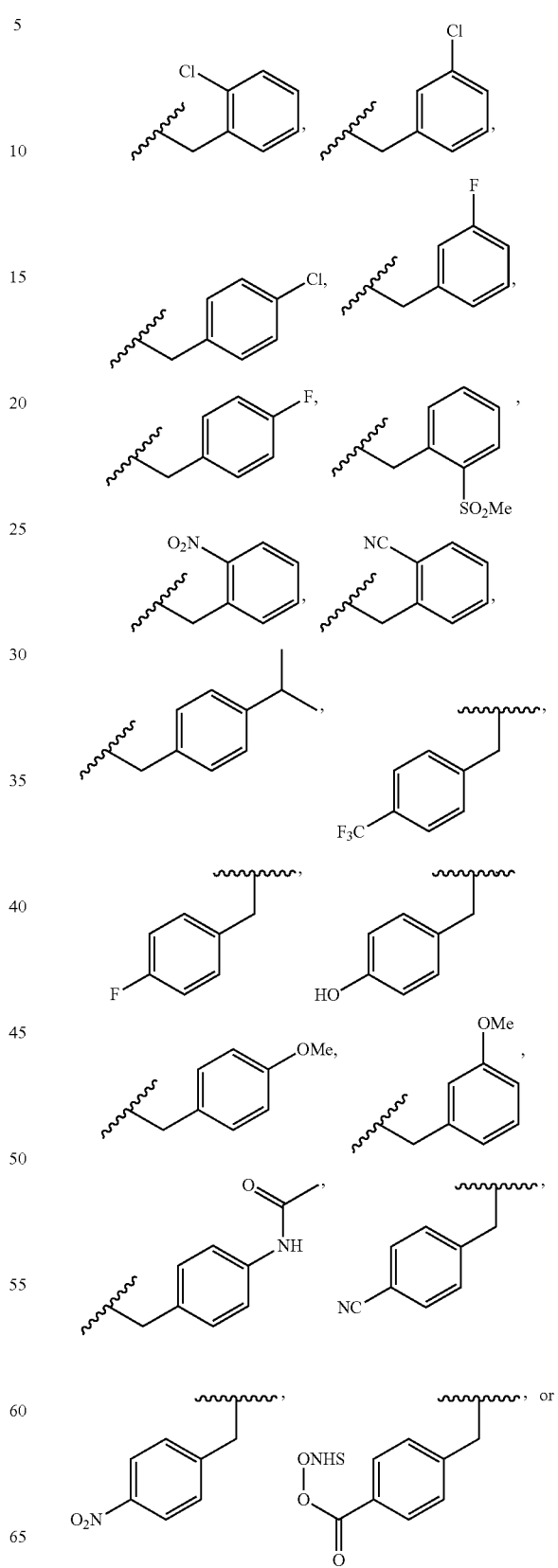

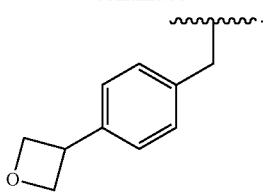 [SMILES: *Cc1ccc(C2COC2)cc1]

20. The compound of claim 1, wherein at least one instance of $R^3$ is of the formula:

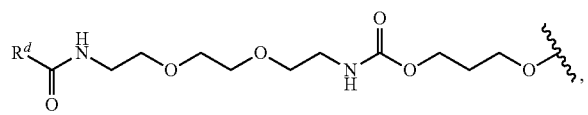

wherein:
$R^d$ is independently substituted or unsubstituted alkyl, substituted or unsubstituted carbocyclyl, substituted or unsubstituted heterocyclyl, substituted or unsubstituted aryl, or substituted or unsubstituted heteroaryl.

21. The compound of claim 1, or a pharmaceutically acceptable salt thereof, wherein at least one instance of $R^3$ is:

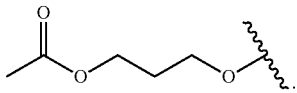 [SMILES: *OCCCOC(C)=O]

22. The compound of claim 1, wherein the compound is of the formula:

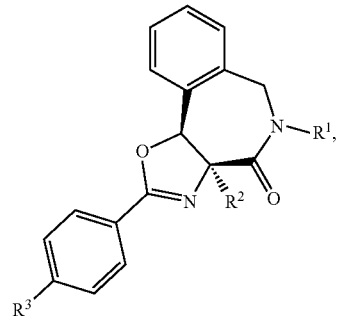

or a pharmaceutically acceptable salt thereof.

23. The compound of claim 1, wherein the compound is of the formula:

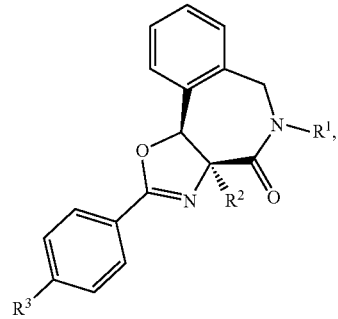

or a pharmaceutically acceptable salt thereof.

* * * * *

UNITED STATES PATENT AND TRADEMARK OFFICE
CERTIFICATE OF CORRECTION

PATENT NO. : 10,106,555 B2  
APPLICATION NO. : 15/435003  
DATED : October 23, 2018  
INVENTOR(S) : Angela N. Koehler et al.

Page 1 of 2

It is certified that error appears in the above-identified patent and that said Letters Patent is hereby corrected as shown below:

In the Claims

In Claim 11, the second compound in Column 218 of formula: 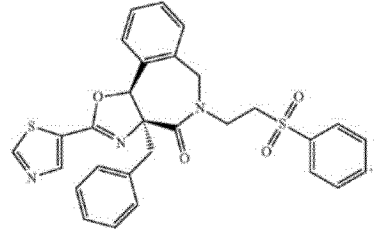 should be replaced with the formula: 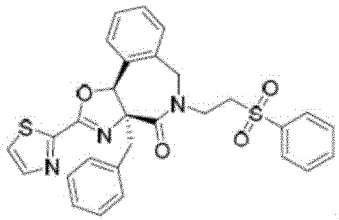 .

Signed and Sealed this  
Sixth Day of August, 2019

Andrei Iancu  
*Director of the United States Patent and Trademark Office*

CERTIFICATE OF CORRECTION (continued)  
U.S. Pat. No. 10,106,555 B2

Page 2 of 2

In Claim 11, the third compound in Columns 225-226 of formula:

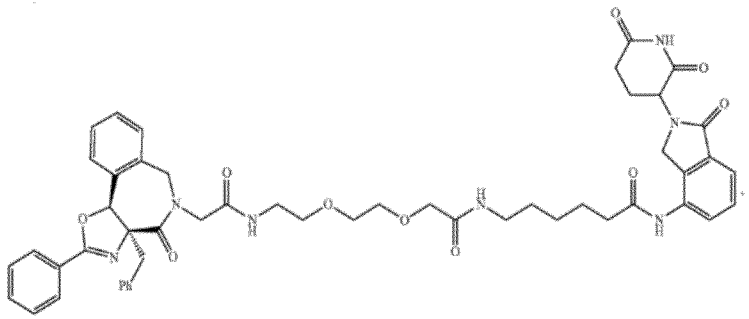

should be replaced with the formula: